US012250931B2

(12) United States Patent
Cheng et al.

(10) Patent No.: US 12,250,931 B2
(45) Date of Patent: Mar. 18, 2025

(54) GENETICALLY MODIFIED MOUSE WITH A HUMANIZED PNPLA3 GENE AND METHODS OF USE

(71) Applicant: Regeneron Pharmaceuticals, Inc., Tarrytown, NY (US)

(72) Inventors: Xiping Cheng, Northvale, NJ (US); Jose F. Rojas, Newburgh, NY (US); Mark Sleeman, New York, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 636 days.

(21) Appl. No.: 17/159,564

(22) Filed: Jan. 27, 2021

(65) Prior Publication Data

US 2021/0227812 A1 Jul. 29, 2021

Related U.S. Application Data

(60) Provisional application No. 62/966,837, filed on Jan. 28, 2020.

(51) Int. Cl.

| | |
|---|---|
| ***A01K 67/027*** | (2024.01) |
| ***A01K 67/0278*** | (2024.01) |
| ***A61K 49/00*** | (2006.01) |
| ***C12N 15/85*** | (2006.01) |

(52) U.S. Cl.

CPC ...... *A01K 67/0278* (2013.01); *A61K 49/0008* (2013.01); *C12N 15/8509* (2013.01); *A01K 2207/15* (2013.01); *A01K 2227/105* (2013.01)

(58) Field of Classification Search

None

See application file for complete search history.

(56) References Cited

U.S. PATENT DOCUMENTS

| | | | | |
|---|---|---|---|---|
| 5,942,435 | A | 8/1999 | Wheeler | |
| 6,586,251 | B2 | 7/2003 | Economides et al. | |
| 7,294,754 | B2 | 11/2007 | Poueymirou et al. | |
| 7,576,259 | B2 | 8/2009 | Poueymirou et al. | |
| 7,659,442 | B2 | 2/2010 | Poueymirou et al. | |
| 8,847,004 | B2 * | 9/2014 | Murphy | A01K 67/0271 800/9 |
| 8,878,001 | B2 * | 11/2014 | Wang | C12N 5/0606 800/25 |
| 8,962,913 | B2 * | 2/2015 | Murphy | A01K 67/0278 800/21 |
| 9,155,290 | B2 * | 10/2015 | Rojas | A01K 67/0278 |
| 9,497,945 | B2 * | 11/2016 | Kyratsous | C12N 5/0606 |
| 9,565,841 | B2 * | 2/2017 | Wang | C07K 14/7155 |
| 9,629,347 | B2 * | 4/2017 | McWhirter | A01K 67/0278 |
| 9,730,435 | B2 * | 8/2017 | McWhirter | C07K 14/47 |
| 10,329,582 | B2 | 6/2019 | Lee et al. | |
| 10,385,359 | B2 | 8/2019 | Lee et al. | |
| 10,390,522 | B2 * | 8/2019 | Burova | A01K 67/0278 |
| 10,577,630 | B2 | 3/2020 | Zhang et al. | |
| 2004/0033497 | A1 * | 2/2004 | Alarcon-Riquelme | C07K 14/70503 435/6.12 |
| 2008/0078000 | A1 | 3/2008 | Poueymirou et al. | |
| 2014/0178879 | A1 | 6/2014 | Economides et al. | |
| 2014/0235933 | A1 | 8/2014 | Lee et al. | |
| 2014/0310828 | A1 | 10/2014 | Lee et al. | |
| 2015/0376628 | A1 | 12/2015 | Schoenherr et al. | |
| 2015/0376651 | A1 | 12/2015 | Frendewey et al. | |
| 2016/0145646 | A1 | 5/2016 | Frendewey et al. | |
| 2017/0347633 | A1 | 12/2017 | Macdonald et al. | |
| 2017/0349903 | A1 | 12/2017 | Liu et al. | |
| 2019/0070213 | A1 * | 3/2019 | Aznarez | C12N 15/1136 |
| 2020/0392541 | A1 | 12/2020 | Zhang et al. | |

FOREIGN PATENT DOCUMENTS

| | | | | |
|---|---|---|---|---|
| EP | 3620524 | A1 | 3/2020 | |
| WO | WO-2005059099 | A2 * | 6/2005 | A61P 3/10 |
| WO | WO 2014/130706 | A1 | 8/2014 | |
| WO | WO 2014/172489 | A2 | 10/2014 | |
| WO | WO 2015/088643 | A1 | 6/2015 | |
| WO | WO 2015/200334 | A1 | 12/2015 | |
| WO | WO 2015/200805 | A2 | 12/2015 | |
| WO | WO 2016/044745 | A1 | 3/2016 | |
| WO | WO 2016/081923 | A2 | 5/2016 | |
| WO | WO 2016/130806 | A2 | 8/2016 | |
| WO | WO 2017/087780 | A1 | 5/2017 | |

(Continued)

OTHER PUBLICATIONS

Smagris (Hepatology, 2015, vol. 61, p. 108-118) plus Supplemental Information (Year: 2015).*

NIH Library of Med. description of the mouse PNPLA3 gene, 2023.*

NIH Library of Med. description of the human PNPLA3 gene, 2023.*

Barthold, "Genetically altered mice: phenotypes, no phenotypes, and Faux phenotypes," Genetica, 122(1):75-88, (2004).

Basuray, et al., "Accumulation of PNPLA3 on Lipid Droplets is the Basis of Associated Hepatic Steatosis," Proc. Natl. Acad. Sci. U.S.A., 116(19):9521-9526, (2019).

Birling, et al., "Modeling human disease in rodents by CRISPR/Cas9 genome editing," Mamm. Genome, 28(7-8):291-301, (2017).

Brevini, et al., "No shortcuts to pig embryonic stem cells," Theriogenology, 74(4):544-550, (2010).

(Continued)

*Primary Examiner* — Michael C Wilson

(74) *Attorney, Agent, or Firm* — Alston & Bird LLP

(57) ABSTRACT

Non-human animal genomes, non-human animal cells, and non-human animals comprising a humanized PNPLA3 locus and methods of making and using such non-human animal genomes, non-human animal cells, and non-human animals are provided. Non-human animal cells or non-human animals comprising a humanized PNPLA3 locus express a human PNPLA3 protein or a chimeric PNPLA3 protein, fragments of which are from human PNPLA3. Methods are provided for using such non-human animals comprising a humanized PNPLA3 locus to assess in vivo efficacy of human-PNPLA3-targeting reagents such as nuclease agents designed to target human PNPLA3.

23 Claims, 7 Drawing Sheets

Specification includes a Sequence Listing.

(56) References Cited

FOREIGN PATENT DOCUMENTS

| | | | |
|---|---|---|---|
| WO | WO 2019/118638 | A2 | 6/2019 |
| WO | WO 2020/123508 | A2 | 6/2020 |
| WO | WO 2015/042557 | A1 | 4/2021 |
| WO | WO 2021/074772 | A1 | 4/2021 |
| WO | 2021/154791 | A1 | 8/2021 |

OTHER PUBLICATIONS

Brevini, et al., "Porcine embryonic stem cells: Facts, challenges and hopes," Theriogenology, 68 Suppl. 1:S206-S213, (2007).
Burova, et al., "Characterization of the Anti-PD-1 Antibody REGN2810 and Its Antitumor Activity in Human PD-1 Knock-In Mice," Mol. Cancer Ther., 16(5):861-870, (2017).
Cao, et al., "Isolation and Culture of Primary Bovine Embryonic Stem Cell Colonies by a Novel Method," J. Exp. Zool. A. Ecol. Genet. Physiol., 311(5):368-376, (2009).
Chen, et al., "PNPLA3 1148M Variant in Nonalcoholic Fatty Liver Disease: Demographic and Ethnic Characteristic and the Role of the Variant in Nonalcoholic Fatty Liver Fibrosis," World J. Gastroenterol., 21(3):794-802, (2015).
Clark, et al., "A future for transgenic livestock," Nat. Rev. Genet., 4(10):825-833, (2003).
Dechiara, T.M., et al., "VelociMouse: Fully ES Cell-Derived FO-Generation Mice Obtained from the Injection of ES Cells into Eight-Cell-Stage Embryos," Jan. 1, 2009, Methods in Molecular Biology, 530(16): 311-324.
Dennis, "Welfare Issues of Genetically Modified Animals," ILAR J., 43(2):100-109, (2002).
Donati, et al., "The rs2294918 E434K Variant Modulates Patatin-Like Phospholipase Domain-Containing 3 Expression and Liver Damage," Hepatology, 63(3):787-798, (2016).
Frendewey, et al., "The Loss-of-Allele Assay for ES Cell Screening and Mouse Genotyping," Methods Enzymol., 476:295-307, (2010).
Genoway, "Humanized Mouse Model," retrieved from https://www.genoway.com/services/customized-mouse/knockin-models/humanisation.htm on May 12, 2018.
Gomez, et al., "Derivation of cat embryonic stem-like cells from in vitro-produced blastocysts on homologous and heterologous feeder cells," Theriogenology, 74(4): 498-515, (2010).
Graham, et al., "Resources for the design of CRISPR gene editing experiments," Genome Biol., 16:260, (2015).
Harari, et al., "Bridging the Species Divide: Transgenic Mice Humanized for Type-I Interferon Response," PLoS One, 9(1): e84259, (2014).
Herndler-Brandstetter, et al., "Humanized mouse model supports development, function, and tissue residency of human natural killer cells," Proc. Natl. Acad. Sci. U.S.A., 114(45):E9626-E9634, (2017).
Houdebine, "Methods to Generate Transgenic Animals," pp. 31-48 in "Genetic Engineering in Livestock: New Applications and Interdisciplinary Perspectives," Ed. Engelhard et al., (2009).
Jean, et al., "Pluripotent genes in avian stem cells," Dev. Growth Differ., 55(1): 41-51, (2013).
Kawamata, et al., "Generation of genetically modified rats from embryonic stem cells," Proc. Natl. Acad. Sci. U.S.A., 7(32):14223-14228, (2010).
Kovalic, et al., "Genetic and Epigenetic Culprits in the Pathogenesis of Nonalcoholic Fatty Liver Disease," J. Clin. Exp. Hepatol., 8(4):390-402, (2018).
Kumar, et al., "Transgenic Mouse Technology: Principles and Methods," Methods Mol. Biol., 590:335-362, (2009).
Linden, et al., "Pnpla3 Silencing with Antisense Oligonucleotides Ameliorates Nonalcoholic Steatohepatitis and Fibrosis in Pnpla3 I148M Knock-In Mice," Mol. Metab., 22:49-61, (2019).
Lute, et al., "Human CTLA4 knock-in mice unravel the quantitative link between tumor immunity and autoimmunity induced by anti-CTLA-4 antibodies," Blood, 106(9):3127-3133, (2005).
Min, et al., "Metabolic profiling reveals that PNPLA3 induces widespread effects on metabolism beyond triacylglycerol remodeling in Huh-7 hepatoma cells," Am. J. Physiol. Gastrointest. Liver Physiol., 307(1):G66-G76, (2014).
Mullins, et al., "Transgenesis in the rat and larger mammals," J. Clin. Invest. 97(7):1557-1560, (1996).
Munoz, et al., "Conventional pluripotency markers are unspecific for bovine embryonic-derived cell-lines," Theriogenology, 69(9): 1159-1164, (2008).
Niemann, "Transgenic farm animals get off the ground. Transgenic Animals in Agriculture, Conference Tahoe City, California, USA. Aug. 24-27, 1997." Transgenic Res., 7(1): 73-75, (1998).
Paris, et al., "Equine embryos and embryonic stem cells: defining reliable markers of pluripotency, " Theriogenology, 74(4): 516-524, (2010).
Poueymirou, et al., "F0 generation mice fully derived from gene-targeted embryonic stem cells allowing immediate phenotypic analyses," Nat. Biotechnol., 25(1):91-99, (2007).
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Romeo, et al., "Genetic Variation in PNPLA3 Confers Susceptibility to Nonalcoholic Fatty Liver Disease," Nat. Genet., 40(12):1461-1465, (2008).
Sigmund, "Viewpoint: Are Studies in Genetically Altered Mice Out of Control?," Arterioscler. Thromb. Vasc. Biol., 20(6):1425-1429, (2000).
Smagris, et al., "Pnpla3I148M Knockin Mice Accumulate PNPLA3 on Lipid Droplets and Develop Hepatic Steatosis," Hepatology, 61(1):108-118, (2015).
Valenzuela, et al., "High-throughput engineering of the mouse genome coupled with high-resolution expression analysis," Nat. Biotechnol., 21(6):652-659, (2003).
Wakchaure, et al., "Transgenic Animals: A Review on its Various Dimensions and Applications in Animal Biotechnology," International Journal of Emerging Technology and Advanced Engineering, 5(11):210-213, (2015).
Zhao, et al., "Inconsistency between hepatic expression and serum concentration of transthyretin in mice humanized at the transthyretin locus," Genes to Cells, 13:1257-1268, (2008).
Zhou, et al., "Developing tTA transgenic rats for inducible and reversible gene expression," Int. J. Biol. Sci., 5(2):171-181, (2009).
Foquet, et al., "LBP-09-Liver humanization of Fah -/-/Rag2 -/-/112eg -/-/andnbsp;NOD mice with human hepatocytes homozygous for M1481 PNPLA3 allos the assessment of specific genotype contribution to NASH development in vivo," Journal of Hepatology, vol. 70, No. 1, pp. e145-e382, p. e145 (Apr. 2019).
Zhu et al., "Humanising the mouse genome piece by piece," Nat. Commun. 10(1):1845, (Apr. 23, 2019).
WIPO Application No. PCT/US2021/015192, PCT International Search Report and Written Opinion of the International Searching Authority mailed Apr. 22, 2021.
Davis et al., "High fat and high sucrose diets impair time-of-day differences in spatial working memory of male mice," Obesity (Silver Spring), 28(12):2347-2356, (2020).
Fairbridge et al., "Loss of CD24 in Mice Leads to Metabolic Dysfunctions and a Reduction in White Adipocyte Tissue," PLoS One, 10(11):e0141966, (2015).
Brenner, "Of Mice and Men and Nonalcoholic Steatohepatitis," Hepatology 68(6):2059-2061, (2018).
Devoy, et al., "Genomically humanized mice: technologies and promises," Nat. Rev. Genet. 13(1):14-20, (2012).
Dong, "PNPLA3—A Potential Therapeutic Target for Personalized Treatment of Chronic Liver Disease," Front. Med. (Lausane) 6:304, (Dec. 2019).
Foquet, et al., "LBP-09-Liver humanization of Fah -/-/Rag2 -/-/I12eg -/-/andnbsp;NOD mice with human hepatocytes homozygous for M1481 PNPLA3 allos the assessment of specific genotype contribution to NASH development in vivo," Journal of Hepatology, vol. 70, No. 1, pp. e145-e382, p. e145 (Apr. 2019).

(56) References Cited

OTHER PUBLICATIONS

Pankowicz, et al., "CRISPR/Cas9: at the cutting edge of hepatology," Gut 66(7):1329-1340, (May 2017).
Zhu, et al., "Humanising the mouse genome piece by piece," Nat. Commun. 10(1):1845, (Apr. 2019).
WIPO Application No. PCT/US2021/015192, PCT International Search Report and Written Opinion of the International Searching Authority mailed Apr. 22, 2021.

* cited by examiner

```
                                       Cytoplasmic Domain                     Transmembrane Domain   Lumenal Domain
mPNPLA3      MYDPERRWSLSFAGCGFLGFYHVGATLCLSERAPHLLRDARTFFGCSAGALHAVTFVCSLPLGRIMEILM
hPNPLA3      MYDAERGWSLSFAGCGFLGFYHVGATRCLSEHAPHLLRDARMLFGASAGALHCVGVLSGIPLEQTLQVLS
hPNPLA3_mut  MYDAERGWSLSFAGCGFLGFYHVGATRCLSEHAPHLLRDARMLFGASAGALHCVGVLSGIPLEQTLQVLS

mPNPLA3      DLVRKARSRNIGTLHPFFNINKCIRDGLQESLPDNVHQVISGKVHISLTRVSDGENVLVSEFHSKDEVVD
hPNPLA3      DLVRKARSRNIGIFHPSFNLSKFLRQGLCKCLPANVHQLISGKIGISLTRVSDGENVLVSDFRSKDEVVD
hPNPLA3_mut  DLVRKARSRNIGIFHPSFNLSKFLRQGLCKCLPANVHQLISGKIGISLTRVSDGENVLVSDFRSKDEVVD
                    I148M
mPNPLA3      ALVCSCFIPLFSGLIPPSFRGERYVDGGVSDNVPVLDAKTTITVSPFYGEHDICPKVKSTNFFHVNITNL
hPNPLA3      ALVCSCFIPFYSGLIPPSFRGVRYVDGGVSDNVPFIDAKTTITVSPFYGEYDICPKVKSTNFLHVDITKL
hPNPLA3_mut  ALVCSCFMPFYSGLIPPSFRGVRYVDGGVSDNVPFIDAKTTITVSPFYGEYDICPKVKSTNFLHVDITKL

mPNPLA3      SLRLCTGNLQLLTRALFPSDVKVMGELCYQGYLDAFRFLEENGICNGPQRSLS-----------------
hPNPLA3      SLRLCTGNLYLLSRAFVPPDLKVLGEICLRGYLDAFRFLEEKGICNRPQPGLKSSSEGMDPEVAMPSWAN
hPNPLA3_mut  SLRLCTGNLYLLSRAFVPPDLKVLGEICLRGYLDAFRFLEEKGICNRPQPGLKSSSEGMDPEVAMPSWAN

mPNPLA3      LSL-VAPEACLENGKLVG----DKVPVSLCFTDENIWETLSPELSTALSEAIKDREGYLSKVCNLLPVRI
hPNPLA3      MSLDSSPESAALAVRLEGDELLDHLRLSILPWDESILDTLSPRLATALSEEMKDKGGYMSKICNLLPIRI
hPNPLA3_mut  MSLDSSPESAALAVRLEGDELLDHLRLSILPWDESILDTLSPRLATALSEEMKDKGGYMSKICNLLPIRI

mPNPLA3      LSYIMLPCSLPVESAIAAVHRLVTWLPDIQDDIQWLQWATSQVCARMTMCLLPSTR--------------
hPNPLA3      MSYVMLPCTLPVESAIAIVQRLVTWLPDMPDDVLWLQWVTSQVFTRVLMCLLPASRSQMPVSSQQASPCT
hPNPLA3_mut  MSYVMLPCTLPVESAIAIVQRLVTWLPDMPDDVLWLQWVTSQVFTRVLMCLLPASRSQMPVSSQQASPCT
                           K434E
mPNPLA3      -----------------------------------------------------------   (SEQ ID NO: 1)
hPNPLA3      PEQDWPCWTPCSPKGCPAETKAEATPRSILRSSLNFFLGNKVPAGAEGLSTFPSFSLEKSL (SEQ ID NO: 5)
hPNPLA3_mut  PEQDWPCWTPCSPEGCPAETKAEATPRSILRSSLNFFLGNKVPAGAEGLSTFPSFSLEKSL (SEQ ID NO: 9)
```

FIG. 3

SEQUENCE LISTING

```
<160> NUMBER OF SEQ ID NOS: 69

<210> SEQ ID NO 1
<211> LENGTH: 384
<212> TYPE: PRT
<213> ORGANISM: Mus musculus
<220> FEATURE:
<221> NAME/KEY: MISC_FEATURE
<222> LOCATION: (1)..(42)
<223> OTHER INFORMATION: Cytoplasmic Domain
<220> FEATURE:
<221> NAME/KEY: MISC_FEATURE
<222> LOCATION: (43)..(63)
<223> OTHER INFORMATION: Transmembrane Domain
<220> FEATURE:
<221> NAME/KEY: MISC_FEATURE
<222> LOCATION: (64)..(413)
<223> OTHER INFORMATION: Lumenal Domain

<400> SEQUENCE: 1

Met Tyr Asp Pro Glu Arg Arg Trp Ser Leu Ser Phe Ala Gly Cys Gly
1               5                   10                  15

Phe Leu Gly Phe Tyr His Val Gly Ala Thr Leu Cys Leu Ser Glu Arg
            20                  25                  30

Ala Pro His Leu Leu Arg Asp Ala Arg Thr Phe Phe Gly Cys Ser Ala
        35                  40                  45

Gly Ala Leu His Ala Val Thr Phe Val Cys Ser Leu Pro Leu Gly Arg
    50                  55                  60

Ile Met Glu Ile Leu Met Asp Leu Val Arg Lys Ala Arg Ser Arg Asn
65                  70                  75                  80

Ile Gly Thr Leu His Pro Phe Phe Asn Ile Asn Lys Cys Ile Arg Asp
                85                  90                  95

Gly Leu Gln Glu Ser Leu Pro Asp Asn Val His Gln Val Ile Ser Gly
            100                 105                 110

Lys Val His Ile Ser Leu Thr Arg Val Ser Asp Gly Glu Asn Val Leu
        115                 120                 125
```

```
Val Ser Glu Phe His Ser Lys Asp Glu Val Val Asp Ala Leu Val Cys
    130                 135                 140

Ser Cys Phe Ile Pro Leu Phe Ser Gly Leu Ile Pro Pro Ser Phe Arg
145                 150                 155                 160

Gly Glu Arg Tyr Val Asp Gly Gly Val Ser Asp Asn Val Pro Val Leu
                165                 170                 175

Asp Ala Lys Thr Thr Ile Thr Val Ser Pro Phe Tyr Gly Glu His Asp
            180                 185                 190

Ile Cys Pro Lys Val Lys Ser Thr Asn Phe Phe His Val Asn Ile Thr
        195                 200                 205

Asn Leu Ser Leu Arg Leu Cys Thr Gly Asn Leu Gln Leu Leu Thr Arg
    210                 215                 220

Ala Leu Phe Pro Ser Asp Val Lys Val Met Gly Glu Leu Cys Tyr Gln
225                 230                 235                 240

Gly Tyr Leu Asp Ala Phe Arg Phe Leu Glu Glu Asn Gly Ile Cys Asn
                245                 250                 255

Gly Pro Gln Arg Ser Leu Ser Leu Ser Leu Val Ala Pro Glu Ala Cys
            260                 265                 270

Leu Glu Asn Gly Lys Leu Val Gly Asp Lys Val Pro Val Ser Leu Cys
        275                 280                 285

Phe Thr Asp Glu Asn Ile Trp Glu Thr Leu Ser Pro Glu Leu Ser Thr
    290                 295                 300

Ala Leu Ser Glu Ala Ile Lys Asp Arg Glu Gly Tyr Leu Ser Lys Val
305                 310                 315                 320

Cys Asn Leu Leu Pro Val Arg Ile Leu Ser Tyr Ile Met Leu Pro Cys
                325                 330                 335

Ser Leu Pro Val Glu Ser Ala Ile Ala Ala Val His Arg Leu Val Thr
            340                 345                 350

Trp Leu Pro Asp Ile Gln Asp Asp Ile Gln Trp Leu Gln Trp Ala Thr
        355                 360                 365

Ser Gln Val Cys Ala Arg Met Thr Met Cys Leu Leu Pro Ser Thr Arg
    370                 375                 380


<210> SEQ ID NO 2
<211> LENGTH: 42
<212> TYPE: PRT
<213> ORGANISM: Mus musculus

<400> SEQUENCE: 2

Met Tyr Asp Pro Glu Arg Arg Trp Ser Leu Ser Phe Ala Gly Cys Gly
1               5                   10                  15

Phe Leu Gly Phe Tyr His Val Gly Ala Thr Leu Cys Leu Ser Glu Arg
            20                  25                  30

Ala Pro His Leu Leu Arg Asp Ala Arg Thr
        35                  40


<210> SEQ ID NO 3
<211> LENGTH: 21
<212> TYPE: PRT
<213> ORGANISM: Mus musculus

<400> SEQUENCE: 3

Phe Phe Gly Cys Ser Ala Gly Ala Leu His Ala Val Thr Phe Val Cys
1               5                   10                  15

Ser Leu Pro Leu Gly
            20
```

<210> SEQ ID NO 4
<211> LENGTH: 321
<212> TYPE: PRT
<213> ORGANISM: Mus musculus

<400> SEQUENCE: 4

Arg Ile Met Glu Ile Leu Met Asp Leu Val Arg Lys Ala Arg Ser Arg
1               5                   10                  15

Asn Ile Gly Thr Leu His Pro Phe Phe Asn Ile Asn Lys Cys Ile Arg
            20                  25                  30

Asp Gly Leu Gln Glu Ser Leu Pro Asp Asn Val His Gln Val Ile Ser
        35                  40                  45

Gly Lys Val His Ile Ser Leu Thr Arg Val Ser Asp Gly Glu Asn Val
    50                  55                  60

Leu Val Ser Glu Phe His Ser Lys Asp Glu Val Val Asp Ala Leu Val
65                  70                  75                  80

Cys Ser Cys Phe Ile Pro Leu Phe Ser Gly Leu Ile Pro Pro Ser Phe
                85                  90                  95

Arg Gly Glu Arg Tyr Val Asp Gly Gly Val Ser Asp Asn Val Pro Val
            100                 105                 110

Leu Asp Ala Lys Thr Thr Ile Thr Val Ser Pro Phe Tyr Gly Glu His
        115                 120                 125

Asp Ile Cys Pro Lys Val Lys Ser Thr Asn Phe Phe His Val Asn Ile
    130                 135                 140

Thr Asn Leu Ser Leu Arg Leu Cys Thr Gly Asn Leu Gln Leu Leu Thr
145                 150                 155                 160

Arg Ala Leu Phe Pro Ser Asp Val Lys Val Met Gly Glu Leu Cys Tyr
                165                 170                 175

Gln Gly Tyr Leu Asp Ala Phe Arg Phe Leu Glu Glu Asn Gly Ile Cys
            180                 185                 190

Asn Gly Pro Gln Arg Ser Leu Ser Leu Ser Leu Val Ala Pro Glu Ala
        195                 200                 205

Cys Leu Glu Asn Gly Lys Leu Val Gly Asp Lys Val Pro Val Ser Leu
    210                 215                 220

Cys Phe Thr Asp Glu Asn Ile Trp Glu Thr Leu Ser Pro Glu Leu Ser
225                 230                 235                 240

Thr Ala Leu Ser Glu Ala Ile Lys Asp Arg Glu Gly Tyr Leu Ser Lys
                245                 250                 255

Val Cys Asn Leu Leu Pro Val Arg Ile Leu Ser Tyr Ile Met Leu Pro
            260                 265                 270

Cys Ser Leu Pro Val Glu Ser Ala Ile Ala Ala Val His Arg Leu Val
        275                 280                 285

Thr Trp Leu Pro Asp Ile Gln Asp Asp Ile Gln Trp Leu Gln Trp Ala
    290                 295                 300

Thr Ser Gln Val Cys Ala Arg Met Thr Met Cys Leu Leu Pro Ser Thr
305                 310                 315                 320

Arg

<210> SEQ ID NO 5
<211> LENGTH: 481
<212> TYPE: PRT
<213> ORGANISM: Homo sapiens
<220> FEATURE:
<221> NAME/KEY: MISC_FEATURE
<222> LOCATION: (1)..(41)

-continued

```
<223> OTHER INFORMATION: Cytoplasmic Domain
<220> FEATURE:
<221> NAME/KEY: MISC_FEATURE
<222> LOCATION: (42)..(62)
<223> OTHER INFORMATION: Transmembrane Domain
<220> FEATURE:
<221> NAME/KEY: MISC_FEATURE
<222> LOCATION: (63)..(481)
<223> OTHER INFORMATION: Lumenal Domain

<400> SEQUENCE: 5

Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125

Val Ser Asp Phe Arg Ser Lys Asp Glu Val Val Asp Ala Leu Val Cys
    130                 135                 140

Ser Cys Phe Ile Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Arg Pro Gln Pro Gly Leu Lys Ser Ser Ser Glu Gly Met Asp Pro Glu
            260                 265                 270

Val Ala Met Pro Ser Trp Ala Asn Met Ser Leu Asp Ser Ser Pro Glu
        275                 280                 285

Ser Ala Ala Leu Ala Val Arg Leu Glu Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
            340                 345                 350

Tyr Val Met Leu Pro Cys Thr Leu Pro Val Glu Ser Ala Ile Ala Ile
```

355 360 365

Val Gln Arg Leu Val Thr Trp Leu Pro Asp Met Pro Asp Asp Val Leu
370 375 380

Trp Leu Gln Trp Val Thr Ser Gln Val Phe Thr Arg Val Leu Met Cys
385 390 395 400

Leu Leu Pro Ala Ser Arg Ser Gln Met Pro Val Ser Ser Gln Gln Ala
405 410 415

Ser Pro Cys Thr Pro Glu Gln Asp Trp Pro Cys Trp Thr Pro Cys Ser
420 425 430

Pro Lys Gly Cys Pro Ala Glu Thr Lys Ala Glu Ala Thr Pro Arg Ser
435 440 445

Ile Leu Arg Ser Ser Leu Asn Phe Phe Leu Gly Asn Lys Val Pro Ala
450 455 460

Gly Ala Glu Gly Leu Ser Thr Phe Pro Ser Phe Ser Leu Glu Lys Ser
465 470 475 480

Leu

<210> SEQ ID NO 6
<211> LENGTH: 41
<212> TYPE: PRT
<213> ORGANISM: Homo sapiens

<400> SEQUENCE: 6

Met Tyr Asp Ala Glu Arg Gly Trp Ser Leu Ser Phe Ala Gly Cys Gly
1 5 10 15

Phe Leu Gly Phe Tyr His Val Gly Ala Thr Arg Cys Leu Ser Glu His
20 25 30

Ala Pro His Leu Leu Arg Asp Ala Arg
35 40

<210> SEQ ID NO 7
<211> LENGTH: 21
<212> TYPE: PRT
<213> ORGANISM: Homo sapiens

<400> SEQUENCE: 7

Met Leu Phe Gly Ala Ser Ala Gly Ala Leu His Cys Val Gly Val Leu
1 5 10 15

Ser Gly Ile Pro Leu
20

<210> SEQ ID NO 8
<211> LENGTH: 419
<212> TYPE: PRT
<213> ORGANISM: Homo sapiens

<400> SEQUENCE: 8

Glu Gln Thr Leu Gln Val Leu Ser Asp Leu Val Arg Lys Ala Arg Ser
1 5 10 15

Arg Asn Ile Gly Ile Phe His Pro Ser Phe Asn Leu Ser Lys Phe Leu
20 25 30

Arg Gln Gly Leu Cys Lys Cys Leu Pro Ala Asn Val His Gln Leu Ile
35 40 45

Ser Gly Lys Ile Gly Ile Ser Leu Thr Arg Val Ser Asp Gly Glu Asn
50 55 60

Val Leu Val Ser Asp Phe Arg Ser Lys Asp Glu Val Val Asp Ala Leu
65 70 75 80

-continued

```
Val Cys Ser Cys Phe Ile Pro Phe Tyr Ser Gly Leu Ile Pro Pro Ser
                85                  90                  95

Phe Arg Gly Val Arg Tyr Val Asp Gly Gly Val Ser Asp Asn Val Pro
            100                 105                 110

Phe Ile Asp Ala Lys Thr Thr Ile Thr Val Ser Pro Phe Tyr Gly Glu
        115                 120                 125

Tyr Asp Ile Cys Pro Lys Val Lys Ser Thr Asn Phe Leu His Val Asp
    130                 135                 140

Ile Thr Lys Leu Ser Leu Arg Leu Cys Thr Gly Asn Leu Tyr Leu Leu
145                 150                 155                 160

Ser Arg Ala Phe Val Pro Pro Asp Leu Lys Val Leu Gly Glu Ile Cys
                165                 170                 175

Leu Arg Gly Tyr Leu Asp Ala Phe Arg Phe Leu Glu Glu Lys Gly Ile
            180                 185                 190

Cys Asn Arg Pro Gln Pro Gly Leu Lys Ser Ser Ser Glu Gly Met Asp
        195                 200                 205

Pro Glu Val Ala Met Pro Ser Trp Ala Asn Met Ser Leu Asp Ser Ser
    210                 215                 220

Pro Glu Ser Ala Ala Leu Ala Val Arg Leu Glu Gly Asp Glu Leu Leu
225                 230                 235                 240

Asp His Leu Arg Leu Ser Ile Leu Pro Trp Asp Glu Ser Ile Leu Asp
                245                 250                 255

Thr Leu Ser Pro Arg Leu Ala Thr Ala Leu Ser Glu Glu Met Lys Asp
            260                 265                 270

Lys Gly Gly Tyr Met Ser Lys Ile Cys Asn Leu Leu Pro Ile Arg Ile
        275                 280                 285

Met Ser Tyr Val Met Leu Pro Cys Thr Leu Pro Val Glu Ser Ala Ile
    290                 295                 300

Ala Ile Val Gln Arg Leu Val Thr Trp Leu Pro Asp Met Pro Asp Asp
305                 310                 315                 320

Val Leu Trp Leu Gln Trp Val Thr Ser Gln Val Phe Thr Arg Val Leu
                325                 330                 335

Met Cys Leu Leu Pro Ala Ser Arg Ser Gln Met Pro Val Ser Ser Gln
            340                 345                 350

Gln Ala Ser Pro Cys Thr Pro Glu Gln Asp Trp Pro Cys Trp Thr Pro
        355                 360                 365

Cys Ser Pro Lys Gly Cys Pro Ala Glu Thr Lys Ala Glu Ala Thr Pro
    370                 375                 380

Arg Ser Ile Leu Arg Ser Ser Leu Asn Phe Phe Leu Gly Asn Lys Val
385                 390                 395                 400

Pro Ala Gly Ala Glu Gly Leu Ser Thr Phe Pro Ser Phe Ser Leu Glu
                405                 410                 415

Lys Ser Leu
```

<210> SEQ ID NO 9
<211> LENGTH: 481
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(41)
<223> OTHER INFORMATION: Cytoplasmic Domain
<220> FEATURE:
<221> NAME/KEY: MISC_FEATURE
<222> LOCATION: (42)..(62)

```
<223> OTHER INFORMATION: Transmembrane Domain
<220> FEATURE:
<221> NAME/KEY: MISC_FEATURE
<222> LOCATION: (63)..(481)
<223> OTHER INFORMATION: Lumenal Domain

<400> SEQUENCE: 9

Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125

Val Ser Asp Phe Arg Ser Lys Asp Glu Val Val Asp Ala Leu Val Cys
    130                 135                 140

Ser Cys Phe Met Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Arg Pro Gln Pro Gly Leu Lys Ser Ser Ser Glu Gly Met Asp Pro Glu
            260                 265                 270

Val Ala Met Pro Ser Trp Ala Asn Met Ser Leu Asp Ser Ser Pro Glu
        275                 280                 285

Ser Ala Ala Leu Ala Val Arg Leu Glu Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
            340                 345                 350

Tyr Val Met Leu Pro Cys Thr Leu Pro Val Glu Ser Ala Ile Ala Ile
        355                 360                 365

Val Gln Arg Leu Val Thr Trp Leu Pro Asp Met Pro Asp Asp Val Leu
    370                 375                 380
```

```
Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
                405                 410                 415

Ser Pro Cys Thr Pro Glu Gln Asp Trp Pro Cys Trp Thr Pro Cys Ser
            420                 425                 430

Pro Glu Gly Cys Pro Ala Glu Thr Lys Ala Glu Ala Thr Pro Arg Ser
        435                 440                 445

Ile Leu Arg Ser Ser Leu Asn Phe Phe Leu Gly Asn Lys Val Pro Ala
    450                 455                 460

Gly Ala Glu Gly Leu Ser Thr Phe Pro Ser Phe Ser Leu Glu Lys Ser
465                 470                 475                 480

Leu


<210> SEQ ID NO 10
<211> LENGTH: 419
<212> TYPE: PRT
<213> ORGANISM: Artificial Sequence
<220> FEATURE:
<223> OTHER INFORMATION: Synthetic

<400> SEQUENCE: 10

Glu Gln Thr Leu Gln Val Leu Ser Asp Leu Val Arg Lys Ala Arg Ser
1               5                   10                  15

Arg Asn Ile Gly Ile Phe His Pro Ser Phe Asn Leu Ser Lys Phe Leu
            20                  25                  30

Arg Gln Gly Leu Cys Lys Cys Leu Pro Ala Asn Val His Gln Leu Ile
        35                  40                  45

Ser Gly Lys Ile Gly Ile Ser Leu Thr Arg Val Ser Asp Gly Glu Asn
    50                  55                  60

Val Leu Val Ser Asp Phe Arg Ser Lys Asp Glu Val Val Asp Ala Leu
65                  70                  75                  80

Val Cys Ser Cys Phe Met Pro Phe Tyr Ser Gly Leu Ile Pro Pro Ser
                85                  90                  95

Phe Arg Gly Val Arg Tyr Val Asp Gly Gly Val Ser Asp Asn Val Pro
            100                 105                 110

Phe Ile Asp Ala Lys Thr Thr Ile Thr Val Ser Pro Phe Tyr Gly Glu
        115                 120                 125

Tyr Asp Ile Cys Pro Lys Val Lys Ser Thr Asn Phe Leu His Val Asp
    130                 135                 140

Ile Thr Lys Leu Ser Leu Arg Leu Cys Thr Gly Asn Leu Tyr Leu Leu
145                 150                 155                 160

Ser Arg Ala Phe Val Pro Pro Asp Leu Lys Val Leu Gly Glu Ile Cys
                165                 170                 175

Leu Arg Gly Tyr Leu Asp Ala Phe Arg Phe Leu Glu Glu Lys Gly Ile
            180                 185                 190

Cys Asn Arg Pro Gln Pro Gly Leu Lys Ser Ser Ser Glu Gly Met Asp
        195                 200                 205

Pro Glu Val Ala Met Pro Ser Trp Ala Asn Met Ser Leu Asp Ser Ser
    210                 215                 220

Pro Glu Ser Ala Ala Leu Ala Val Arg Leu Glu Gly Asp Glu Leu Leu
225                 230                 235                 240

Asp His Leu Arg Leu Ser Ile Leu Pro Trp Asp Glu Ser Ile Leu Asp
                245                 250                 255
```

-continued

```
Thr Leu Ser Pro Arg Leu Ala Thr Ala Leu Ser Glu Glu Met Lys Asp
            260                 265                 270

Lys Gly Gly Tyr Met Ser Lys Ile Cys Asn Leu Leu Pro Ile Arg Ile
        275                 280                 285

Met Ser Tyr Val Met Leu Pro Cys Thr Leu Pro Val Glu Ser Ala Ile
    290                 295                 300

Ala Ile Val Gln Arg Leu Val Thr Trp Leu Pro Asp Met Pro Asp Asp
305                 310                 315                 320

Val Leu Trp Leu Gln Trp Val Thr Ser Gln Val Phe Thr Arg Val Leu
                325                 330                 335

Met Cys Leu Leu Pro Ala Ser Arg Ser Gln Met Pro Val Ser Ser Gln
            340                 345                 350

Gln Ala Ser Pro Cys Thr Pro Glu Gln Asp Trp Pro Cys Trp Thr Pro
        355                 360                 365

Cys Ser Pro Glu Gly Cys Pro Ala Glu Thr Lys Ala Glu Ala Thr Pro
    370                 375                 380

Arg Ser Ile Leu Arg Ser Ser Leu Asn Phe Phe Leu Gly Asn Lys Val
385                 390                 395                 400

Pro Ala Gly Ala Glu Gly Leu Ser Thr Phe Pro Ser Phe Ser Leu Glu
                405                 410                 415

Lys Ser Leu
```

<210> SEQ ID NO 11
<211> LENGTH: 1155
<212> TYPE: DNA
<213> ORGANISM: Mus musculus
<220> FEATURE:
<221> NAME/KEY: misc_feature
<222> LOCATION: (1)..(126)
<223> OTHER INFORMATION: Cytoplasmic Domain
<220> FEATURE:
<221> NAME/KEY: misc_feature
<222> LOCATION: (127)..(189)
<223> OTHER INFORMATION: Transmembrane Domain
<220> FEATURE:
<221> NAME/KEY: misc_feature
<222> LOCATION: (190)..(1152)
<223> OTHER INFORMATION: Lumenal Domain

<400> SEQUENCE: 11

```
atgtatgacc cagagcgccg ctggagcctg tcgtttgcag gctgcggctt cctgggcttc      60

taccacgtcg gggctacgct atgtctgagc gagcgcgccc cgcacctcct ccgcgatgcg     120

cgcactttct ttggctgctc ggccggtgca ctgcacgcgg tcaccttcgt gtgcagtctc     180

cctctcggcc gtataatgga gatcctcatg gacctcgtgc ggaaagccag gagccgcaac     240

atcggcaccc tccacccgtt cttcaacatt aacaagtgca tcagagacgg gctccaggag     300

agcctcccag acaatgtcca ccaggtcatt tctggcaagg ttcacatctc actcaccagg     360

gtgtcggatg gggagaacgt gctggtgtct gagttccatt ccaaagacga agtcgtggat     420

gccctggtgt gttcctgctt cattcccctc ttctctggcc taatccctcc ttccttccga     480

ggcgagcggt acgtggacgg aggagtgagc gacaacgtcc ctgtgctgga tgccaaaacc     540

accatcacgg tgtcaccttt ctacggtgag catgacatct gccccaaagt caagtccacc     600

aacttcttcc acgtgaatat caccaacctc agcctccgcc tctgcactgg gaacctccaa     660

cttctgacca gagcgctctt cccgtctgat gtgaaggtga tgggagagct gtgctatcaa     720

gggtacctgg acgccttccg gttcctggag gagaatggca tctgtaacgg gccacagcgc     780

agcctgagtc tgtccttggt ggcgccagaa gcctgcttgg aaaatggcaa acttgtggga     840
```

-continued gacaaggtgc cagtcagcct atgctttaca gatgagaaca tctgggagac actgtccccc 900
gagctcagca cagctctgag tgaagcgatt aaggacaggg agggctacct gagcaaagtc 960
tgcaacctcc tgcccgtcag gatcctgtcc tacatcatgc tgccctgcag tctgcccgtg 1020
gagtcggcta tcgctgcagt ccacaggctg gtgacatggc tccctgatat ccaggatgat 1080
atccagtggc tacaatgggc gacatcccag gtttgtgccc gaatgacgat gtgcctgctc 1140
ccctctacca ggtaa 1155

<210> SEQ ID NO 12
<211> LENGTH: 126
<212> TYPE: DNA
<213> ORGANISM: Mus musculus

<400> SEQUENCE: 12
atgtatgacc cagagcgccg ctggagcctg tcgtttgcag gctgcggctt cctgggcttc 60
taccacgtcg ggctacgct atgtctgagc gagcgcgccc cgcacctcct ccgcgatgcg 120
cgcact 126

<210> SEQ ID NO 13
<211> LENGTH: 63
<212> TYPE: DNA
<213> ORGANISM: Mus musculus

<400> SEQUENCE: 13
ttctttggct gctcggccgg tgcactgcac gcggtcacct tcgtgtgcag tctccctctc 60
ggc 63

<210> SEQ ID NO 14
<211> LENGTH: 963
<212> TYPE: DNA
<213> ORGANISM: Mus musculus

<400> SEQUENCE: 14
cgtataatgg agatcctcat ggacctcgtg cggaaagcca ggagccgcaa catcggcacc 60
ctccacccgt tcttcaacat taacaagtgc atcagagacg ggctccagga gagcctccca 120
gacaatgtcc accaggtcat ttctggcaag gttcacatct cactcaccag ggtgtcggat 180
ggggagaacg tgctggtgtc tgagttccat tccaaagacg aagtcgtgga tgccctggtg 240
tgttcctgct tcattcccct cttctctggc ctaatccctc cttccttccg aggcgagcgg 300
tacgtggacg gaggagtgag cgacaacgtc cctgtgctgg atgccaaaac caccatcacg 360
gtgtcacctt tctacggtga gcatgacatc tgccccaaag tcaagtccac caacttcttc 420
cacgtgaata tcaccaacct cagcctccgc ctctgcactg ggaacctcca acttctgacc 480
agagcgctct tcccgtctga tgtgaaggtg atgggagagc tgtgctatca agggtacctg 540
gacgccttcc ggttcctgga ggagaatggc atctgtaacg ggccacagcg cagcctgagt 600
ctgtccttgg tggcgccaga agcctgcttg gaaaatggca aacttgtggg agacaaggtg 660
ccagtcagcc tatgctttac agatgagaac atctgggaga cactgtcccc cgagctcagc 720
acagctctga gtgaagcgat taaggacagg gagggctacc tgagcaaagt ctgcaacctc 780
ctgcccgtca ggatcctgtc ctacatcatg ctgccctgca gtctgcccgt ggagtcggct 840
atcgctgcag tccacaggct ggtgacatgg ctccctgata tccaggatga tatccagtgg 900
ctacaatggg cgacatccca ggtttgtgcc cgaatgacga tgtgcctgct cccctctacc 960
agg 963

<210> SEQ ID NO 15
<211> LENGTH: 1446
<212> TYPE: DNA
<213> ORGANISM: Homo sapiens
<220> FEATURE:
<221> NAME/KEY: misc_feature
<222> LOCATION: (1)..(123)
<223> OTHER INFORMATION: Cytoplasmic Domain
<220> FEATURE:
<221> NAME/KEY: misc_feature
<222> LOCATION: (124)..(186)
<223> OTHER INFORMATION: Transmembrane Domain
<220> FEATURE:
<221> NAME/KEY: misc_feature
<222> LOCATION: (187)..(1443)
<223> OTHER INFORMATION: Lumenal Domain

<400> SEQUENCE: 15
atgtacgacg cagagcgcgg ctggagcttg tccttcgcgg gctgcggctt cctgggcttc 60
taccacgtcg gggcgacccg ctgcctgagc gagcacgccc cgcacctcct ccgcgacgcg 120
cgcatgttgt tcggcgcttc ggccggggcg ttgcactgcg tcggcgtcct ctccggtatc 180
ccgctggagc agactctgca ggtcctctca gatcttgtgc ggaaggccag gagtcggaac 240
attggcatct tccatccatc cttcaactta agcaagttcc tccgacaggg tctctgcaaa 300
tgcctcccgg ccaatgtcca ccagctcatc tccggcaaaa taggcatctc tcttaccaga 360
gtgtctgatg gggaaaacgt tctggtgtct gactttcggt ccaaagacga agtcgtggat 420
gccttggtat gttcctgctt catccccttc tacagtggcc ttatccctcc ttccttcaga 480
ggcgtgcgat atgtggatgg aggagtgagt gacaacgtac ccttcattga tgccaaaaca 540
accatcaccg tgtcccccctt ctatggggag tacgacatct gccctaaagt caagtccacg 600
aactttcttc atgtggacat caccaagctc agtctacgcc tctgcacagg gaacctctac 660
cttctctcga gagcttttgt ccccccggat ctcaaggtgc tgggagagat atgccttcga 720
ggatatttgg atgcattcag gttcttggaa gagaagggca tctgcaacag gccccagcca 780
ggcctgaagt catcctcaga agggatggat cctgaggtcg ccatgcccag ctgggcaaac 840
atgagtctgg attcttcccc ggagtcggct gccttggctg tgaggctgga gggagatgag 900
ctgctagacc acctgcgtct cagcatcctg ccctgggatg agagcatcct ggacaccctc 960
tcgcccaggc tcgctacagc actgagtgaa gaaatgaaag acaaaggtgg atacatgagc 1020
aagatttgca acttgctacc cattaggata atgtcttatg taatgctgcc ctgtaccctg 1080
cctgtggaat ctgccattgc gattgtccag agactggtga catggcttcc agatatgccc 1140
gacgatgtcc tgtggttgca gtgggtgacc tcacaggtgt tcactcgagt gctgatgtgt 1200
ctgctccccg cctccaggtc ccaaatgcca gtgagcagcc aacaggcctc cccatgcaca 1260
cctgagcagg actggccctg ctggactccc tgctccccca agggctgtcc agcagagacc 1320
aaagcagagg ccaccccgcg gtccatcctc aggtccagcc tgaacttctt cttgggcaat 1380
aaagtacctg ctggtgctga ggggctctcc acctttccca gtttttcact agagaagagt 1440
ctgtga 1446

<210> SEQ ID NO 16
<211> LENGTH: 123
<212> TYPE: DNA
<213> ORGANISM: Homo sapiens

<400> SEQUENCE: 16
atgtacgacg cagagcgcgg ctggagcttg tccttcgcgg gctgcggctt cctgggcttc 60
taccacgtcg ggcgacccg ctgcctgagc gagcacgccc cgcacctcct ccgcgacgcg 120
cgc 123

<210> SEQ ID NO 17
<211> LENGTH: 63
<212> TYPE: DNA
<213> ORGANISM: Homo sapiens

<400> SEQUENCE: 17
atgttgttcg gcgcttcggc cggggcgttg cactgcgtcg gcgtcctctc cggtatcccg 60
ctg 63

<210> SEQ ID NO 18
<211> LENGTH: 1257
<212> TYPE: DNA
<213> ORGANISM: Homo sapiens

<400> SEQUENCE: 18
gagcagactc tgcaggtcct ctcagatctt gtgcggaagg ccaggagtcg gaacattggc 60
atcttccatc catccttcaa cttaagcaag ttcctccgac agggtctctg caaatgcctc 120
ccggccaatg tccaccagct catctccggc aaaataggca tctctcttac cagagtgtct 180
gatggggaaa acgttctggt gtctgacttt cggtccaaag acgaagtcgt ggatgccttg 240
gtatgttcct gcttcatccc cttctacagt ggccttatcc ctccttcctt cagaggcgtg 300
cgatatgtgg atggaggagt gagtgacaac gtacccttca ttgatgccaa aacaaccatc 360
accgtgtccc ccttctatgg ggagtacgac atctgcccta aagtcaagtc cacgaacttt 420
cttcatgtgg acatcaccaa gctcagtcta cgcctctgca cagggaacct ctaccttctc 480
tcgagagctt ttgtcccccc ggatctcaag gtgctgggag agatatgcct tcgaggatat 540
ttggatgcat tcaggttctt ggaagagaag ggcatctgca acaggcccca gccaggcctg 600
aagtcatcct cagaagggat ggatcctgag gtcgccatgc ccagctgggc aaacatgagt 660
ctggattctt ccccggagtc ggctgccttg gctgtgaggc tggagggaga tgagctgcta 720
gaccacctgc gtctcagcat cctgccctgg gatgagagca tcctggacac cctctcgccc 780
aggctcgcta cagcactgag tgaagaaatg aaagacaaag gtggatacat gagcaagatt 840
tgcaacttgc tacccattag gataatgtct tatgtaatgc tgccctgtac cctgcctgtg 900
gaatctgcca ttgcgattgt ccagagactg gtgacatggc ttccagatat gcccgacgat 960
gtcctgtggt tgcagtgggt gacctcacag gtgttcactc gagtgctgat gtgtctgctc 1020
cccgcctcca ggtcccaaat gccagtgagc agccaacagg cctccccatg cacacctgag 1080
caggactggc cctgctggac tccctgctcc cccaagggct gtccagcaga gaccaaagca 1140
gaggccaccc cgcggtccat cctcaggtcc agcctgaact tcttcttggg caataaagta 1200
cctgctggtg ctgaggggct ctccaccttt cccagttttt cactagagaa gagtctg 1257

<210> SEQ ID NO 19
<211> LENGTH: 1446
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(123)

<223> OTHER INFORMATION: Cytoplasmic Domain
<220> FEATURE:
<221> NAME/KEY: misc_feature
<222> LOCATION: (124)..(186)
<223> OTHER INFORMATION: Transmembrane Domain
<220> FEATURE:
<221> NAME/KEY: misc_feature
<222> LOCATION: (187)..(1443)
<223> OTHER INFORMATION: Lumenal Domain

<400> SEQUENCE: 19
atgtacgacg cagagcgcgg ctggagcttg tccttcgcgg gctgcggctt cctgggcttc 60
taccacgtcg gggcgacccg ctgcctgagc gagcacgccc cgcacctcct ccgcgacgcg 120
cgcatgttgt tcggcgcttc ggccggggcg ttgcactgcg tcggcgtcct ctccggtatc 180
ccgctggagc agactctgca ggtcctctca gatcttgtgc ggaaggccag gagtcggaac 240
attggcatct tccatccatc cttcaactta agcaagttcc tccgacaggg tctctgcaaa 300
tgcctcccgg ccaatgtcca ccagctcatc tccggcaaaa taggcatctc tcttaccaga 360
gtgtctgatg ggaaaacgt tctggtgtct gactttcggt ccaaagacga agtcgtggat 420
gccttggtat gttcctgctt catgcctttc tacagtggcc ttatccctcc ttccttcaga 480
ggcgtgcgat atgtggatgg aggagtgagt gacaacgtac ccttcattga tgccaaaaca 540
accatcaccg tgtccccctt ctatggggag tacgacatct gccctaaagt caagtccacg 600
aactttcttc atgtggacat caccaagctc agtctacgcc tctgcacagg gaacctctac 660
cttctctcga gagcttttgt ccccccggat ctcaaggtgc tgggagagat atgccttcga 720
ggatatttgg atgcattcag gttcttggaa gagaagggca tctgcaacag gccccagcca 780
ggcctgaagt catcctcaga agggatggat cctgaggtcg ccatgcccag ctgggcaaac 840
atgagtctgg attcttcccc ggagtcggct gccttggctg tgaggctgga gggagatgag 900
ctgctagacc acctgcgtct cagcatcctg ccctgggatg agagcatcct ggacaccctc 960
tcgcccaggc tcgctacagc actgagtgaa gaaatgaaag acaaaggtgg atacatgagc 1020
aagatttgca acttgctacc cattaggata atgtcttatg taatgctgcc ctgtaccctg 1080
cctgtggaat ctgccattgc gattgtccag agactggtga catggcttcc agatatgccc 1140
gacgatgtcc tgtggttgca gtgggtgacc tcacaggtgt tcactcgagt gctgatgtgt 1200
ctgctccccg cctccaggtc ccaaatgcca gtgagcagcc aacaggcctc cccatgcaca 1260
cctgagcagg actggccctg ctggactccc tgctccccg agggctgtcc agcagagacc 1320
aaagcagagg ccaccccgcg gtccatcctc aggtccagcc tgaacttctt cttgggcaat 1380
aaagtacctg ctggtgctga ggggctctcc acctttccca gtttttcact agagaagagt 1440
ctgtga 1446

<210> SEQ ID NO 20
<211> LENGTH: 1257
<212> TYPE: DNA
<213> ORGANISM: Artificial Sequence
<220> FEATURE:
<223> OTHER INFORMATION: Synthetic

<400> SEQUENCE: 20
gagcagactc tgcaggtcct ctcagatctt gtgcggaagg ccaggagtcg gaacattggc 60
atcttccatc catccttcaa cttaagcaag ttcctccgac agggtctctg caaatgcctc 120
ccggccaatg tccaccagct catctccggc aaaataggca tctctcttac cagagtgtct 180
gatggggaaa acgttctggt gtctgacttt cggtccaaag acgaagtcgt ggatgccttg 240

-continued gtatgttcct gcttcatgcc tttctacagt ggccttatcc ctccttcctt cagaggcgtg 300
cgatatgtgg atggaggagt gagtgacaac gtacccttca ttgatgccaa aacaaccatc 360
accgtgtccc ccttctatgg ggagtacgac atctgcccta aagtcaagtc cacgaacttt 420
cttcatgtgg acatcaccaa gctcagtcta cgcctctgca cagggaacct ctaccttctc 480
tcgagagctt ttgtcccccc ggatctcaag gtgctgggag agatatgcct tcgaggatat 540
ttggatgcat tcaggttctt ggaagagaag ggcatctgca acaggcccca gccaggcctg 600
aagtcatcct cagaagggat ggatcctgag gtcgccatgc ccagctgggc aaacatgagt 660
ctggattctt ccccggagtc ggctgccttg gctgtgaggc tggagggaga tgagctgcta 720
gaccacctgc gtctcagcat cctgccctgg gatgagagca tcctggacac cctctcgccc 780
aggctcgcta cagcactgag tgaagaaatg aaagacaaag gtggatacat gagcaagatt 840
tgcaacttgc tacccattag gataatgtct tatgtaatgc tgccctgtac cctgcctgtg 900
gaatctgcca ttgcgattgt ccagagactg gtgacatggc ttccagatat gcccgacgat 960
gtcctgtggt tgcagtgggt gacctcacag gtgttcactc gagtgctgat gtgtctgctc 1020
cccgcctcca ggtcccaaat gccagtgagc agccaacagg cctccccatg cacacctgag 1080
caggactggc cctgctggac tccctgctcc cccgagggct gtccagcaga gaccaaagca 1140
gaggccaccc cgcggtccat cctcaggtcc agcctgaact tcttcttggg caataaagta 1200
cctgctggtg ctgaggggct ctccaccttt cccagttttt cactagagaa gagtctg 1257

<210> SEQ ID NO 21
<211> LENGTH: 36433
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(58)
<223> OTHER INFORMATION: Mouse Sequence
<220> FEATURE:
<221> NAME/KEY: misc_feature
<222> LOCATION: (59)..(23322)
<223> OTHER INFORMATION: Human Sequence
<220> FEATURE:
<221> NAME/KEY: misc_feature
<222> LOCATION: (59)..(61)
<223> OTHER INFORMATION: Start Codon
<220> FEATURE:
<221> NAME/KEY: misc_feature
<222> LOCATION: (4994)..(4994)
<223> OTHER INFORMATION: I148M (C>G)
<220> FEATURE:
<221> NAME/KEY: misc_feature
<222> LOCATION: (22383)..(22383)
<223> OTHER INFORMATION: K434E (A>G)
<220> FEATURE:
<221> NAME/KEY: misc_feature
<222> LOCATION: (22527)..(22529)
<223> OTHER INFORMATION: Stop Codon
<220> FEATURE:
<221> NAME/KEY: misc_feature
<222> LOCATION: (23323)..(28133)
<223> OTHER INFORMATION: Neo Self-Deleting Cassette
<220> FEATURE:
<221> NAME/KEY: misc_feature
<222> LOCATION: (23323)..(23328)
<223> OTHER INFORMATION: XhoI
<220> FEATURE:
<221> NAME/KEY: misc_feature
<222> LOCATION: (23329)..(23362)
<223> OTHER INFORMATION: LoxP1
<220> FEATURE:

<221> NAME/KEY: misc_feature
<222> LOCATION: (28061)..(28094)
<223> OTHER INFORMATION: LoxP2
<220> FEATURE:
<221> NAME/KEY: misc_feature
<222> LOCATION: (28102)..(28127)
<223> OTHER INFORMATION: I_Ceu
<220> FEATURE:
<221> NAME/KEY: misc_feature
<222> LOCATION: (28128)..(28133)
<223> OTHER INFORMATION: NheI
<220> FEATURE:
<221> NAME/KEY: misc_feature
<222> LOCATION: (28134)..(36433)
<223> OTHER INFORMATION: Mouse Sequence

<400> SEQUENCE: 21
agagcagcaa caccgggagc agagctgaac tgcagcgccg cccggagctt caagcaccat 60
gtacgacgca gagcgcggct ggagcttgtc cttcgcgggc tgcggcttcc tgggcttcta 120
ccacgtcggg gcgacccgct gcctgagcga gcacgccccg cacctcctcc gcgacgcgcg 180
catgttgttc ggcgcttcgg ccggggcgtt gcactgcgtc ggcgtcctct ccggtatccc 240
gctgggtgcg tctggggacg ctgcccgggc tccacgtgcg gagtgggtgc cccctaggcc 300
ggggagcggg ggatccccag gggtcgcggg gccctggagg agcgggcatc ggacgcggac 360
acggcggggt gcatcccgag ggccccctcc gaggcagatg cttcctgcgg gggcgctgtt 420
cctgggcccg ggaagggggc gttggaaccc cgagcggtcc gggccgaagc ctgggactct 480
cgtgcgtccc cacccctacc cccatcaggc gcccgtgcat gaagggagac cctcacctcc 540
ggactgagag tcggagcgtc tcggagcgac ggggagtagg gagcgggacc cggggcggag 600
ggtagtgctg gcccctgcgg actccgggtc ccctgtgtcc tctcgggagg ggctggacgg 660
gctgagctgc cgaggggccg atttgccctg ggccggacaa agagtggggc tttggccggt 720
cccccacggt gggctccttc cctctgggga ttgagggact caagacaccc cgcgcctgcg 780
cttttctttt cttttttctt ttttttttt ttgagacgga gtttcgctca gtcgcccagg 840
ctggagtgca gtggcgtgat ctcaactcac tgcaagctcc acctcccagg ttcacgccat 900
tctcctgcct cagcctcccg agtagctggg actacaggcg ccagccacca agcccggcta 960
attttttgta tttttagta gagacggggt ttcaccgtgt tagccaggat ggtctcgatc 1020
tcctgacctc gtgatctgcc cacctcggcc tcccagaatg ctggggttac aggcgtgagc 1080
cactgctccc tgctgcctac gctctctggg tcgcagccca gccttctggg ggctgggtag 1140
cctcccagaa gggcaaccct gggcatcctc cagggcaggc taactggagt ctagtgggga 1200
ggggtacctt gaaagaggaa agttgtttcc tcctcctcct cctcctccag tgtttgggac 1260
ccttcctggg ggctggagtg catccctgga caccccccaa tcccatcctc ttctctagtt 1320
tccactgacc taggcccacc ctcccctctc cggctcagta ctcctggaaa tgagattccg 1380
tacatttgaa tcttgtccta atgaaatatt tgtccatgtg ggtacctgtg tgtgtgtggt 1440
gggggtgcag acggagggtt tgtttctcac tagctggaac tactggggtg tggtatgctt 1500
cctgggaatt tgtgtgccac agtcctggag gcgaggaggg ggttgtgagc cagtaggcag 1560
gggctggggc aagtagcatt gtgaagctat tgacacccag acgtccccag gcaggagatt 1620
atgcccccat tagccccctt ttatctgggc ttccttaaca atggactctt tgccctgcct 1680
gccagagcca gcagggagtg actgttcagt ggtgaggaag cgggcagagg aagccctgcc 1740
attgggtagg agcagtgggc agcccctggg ctgactggga ggtggggatt agggattaga 1800
cagtcctggc tgtctgcctt cccctaagcc agggggagag gagcaaaggg cacgaaatgt 1860

-continued

```
ggcctccagg aggattagac cgccacatga tcatttgcac accctggggt ttagcaacaa   1920
taaaagtcag ctttttgta tcccaaggtg gcctgtggac acccacatgg acaaatgttt    1980
acactgggac agaattcaaa tgcagaggtc ccaggagcct aaagtacact cactctggta   2040
tagaaaggat tccttactgg gcagaggaca ggtgcagcct ggggctttcc caggcaggac   2100
acagggaggc tcaggaacca ccaagtccct ggaaggtgga tctggaggtg ttggcaggag   2160
ccactccctg ggttccaggg ctccaggttc ctgctttaac cccctgtctc acagagggct   2220
gtgcacttgg gggctgctga gcatgtccca gaggctgcat cctggacaca gcacctcagt   2280
gcatctgagc tgaggctaac ttggcaggag ggacaggcag aacctgccag ccacgtgcaa   2340
ttccacccct ctggccactc agggaaggag agctgtgagt caagatcaga tttgggtcag   2400
gacaggctgg ggcctgcctg tccctgtgca tcccaagatt tatggctggc caggggttgg   2460
gctgggaggg gtggtcttgc atgccaggag agtgcagatc agcctgagag gccaggccag   2520
taagtgaggt cagatctcct gcacctgata gcattaaggc catctacacc aaagctctaa   2580
tgctgatatg ttcctggcct ctatgtgggg catggaggtg gggcatggag gtgaggcctg   2640
ctcgcctggg cttctggaag tgggagactc attcctgtgg ctgaggccta cagcagtgct   2700
gtgtggtagg aatacactgg aagccatgat gtcattgtgc attttctaga agccacattg   2760
aataaagtaa aagacacagg tagaattaat ttcattgagc ccaatatatc caaaataata   2820
tcattttcac atctattcaa tataaaaatt tactaatgag atatttcata ctaagccact   2880
gaaatccagt ttgtatctta cacatctcag ttttgacgag ccacatttca agggcgtgat   2940
agccacatgt ggctcccata gtagacagta ctggtctaga gaaatgttgg tggcatcctt   3000
gctgtctggt ttctggcctt gccaaaagta ttaccatccc agtgtggtac attctttcat   3060
gtatttgtct cctgtcccca gagcagactc tgcaggtcct ctcagatctt gtgcggaagg   3120
ccaggagtcg gaacattggc atcttccatc catccttcaa cttaagcaag ttcctccgac   3180
agggtctctg caaatgcctc ccggccaatg tccaccagct catctccggc aaaataggca   3240
tctctcttac cagagtgtct gatggggaaa acgttctggt gtctgacttt cggtccaaag   3300
acgaagtcgt ggatgtaagc agtttgctta tctggacgtt gtcaagttag aaaagctgtt   3360
ttgggatggg tgtggtggct catgcctgtc atcccggcac tttgggaggc cgaagcgggt   3420
gggttgcttg agcccaggag ctcgagacca acatgatgaa acccagtctc tacaaaaatt   3480
acagaaaaat tagctaggca tggtgttgtg ggcccatagt cccagctact agggaggctg   3540
aggcaggaga attgcttgag cctgggaggt ggaggttgca gtaagtcatg atcatgccac   3600
tgtactccag cccgggtgac agtgagatgc tgtctggaaa aaaaaaaaaa agaaagactg   3660
ttttgttttg gaagcaacac aggcagttgt aggccccctg tgccagagtg acataaactc   3720
tgtacacctc cagtgatttg gtccatgttt gtaaaccctg aatgttccag ggcagtttct   3780
tttcttcact ttttatctct ttttttggg tggggggcg gggtacagag tcttgctctg      3840
tctcccaggc tggagtgcag tggcgcaatc tcaacctccc gaggagctgg gactacaggc   3900
acaggccatc acaccttgct aatgtttgta ctttttgtag agacggggtt ttgccctgtt   3960
gcccaggctg gtcccaaact cctgcaccca agtaatctgc ccacctctgc ctggcagtta   4020
caatttcaaa taattcctcc ctttccttca acacttggct catgaccgtc cagtccaagg   4080
aacctgtcct gcaggtgtgc ctctcccgag cttcctctat gcatcttcca taatgaagat   4140
gccttctcac tggaaaccct acaagggtgg gaacgtgcct tatttgcctg tatcctcagg   4200
```

-continued

```
gtctagcaga gagaagataa tctgtaatac caaaacacca ttaaattcag ctgatgcttt   4260
cataagcgct ccttggagga aggactccat ttacttgaca gatctgtgca agacagcagc   4320
ctggcgcgtc taacctgcag ccagttgcat cctctgttta accttgtttg tggaagcttt   4380
ctctaaacag ccagcacttg tctgttccca catgggtccg ttctcccagt gaatcaccgt   4440
ggtgcctact gactgctctg tagcacagtg cttcgcaaag tgtgatcctg ggaccagcag   4500
agcagcagct cctttgagct tattggaatg gcagaccctc aggtcccacc tctgacctgc   4560
tgcatgggaa ttctggggag ggacgcagaa tctctggttc cacaggctct ccggtgatgc   4620
taatgaatac cggcatttga acagcaccga tctagcccct ttcagtccat gagccaacaa   4680
cccttggtcc tgtctgtggt gacccagtgt gactctcatg gggagcaagg agaggaagtt   4740
gaagttcact gacagggttg ttaaggggat tatgcaatag atgagaccca tgggcctgaa   4800
gtccgagggt gtatgttagt tccccgttct tttgacccat ggattaacct actctgtgca   4860
aagggcattt tcaagtttgt tgccctgctc acttggagaa agcttatgaa ggatcaggaa   4920
aattaaaagg gtgctctcgc ctataacttc tctctccttt gctttcacag gccttggtat   4980
gttcctgctt catgcctttc tacagtggcc ttatccctcc ttccttcaga ggcgtggtaa   5040
gtcggctttc tctgctagcg ctgagtcctg ggggcctctg aagtgtgctc acacatctcc   5100
tgcctgcagg gcactggtgt caggcacctc agggtctgtc ccatggtgga gccccatgcc   5160
tcactgcctt tcagacagag tagccacagc tggccctatt tccaggctac ccgggcagca   5220
aaacttactg catgtgtaat taattatttg gctatctgta aggtaaactg gctggttcac   5280
ttaatctgca ccttaagcat cagatagctt ctcagtgatc tagttaaact atatgatgtt   5340
ggccaggcgc ggtggctcat gtctgtaatc ccagcacttt gggagcctga agcaggcaga   5400
tcacttgagg tcaggagttc gagaccagcc tggccaacag tgtgaaactc tgtctctcct   5460
aaaaatacaa aaattagctg ggcatggtgg tgtgcacctg taatcccagc tgctcgggag   5520
gctgaggcag gagaattgct tgaacttggg aggcggaagt tgcagtgagc caagatcgca   5580
ccactgcact ccatcctggg tgacagagcg agactctatc tcaaaaagaa aaaaaaaaaa   5640
aaggtaaata aagtatatga cactgaagaa tctgttaccc ctggaaggtg gagctttact   5700
cttaggggga actataacag tcatatatat atattttttt cttttctttt tttttttttt   5760
tgagatggag tctsgctctg tctcccaggc tggagtgcag tggtgcaatc tcggctcact   5820
gcaacctcca cttcacaggt tcaggcaatt ctcctgcctc aacctcccga gtagctggga   5880
ttacaggtgc ctgccgttac gccaagctaa tttttgtatt tttagtagag acagggtttc   5940
atcatattgg ccaggctggt ctccaactcc tgacctcagg tgatccgccc gccttggcct   6000
cccaaagtgc tgagattaca ggcgtgagcc atggtgcccg gccaacaatc acatgtgttg   6060
taaacaacaa caaaaatctg tcagcctggt ctaacctaga tttgtgcttt gttttgtttt   6120
gccactttgt gatgcacagg aggaagttta ggctgtaaaa tactagcctt ttagggtaat   6180
ttttgaactc acaagagcag cagcggaacc tttgatgcaa tcctgtatgt agcaccagca   6240
gagccacgtg gcagagggac tcacattagg agcctcccat tacagactac gtgctcctgt   6300
gcgttatctt atagggtccc cacaaccaag gggagatgtg attattcatc ctgtgtggct   6360
gtggggaact tgagagtcat acttgcccaa agagcacggc cagcgagctt gcacccaggt   6420
cactctctgc tcctctgtca gaacagggca tgtcttggtt cactgcaggg cggctcttct   6480
cattctctgt agtttggggt ccaggatagt ggtccacgga gccactggag tgcccagcca   6540
ctgagtgacc aaagcatatt ttggatttcc gacattgcca cagcatggtt gggcatcagc   6600
```

-continued

```
aggaccccaa ccccttgtta tgctggtggc tttatgtggt tatttgatct tccccagaac   6660
tcagcaggag tgcacccagc agcaccgtag tgatgctctc tggctcccca gtgcacggtt   6720
ctggctttcc ttcctggtcg agagtttcaa gccctctggg tcctactctg tccttttcag   6780
cccatagctt tgttcaaaag ctgctggcag tgttcagatt tggctgagtt cagtgaatat   6840
gtgcattggc tgatttctga gccatgccag gggatggag  aagccgaagc aggagtgttt   6900
gttctgcagg ctctggagta ggcattgggt ctgtgccggc tcacttgcta gtcttgcatc   6960
cttccctaac cccctctggg gatgtctggc cacatcagaa gacagtttgg gttgtcagaa   7020
ctgggggagt accaggccga ggtgggtgga tcatgaggtc aggagatcga gaccatcctg   7080
gctaacacag tgaaacctca tctctactaa acatacgaaa aaaattagct gggcgtggtg   7140
gcgggcgcct gtagtcccag ctactcggga ggctgaggca ggagaatggt gtgaacccgg   7200
ggggcggagc ttgcagtgag ctgagatcct gccactgcac tccagcctgg gcaacaaagc   7260
gagactccgt ctcacaaaaa aaacaaaaca aaacaaaaca aaatctgggg gagtgccact   7320
ggcatctgat gtatagaggc ccgagatgct gtgtcatcac ccgttgagtg cgctcatagg   7380
catcttcctg acaattagaa cccattattc ttcaaattca atgcaagcaa attcaaagca   7440
ttactatgta cataccgcgt gctaatcaat tgcaccactg gagctcctaa attcaaaaca   7500
ttactataaa aaagttcaaa atgcatggaa aagttgtacg tggcaggaga atatttgggc   7560
ttctgactac cccttgaatg aagatgatcc accagccgcc ttcctccttg gtcttcactc   7620
cagattccta gcatttcatt ctgtgtctct ttatgcagtg aggtttttgt ttgtttttg    7680
agacagagtc tcactgtatc acctaggcct ggagtgcagt ggcgcgatct cagctcactg   7740
caaccctcgg ctcctgggtt taagcgattc tcctgcctca gcctcccgag cagctgagat   7800
tacaagcaca catccccatg cccagctaat ttttgtattt ttagcagaga cagggtttca   7860
ccatgttgcc caggctggtc tcgaactcct ggcctcaagt gatccatgtg cctcagcctt   7920
ccaaagtgct gggattacag gcgtgagcca ccatgcccag ctcctagtga ggtttttgat   7980
gccttgctac atctgcccta gaaattgtgt gactacgatt ttggaaatgt tgctgtgtaa   8040
acttgtgatc atttctggac tccaggcaag aatcttgatg gctaaggtgt ggctgaacat   8100
gtctgattct ctcctggacc tgttttaggc caaactctgc tctgaaattc ctccgtgtgg   8160
aagggcgggc tggggagagc ctcccagctg gaatcttttg gatgcctttc tctgtgggta   8220
tctgatggct ggctctgatg gctggctgtg atggctgtgg ctggaaatca ttgttgacat   8280
gagtttcaca gatgcaggct ctgtccaaac tgtagcaaaa gctgcctgcc ccagccgagc   8340
tatgggcaat aaggtggttt aaggatatag atgaaggaaa actcaccctt agaataattt   8400
atccaaaatg ctgctgtgtt gtgggttaga ggacattttc tgaggtccca ggttcattgt   8460
ttcatttaag tctcaaaagt ccctccaggt gttggttcta attgtcaaag catgggggga   8520
gatgggctca tgggttaaag gtcttatccc agatttctgt atcctccttg caagcagcaa   8580
aggggtctgg atttgaatcc atgaccatgt ttctcctttg ggtttccatc acactctgtc   8640
cccgtgcact gagcaccctt tagttcatat gaccccctta ggcatgttac atgggcactc   8700
ctataggtgc ccatctggcc ctaggacttg gccaacacaa catggactcc agtttccatc   8760
tgcctctttg ccaggcactt ttgtgcagtg cacacactgt acaacagtag acggcaaccc   8820
tgagagccag agtagagcct gtcctagcac cggaatgctc ggtaaggatt tgtcgcagga   8880
gtgattccaa agccaatgtc ctccctccat atcagcctgt ttgtggctct gagaagctct   8940
```

-continued

```
gcccacatgt gaaagcttgt taagcactta agcactaacc cagagcttca gacagtacca   9000
gtccttttc cccttcttta aaagcgatat gtggatggag gagtgagtga caacgtaccc   9060
ttcattgatg ccaaaacaac catcaccgtg tccccttct atggggagta cgacatctgc   9120
cctaaagtca agtccacgaa ctttcttcat gtggacatca ccaagctcag tctacgcctc   9180
tgcacaggga acctctacct tctctcgaga gcttttgtcc ccccggatct caaggtgagt   9240
tggtggtgag ggggcaggtg ttctggggtg cagctcttct ttgcctccct gattgccagg   9300
agctaccagt tactgtctgc acaatcaaac agaaatagac ctgttcttga tggttaacgg   9360
aaataaaagg cgcttgtccc agaagctcag gtgaggcacc accctgatta tgggaatcac   9420
ctgggaacat atacccagac ctaaaactca gatccacttc ccaggctgtg gttatatagt   9480
caggggggtg cagtatgggt attaggattt tttattttt agttataaag attttttttt   9540
gatttgtttt tgagacaggg tcttgctctg ccgcttaggc tggagtgcag tggtgcaatc   9600
atagctcact gaagcctcag actcctgggt tcaagcagtc ctcccacctc agcctcctaa   9660
ggagctggga cccacaggca tgcagcacca cacctggcta atttttaaaa attttgtgga   9720
gtgttgccca ggctggtctc acactcctgg cctcaagcga tcctcccacc ccagcctccc   9780
aatgtgttgg gattacaggc atgagccatt gtacccagcc actaagatga ttcttatttg   9840
gaaacacggt caagaacaac tgcgttcggt agtttaacct tttttgattg tggtggtttt   9900
agtatgcctt accactctac catagtaaga aatttgcaga ccatgtacac caacctttgg   9960
tgctcctggg gagaaagaaa gaaggctatg caatgcaatg catgctcaca gtccaaggga  10020
gagggaaagc tgtctaacag gattggtttt cccgtgtgct ttataagcag atgagtagag  10080
gagacagctc ttattgtcct agtggcaatt gggataggct gcaaagtttg ttagggtgga  10140
ggcttattcc gggaccaagg gagcccaaag aaacaagctc ctgccaggcg cggtggctca  10200
cgcctgtaat cccagcactt tgggaggctg aggcaggtgg atcacctgag gtcaggagtt  10260
tgagaccagc ctggccaaca tggtgaaacc ccgtctctat gaaaaataca aaaattaccc  10320
gggcatggtg gcgggcacct gtaatcccag ctactaggga ggctgaggca ggaaaatggc  10380
ttgaacctcg gaagcggagg tggccgttag ccgagatcac gccactgcac tccagcctgg  10440
gcaacagagc aagactctgc cttaaaaaaa aaaaaaaaaa aaagaaaagt aaaaggaaaa  10500
aaaagaggct ctggcctgct ggggtgcctg caaagtctcc gtggaagggt gacattcaag  10560
ccgagacctc cagggaactg tctcctggga gcacagagcc ctttgctcag cccccaggtg  10620
gctcagtgcc cccagccagc agactcagag cttgcatgat tctttggtgc tctctgcggt  10680
cttccaatga tgctgaaata aatggtgctt ggtgtctccc tgctgtagtc cccttgcttg  10740
ctttgctcac aggtgctggg agagatatgc cttcgaggat atttggatgc attcaggttc  10800
ttggaagaga agggtatgta tgggctggga ggatcagcca tgcccttttg acaagcattt  10860
actagcggtc ttggtaaaga cttgagattt gccttagttc taacacttag tgcccaacgc  10920
cttccttgtg ttgctcaacc tactcatgag cccaggagat aggaaatctc cgtcccattg  10980
tacagatggg gaaacagaat tttggaaagg agagccaagc agcacacacc cctccctgag  11040
gggcagagcc gagatttgaa ctgggatgtc atgactccag ggccctctcc ctccccaggg  11100
tccccttatc tgaaggcggt ttttctttcc agctcgacct cttgtgaccc ttagtttaac  11160
aagggccgaa gttaaagagt ttctgcgcct ggaccccaaa tgaagcaatc agatttctca  11220
tctccagtca ggtgtgggtc caagcccact agacaagttt gctcttccca gagcacattt  11280
ctgccttcaa gtcatcctgg cttgtcaggg ctgggggagt tctgctctag aaatattaga  11340
```

```
gtggaaggaa aaagatgtgt tgggagctat ttttctttaa tactaaaagt tggttgatga  11400
atttgtcgtt ggccaagacc aaggagactg catttttaag gacatatgtg tatttatctg  11460
ctcagaaaat gttcattgct gtgtgctagg gatactgcag tgaacacaga ggtgtgaccc  11520
ttgccagcct tgtgagagaa gtgagcagat aagtaagcag aagggtgatg ctgtgtcgat  11580
gggaaagtac aggtgccaat gagaaggcac aggtgtcaag gagaagacac aggatgctgg  11640
aggctcatgc aggatggatc tccaaggccc aggggaagaa gggcctctcg gaggacgtga  11700
atccacatta agactttggg gataagtagg agcgccttag gcatggggac ccatggatgc  11760
gaggcctgta ggacacagag aggatggcat gaaggcctgt gcaactggag gggtggggat  11820
ggggacacta agagatggct ggaagtgtgg gggtggggac actaagagat gactggagaa  11880
gagggggtca ggagtggtga aaaatgggag aggagggcag gctgggcctt ttggatacag  11940
ggggattgca tcctgcagtg gtagggagcc actgagggct gctgcagtag gagtgagggg  12000
atcagaggag agctttggaa gccccctgga tgcgggacag gaagggagat accagtgtct  12060
aggaggccag tgaggcagcc agaggctcca ccaggatcag ggctgcgagg gtcatgagga  12120
ggaaaccaat ttgaaggagt ccaggggaat aggacttgga aatgaccgat gggacatttg  12180
ggaagaggaa gacagaagag cgcagtccca gcttctggct ttagcagttg ggcaagggga  12240
gatggggaga tgtgcccatg ggttgagggt tgaggacatt aggagggagc cggtatggca  12300
ggaagagctg gtgtgccaga gatgctggaa gcagcatctg cctgagaaca gatacctggc  12360
aatattccta agggaaagtg acatctcgga gggtgaggag ggcatctgat agggcctgga  12420
aagagccggg gcaagcatga atgtgaggtt atcttggggg gcaaggctca ggcgttgagg  12480
agcagcccct ggtctcttca gcctgaagtt ggaagccaga gttgggccag gtgcagctgt  12540
ggttgtctga agtccccctc ccccagccca gtgtgccaat gctgtaagag caagggccgc  12600
tcactggtgc tggtggctga gtcccagcac ccaggacagg gcctggcaca tactggtgcc  12660
caatcctccc ttctgggtgc ttcttccaag gccttgtgat ggaagtgagt accctcttcg  12720
acatcagacc cagcttcaaa tcccggctct gctatgtatc ggctgcgtgg ctttagacaa  12780
gtcttttaac cttgctgtgc ttctgatttc tcagctgaaa aatggagatg atgataatgg  12840
tttctgtaag gccttatggt gaagcaccta gctcagggcc tggaaggcag gtgtaaccag  12900
tggttcagtt gttataaacg aacactaacc ctcgcctttg cacctcatga atccagatat  12960
gtagatggag cccacaaagc tagcaggagc caagctcacg tgtgtcctgc tttaaagccc  13020
catacccctt tctccgggtg acaaacacct gtgctcgttc tcttcccttc ccctcttccc  13080
cttgcatttg gctaataaca ggccagctgc ctgcctccct gcagtttggt agatgggtgg  13140
gtaatgacca ccactcccac gttcgcctga tgggcttgtt ttccgtgccc ttcacaggca  13200
tctgcaacag gccccagcca ggcctgaagt catcctcaga agggatggat cctgaggtcg  13260
ccatgcccag ctgggcaaac atgagtctgg attcttcccc ggagtcggct gccttggctg  13320
tgaggctgga gggagatgag ctgctagacc acctgcgtct cagcatcctg ccctgggatg  13380
agagcatcct ggacaccctc tcgcccaggc tcgctacagg tacccactcc tcggggtggg  13440
cacgggcagc accttgtttt ctttcttgtg cattatggag gaagatggta ctgccacatg  13500
ggagcgatag ggtgaggcaa ccatgacagg tggttgggaa catctccttc catgtgtaca  13560
gcctgggctg ctgccatcac tcccagcaca gcccccaacc cccccaatcc tggaaccttg  13620
ccaagtctcc cttcccgtgg ggtcatgacc aggaggaaaa caaactccag ctgagcccct  13680
```

-continued

```
tggggttccc catataggct cctgcctgtg gcagctgggc cctctgtacc cctttccaac  13740
tctgtgtccc taacatggca cctgagctcc tgccatcctg gatttcatgg accccaagga  13800
tgggggtcct gcatctggga cttggcctat tactcggagc tccttttcag ccgcctccct  13860
ccacctgtcc acccacctca aggctccttt cttgagacct ctcctaattt ctcccttccc  13920
ctaaacccac aattttgaac ctccatcgaa tggtgctgta gtttataatg tcatcaaata  13980
tcaaatggag acagtgctat ggtccaaatg attgtgtacc ccccagaatt tgtcttttga  14040
aatcctaacc cccaacatga tggtcttagg aggtggggcc tttgggagga gattaggtca  14100
tgaggaaagg gctgtcatga atgggattgg tgcccttatt aaacagaccc aagagaggtc  14160
ccttgtccct tctactgtgt gaggactcag aaggtggtgt ctatgaagaa ggaggccctc  14220
accagacacc aacacgtctg ctgccccttg atctgggacc ttgcagcctc tagaactctg  14280
aaaaatcgat gtttgttgtt ttataagcca ctcagttggt ggcattttgt tagagtagcc  14340
tgaacacgga ctaagtcaaa cagaagaacc cacaaaccag ctacagagtt gggcatttgg  14400
agaaattcaa aaatgagtca gacataactc cttattcttg aggtgcccta agagatggga  14460
cacagcagct gcccaggtgc attagtttgt tctcacattg ctataaagaa atacctgaga  14520
ctgggtaact cataaagaaa gaggttgaat tggctcacag ttgcacaggc tggacaggaa  14580
gcatggtgct ggcatctgct cagcttctgg ggaggcctca ggaaacttac aatcatggca  14640
gaaggtgaac gggaagcatg cacatcccat gactggagca ggagtgagag agagagggaa  14700
atagagggaa ggtgccatac acttttaaac aaccagatct cacgagaaca cactcactat  14760
caagagaaca gcaccagtgg ggaaatccgc ccccacgatc caatcacctc ccatcaggct  14820
ccgcctccaa cactgggaat tacaatttga catgagatgt gggcagggac acagatccaa  14880
accatatgac cagattaata cgatttgagg catcacgagg tcattaaaga gagggaataa  14940
aagactgggg ctccaggaag aaggctctgg aatccagcag agggtcaagg accagcttgt  15000
aaagctggtg gtgcctgaga agtacctagg agaacataga tgctgtgacg tttgatgtag  15060
ctgtttttttg ttttgtgttt tggtttttga gacagagtct cactctgtcg cccaggctgg  15120
agtgtgcagt ggcgtgatct tggctcactg gagcctccat ctcccaggtt caaatgatcc  15180
tcatgcctca gcctcctgag ttgctgggat tacaggtgca caccaccacg cctggctaat  15240
ttttgtgttt tcagtagaga cagggtttca ccatgttggc caggctggtc ttgaactcct  15300
gacctcaagt gatccaacaa cttcagcctc ccaaagtgct gggatgacag gcatgagcca  15360
ccatgcccag cctgatgtag ctgtttctgt gcacattatt tgctgtgggg tatattcaga  15420
tttcttaata caagatgatt ctttgcctca tgacttacac accattttct atttaatttc  15480
agctatgata ttggaaatgg acatgtcttt tcaaggaaaa taaaagcagg ctttctggaa  15540
tggcgacttc caaacatatt tgtcaattta aaggagctgg gagtggggac cctatgcccc  15600
gtaagcactc tcttagctgt tcttggctgt gctccccgct tcagcttcac actgcccttg  15660
ctgtgaaggg agaagcctgg gctgggcgcg gtggcttaca cctgtaatcc tagcactttt  15720
ggaggccgag gtgggtggat cacctgaggt caggagttca agaccagcct ggccaacatg  15780
gtgaaactcc atctctacta aaaatacaaa aaattagctg ggcatggtgg caggtgcctg  15840
taatcccagc tacttgggag gctgaggcag aagaatcgct tgaacccagg aggcggaggt  15900
tgcagtgagc cgagattgcg ccattgcact ccagcctggg ggcaacaaga gcaaaactct  15960
gtctggaaaa aaaagaaagg agcagcttgg caaaccccac cttgtcgctt ctgtgagtgc  16020
ctctgaccct ttggctgcca ggacgggcgt attttatgga aatgctaagc accaacagag  16080
```

taaagtggtt tggtttttca cagtggtggg agataatagc tccaaattgt ctttttcagc 16140
actgagtgaa gaaatgaaag acaaaggtgg atacatgagc aagatttgca acttgctacc 16200
cattaggata atgtcttatg taatgctgcc ctgtaccctg cctgtggaat ctgccattgc 16260
gattgtccag aggtgagcat tttaggtggc tccgtgtctt cctcacaggg ttgatatgag 16320
gatgaaacaa gatgatagat catggtggca tgtagtctgg gacccggatt gtcgtgccac 16380
agatcacagc tcacagtcta tgtgcaatgc ccctgaatgt tgcccacctg tcctcaagcc 16440
acacatgcac ctgtaactca gtgcaagccc agaaactccc cgtggggact cctagagctg 16500
tcagtggcct cacatagcag ctggtccagt ctcttgtgat tgcccaagga aactgaggcc 16560
tggagagctt ggggtcgctg ctctgaggcc atagagatgc ctagtagaag ggccaggcct 16620
agaagcagga tccttgctgc ccctctgagc tgtttccatt taaaatcaca tgaaggccgg 16680
cgccgtggct cacggctgta atcccagcat tttgggaggc caaggtgggt ggatcatgtg 16740
aggtcaggag tttgagacca gcctggccaa catggtgaaa tgccatctgt actaaaaata 16800
caaaaattag tggagcatgg tggcacgtgc ctgtactccc agctacttgg aaggctgggg 16860
cagaagaatc gcttgagcct gggaggcaga ggttgtagtg agccaagatt gtaccactgc 16920
actccagcct gggtgacagg agagaaaccc tatctcaaaa taaaatgaaa ggtaatgaaa 16980
tgaataaaat aataaatcaa gtcacggccg ggcacggtgg ctcacacctg taatcccagc 17040
gctttgggag gccgaggtgg gtggataatg aggtcaggag ttcaagacca gcctggccaa 17100
catggtgaaa ccatgtctct actaaaaata caaaaattag ctgggcatgg tggtgcatgc 17160
ctgtaatccc agctactccg gaggctaagg caggagaatt gcttgaagca ggacctagga 17220
ggcagaggtt ggttgcagtg agccgagatc atgccactgc actctagcct gggctacaga 17280
gcgaaactcc gactcaaaaa aaaaaaaaaa aaaaaatcaa atcacatgaa agtagaacat 17340
agggaattcc atctttcgtt ctaggcatag tttgttaata tgattcagag ccagcagtta 17400
ggagaacaca gtgtgactct cctagaactt cttgattggg cttcctctga ttgggtttcc 17460
tctgattggg cttcctctga aagtgggggg gatggggggt ggggagcaga atggtcagag 17520
cttggctcag cagtcagact gctcttcttc aaatcctggc tgcattgctt actacagctg 17580
tgtgactcca gatgactgaa tccacctctc tgtgctgcag cttcccgtct agagagatca 17640
cctggagcag agggtggtca ggagactcaa tctggttact gactcacagt gcaggagtac 17700
tcatcccata gtaagcatcc agctagagat gttgatttct attttcaggt aataatgatg 17760
atcgtaaaat tagagacaga taaaaggtat gggcattaga ccagggcact gcaatttcta 17820
agctgtgtga cctcaggcaa gttactcgac ttctctgagc ctcagcggtt tcatccgcaa 17880
tatatggata ggaaaaccga cctcagtggg ttgtctgaca gtggagggca cttgattaaa 17940
aaaaaaaaaa ttaccctggt ctgaatatta ccctggactg aaagaaaaat attgagctaa 18000
tacaggcatc aggaatgggg ctgcagggag tccagggaag ggagaacgaa gagcctgaag 18060
gtgtgaggag gtgcgagtgc tgatctgtct gctacaaaga ggctgctgag cctcctgtgg 18120
atgtggccct ggacttggca gtttaatacc tgagctgtta aaataacctc agatgctgtg 18180
ttctttaagg ggtaggattc agattcctgc tgaaatgctt ctgaaaggga gggaatgagc 18240
cagcccatcc ccagttgctt tttaagatca ttgggaagtt ctggtcttgc catttgtccc 18300
tggaccactc ttaggtcctc ctgccccact tccatctggg tgtgtgccct gggctgtcca 18360
ccacacagct acatcctgcc atcttccctc ctggagccac tgtgccatgc atggatctgt 18420

-continued

```
agcttcattt ttcttggctt ttccctggtt tttctggagc agagtctcta gtaaactccc  18480
aaggaagaaa acgtttgact ttatgtgtgt tgggaaacgt gctttttttc tattacatct  18540
cagtgatagg ttggccatgt ctagaattgc aggttgaaaa tcatttcctc tcagtatatt  18600
ggttagtgag aagcctggga ctgagacagt cacattctca cttctttgca ggtgagtgct  18660
cttaggactg tctttttatc ccttatactc tgaaatgtca tatgtcttgg tgtaagtcct  18720
tatttcagtt attgagctgg acaagtactg gagacccctt cagtcaaagc cttctgtcat  18780
tctccagctc taggaaatta tcttctattg ttatttctgt tattccttcc cttccatttt  18840
ctttttcttt tttttttttt ttttttgag acagggtctt actctggtgc ccaggctgga  18900
atgcagtgac ctgatcatgg tacactgcag cctgaacctc ccagactcaa gtgatcctcc  18960
cacctcaacc tcctaagtag ctgggactgc aagcacacat caccacaccc aacaaatatt  19020
ttttaaaaat tttgtaagat gggatcttac tatgttgccc agactttttc ttcctcttcc  19080
tggggctctt attaggaaga tgtttgactt cctgggttgg attcctgtct ccgtgtctga  19140
ctttctctct ttgtcatatt tttcatcact cgttgtcttt ttgcgtctgc tctgacagat  19200
ttcctcaaat tttgtcttct agtcctatcc tacagttttt actttcagca aatataattt  19260
aatctccaag agtactctct tgttcttttt tcttagcatt ctgttcttgt tttatggatg  19320
taacattctc ttggaatatt tgctgtcctc tagatcatcc cttctccatt tcttcttggg  19380
ctagtttttc tgtttcttca tctttctctt ttatgctact tattctgggc gtgttcttgg  19440
tgggtttttt cccatatagc aacagaggac ttggagctca gggagaaaag ggtaggtgca  19500
tcacctggca gagctcccag acagtgacag gcaggctgcg ggaaggatgt ctacttggcg  19560
gtgctaccgc tttcctagaa accctttccc tggagctggt tgaactgttg ggtttttgccc  19620
tggtggtgaa cgctggctcc ccgtgctctg cctgtttcat caccagcccc ctccccttct  19680
gcctggggtc cagtaatctg ttgaaatata tatcttgctc attggtgagc tcctgctcct  19740
tcctcgttgc tcttgcagat ttatcacttc tcgtaaggct gcgcttgtac ttggggattt  19800
tctctgtgcc acactgggaa acatagggtg gttgcatgct gcagtcctga gcacttattt  19860
cactcacatc tttacacgaa gatttggtgg gtgtttactt tgtttttagt aagttagtct  19920
gtcatgtcct ttgatccttt ttttttgttt tttgagatgg agtctctctg tgtcctccag  19980
gctggagtgc aatgtcgcga tctcagctca ctgcaacctc cacctcctgg gctcaagaga  20040
ttctcctgct tcagtctcct gagtagctgg gattacaggc atgtgccacc acacctggct  20100
aatttttgta tttttagtag aggtggggtt tggcatgttg gccagcctgg tctcaaactc  20160
ctgacctcct gacctgcctg ccttggcctc ccaaagtgct gggattacag gtgtgagcca  20220
ccacacctgg ccctgattaa tcttttaatg cccagtctct ccttcaaaag ccggctcctt  20280
tctctccctc gccttcctag attccttctc cactccccag gatcagcctc ctcctcccca  20340
ccccaccact gctgggggga tgtctgtggt caggcattta tcagagaccc tgaggtgggg  20400
gtcctttatg tgtctggggg atggagagtc tagaggaggt agcgttcaga cctctccatg  20460
gtgcctctgc tgggctcaca tgtgaccaag cacagcaaac catgaggcag gggatggtct  20520
tgaccatgag agcccttgca gcagctgcca tgggcctcag ctcctctcca agctgggaag  20580
agccctgaaa agccaaggtg tttttttttc cctctttatt tcagtgtaag tcccttgagc  20640
tttcttgaac cagaagtggg ctcattttgc tttagagatt tcaggtgggc ttgtccttgt  20700
cctagcatcc cagatccacc ttctgggaag tcatcagatt ggaggtgatg ttggcagctt  20760
ttgtaaacaa agggtagtgt tgtaagctgt tgtgtctgcc tatgtgtgtg tttgtgtact  20820
```

```
tggtctcatc tctgcagact ggtgacatgg cttccagata tgcccgacga tgtcctgtgg  20880
ttgcagtggg tgacctcaca ggtgttcact cgagtgctga tgtgtctgct ccccgcctcc  20940
aggtaaatac tttggctgtg ggtgtgtggg ccggacgggc acctctctca tctgatgagg  21000
cctcacacga cattctagaa acagctggct gaacaccaag caaggagctt gcccttgggt  21060
gtggggaccc tgtctcatgg gaggcagctg agtcagtcag aggtcctggc acacctgctg  21120
agagctgcca cccaggccaa cctgaaccgg agcctgggaa gacttcccgt tggatgagtc  21180
tctttgaggg cagcattgat ggtggaagag cagagaggcc ccagataagc agggaaaggt  21240
gcttcagaca gagtggctgg gatgaggact ggggagtgtc agatagcgct ggcgtgtctg  21300
agcgaaggag ctctggcacc catggcacag gaaggaggtg ggaccctgga ggggcagggc  21360
tagcagagct cctcggagcg tgtggctagg tgcctggtaa tgcaagcccc ctgtcctcca  21420
ccctctgttg tactgagtca cagtctccgg ggtgaagccc agcagtctgc gttgacaggc  21480
cccaggggat gccgctactt cctgaattct gaattctgga aactgagccg gagttcaggg  21540
cctggctccc attaccaggg ttggacgtta tcctgaaaat cataggcctt ggtttcctca  21600
cttggctaac aggggtgatc cccatcccct caatgggttt ccgtgagctc ctgagagccc  21660
gtagcatggt acttggcaca tgctgggcat caggaggtat ggcctctctt gctattgttg  21720
ttattggtag acacagaagg atttaaaagt aggggaatgc aaagatccga tttgctaggg  21780
aagagggcag tagtggccaa gtagagggtg gatcctgggc cctggctggc agcaggcagc  21840
aagggggct gccagggccc aggcagggac gacctgtaga ccgagaggct tcctaaggct  21900
cttggacagg aggaggtgtc ggttccaagc ctgaggagcg gggcagccct ggtgactggt  21960
ggtcagtggt gccaggcggt gggtggtagg acaccctggc aggcaagtag gtttgtgtgg  22020
gggaaactga taggcccctc cagggattcg ttggtggaca acacctgtga tgtccagtgg  22080
gaggtgtcca ggtagctggg agggccacag gcttggaaga cctaggtggt gacatcagcc  22140
cagcactgag ggctagaaga agctgtgtct ctggctgtga cggcacccta gagtgtgtgt  22200
ggtgccctct actggccggc aatgtgggtc caccgtagct cagactgcac actgcagcag  22260
cgggaacggc ctctaagcca acttcctcca tgtgtttcag gtcccaaatg ccagtgagca  22320
gccaacaggc ctccccatgc acacctgagc aggactggcc ctgctggact ccctgctccc  22380
ccgagggctg tccagcagag accaaagcag aggccacccc gcggtccatc ctcaggtcca  22440
gcctgaactt cttcttgggc aataaagtac ctgctggtgc tgaggggctc tccacctttc  22500
ccagtttttc actagagaag agtctgtgag tcacttgagg aggcgagtct agcagattct  22560
ttcagaggtg ctaaagtttc ccatctttgt gcagctacct ccgcattgct gtgtagtgac  22620
ccctgcctgt gacgtggagg atcccagcct ctgagctgag ttggttttat gaaaagctag  22680
gaagcaacct ttcgcctgtg cagcggtcca gcacttaact ctaatacatc agcatgcgtt  22740
aattcagctg gttgggaaat gacaccagga agcccagtgc agagggtccc ttactgactg  22800
tttcgtggcc ctattaatgg tcagactgtt ccagcatgag gttcttagaa tgacaggtgt  22860
ttggatgggt gggggccttg tgatgggggg taggctggcc catgtgtgat cttgtggggt  22920
ggagggaaga gaatagcatg atcccacttc cccatgctgt gggaaggggt gcagttcgtc  22980
cccaagaacg acactgcctg tcaggtggtc tgcaaagatg ataaccttga ctactaaaaa  23040
cgtctccatg gcgggggtaa caagatgata atctacttaa ttttagaaca cctttttcac  23100
ctaactaaaa taatgtttaa agagttttgt ataaaaatgt aaggaagcgt tgttacctgt  23160
```

-continued

```
tgaattttgt attatgtgaa tcagtgagat gttagtagaa taagccttaa aaaaaaaaaa  23220
atcggttggg tgcagcggca cacggctgta atcccagcac tttgggaggc caaggttggc  23280
agatcacctg aggtcaggag ttcaagacca gtctggccaa cactcgagat aacttcgtat  23340
aatgtatgct atacgaagtt atatgcatgc cagtagcagc acccacgtcc accttctgtc  23400
tagtaatgtc caacacctcc ctcagtccaa acactgctct gcatccatgt ggctcccatt  23460
tatacctgaa gcacttgatg gggcctcaat gttttactag agcccacccc cctgcaactc  23520
tgagaccctc tggatttgtc tgtcagtgcc tcactggggc gttggataat ttcttaaaag  23580
gtcaagttcc ctcagcagca ttctctgagc agtctgaaga tgtgtgcttt tcacagttca  23640
aatccatgtg gctgtttcac ccacctgcct ggccttgggt tatctatcag gacctagcct  23700
agaagcaggt gtgtggcact taacacctaa gctgagtgac taactgaaca ctcaagtgga  23760
tgccatcttt gtcacttctt gactgtgaca caagcaactc ctgatgccaa agccctgccc  23820
acccctctca tgcccatatt tggacatggt acaggtcctc actggccatg gtctgtgagg  23880
tcctggtcct ctttgacttc ataattccta ggggccacta gtatctataa gaggaagagg  23940
gtgctggctc ccaggccaca gcccacaaaa ttccacctgc tcacaggttg gctggctcga  24000
cccaggtggt gtcccctgct ctgagccagc tcccggccaa gccagcacca tgggaacccc  24060
caagaagaag aggaaggtgc gtaccgattt aaattccaat ttactgaccg tacaccaaaa  24120
tttgcctgca ttaccggtcg atgcaacgag tgatgaggtt cgcaagaacc tgatggacat  24180
gttcagggat cgccaggcgt tttctgagca tacctggaaa atgcttctgt ccgtttgccg  24240
gtcgtgggcg gcatggtgca agttgaataa ccggaaatgg tttcccgcag aacctgaaga  24300
tgttcgcgat tatcttctat atcttcaggc gcgcggtctg gcagtaaaaa ctatccagca  24360
acatttgggc cagctaaaca tgcttcatcg tcggtccggg ctgccacgac caagtgacag  24420
caatgctgtt tcactggtta tgcggcggat ccgaaaagaa aacgttgatg ccggtgaacg  24480
tgcaaaacag gtaaatataa aatttttaag tgtataatga tgttaaacta ctgattctaa  24540
ttgtttgtgt attttaggct ctagcgttcg aacgcactga tttcgaccag gttcgttcac  24600
tcatggaaaa tagcgatcgc tgccaggata tacgtaatct ggcatttctg gggattgctt  24660
ataacaccct gttacgtata gccgaaattg ccaggatcag ggttaaagat atctcacgta  24720
ctgacggtgg gagaatgtta atccatattg gcagaacgaa aacgctggtt agcaccgcag  24780
gtgtagagaa ggcacttagc ctgggggtaa ctaaactggt cgagcgatgg atttccgtct  24840
ctggtgtagc tgatgatccg aataactacc tgttttgccg ggtcagaaaa aatggtgttg  24900
ccgcgccatc tgccaccagc cagctatcaa ctcgcgccct ggaagggatt tttgaagcaa  24960
ctcatcgatt gatttacggc gctaaggatg actctggtca gagatacctg gcctggtctg  25020
gacacagtgc ccgtgtcgga gccgcgcgag atatggcccg cgctggagtt tcaataccgg  25080
agatcatgca agctggtggc tggaccaatg taaatattgt catgaactat atccgtaacc  25140
tggatagtga aacaggggca atggtgcgcc tgctggaaga tggcgattag gcggccggcc  25200
gctaatcagc cataccacat ttgtagaggt tttacttgct ttaaaaaacc tcccacacct  25260
ccccctgaac ctgaaacata aaatgaatgc aattgttgtt gttaacttgt ttattgcagc  25320
ttataatggt tacaaataaa gcaatagcat cacaaatttc acaaataaag catttttttc  25380
actgcattct agttgtggtt tgtccaaact catcaatgta tcttatcatg tctggatccc  25440
ccggctagag tttaaacact agaactagtg gatcccccgg gatcatggcc tccgcgccgg  25500
gttttggcgc ctcccgcggg cgccccccctc ctcacggcga gcgctgccac gtcagacgaa  25560
```

-continued gggcgcagcg agcgtcctga tccttccgcc cggacgctca ggacagcggc ccgctgctca 25620
taagactcgg ccttagaacc ccagtatcag cagaaggaca ttttaggacg ggacttgggt 25680
gactctaggg cactggtttt ctttccagag agcggaacag gcgaggaaaa gtagtccctt 25740
ctcggcgatt ctgcggaggg atctccgtgg ggcggtgaac gccgatgatt atataaggac 25800
gcgccgggtg tggcacagct agttccgtcg cagccgggat ttgggtcgcg gttcttgttt 25860
gtggatcgct gtgatcgtca cttggtgagt agcgggctgc tgggctggcc ggggctttcg 25920
tggccgccgg gccgctcggt gggacggaag cgtgtggaga gaccgccaag ggctgtagtc 25980
tgggtccgcg agcaaggttg ccctgaactg ggggttgggg ggagcgcagc aaaatggcgg 26040
ctgttcccga gtcttgaatg gaagacgctt gtgaggcggg ctgtgaggtc gttgaaacaa 26100 ggtgggggc atggtgggcg gcaagaaccc aaggtcttga ggccttcgct aatgcgggaa 26160
agctcttatt cgggtgagat gggctggggc accatctggg gaccctgacg tgaagtttgt 26220
cactgactgg agaactcggt ttgtcgtctg ttgcgggggc ggcagttatg gcggtgccgt 26280
tgggcagtgc acccgtacct ttgggagcgc gcgccctcgt cgtgtcgtga cgtcacccgt 26340
tctgttggct tataatgcag ggtggggcca cctgccggta ggtgtgcggt aggcttttct 26400
ccgtcgcagg acgcagggtt cgggcctagg gtaggctctc ctgaatcgac aggcgccgga 26460
cctctggtga ggggagggat aagtgaggcg tcagtttctt tggtcggttt tatgtaccta 26520
tcttcttaag tagctgaagc tccggttttg aactatgcgc tcggggttgg cgagtgtgtt 26580
ttgtgaagtt ttttaggcac cttttgaaat gtaatcattt gggtcaatat gtaattttca 26640
gtgttagact agtaaattgt ccgctaaatt ctggccgttt ttggcttttt tgttagacgt 26700
gttgacaatt aatcatcggc atagtatatc ggcatagtat aatacgacaa ggtgaggaac 26760
taaaccatgg gatcggccat tgaacaagat ggattgcacg caggttctcc ggccgcttgg 26820
gtggagaggc tattcggcta tgactgggca caacagacaa tcggctgctc tgatgccgcc 26880
gtgttccggc tgtcagcgca ggggcgcccg gttctttttg tcaagaccga cctgtccggt 26940
gccctgaatg aactgcagga cgaggcagcg cggctatcgt ggctggccac gacgggcgtt 27000
ccttgcgcag ctgtgctcga cgttgtcact gaagcgggaa gggactggct gctattgggc 27060
gaagtgccgg ggcaggatct cctgtcatct caccttgctc ctgccgagaa agtatccatc 27120
atggctgatg caatgcggcg gctgcatacg cttgatccgg ctacctgccc attcgaccac 27180
caagcgaaac atcgcatcga gcgagcacgt actcggatgg aagccggtct tgtcgatcag 27240
gatgatctgg acgaagagca tcaggggctc gcgccagccg aactgttcgc caggctcaag 27300
gcgcgcatgc ccgacggcga tgatctcgtc gtgacccatg gcgatgcctg cttgccgaat 27360
atcatggtgg aaaatggccg cttttctgga ttcatcgact gtggccggct gggtgtggcg 27420
gaccgctatc aggacatagc gttggctacc cgtgatattg ctgaagagct tggcggcgaa 27480
tgggctgacc gcttcctcgt gctttacggt atcgccgctc ccgattcgca gcgcatcgcc 27540
ttctatcgcc ttcttgacga gttcttctga ggggatccgc tgtaagtctg cagaaattga 27600
tgatctatta aacaataaag atgtccacta aaatggaagt ttttcctgtc atactttgtt 27660
aagaagggtg agaacagagt acctacattt tgaatggaag gattggagct acgggggtgg 27720
gggtggggtg ggattagata aatgcctgct ctttactgaa ggctctttac tattgcttta 27780
tgataatgtt tcatagttgg atatcataat ttaaacaagc aaaaccaaat taagggccag 27840
ctcattcctc ccactcatga tctatagatc tatagatctc tcgtgggatc attgtttttc 27900

```
tcttgattcc cactttgtgg ttctaagtac tgtggtttcc aaatgtgtca gtttcatagc  27960
ctgaagaacg agatcagcag cctctgttcc acatacactt cattctcagt attgttttgc  28020
caagttctaa ttccatcaga cctcgacctg cagcccctag ataacttcgt ataatgtatg  28080
ctatacgaag ttatgctagg gtaactataa cggtcctaag gtagcgagct agccatgtgt  28140
ccagttcgca ggggggattt gtttgcatgt tgacttccct cgttggaaac ttcagagggt  28200
ttggttttgt tgttgctact tgggaattcg gggtgtttgc acaggcttac cagttaagca  28260
agttcaaaca ggtaaacatc tcagacgtgt tttgagcatc acaccaacgc tcagaaggct  28320
tctgactttt acactgggtg tggcggcaca cacctgtggt cccagcactg tggatggagg  28380
ctgaggcaga agagtcagga attcaaacct atcctgggcc acagagttag tcaaggccag  28440
cttgggcttt gtatagagac catgtctcat aactaagatg tgtctgggga cgtaactcag  28500
tggatagttt gcatggttca atccctgtgc taccattagg aaggagaagg gagggaagga  28560
gaaagagagg aagggaaaga gggaaagggg ggaaagagag agaagaaagg agaggggag  28620
aagaagagag ggaaggagag agggagaggg gaaaaacaga aagggcaaga ggaagagagt  28680
gagagggagg gaaggagaga gggaagaagg gggagaggaa gggagaaaac aagaggggaa  28740
gagagagtag gagggaggga aggagggaga ggaaggaagg gagaagaagg aagggaagga  28800
aggagagaaa aagaggaaag gagaggggag agaaggagag agagaggaag aagaggagga  28860
ggaagaggag gaggaggagg aaagaaagag gagggtgtgt tatctagagg ctctggatgt  28920
accttctgcc ctggactact cctggtctcc ttatcctgtc caatctgggc ccatgcctca  28980
gggacatgac ccagccctgc ccttccattt ctttgcaccc tctttttctt ggcactctcc  29040
cttgtttttc tgaagcgaag ccttcctaaa tccccaggga aacagcagcc tgccagcctc  29100
ctcagagcct cacctgttcc tgcactggct gctgggcagc tgctcgcagg cctgcgggca  29160
cagtctgtcc tctgagagcc tagctggggc tccgtaagat tatttattca cgacttccac  29220
ctgctcttct cctctgtggc ctgtaggttc ttggtctttc tttccaccga ctgctacttt  29280
ctcagtcaaa ggccctctct ctcctggttt ggggacatga ccatctgtaa ttaatgcctg  29340
tagtttcgtc tttcctgggg ctgtttcttc tctcttatga gactcttgtg agatgctttg  29400
cctggaactc tgtagaccag gctgacctta gactcacaga gatccacctg gttctggctt  29460
ctgagtgctg ggttaaagg aatgcaccat cgttgcctga catagaaact tctttattgg  29520
ggcagatggg aaatgagaaa cagatgtctt cagggtctga gggaaagcct agagcagaga  29580
agccttcatc ctgggagaaa gaacagatca gcagcttatg aagttgttag ggagtgccca  29640
ggggaatggt gaaggagagg tagtccccaa gagcgcccca gcggggccgg tagatctgga  29700
agatggtgat ccaggtggtg agaatgaatg atcaccaaga agaggaagcc cacagctgag  29760
cgccaaacat agcctttgat ttggctctgc tctgtgtagg ctggggcgag gaaagcctct  29820
ctaaagaacc agaaaatgtt gaccaaccaa agaaaaggca ggaacgcaaa tccaccaaga  29880
tagtacttcc ggcacaggtt caacttctcc tcattggata cccgctccaa gttcatagtt  29940
gcgctggagc ccggtggtcc taagggtctg cagagcaaga cccaaatgac aggcgcaaga  30000
tcacgagcaa ccacgcccca gtgcggttta tcccttctgc ctgggattcc tttgtgggag  30060
atttgcggga gatgccgcag ttttcagtgg agtttgttgt cgctttattt ttttcttctc  30120
ctgcccagcc cccctcgcac cccaccctct ccgccagttt tcagtggagt ttgttgtcgc  30180
tttatttttt tcttctcctg cccagccccc ctcgcactcc accccctccg ccgaaacttc  30240
tctttcttac atatttcagc cctttggctt tttgcctcca atctgaagtc ttctcagctt  30300
```

-continued

```
taccctccag ttctaccctt cggggtttta acattagcag catgagtgag catgctggtc  30360
ctttcttctg gttcctttac ttgagcattc tcagcttggt ttgtgggtgt tgggagaagt  30420
gtattggggg tgtgtctgtg gaagtgggtg tgtctgtatg ttgaggggta tttttacttt  30480
tatttatgtc tgtgtgcact gattggttga ttgattttgt gtgtgtgtgt gtgtgtgtgc  30540
gcgcgcacgc acacacacac aaactgtttg agcagacagg ctagccttga cttctagatc  30600
ctcctgcttc accctcttag cactaggata atagatatgc gcctctgtgc ttaggtgagt  30660
gtcctgccgt cctgtctttc tttcctggct atagcagggc cacagcctat gtgtggaggt  30720
cagaggacaa ctctcagaag gagttggccc tctccttcca ttttctgggt cctaaagatc  30780
agactcaagt tgtgagacag ggcagaaaac gtcattaccc tgtgaaccat gtctgcctcc  30840
tgtgtaagta cttctgagac agaattctag ttctgtagcc caagctggcc tagaacttac  30900
tgtgtagacc agactgacct tcaactcaag tcggacctct cccctgcatg cagggtgtag  30960
ggcttgattc accccctcccc catcccactc aaggtcttgt attaggggca tcagcctagc  31020
tcccaggcag ggagtagtgc tgagtcagcc tgcttctgga ggaagaaggg ctcccttgtg  31080
agggtggggg tgggggggtg cttcctcctt gtccttcctg gaggattaga cacaaggcca  31140
agtttgactg tagtaccagt gctttgtggt gtctggctcc ctcccctctg gctgaggcta  31200
tgggatctca tagccagatc agtagttcac acttgcagcc agctcagctg cttaggggga  31260
agcccaggag gtctagacca gcctgtggag agagactccg tcctccctgc tccccgtcac  31320
tgtgctccct tagcatggga gcacctctgg ataagaggtg cagcaagcta ggcttagctt  31380
gtcctcaccc caccccacgt cctcgaattt gtatcttagc acattgcaca ggcccaacct  31440
ttagtttctc tatccaaacc ctggggcagc tttactgatc cagtgttccc cttcaacagc  31500
ttccccaccg acgtcatgat aaatcgaatt aagtcgaagt tgtaaaaagt caggtttatt  31560
ggggcagctc tgggtgggct caccaatgtc acaggaaggg gtcagcaaag ttgtagaagt  31620
tgccgggctg agctccagta gaggctgctg ggggagtggg ggaggggagt cgtgaagtga  31680
tggttattca tttggtaagt ttagggccct gtaggtgggt ctttaggtcc agcggttact  31740
ttggaatctg gaactgggag ctgactttgt ccagtgtttt agatgggctt ttgcaagcat  31800
gggcgcctgg tcagaagaga aagggggtag ggtctcttgg cccataccat cttaccggtg  31860
ttccaaactt ccagtctgcc accccctcaag ggaagttctt accagcaact tacctcttgc  31920
cagagtctac agagggtttt ggccccggtg gctccagttg gattcctagt ggccctgcac  31980
cgctggcttc tatggagcct aggcctcggc cagcacttgc cctcaaccct tgagaaatta  32040
ggtagaccca ccccacgctg ctgcctttcc cgttcattcc caggagcttt ctggaacctt  32100
atatggcctg tgtgctttaa gagatattct cagaggttca cctttgtgct gatatcccac  32160
atatgcctta gggaaggtat cagattgcgg ttagaggcga tacaggcagc tcactaggat  32220
taaggtcgcg gttgtctagt tggttgtgag ccaccacttg gttgctggga tttgaactta  32280
gaacctctga aagagcggcc cgtgctctta gccactgagc catctctcca gcaatgggac  32340
tgctttttat tgcagtgttg gctgcttttt attgacctct tttttttttt ttttctggtt  32400
taatctttac agtgaaccct tgtgtccatg tgatatttgt gcacatgtac atatatctgc  32460
atctgtgttt ctatgtgaag tatacatgca tggtgtctgt tatgaaaaat aacacaggat  32520
taaagggcca cctggagggc ccatgccaag gtgtctccct gagaaatccc accatgtgac  32580
agacctggct ggtataaggg aggtctattg tggggcaagg gaggggagac agaaaggggg  32640
```

-continued

```
agacagagac agggaggctg gcagggaaca tgtggggaca gagaaagaga gagagaataa  32700
gaaaggggag atagagaagg ggaccggggt aacatggtcc tcttacaagc tcccaggcca  32760
cccacacctg gtggcagctc aggtagcaat ggaggcaggt gatgacctaa gctgttgcta  32820
ggtctctgtt gttaggtccc tgggaggaaa ccagaatcac ctgtaagcca atagtgtcct  32880
tggcttcctt cccacaggct ggtgacatgg ctccctgata tccaggatga tatccagtgg  32940
ctacaatggg cgacatccca ggtttgtgcc cgaatgacga tgtgcctgct cccctctacc  33000
aggtaaatac ttgggcccag ggtgtgtggg ccagataggc atccctcccg gttgttccca  33060
gagctcttag ggtcagagct tgggtggtga cagccttaac aagccaggct cagccgcctg  33120
tccccagcat gccattaaag aaaccggtag cagagaaagc aggtttattc gaatataaaa  33180
aggttcaagc ccccacccgg ttaatcttta agataccaac aggaggctta agtttaaaca  33240
gagttacaca taaacagtct gaatcagggc gtggtcctgc ccaccattgt ctgggcttca  33300
aggttccttc tttctctccc tagcatgaga ttcctgggac aatcccaatt ccttggcctc  33360
cattgtatca aagggctgaa aaccaaaggg aaggcacagc tgtctcttca gcatgcctct  33420
tctgccagaa ccactgcaag gtttggtgct caggctgtgc aaacattcta gcaatgtttg  33480
actcagtgtc aagcaggtga caaggaacat ggtgctgtgt ggggggaacc catggcccag  33540
gtgagggctt attggtgggt gaagctgtgg gtgttcaggt ggtggagaag gccttaaggg  33600
atgggactga cacctcagca ctgaaggcag gaggaagctg tggctctggg ttgcacccct  33660
gcctggctcc accctctctg gcatctgtag aagttacagc tggttcttcc tctcagcccc  33720
atgctcccag aaataagact cagacccaaa ttatagttac aaataccttg gccatatagc  33780
taggctcttc tcagactagc tcataactta actcattaat tttaacctcc atcctgccac  33840
atggctggtg gcctgtgctc aggtaccatg agtccagctc ttcacatctt tccggatgaa  33900
tcttccataa ttctttctgc ctcctggatg ttccaccttc tattccacct tttcctatag  33960
gccatggttt tgtttttgtt tttttttcc aaatttaatt taattaatta atttatttat  34020
ttttggtttt tcgagacagg gtttctctgt atcgccctgg ctgtcctgga actcactatg  34080
taagccaggc tggcctcaaa ctcagaaatc cgcctgcctc tgcctcctga gtgctgggat  34140
taaaggcgtg cgcaaccatg cccggtgtgg tttttttttt tttttaattg acaggtggat  34200
gcatctatat aatccataac atattctctc tacaggtatc tattaggttt tgggtgaggt  34260
gtggagttct agggaactct gagagaaatt cctggggagt aagtggttta tcaagttgat  34320
tggaggagtt tttaatgcta tggacagaca gacagaagga caacagcata gtcggggcta  34380
ccagggagtt caggccccgg catcggagat agaagcagga tggggtcttt gaagagattc  34440
tgagcccaca cagcagagga gggactctct ctttagagct tttgaggatg agggaggttg  34500
actgcaagag cctacagcca ggctcgaggc aggcaggggg tggggagcag gatgtaaacc  34560
ccttcgatgc tgacagactc acttctgggg taaaatatta tgagatgcct gtcagtgtct  34620
gtgaagagac ctgagcagag tctggattct gacatcaatc atgttcttac aatactgaag  34680
acctgagagc ctgcaatctt ggtttgtaaa ttgctggtct ccgtgcttcc agtgaacttg  34740
gacattcttc tcatggttgg tccaggagag gccaaagctg agggcaccct gccttccacc  34800
cccagtccag cttgaccttt tatctggagc aacagtgtct agatgatggg tgggtgaggg  34860
gtgctatact gtctgtccct ctgggaaggg ttctgttact tttggaggca gctaggaagt  34920
ttctctgtgc agctgccccc tggtgctgtg tggtgacctc attgcctgtg accccaggat  34980
cacaggatct gggctaaagt ggtagtccat agaaaccaaa gacaatgatt tggtgtttag  35040
```

aaagctactc ttggtctggg tgaagtctgg tgcttaaggg ctatcacaaa gagcgtgtca 35100
aaccatctct cagcctgtga gtcagtgggg agcccaaggg catcagtgtt tggaaactgg 35160
aatccaaacc gggcaatctc ggaaggaaac tgtttaggaa ttgtgatggg acgggccgtg 35220
gctgtctctg aaaagggcct gccagataac ttattacttt taaggacacc tttggctctt 35280
actaatttat aaagcatttt atataaacac accagggagt gcatggtgaa ctacacgtat 35340
gatcagttaa gtggggctag aattaggtag ggagagcatc ggacctctgc ctcctcaacc 35400
tcaacttgct tgctttctcc actggctcca aatctttgta tagtcatcag ccatgaccac 35460
ctctctccct ccccatctac taccagcagc gttaatggga ataagtaccc acttctctca 35520
ggtgtactat acagctgtgg gtgtggtgtg tgtttcctgt aattcacact ttagaaagga 35580
aacaagcaaa caaaagaaac caggtgctgc ccatactcct aagtgtagac agtgaaggtg 35640
tgtgtctccc atgcctgagt ctcctggagg cctagtgagc tccaggttca tgcaagcaca 35700
tcaggaggaa tcatataatc tcagcacggt tgatccagat gggataagaa aggactctgg 35760
gagagagaat gtggttctag agacaaagtg tctaggctac acagaagata agactgtccc 35820
aaggaaagaa aagaaaccag gaactagggt gcagctcagt tgtcagagga cttctctagg 35880
cttgaagccc agagtccaat ctcagcacct tataaactgt ggagtgacag gcagtgacat 35940
cggcctgtaa tcccaacact caagcagtag aggcaagagg atcataagtt caaggtcttc 36000
cttggctatt tagggagttg gaggttagct ctggctacat gagaccctgt ctcaaaaaaa 36060
aaaaaaaaaa aaagtagaaa cttctgcctt gctttgagct gccccttct ggacgtttct 36120 catcagtaga gaatattcct gccaccctat cagacaaaac tcccactggt ttggagtctc 36180
tccattctca ggaacacctc aggagtcaga cagtgagcag cagggagcaa tgtcttgact 36240
tgtaagcccc ttagcaaggc tggttcattt gtttattaaa agcaggtgtg ggtgaattta 36300
tgcaaatgag tatgcaaact agtggaacag cagaaggatt gaatggatac accaaaaata 36360
accacaactg tttaagggaa aagggtccat aataaatgtg gggaacaaaa aacaaataaa 36420
tgtgattttt ttt 36433

<210> SEQ ID NO 22
<211> LENGTH: 31701
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(58)
<223> OTHER INFORMATION: Mouse Sequence
<220> FEATURE:
<221> NAME/KEY: misc_feature
<222> LOCATION: (59)..(23322)
<223> OTHER INFORMATION: Human Sequence
<220> FEATURE:
<221> NAME/KEY: misc_feature
<222> LOCATION: (59)..(61)
<223> OTHER INFORMATION: Start Codon
<220> FEATURE:
<221> NAME/KEY: misc_feature
<222> LOCATION: (4994)..(4994)
<223> OTHER INFORMATION: I148M (C>G)
<220> FEATURE:
<221> NAME/KEY: misc_feature
<222> LOCATION: (22383)..(22383)
<223> OTHER INFORMATION: K434E (A>G)
<220> FEATURE:
<221> NAME/KEY: misc_feature
<222> LOCATION: (22527)..(22529)

-continued

<223> OTHER INFORMATION: Stop Codon
<220> FEATURE:
<221> NAME/KEY: misc_feature
<222> LOCATION: (23323)..(23328)
<223> OTHER INFORMATION: XhoI
<220> FEATURE:
<221> NAME/KEY: misc_feature
<222> LOCATION: (23329)..(23362)
<223> OTHER INFORMATION: LoxP
<220> FEATURE:
<221> NAME/KEY: misc_feature
<222> LOCATION: (23370)..(23395)
<223> OTHER INFORMATION: I_Ceu
<220> FEATURE:
<221> NAME/KEY: misc_feature
<222> LOCATION: (23396)..(23401)
<223> OTHER INFORMATION: NheI
<220> FEATURE:
<221> NAME/KEY: misc_feature
<222> LOCATION: (23402)..(31701)
<223> OTHER INFORMATION: Mouse Sequence

<400> SEQUENCE: 22
agagcagcaa caccgggagc agagctgaac tgcagcgccg cccggagctt caagcaccat 60
gtacgacgca gagcgcggct ggagcttgtc cttcgcgggc tgcggcttcc tgggcttcta 120
ccacgtcggg gcgacccgct gcctgagcga gcacgccccg cacctcctcc gcgacgcgcg 180
catgttgttc ggcgcttcgg ccggggcgtt gcactgcgtc ggcgtcctct ccggtatccc 240
gctgggtgcg tctggggacg ctgcccgggc tccacgtgcg gagtgggtgc cccctaggcc 300
ggggagcggg ggatccccag gggtcgcggg gccctggagg agcgggcatc ggacgcggac 360
acggcggggt gcatcccgag ggccccctcc gaggcagatg cttcctgcgg gggcgctgtt 420
cctgggcccg ggaagggggc gttggaaccc cgagcggtcc gggccgaagc ctgggactct 480
cgtgcgtccc cacccctacc cccatcaggc gcccgtgcat gaagggagac cctcacctcc 540
ggactgagag tcggagcgtc tcggagcgac ggggagtagg gagcgggacc cggggcggag 600
ggtagtgctg gcccctgcgg actccgggtc ccctgtgtcc tctcgggagg ggctggacgg 660
gctgagctgc cgaggggccg atttgccctg ggccggacaa agagtggggc tttggccggt 720
cccccacggt gggctccttc cctctgggga ttgagggact caagacaccc cgcgcctgcg 780
cttttctttt cttttttct ttttttttt ttgagacgga gtttcgctca gtcgcccagg 840
ctggagtgca gtggcgtgat ctcaactcac tgcaagctcc acctcccagg ttcacgccat 900
tctcctgcct cagcctcccg agtagctggg actacaggcg ccagccacca agcccggcta 960
attttttgta tttttagta gagacggggt ttcaccgtgt tagccaggat ggtctcgatc 1020
tcctgacctc gtgatctgcc cacctcggcc tcccagaatg ctggggttac aggcgtgagc 1080
cactgctccc tgctgcctac gctctctggg tcgcagccca gccttctggg ggctgggtag 1140
cctcccagaa gggcaaccct gggcatcctc cagggcaggc taactggagt ctagtgggga 1200
ggggtacctt gaaagaggaa agttgtttcc tcctcctcct cctcctccag tgtttgggac 1260
ccttcctggg ggctggagtg catccctgga caccccccaa tcccatcctc ttctctagtt 1320
tccactgacc taggcccacc ctcccctctc cggctcagta ctcctggaaa tgagattccg 1380
tacatttgaa tcttgtccta atgaaatatt tgtccatgtg ggtacctgtg tgtgtgtggt 1440
gggggtgcag acggagggtt tgtttctcac tagctggaac tactggggtg tggtatgctt 1500
cctgggaatt tgtgtgccac agtcctggag gcgaggaggg ggttgtgagc cagtaggcag 1560
gggctggggc aagtagcatt gtgaagctat tgacacccag acgtccccag gcaggagatt 1620
atgcccccat tagccccctt ttatctgggc ttccttaaca atggactctt tgccctgcct 1680

```
gccagagcca gcagggagtg actgttcagt ggtgaggaag cgggcagagg aagccctgcc   1740
attgggtagg agcagtgggc agcccctggg ctgactggga ggtggggatt agggattaga   1800
cagtcctggc tgtctgcctt cccctaagcc agggggagag gagcaaaggg cacgaaatgt   1860
ggcctccagg aggattagac cgccacatga tcatttgcac accctggggt ttagcaacaa   1920
taaaagtcag ctttttttgta tcccaaggtg gcctgtggac acccacatgg acaaatgttt  1980
acactgggac agaattcaaa tgcagaggtc ccaggagcct aaagtacact cactctggta   2040
tagaaaggat tccttactgg gcagaggaca ggtgcagcct ggggctttcc caggcaggac   2100
acagggaggc tcaggaacca ccaagtccct ggaaggtgga tctggaggtg ttggcaggag   2160
ccactccctg ggttccaggg ctccaggttc ctgctttaac cccctgtctc acagagggct   2220
gtgcacttgg gggctgctga gcatgtccca gaggctgcat cctggacaca gcacctcagt   2280
gcatctgagc tgaggctaac ttggcaggag ggacaggcag aacctgccag ccacgtgcaa   2340
ttccacccct ctggccactc agggaaggag agctgtgagt caagatcaga tttgggtcag   2400
gacaggctgg ggcctgcctg tccctgtgca tcccaagatt tatggctggc caggggttgg   2460
gctgggaggg gtggtcttgc atgccaggag agtgcagatc agcctgagag gccaggccag   2520
taagtgaggt cagatctcct gcacctgata gcattaaggc catctacacc aaagctctaa   2580
tgctgatatg ttcctggcct ctatgtgggg catggaggtg gggcatggag gtgaggcctg   2640
ctcgcctggg cttctggaag tgggagactc attcctgtgg ctgaggccta cagcagtgct   2700
gtgtggtagg aatacactgg aagccatgat gtcattgtgc attttctaga agccacattg   2760
aataaagtaa aagacacagg tagaattaat ttcattgagc ccaatatatc caaaataata   2820
tcattttcac atctattcaa tataaaaatt tactaatgag atatttcata ctaagccact   2880
gaaatccagt ttgtatctta cacatctcag ttttgacgag ccacatttca agggcgtgat   2940
agccacatgt ggctcccata gtagacagta ctggtctaga gaaatgttgg tggcatcctt   3000
gctgtctggt ttctggcctt gccaaaagta ttaccatccc agtgtggtac attctttcat   3060
gtatttgtct cctgtcccca gagcagactc tgcaggtcct ctcagatctt gtgcggaagg   3120
ccaggagtcg gaacattggc atcttccatc catccttcaa cttaagcaag ttcctccgac   3180
agggtctctg caaatgcctc ccggccaatg tccaccagct catctccggc aaaataggca   3240
tctctcttac cagagtgtct gatggggaaa acgttctggt gtctgacttt cggtccaaag   3300
acgaagtcgt ggatgtaagc agtttgctta tctggacgtt gtcaagttag aaaagctgtt   3360
ttgggatggg tgtggtggct catgcctgtc atcccggcac tttgggaggc cgaagcgggt   3420
gggttgcttg agcccaggag ctcgagacca acatgatgaa acccagtctc tacaaaaatt   3480
acagaaaaat tagctaggca tggtgttgtg ggcccatagt cccagctact agggaggctg   3540
aggcaggaga attgcttgag cctgggaggt ggaggttgca gtaagtcatg atcatgccac   3600
tgtactccag cccgggtgac agtgagatgc tgtctggaaa aaaaaaaaaa agaaagactg   3660
ttttgttttg gaagcaacac aggcagttgt aggcccccctg tgccagagtg acataaactc  3720
tgtacacctc cagtgatttg gtccatgttt gtaaaccctg aatgttccag ggcagtttct   3780
tttcttcact ttttatctct ttttttggg tggggggggcg gggtacagag tcttgctctg   3840
tctcccaggc tggagtgcag tggcgcaatc tcaacctccc gaggagctgg gactacaggc   3900
acaggccatc acaccttgct aatgtttgta ctttttgtag agacggggtt ttgccctgtt   3960
gcccaggctg gtcccaaact cctgcaccca agtaatctgc ccacctctgc ctggcagtta   4020
```

-continued

```
caatttcaaa taattcctcc ctttccttca acacttggct catgaccgtc cagtccaagg   4080
aacctgtcct gcaggtgtgc ctctcccgag cttcctctat gcatcttcca taatgaagat   4140
gccttctcac tggaaaccct acaagggtgg gaacgtgcct tatttgcctg tatcctcagg   4200
gtctagcaga gagaagataa tctgtaatac caaaacacca ttaaattcag ctgatgcttt   4260
cataagcgct ccttggagga aggactccat ttacttgaca gatctgtgca agacagcagc   4320
ctggcgcgtc taacctgcag ccagttgcat cctctgttta accttgtttg tggaagcttt   4380
ctctaaacag ccagcacttg tctgttccca catgggtccg ttctcccagt gaatcaccgt   4440
ggtgcctact gactgctctg tagcacagtg cttcgcaaag tgtgatcctg ggaccagcag   4500
agcagcagct cctttgagct tattggaatg gcagaccctc aggtcccacc tctgacctgc   4560
tgcatgggaa ttctggggag ggacgcagaa tctctggttc cacaggctct ccggtgatgc   4620
taatgaatac cggcatttga acagcaccga tctagcccct ttcagtccat gagccaacaa   4680
cccttggtcc tgtctgtggt gacccagtgt gactctcatg gggagcaagg agaggaagtt   4740
gaagttcact gacagggttg ttaaggggat tatgcaatag atgagaccca tgggcctgaa   4800
gtccgagggt gtatgttagt tccccgttct tttgacccat ggattaacct actctgtgca   4860
aagggcattt tcaagtttgt tgccctgctc acttggagaa agcttatgaa ggatcaggaa   4920
aattaaaagg gtgctctcgc ctataacttc tctctccttt gctttcacag gccttggtat   4980
gttcctgctt catgcctttc tacagtggcc ttatccctcc ttccttcaga ggcgtggtaa   5040
gtcggctttc tctgctagcg ctgagtcctg ggggcctctg aagtgtgctc acacatctcc   5100
tgcctgcagg gcactggtgt caggcacctc agggtctgtc ccatggtgga gccccatgcc   5160
tcactgcctt tcagacagag tagccacagc tggccctatt tccaggctac ccggcagcca   5220
aaacttactg catgtgtaat taattatttg gctatctgta aggtaaactg gctggttcac   5280
ttaatctgca ccttaagcat cagatagctt ctcagtgatc tagttaaact atatgatgtt   5340
ggccaggcgc ggtggctcat gtctgtaatc ccagcacttt gggagcctga agcaggcaga   5400
tcacttgagg tcaggagttc gagaccagcc tggccaacag tgtgaaactc tgtctctcct   5460
aaaaatacaa aaattagctg ggcatggtgg tgtgcacctg taatcccagc tgctcgggag   5520
gctgaggcag gagaattgct tgaacttggg aggcggaagt tgcagtgagc caagatcgca   5580
ccactgcact ccatcctggg tgacagagcg agactctatc tcaaaaagaa aaaaaaaaaa   5640
aaggtaaata aagtatatga cactgaagaa tctgttaccc ctggaaggtg gagctttact   5700
cttaggggga actataacag tcatatatat atattttttt cttttctttt tttttttttt   5760
tgagatggag tctsgctctg tctcccaggc tggagtgcag tggtgcaatc tcggctcact   5820
gcaacctcca cttcacaggt tcaggcaatt ctcctgcctc aacctcccga gtagctggga   5880
ttacaggtgc ctgccgttac gccaagctaa tttttgtatt tttagtagag acagggtttc   5940
atcatattgg ccaggctggt ctccaactcc tgacctcagg tgatccgccc gccttggcct   6000
cccaaagtgc tgagattaca ggcgtgagcc atggtgcccg gccaacaatc acatgtgttg   6060
taaacaacaa caaaaatctg tcagcctggt ctaacctaga tttgtgcttt gttttgtttt   6120
gccactttgt gatgcacagg aggaagttta ggctgtaaaa tactagcctt ttagggtaat   6180
ttttgaactc acaagagcag cagcggaacc tttgatgcaa tcctgtatgt agcaccagca   6240
gagccacgtg gcagagggac tcacattagg agcctcccat tacagactac gtgctcctgt   6300
gcgttatctt atagggtccc cacaaccaag gggagatgtg attattcatc ctgtgtggct   6360
gtggggaact tgagagtcat acttgcccaa agagcacggc cagcgagctt gcacccaggt   6420
```

-continued

```
cactctctgc tcctctgtca gaacagggca tgtcttggtt cactgcaggg cggctcttct   6480
cattctctgt agtttggggt ccaggatagt ggtccacgga gccactggag tgcccagcca   6540
ctgagtgacc aaagcatatt ttggatttcc gacattgcca cagcatggtt gggcatcagc   6600
aggaccccaa cccccttgtta tgctggtggc tttatgtggt tatttgatct tccccagaac   6660
tcagcaggag tgcacccagc agcaccgtag tgatgctctc tggctcccca gtgcacggtt   6720
ctggctttcc ttcctggtcg agagtttcaa gccctctggg tcctactctg tccttttcag   6780
cccatagctt tgttcaaaag ctgctggcag tgttcagatt tggctgagtt cagtgaatat   6840
gtgcattggc tgatttctga gccatgccag ggggatggag aagccgaagc aggagtgttt   6900
gttctgcagg ctctggagta ggcattgggt ctgtgccggc tcacttgcta gtcttgcatc   6960
cttccctaac cccctctggg gatgtctggc cacatcagaa gacagtttgg gttgtcagaa   7020
ctgggggagt accaggccga ggtgggtgga tcatgaggtc aggagatcga gaccatcctg   7080
gctaacacag tgaaacctca tctctactaa acatacgaaa aaaattagct gggcgtggtg   7140
gcgggcgcct gtagtcccag ctactcggga ggctgaggca ggagaatggt gtgaacccgg   7200
ggggcggagc ttgcagtgag ctgagatcct gccactgcac tccagcctgg gcaacaaagc   7260
gagactccgt ctcacaaaaa aaacaaaaca aaacaaaaca aaatctgggg gagtgccact   7320
ggcatctgat gtatagaggc ccgagatgct gtgtcatcac ccgttgagtg cgctcatagg   7380
catcttcctg acaattagaa cccattattc ttcaaattca atgcaagcaa attcaaagca   7440
ttactatgta cataccgcgt gctaatcaat tgcaccactg gagctcctaa attcaaaaca   7500
ttactataaa aaagttcaaa atgcatggaa aagttgtacg tggcaggaga atatttgggc   7560
ttctgactac cccttgaatg aagatgatcc accagccgcc ttcctccttg gtcttcactc   7620
cagattccta gcatttcatt ctgtgtctct ttatgcagtg aggtttttgt ttgtttttttg   7680
agacagagtc tcactgtatc acctaggcct ggagtgcagt ggcgcgatct cagctcactg   7740
caaccctcgg ctcctgggtt taagcgattc tcctgcctca gcctcccgag cagctgagat   7800
tacaagcaca catccccatg cccagctaat ttttgtattt ttagcagaga cagggtttca   7860
ccatgttgcc caggctggtc tcgaactcct ggcctcaagt gatccatgtg cctcagcctt   7920
ccaaagtgct gggattacag gcgtgagcca ccatgcccag ctcctagtga ggtttttgat   7980
gccttgctac atctgcccta gaaattgtgt gactacgatt ttggaaatgt tgctgtgtaa   8040
acttgtgatc atttctggac tccaggcaag aatcttgatg gctaaggtgt ggctgaacat   8100
gtctgattct ctcctggacc tgttttaggc caaactctgc tctgaaattc ctccgtgtgg   8160
aagggcgggc tggggagagc ctcccagctg gaatcttttg gatgcctttc tctgtgggta   8220
tctgatggct ggctctgatg gctggctgtg atggctgtgg ctggaaatca ttgttgacat   8280
gagtttcaca gatgcaggct ctgtccaaac tgtagcaaaa gctgcctgcc ccagccgagc   8340
tatgggcaat aaggtggttt aaggatatag atgaaggaaa actcaccctt agaataattt   8400
atccaaaatg ctgctgtgtt gtgggttaga ggacattttc tgaggtccca ggttcattgt   8460
ttcatttaag tctcaaaagt ccctccaggt gttggttcta attgtcaaag catgggggga   8520
gatgggctca tgggttaaag gtcttatccc agatttctgt atcctccttg caagcagcaa   8580
aggggtctgg atttgaatcc atgaccatgt ttctcctttg ggtttccatc acactctgtc   8640
cccgtgcact gagcaccctt tagttcatat gacccccctta ggcatgttac atgggcactc   8700
ctataggtgc ccatctggcc ctaggacttg gccaacacaa catggactcc agtttccatc   8760
```

tgcctctttg ccaggcactt ttgtgcagtg cacacactgt acaacagtag acggcaaccc 8820
tgagagccag agtagagcct gtcctagcac cggaatgctc ggtaaggatt tgtcgcagga 8880
gtgattccaa agccaatgtc ctccctccat atcagcctgt ttgtggctct gagaagctct 8940
gcccacatgt gaaagcttgt taagcactta agcactaacc cagagcttca gacagtacca 9000 gtccttttc cccttcttta aaagcgatat gtggatggag gagtgagtga caacgtaccc 9060
ttcattgatg ccaaaacaac catcaccgtg tccccttct atggggagta cgacatctgc 9120
cctaaagtca agtccacgaa ctttcttcat gtggacatca ccaagctcag tctacgcctc 9180
tgcacaggga acctctacct tctctcgaga gcttttgtcc ccccggatct caaggtgagt 9240
tggtggtgag gggcaggtg ttctggggtg cagctcttct ttgcctccct gattgccagg 9300
agctaccagt tactgtctgc acaatcaaac agaaatagac ctgttcttga tggttaacgg 9360
aaataaaagg cgcttgtccc agaagctcag gtgaggcacc accctgatta tgggaatcac 9420
ctgggaacat atacccagac ctaaaactca gatccacttc ccaggctgtg gttatatagt 9480
caggggggtg cagtatgggt attaggattt tttattttt agttataaag atttttttt 9540 gatttgtttt tgagacaggg tcttgctctg ccgcttaggc tggagtgcag tggtgcaatc 9600
atagctcact gaagcctcag actcctgggt tcaagcagtc ctcccacctc agcctcctaa 9660
ggagctggga cccacaggca tgcagcacca cacctggcta atttttaaaa attttgtgga 9720
gtgttgccca ggctggtctc acactcctgg cctcaagcga tcctcccacc ccagcctccc 9780
aatgtgttgg gattacaggc atgagccatt gtacccagcc actaagatga ttcttatttg 9840
gaaacacggt caagaacaac tgcgttcggt agtttaacct tttttgattg tggtggtttt 9900
agtatgcctt accactctac catagtaaga aatttgcaga ccatgtacac caacctttgg 9960
tgctcctggg gagaaagaaa gaaggctatg caatgcaatg catgctcaca gtccaaggga 10020
gagggaaagc tgtctaacag gattggtttt cccgtgtgct ttataagcag atgagtagag 10080
gagacagctc ttattgtcct agtggcaatt gggataggct gcaaagtttg ttagggtgga 10140
ggcttattcc gggaccaagg gagcccaaag aaacaagctc ctgccaggcg cggtggctca 10200
cgcctgtaat cccagcactt tgggaggctg aggcaggtgg atcacctgag gtcaggagtt 10260
tgagaccagc ctggccaaca tggtgaaacc ccgtctctat gaaaaataca aaaattaccc 10320
gggcatggtg gcgggcacct gtaatcccag ctactaggga ggctgaggca ggaaaatggc 10380
ttgaacctcg gaagcggagg tggccgttag ccgagatcac gccactgcac tccagcctgg 10440
gcaacagagc aagactctgc cttaaaaaaa aaaaaaaaaa aaagaaaagt aaaaggaaaa 10500
aaaagaggct ctggcctgct ggggtgcctg caaagtctcc gtggaagggt gacattcaag 10560
ccgagacctc cagggaactg tctcctggga gcacagagcc ctttgctcag cccccaggtg 10620
gctcagtgcc cccagccagc agactcagag cttgcatgat tctttggtgc tctctgcggt 10680
cttccaatga tgctgaaata aatggtgctt ggtgtctccc tgctgtagtc cccttgcttg 10740
ctttgctcac aggtgctggg agagatatgc cttcgaggat atttggatgc attcaggttc 10800
ttggaagaga agggtatgta tgggctggga ggatcagcca tgcccttttg acaagcattt 10860
actagcggtc ttggtaaaga cttgagattt gccttagttc taacacttag tgcccaacgc 10920
cttccttgtg ttgctcaacc tactcatgag cccaggagat aggaaatctc cgtcccattg 10980
tacagatggg gaaacagaat tttggaaagg agagccaagc agcacacacc cctccctgag 11040
gggcagagcc gagatttgaa ctgggatgtc atgactccag ggccctctcc ctccccaggg 11100
tccccttatc tgaaggcggt tttctttcc agctcgacct cttgtgaccc ttagtttaac 11160

-continued aagggccgaa gttaaagagt ttctgcgcct ggaccccaaa tgaagcaatc agatttctca 11220
tctccagtca ggtgtgggtc caagcccact agacaagttt gctcttccca gagcacattt 11280
ctgccttcaa gtcatcctgg cttgtcaggg ctgggggagt tctgctctag aaatattaga 11340
gtggaaggaa aaagatgtgt tgggagctat ttttctttaa tactaaaagt tggttgatga 11400
atttgtcgtt ggccaagacc aaggagactg catttttaag gacatatgtg tatttatctg 11460
ctcagaaaat gttcattgct gtgtgctagg gatactgcag tgaacacaga ggtgtgaccc 11520
ttgccagcct tgtgagagaa gtgagcagat aagtaagcag aagggtgatg ctgtgtcgat 11580
gggaaagtac aggtgccaat gagaaggcac aggtgtcaag gagaagacac aggatgctgg 11640
aggctcatgc aggatggatc tccaaggccc aggggaagaa gggcctctcg gaggacgtga 11700
atccacatta agactttggg gataagtagg agcgccttag gcatggggac ccatggatgc 11760
gaggcctgta ggacacagag aggatggcat gaaggcctgt gcaactggag gggtggggat 11820
ggggacacta agagatggct ggaagtgtgg gggtggggac actaagagat gactggagaa 11880
gagggggtca ggagtggtga aaaatgggag aggagggcag gctgggcctt ttggatacag 11940
ggggattgca tcctgcagtg gtagggagcc actgagggct gctgcagtag gagtgagggg 12000
atcagaggag agctttggaa gccccctgga tgcgggacag gaagggagat accagtgtct 12060
aggaggccag tgaggcagcc agaggctcca ccaggatcag ggctgcgagg gtcatgagga 12120
ggaaaccaat ttgaaggagt ccaggggaat aggacttgga aatgaccgat gggacatttg 12180
ggaagaggaa gacagaagag cgcagtccca gcttctggct ttagcagttg ggcaagggga 12240
gatggggaga tgtgcccatg ggttgagggt tgaggacatt aggagggagc cggtatggca 12300
ggaagagctg gtgtgccaga gatgctggaa gcagcatctg cctgagaaca gatacctggc 12360
aatattccta agggaaagtg acatctcgga gggtgaggag ggcatctgat agggcctgga 12420
aagagccggg gcaagcatga atgtgaggtt atcttggggg gcaaggctca ggcgttgagg 12480
agcagcccct ggtctcttca gcctgaagtt ggaagccaga gttgggccag gtgcagctgt 12540
ggttgtctga agtccccctc ccccagccca gtgtgccaat gctgtaagag caagggccgc 12600
tcactggtgc tggtggctga gtcccagcac ccaggacagg gcctggcaca tactggtgcc 12660
caatcctccc ttctgggtgc ttcttccaag gccttgtgat ggaagtgagt accctcttcg 12720
acatcagacc cagcttcaaa tcccggctct gctatgtatc ggctgcgtgg ctttagacaa 12780
gtcttttaac cttgctgtgc ttctgatttc tcagctgaaa aatggagatg atgataatgg 12840
tttctgtaag gccttatggt gaagcaccta gctcagggcc tggaaggcag gtgtaaccag 12900
tggttcagtt gttataaacg aacactaacc ctcgcctttg cacctcatga atccagatat 12960
gtagatggag cccacaaagc tagcaggagc caagctcacg tgtgtcctgc tttaaagccc 13020
catacccctt tctccgggtg acaaacacct gtgctcgttc tcttcccttc ccctcttccc 13080
cttgcatttg gctaataaca ggccagctgc ctgcctccct gcagtttggt agatgggtgg 13140
gtaatgacca ccactcccac gttcgcctga tgggcttgtt ttccgtgccc ttcacaggca 13200
tctgcaacag gccccagcca ggcctgaagt catcctcaga agggatggat cctgaggtcg 13260
ccatgcccag ctgggcaaac atgagtctgg attcttcccc ggagtcggct gccttggctg 13320
tgaggctgga gggagatgag ctgctagacc acctgcgtct cagcatcctg ccctgggatg 13380
agagcatcct ggacaccctc tcgcccaggc tcgctacagg tacccactcc tcggggtggg 13440
cacgggcagc accttgtttt ctttcttgtg cattatggag gaagatggta ctgccacatg 13500

```
ggagcgatag ggtgaggcaa ccatgacagg tggttgggaa catctccttc catgtgtaca  13560
gcctgggctg ctgccatcac tcccagcaca gcccccaacc cccccaatcc tggaaccttg  13620
ccaagtctcc cttcccgtgg ggtcatgacc aggaggaaaa caaactccag ctgagcccct  13680
tggggttccc catataggct cctgcctgtg gcagctgggc cctctgtacc cctttccaac  13740
tctgtgtccc taacatggca cctgagctcc tgccatcctg gatttcatgg accccaagga  13800
tgggggtcct gcatctggga cttggcctat tactcggagc tccttttcag ccgcctccct  13860
ccacctgtcc acccacctca aggctccttt cttgagacct ctcctaattt ctcccttccc  13920
ctaaacccac aattttgaac ctccatcgaa tggtgctgta gtttataatg tcatcaaata  13980
tcaaatggag acagtgctat ggtccaaatg attgtgtacc ccccagaatt tgtcttttga  14040
aatcctaacc cccaacatga tggtcttagg aggtggggcc tttgggagga gattaggtca  14100
tgaggaaagg gctgtcatga atgggattgg tgcccttatt aaacagaccc aagagaggtc  14160
ccttgtccct tctactgtgt gaggactcag aaggtggtgt ctatgaagaa ggaggccctc  14220
accagacacc aacacgtctg ctgccccttg atctgggacc ttgcagcctc tagaactctg  14280
aaaaatcgat gtttgttgtt ttataagcca ctcagttggt ggcattttgt tagagtagcc  14340
tgaacacgga ctaagtcaaa cagaagaacc cacaaaccag ctacagagtt gggcatttgg  14400
agaaattcaa aaatgagtca gacataactc cttattcttg aggtgcccta agagatggga  14460
cacagcagct gcccaggtgc attagtttgt tctcacattg ctataaagaa atacctgaga  14520
ctgggtaact cataaagaaa gaggttgaat tggctcacag ttgcacaggc tggacaggaa  14580
gcatggtgct ggcatctgct cagcttctgg ggaggcctca ggaaacttac aatcatggca  14640
gaaggtgaac gggaagcatg cacatcccat gactggagca ggagtgagag agagagggaa  14700
atagagggaa ggtgccatac acttttaaac aaccagatct cacgagaaca cactcactat  14760
caagagaaca gcaccagtgg ggaaatccgc ccccacgatc caatcacctc ccatcaggct  14820
ccgcctccaa cactgggaat tacaatttga catgagatgt gggcagggac acagatccaa  14880
accatatgac cagattaata cgatttgagg catcacgagg tcattaaaga gagggaataa  14940
aagactgggg ctccaggaag aaggctctgg aatccagcag agggtcaagg accagcttgt  15000
aaagctggtg gtgcctgaga agtacctagg agaacataga tgctgtgacg tttgatgtag  15060
ctgtttttttg ttttgtgttt tggtttttga gacagagtct cactctgtcg cccaggctgg  15120
agtgtgcagt ggcgtgatct tggctcactg gagcctccat ctcccaggtt caaatgatcc  15180
tcatgcctca gcctcctgag ttgctgggat tacaggtgca caccaccacg cctggctaat  15240
ttttgtgttt tcagtagaga cagggtttca ccatgttggc caggctggtc ttgaactcct  15300
gacctcaagt gatccaacaa cttcagcctc ccaaagtgct gggatgacag gcatgagcca  15360
ccatgcccag cctgatgtag ctgtttctgt gcacattatt tgctgtgggg tatattcaga  15420
tttcttaata caagatgatt ctttgcctca tgacttacac accattttct atttaatttc  15480
agctatgata ttggaaatgg acatgtcttt tcaaggaaaa taaaagcagg ctttctggaa  15540
tggcgacttc caaacatatt tgtcaattta aaggagctgg gagtggggac cctatgcccc  15600
gtaagcactc tcttagctgt tcttggctgt gctccccgct tcagcttcac actgcccttg  15660
ctgtgaaggg agaagcctgg gctgggcgcg gtggcttaca cctgtaatcc tagcactttt  15720
ggaggccgag gtgggtggat cacctgaggt caggagttca agaccagcct ggccaacatg  15780
gtgaaactcc atctctacta aaaatacaaa aaattagctg ggcatggtgg caggtgcctg  15840
taatcccagc tacttgggag gctgaggcag aagaatcgct tgaacccagg aggcggaggt  15900
```

tgcagtgagc cgagattgcg ccattgcact ccagcctggg ggcaacaaga gcaaaactct 15960
gtctggaaaa aaaagaaagg agcagcttgg caaaccccac cttgtcgctt ctgtgagtgc 16020
ctctgaccct ttggctgcca ggacgggcgt attttatgga aatgctaagc accaacagag 16080
taaagtggtt tggtttttca cagtggtggg agataatagc tccaaattgt ctttttcagc 16140
actgagtgaa gaaatgaaag acaaaggtgg atacatgagc aagatttgca acttgctacc 16200
cattaggata atgtcttatg taatgctgcc ctgtaccctg cctgtggaat ctgccattgc 16260
gattgtccag aggtgagcat tttaggtggc tccgtgtctt cctcacaggg ttgatatgag 16320
gatgaaacaa gatgatagat catggtggca tgtagtctgg gacccggatt gtcgtgccac 16380
agatcacagc tcacagtcta tgtgcaatgc ccctgaatgt tgcccacctg tcctcaagcc 16440
acacatgcac ctgtaactca gtgcaagccc agaaactccc cgtggggact cctagagctg 16500
tcagtggcct cacatagcag ctggtccagt ctcttgtgat tgcccaagga aactgaggcc 16560
tggagagctt ggggtcgctg ctctgaggcc atagagatgc ctagtagaag ggccaggcct 16620
agaagcagga tccttgctgc ccctctgagc tgtttccatt taaaatcaca tgaaggccgg 16680
cgccgtggct cacggctgta atcccagcat tttgggaggc caaggtgggt ggatcatgtg 16740
aggtcaggag tttgagacca gcctggccaa catggtgaaa tgccatctgt actaaaaata 16800
caaaaattag tggagcatgg tggcacgtgc ctgtactccc agctacttgg aaggctgggg 16860
cagaagaatc gcttgagcct gggaggcaga ggttgtagtg agccaagatt gtaccactgc 16920
actccagcct gggtgacagg agagaaaccc tatctcaaaa taaaatgaaa ggtaatgaaa 16980
tgaataaaat aataaatcaa gtcacggccg ggcacggtgg ctcacacctg taatcccagc 17040
gctttgggag gccgaggtgg gtggataatg aggtcaggag ttcaagacca gcctggccaa 17100
catggtgaaa ccatgtctct actaaaaata caaaaattag ctgggcatgg tggtgcatgc 17160
ctgtaatccc agctactccg gaggctaagg caggagaatt gcttgaagca ggacctagga 17220
ggcagaggtt ggttgcagtg agccgagatc atgccactgc actctagcct gggctacaga 17280
gcgaaactcc gactcaaaaa aaaaaaaaaa aaaaaaatcaa atcacatgaa agtagaacat 17340
agggaattcc atctttcgtt ctaggcatag tttgttaata tgattcagag ccagcagtta 17400
ggagaacaca gtgtgactct cctagaactt cttgattggg cttcctctga ttgggtttcc 17460
tctgattggg cttcctctga aagtgggggg gatggggggt ggggagcaga atggtcagag 17520
cttggctcag cagtcagact gctcttcttc aaatcctggc tgcattgctt actacagctg 17580
tgtgactcca gatgactgaa tccacctctc tgtgctgcag cttcccgtct agagagatca 17640
cctggagcag agggtggtca ggagactcaa tctggttact gactcacagt gcaggagtac 17700
tcatcccata gtaagcatcc agctagagat gttgatttct attttcaggt aataatgatg 17760
atcgtaaaat tagagacaga taaaaggtat gggcattaga ccagggcact gcaatttcta 17820
agctgtgtga cctcaggcaa gttactcgac ttctctgagc ctcagcggtt tcatccgcaa 17880
tatatggata ggaaaaccga cctcagtggg ttgtctgaca gtggagggca cttgattaaa 17940
aaaaaaaaaa ttaccctggt ctgaatatta ccctggactg aaagaaaaat attgagctaa 18000
tacaggcatc aggaatgggg ctgcagggag tccagggaag ggagaacgaa gagcctgaag 18060
gtgtgaggag gtgcgagtgc tgatctgtct gctacaaaga ggctgctgag cctcctgtgg 18120
atgtggccct ggacttggca gtttaatacc tgagctgtta aaataacctc agatgctgtg 18180
ttctttaagg ggtaggattc agattcctgc tgaaatgctt ctgaaaggga gggaatgagc 18240

-continued

```
cagcccatcc ccagttgctt tttaagatca ttgggaagtt ctggtcttgc catttgtccc  18300
tggaccactc ttaggtcctc ctgccccact tccatctggg tgtgtgccct gggctgtcca  18360
ccacacagct acatcctgcc atcttccctc ctggagccac tgtgccatgc atggatctgt  18420
agcttcattt ttcttggctt ttccctggtt tttctggagc agagtctcta gtaaactccc  18480
aaggaagaaa acgtttgact ttatgtgtgt tgggaaacgt gctttttttc tattacatct  18540
cagtgatagg ttggccatgt ctagaattgc aggttgaaaa tcatttcctc tcagtatatt  18600
ggttagtgag aagcctggga ctgagacagt cacattctca cttctttgca ggtgagtgct  18660
cttaggactg tctttttatc ccttatactc tgaaatgtca tatgtcttgg tgtaagtcct  18720
tatttcagtt attgagctgg acaagtactg gagacccctt cagtcaaagc cttctgtcat  18780
tctccagctc taggaaatta tcttctattg ttatttctgt tattccttcc cttccatttt  18840
ctttttcttt tttttttttt tttttttgag acagggtctt actctggtgc ccaggctgga  18900
atgcagtgac ctgatcatgg tacactgcag cctgaacctc ccagactcaa gtgatcctcc  18960
cacctcaacc tcctaagtag ctgggactgc aagcacacat caccacaccc aacaaatatt  19020
ttttaaaaat tttgtaagat gggatcttac tatgttgccc agactttttc ttcctcttcc  19080
tggggctctt attaggaaga tgtttgactt cctgggttgg attcctgtct ccgtgtctga  19140
ctttctctct ttgtcatatt tttcatcact cgttgtcttt ttgcgtctgc tctgacagat  19200
ttcctcaaat tttgtcttct agtcctatcc tacagttttt actttcagca aatataattt  19260
aatctccaag agtactctct tgttcttttt tcttagcatt ctgttcttgt tttatggatg  19320
taacattctc ttggaatatt tgctgtcctc tagatcatcc cttctccatt tcttcttggg  19380
ctagtttttc tgtttcttca tctttctctt ttatgctact tattctgggc gtgttcttgg  19440
tgggtttttt cccatatagc aacagaggac ttggagctca gggagaaaag ggtaggtgca  19500
tcacctggca gagctcccag acagtgacag gcaggctgcg ggaaggatgt ctacttggcg  19560
gtgctaccgc tttcctagaa accctttccc tggagctggt tgaactgttg ggttttgccc  19620
tggtggtgaa cgctggctcc ccgtgctctg cctgtttcat caccagcccc ctccccttct  19680
gcctggggtc cagtaatctg ttgaaatata tatcttgctc attggtgagc tcctgctcct  19740
tcctcgttgc tcttgcagat ttatcacttc tcgtaaggct gcgcttgtac ttggggattt  19800
tctctgtgcc acactgggaa acatagggtg gttgcatgct gcagtcctga gcacttattt  19860
cactcacatc tttacacgaa gatttggtgg gtgtttactt tgtttttagt aagttagtct  19920
gtcatgtcct ttgatccttt ttttttgttt tttgagatgg agtctctctg tgtcctccag  19980
gctggagtgc aatgtcgcga tctcagctca ctgcaacctc cacctcctgg gctcaagaga  20040
ttctcctgct tcagtctcct gagtagctgg gattacaggc atgtgccacc acacctggct  20100
aatttttgta tttttagtag aggtggggtt tggcatgttg gccagcctgg tctcaaactc  20160
ctgacctcct gacctgcctg ccttggcctc ccaaagtgct gggattacag gtgtgagcca  20220
ccacacctgg ccctgattaa tcttttaatg cccagtctct ccttcaaaag ccggctcctt  20280
tctctccctc gccttcctag attccttctc cactccccag gatcagcctc ctcctcccca  20340
ccccaccact gctgggggga tgtctgtggt caggcattta tcagagaccc tgaggtgggg  20400
gtcctttatg tgtctggggg atggagagtc tagaggaggt agcgttcaga cctctccatg  20460
gtgcctctgc tgggctcaca tgtgaccaag cacagcaaac catgaggcag gggatggtct  20520
tgaccatgag agcccttgca gcagctgcca tgggcctcag ctcctctcca agctgggaag  20580
agccctgaaa agccaaggtg tttttttttc cctctttatt tcagtgtaag tcccttgagc  20640
```

```
tttcttgaac cagaagtggg ctcattttgc tttagagatt tcaggtgggc ttgtccttgt  20700
cctagcatcc cagatccacc ttctgggaag tcatcagatt ggaggtgatg ttggcagctt  20760
ttgtaaacaa agggtagtgt tgtaagctgt tgtgtctgcc tatgtgtgtg tttgtgtact  20820
tggtctcatc tctgcagact ggtgacatgg cttccagata tgcccgacga tgtcctgtgg  20880
ttgcagtggg tgacctcaca ggtgttcact cgagtgctga tgtgtctgct ccccgcctcc  20940
aggtaaatac tttggctgtg ggtgtgtggg ccggacgggc acctctctca tctgatgagg  21000
cctcacacga cattctagaa acagctggct gaacaccaag caaggagctt gcccttgggt  21060
gtggggaccc tgtctcatgg gaggcagctg agtcagtcag aggtcctggc acacctgctg  21120
agagctgcca cccaggccaa cctgaaccgg agcctgggaa gacttcccgt tggatgagtc  21180
tctttgaggg cagcattgat ggtggaagag cagagaggcc ccagataagc agggaaaggt  21240
gcttcagaca gagtggctgg gatgaggact ggggagtgtc agatagcgct ggcgtgtctg  21300
agcgaaggag ctctggcacc catggcacag gaaggaggtg ggaccctgga ggggcagggc  21360
tagcagagct cctcggagcg tgtggctagg tgcctggtaa tgcaagcccc ctgtcctcca  21420
ccctctgttg tactgagtca cagtctccgg ggtgaagccc agcagtctgc gttgacaggc  21480
cccaggggat gccgctactt cctgaattct gaattctgga aactgagccg gagttcaggg  21540
cctggctccc attaccaggg ttggacgtta tcctgaaaat cataggcctt ggtttcctca  21600
cttggctaac aggggtgatc cccatcccct caatgggttt ccgtgagctc ctgagagccc  21660
gtagcatggt acttggcaca tgctgggcat caggaggtat ggcctctctt gctattgttg  21720
ttattggtag acacagaagg atttaaaagt aggggaatgc aaagatccga tttgctaggg  21780
aagagggcag tagtggccaa gtagagggtg gatcctgggc cctggctggc agcaggcagc  21840
aagggggggct gccagggccc aggcagggac gacctgtaga ccgagaggct tcctaaggct  21900
cttggacagg aggaggtgtc ggttccaagc ctgaggagcg gggcagccct ggtgactggt  21960
ggtcagtggt gccaggcggt gggtggtagg acaccctggc aggcaagtag gtttgtgtgg  22020
gggaaactga taggcccctc cagggattcg ttggtggaca acacctgtga tgtccagtgg  22080
gaggtgtcca ggtagctggg agggccacag gcttggaaga cctaggtggt gacatcagcc  22140
cagcactgag ggctagaaga agctgtgtct ctggctgtga cggcacccta gagtgtgtgt  22200
ggtgccctct actggccggc aatgtgggtc caccgtagct cagactgcac actgcagcag  22260
cgggaacggc ctctaagcca acttcctcca tgtgtttcag gtcccaaatg ccagtgagca  22320
gccaacaggc ctccccatgc acacctgagc aggactggcc ctgctggact ccctgctccc  22380
ccgagggctg tccagcagag accaaagcag aggccacccc gcggtccatc ctcaggtcca  22440
gcctgaactt cttcttgggc aataaagtac ctgctggtgc tgaggggctc tccacctttc  22500
ccagtttttc actagagaag agtctgtgag tcacttgagg aggcgagtct agcagattct  22560
ttcagaggtg ctaaagtttc ccatctttgt gcagctacct ccgcattgct gtgtagtgac  22620
ccctgcctgt gacgtggagg atcccagcct ctgagctgag ttggttttat gaaaagctag  22680
gaagcaacct ttcgcctgtg cagcggtcca gcacttaact ctaatacatc agcatgcgtt  22740
aattcagctg gttgggaaat gacaccagga agcccagtgc agagggtccc ttactgactg  22800
tttcgtggcc ctattaatgg tcagactgtt ccagcatgag gttcttagaa tgacaggtgt  22860
ttggatgggt gggggccttg tgatgggggg taggctggcc catgtgtgat cttgtggggt  22920
ggagggaaga gaatagcatg atcccacttc cccatgctgt gggaaggggt gcagttcgtc  22980
```

-continued cccaagaacg acactgcctg tcaggtggtc tgcaaagatg ataaccttga ctactaaaaa 23040
cgtctccatg gcgggggtaa caagatgata atctacttaa ttttagaaca ccttttttcac 23100 ctaactaaaa taatgtttaa agagttttgt ataaaaatgt aaggaagcgt tgttacctgt 23160
tgaattttgt attatgtgaa tcagtgagat gttagtagaa taagccttaa aaaaaaaaaa 23220
atcggttggg tgcagcggca cacggctgta atcccagcac tttgggaggc caaggttggc 23280
agatcacctg aggtcaggag ttcaagacca gtctggccaa cactcgagat aacttcgtat 23340
aatgtatgct atacgaagtt atgctagggt aactataacg gtcctaaggt agcgagctag 23400
ccatgtgtcc agttcgcagg ggggatttgt ttgcatgttg acttccctcg ttggaaactt 23460
cagagggttt ggttttgttg ttgctacttg ggaattcggg gtgtttgcac aggcttacca 23520
gttaagcaag ttcaaacagg taaacatctc agacgtgttt tgagcatcac accaacgctc 23580
agaaggcttc tgacttttac actgggtgtg gcggcacaca cctgtggtcc cagcactgtg 23640
gatggaggct gaggcagaag agtcaggaat tcaaacctat cctgggccac agagttagtc 23700
aaggccagct tgggctttgt atagagacca tgtctcataa ctaagatgtg tctggggacg 23760
taactcagtg gatagtttgc atggttcaat ccctgtgcta ccattaggaa ggagaaggga 23820
gggaaggaga aagagaggaa gggaaagagg gaaagggggg aaagagagag aagaaaggag 23880
agggggagaa gaagagaggg aaggagagag ggagagggga aaaacagaaa gggcaagagg 23940
aagagagtga gagggaggga aggagagagg gaagaagggg gagaggaagg gagaaaacaa 24000
gaggggaaga gagagtagga gggagggaag gagggagagg aaggaaggga gaagaaggaa 24060
gggaaggaag gagagaaaaa gaggaaagga gaggggagag aaggagagag agaggaagaa 24120
gaggaggagg aagaggagga ggaggaggaa agaaagagga gggtgtgtta tctagaggct 24180
ctggatgtac cttctgccct ggactactcc tggtctcctt atcctgtcca atctgggccc 24240
atgcctcagg gacatgaccc agccctgccc ttccatttct ttgcaccctc tttttcttgg 24300
cactctccct tgtttttctg aagcgaagcc ttcctaaatc cccagggaaa cagcagcctg 24360
ccagcctcct cagagcctca cctgttcctg cactggctgc tgggcagctg ctcgcaggcc 24420
tgcgggcaca gtctgtcctc tgagagccta gctggggctc cgtaagatta tttattcacg 24480
acttccacct gctcttctcc tctgtggcct gtaggttctt ggtctttctt tccaccgact 24540
gctactttct cagtcaaagg ccctctctct cctggtttgg ggacatgacc atctgtaatt 24600
aatgcctgta gtttcgtctt tcctggggct gtttcttctc tcttatgaga ctcttgtgag 24660
atgctttgcc tggaactctg tagaccaggc tgaccttaga ctcacagaga tccacctggt 24720
tctggcttct gagtgctggg gttaaaggaa tgcaccatcg ttgcctgaca tagaaacttc 24780
tttattgggg cagatgggaa atgagaaaca gatgtcttca gggtctgagg gaaagcctag 24840
agcagagaag ccttcatcct gggagaaaga acagatcagc agcttatgaa gttgttaggg 24900
agtgcccagg ggaatggtga aggagaggta gtccccaaga gcgccccagc ggggccggta 24960
gatctggaag atggtgatcc aggtggtgag aatgaatgat caccaagaag aggaagccca 25020
cagctgagcg ccaaacatag cctttgattt ggctctgctc tgtgtaggct ggggcgagga 25080
aagcctctct aaagaaccag aaaatgttga ccaaccaaag aaaaggcagg aacgcaaatc 25140
caccaagata gtacttccgg cacaggttca acttctcctc attggatacc cgctccaagt 25200
tcatagttgc gctggagccc ggtggtccta agggtctgca gagcaagacc caaatgacag 25260
gcgcaagatc acgagcaacc acgccccagt gcggtttatc ccttctgcct gggattcctt 25320
tgtgggagat ttgcgggaga tgccgcagtt ttcagtggag tttgttgtcg ctttattttt 25380

-continued

```
ttcttctcct gcccagcccc cctcgcaccc caccctctcc gccagttttc agtggagttt  25440
gttgtcgctt tattttttc ttctcctgcc cagcccccct cgcactccac cccctccgcc  25500
gaaacttctc tttcttacat atttcagccc tttggctttt tgcctccaat ctgaagtctt  25560
ctcagcttta ccctccagtt ctacccttcg gggttttaac attagcagca tgagtgagca  25620
tgctggtcct ttcttctggt tcctttactt gagcattctc agcttggttt gtgggtgttg  25680
ggagaagtgt attgggggtg tgtctgtgga agtgggtgtg tctgtatgtt gaggggtatt  25740
tttactttta tttatgtctg tgtgcactga ttggttgatt gattttgtgt gtgtgtgtgt  25800
gtgtgtgcgc gcgcacgcac acacacacaa actgtttgag cagacaggct agccttgact  25860
tctagatcct cctgcttcac cctcttagca ctaggataat agatatgcgc ctctgtgctt  25920
aggtgagtgt cctgccgtcc tgtctttctt tcctggctat agcagggcca cagcctatgt  25980
gtggaggtca gaggacaact ctcagaagga gttggccctc tccttccatt ttctgggtcc  26040
taaagatcag actcaagttg tgagacaggg cagaaaacgt cattaccctg tgaaccatgt  26100
ctgcctcctg tgtaagtact tctgagacag aattctagtt ctgtagccca agctggccta  26160
gaacttactg tgtagaccag actgaccttc aactcaagtc ggacctctcc cctgcatgca  26220
gggtgtaggg cttgattcac ccctccccca tcccactcaa ggtcttgtat taggggcatc  26280
agcctagctc ccaggcaggg agtagtgctg agtcagcctg cttctggagg aagaagggct  26340
cccttgtgag ggtgggggtg ggggggtgct tcctccttgt ccttcctgga ggattagaca  26400
caaggccaag tttgactgta gtaccagtgc tttgtggtgt ctggctccct cccctctggc  26460
tgaggctatg ggatctcata gccagatcag tagttcacac ttgcagccag ctcagctgct  26520
tagggggaag cccaggaggt ctagaccagc ctgtggagag agactccgtc ctccctgctc  26580
cccgtcactg tgctccctta gcatgggagc acctctggat aagaggtgca gcaagctagg  26640
cttagcttgt cctcacccca ccccacgtcc tcgaatttgt atcttagcac attgcacagg  26700
cccaaccttt agtttctcta tccaaaccct ggggcagctt tactgatcca gtgttcccct  26760
tcaacagctt ccccaccgac gtcatgataa atcgaattaa gtcgaagttg taaaaagtca  26820
ggtttattgg ggcagctctg ggtgggctca ccaatgtcac aggaaggggt cagcaaagtt  26880
gtagaagttg ccgggctgag ctccagtaga ggctgctggg ggagtggggg aggggagtcg  26940
tgaagtgatg gttattcatt tggtaagttt agggccctgt aggtgggtct ttaggtccag  27000
cggttacttt ggaatctgga actgggagct gactttgtcc agtgttttag atgggctttt  27060
gcaagcatgg gcgcctggtc agaagagaaa gggggtaggg tctcttggcc cataccatct  27120
taccggtgtt ccaaacttcc agtctgccac ccctcaaggg aagttcttac cagcaactta  27180
cctcttgcca gagtctacag agggttttgg ccccggtggc tccagttgga ttcctagtgg  27240
ccctgcaccg ctggcttcta tggagcctag gcctcggcca gcacttgccc tcaacccttg  27300
agaaattagg tagacccacc ccacgctgct gcctttcccg ttcattccca ggagctttct  27360
ggaaccttat atggcctgtg tgctttaaga gatattctca gaggttcacc tttgtgctga  27420
tatcccacat atgccttagg gaaggtatca gattgcggtt agaggcgata caggcagctc  27480
actaggatta aggtcgcggt tgtctagttg gttgtgagcc accacttggt tgctgggatt  27540
tgaacttaga acctctgaaa gagcggcccg tgctcttagc cactgagcca tctctccagc  27600
aatgggactg ctttttattg cagtgttggc tgctttttat tgacctcttt tttttttttt  27660
ttctggttta atctttacag tgaacccttg tgtccatgtg atatttgtgc acatgtacat  27720
```

-continued

```
atatctgcat ctgtgtttct atgtgaagta tacatgcatg gtgtctgtta tgaaaaataa  27780
cacaggatta aagggccacc tggagggccc atgccaaggt gtctccctga gaaatcccac  27840
catgtgacag acctggctgg tataagggag gtctattgtg gggcaaggga ggggagacag  27900
aaagggggag acagagacag ggaggctggc agggaacatg tggggacaga gaaagagaga  27960
gagaataaga aaggggagat agagaagggg accggggtaa catggtcctc ttacaagctc  28020
ccaggccacc cacacctggt ggcagctcag gtagcaatgg aggcaggtga tgacctaagc  28080
tgttgctagg tctctgttgt taggtccctg ggaggaaacc agaatcacct gtaagccaat  28140
agtgtccttg gcttccttcc cacaggctgg tgacatggct ccctgatatc caggatgata  28200
tccagtggct acaatgggcg acatcccagg tttgtgcccg aatgacgatg tgcctgctcc  28260
cctctaccag gtaaatactt gggcccaggg tgtgtgggcc agataggcat ccctcccggt  28320
tgttcccaga gctcttaggg tcagagcttg ggtggtgaca gccttaacaa gccaggctca  28380
gccgcctgtc cccagcatgc cattaaagaa accggtagca gagaaagcag gtttattcga  28440
atataaaaag gttcaagccc ccacccggtt aatctttaag ataccaacag gaggcttaag  28500
tttaaacaga gttacacata aacagtctga atcagggcgt ggtcctgccc accattgtct  28560
gggcttcaag gttccttctt tctctcccta gcatgagatt cctgggacaa tcccaattcc  28620
ttggcctcca ttgtatcaaa gggctgaaaa ccaaagggaa ggcacagctg tctcttcagc  28680
atgcctcttc tgccagaacc actgcaaggt ttggtgctca ggctgtgcaa acattctagc  28740
aatgtttgac tcagtgtcaa gcaggtgaca aggaacatgg tgctgtgtgg ggggaaccca  28800
tggcccaggt gagggcttat tggtgggtga agctgtgggt gttcaggtgg tggagaaggc  28860
cttaagggat gggactgaca cctcagcact gaaggcagga ggaagctgtg gctctgggtt  28920
gcacccctgc ctggctccac cctctctggc atctgtagaa gttacagctg gttcttcctc  28980
tcagccccat gctcccagaa ataagactca gacccaaatt atagttacaa ataccttggc  29040
catatagcta ggctcttctc agactagctc ataacttaac tcattaattt taacctccat  29100
cctgccacat ggctggtggc ctgtgctcag gtaccatgag tccagctctt cacatctttc  29160
cggatgaatc ttccataatt ctttctgcct cctggatgtt ccaccttcta ttccaccttt  29220
tcctataggc catggttttg tttttgtttt ttttttccaa atttaattta attaattaat  29280
ttatttattt ttggtttttc gagacagggt ttctctgtat cgccctggct gtcctggaac  29340
tcactatgta agccaggctg gcctcaaact cagaaatccg cctgcctctg cctcctgagt  29400
gctgggatta aaggcgtgcg caaccatgcc cggtgtggtt tttttttttt tttaattgac  29460
aggtggatgc atctatataa tccataacat attctctcta caggtatcta ttaggttttg  29520
ggtgaggtgt ggagttctag ggaactctga gagaaattcc tggggagtaa gtggtttatc  29580
aagttgattg gaggagtttt taatgctatg gacagacaga cagaaggaca acagcatagt  29640
cggggctacc agggagttca ggccccggca tcggagatag aagcaggatg gggtctttga  29700
agagattctg agcccacaca gcagaggagg gactctctct ttagagcttt tgaggatgag  29760
ggaggttgac tgcaagagcc tacagccagg ctcgaggcag gcagggggtg gggagcagga  29820
tgtaaacccc ttcgatgctg acagactcac ttctggggta aaatattatg agatgcctgt  29880
cagtgtctgt gaagagacct gagcagagtc tggattctga catcaatcat gttcttacaa  29940
tactgaagac ctgagagcct gcaatcttgg tttgtaaatt gctggtctcc gtgcttccag  30000
tgaacttgga cattcttctc atggttggtc caggagaggc caaagctgag ggcaccctgc  30060
cttccacccc cagtccagct tgacctttta tctggagcaa cagtgtctag atgatgggtg  30120
```

-continued

```
ggtgaggggt gctatactgt ctgtccctct gggaagggtt ctgttacttt tggaggcagc  30180
taggaagttt ctctgtgcag ctgccccctg gtgctgtgtg gtgacctcat tgcctgtgac  30240
cccaggatca caggatctgg gctaaagtgg tagtccatag aaaccaaaga caatgatttg  30300
gtgtttagaa agctactctt ggtctgggtg aagtctggtg cttaagggct atcacaaaga  30360
gcgtgtcaaa ccatctctca gcctgtgagt cagtggggag cccaagggca tcagtgtttg  30420
gaaactggaa tccaaaccgg gcaatctcgg aaggaaactg tttaggaatt gtgatgggac  30480
gggccgtggc tgtctctgaa aagggcctgc cagataactt attactttta aggacacctt  30540
tggctcttac taatttataa agcattttat ataaacacac cagggagtgc atggtgaact  30600
acacgtatga tcagttaagt ggggctagaa ttaggtaggg agagcatcgg acctctgcct  30660
cctcaacctc aacttgcttg ctttctccac tggctccaaa tctttgtata gtcatcagcc  30720
atgaccacct ctctccctcc ccatctacta ccagcagcgt taatgggaat aagtacccac  30780
ttctctcagg tgtactatac agctgtgggt gtggtgtgtg tttcctgtaa ttcacacttt  30840
agaaaggaaa caagcaaaca aaagaaacca ggtgctgccc atactcctaa gtgtagacag  30900
tgaaggtgtg tgtctcccat gcctgagtct cctggaggcc tagtgagctc caggttcatg  30960
caagcacatc aggaggaatc atataatctc agcacggttg atccagatgg gataagaaag  31020
gactctggga gagagaatgt ggttctagag acaaagtgtc taggctacac agaagataag  31080
actgtcccaa ggaaagaaaa gaaaccagga actagggtgc agctcagttg tcagaggact  31140
tctctaggct tgaagcccag agtccaatct cagcacctta taaactgtgg agtgacaggc  31200
agtgacatcg gcctgtaatc ccaacactca agcagtagag gcaagaggat cataagttca  31260
aggtcttcct tggctattta gggagttgga ggttagctct ggctacatga gaccctgtct  31320
caaaaaaaaa aaaaaaaaaa agtagaaact tctgccttgc tttgagctgc ccctttctgg  31380
acgtttctca tcagtagaga atattcctgc caccctatca gacaaaactc ccactggttt  31440
ggagtctctc cattctcagg aacacctcag gagtcagaca gtgagcagca gggagcaatg  31500
tcttgacttg taagcccctt agcaaggctg gttcatttgt ttattaaaag caggtgtggg  31560
tgaatttatg caaatgagta tgcaaactag tggaacagca gaaggattga atggatacac  31620
caaaaataac cacaactgtt taagggaaaa gggtccataa taaatgtggg gaacaaaaaa  31680
caaataaatg tgattttttt t                                            31701
```

<210> SEQ ID NO 23
<211> LENGTH: 4649
<212> TYPE: DNA
<213> ORGANISM: Mus musculus

<400> SEQUENCE: 23

```
agagcagcaa caccgggagc agagctgaac tgcagcgccg cccggagctt caagcaccat     60
gtatgaccca gagcgccgct ggagcctgtc gtttgcaggc tgcggcttcc tgggcttcta    120
ccacgtcggg gctacgctat gtctgagcga gcgcgccccg cacctcctcc gcgatgcgcg    180
cactttcttt ggctgctcgg ccggtgcact gcacgcggtc accttcgtgt gcagtctccc    240
tctcggccgt ataatggaga tcctcatgga cctcgtgcgg aaagccagga gccgcaacat    300
cggcaccctc cacccgttct tcaacattaa caagtgcatc agagacgggc tccaggagag    360
cctcccagac aatgtccacc aggtcatttc tggcaaggtt cacatctcac tcaccagggt    420
gtcggatggg gagaacgtgc tggtgtctga gttccattcc aaagacgaag tcgtggatgc    480
```

-continued

```
cctggtgtgt tcctgcttca ttcccctctt ctctggccta atccctcctt ccttccgagg    540
cgagcggtac gtggacggag gagtgagcga caacgtccct gtgctggatg ccaaaaccac    600
catcacggtg tcacctttct acggtgagca tgacatctgc cccaaagtca agtccaccaa    660
cttcttccac gtgaatatca ccaacctcag cctccgcctc tgcactggga acctccaact    720
tctgaccaga gcgctcttcc cgtctgatgt gaaggtgatg ggagagctgt gctatcaagg    780
gtacctggac gccttccggt tcctggagga gaatggcatc tgtaacgggc cacagcgcag    840
cctgagtctg tccttggtgg cgccagaagc ctgcttggaa aatggcaaac ttgtgggaga    900
caaggtgcca gtcagcctat gctttacaga tgagaacatc tgggagacac tgtcccccga    960
gctcagcaca gctctgagtg aagcgattaa ggacagggag ggctacctga gcaaagtctg   1020
caacctcctg cccgtcagga tcctgtccta catcatgctg ccctgcagtc tgcccgtgga   1080
gtcggctatc gctgcagtcc acaggctggt gacatggctc cctgatatcc aggatgatat   1140
ccagtggcta caatgggcga catcccaggt ttgtgcccga atgacgatgt gcctgctccc   1200
ctctaccagg taaatacttg ggcccagggt gtgtgggcca gataggcatc cctcccggtt   1260
gttcccagag ctcttagggt cagagcttgg gtggtgacag ccttaacaag ccaggctcag   1320
ccgcctgtcc ccagcatgcc attaaagaaa ccggtagcag agaaagcagg tttattcgaa   1380
tataaaaagg ttcaagcccc cacccggtta atctttaaga taccaacagg aggcttaagt   1440
ttaaacagag ttacacataa acagtctgaa tcagggcgtg gtcctgccca ccattgtctg   1500
ggcttcaagg ttccttcttt ctctccctag catgagattc ctgggacaat cccaattcct   1560
tggcctccat tgtatcaaag ggctgaaaac caaagggaag gcacagctgt ctcttcagca   1620
tgcctcttct gccagaacca ctgcaaggtt tggtgctcag gctgtgcaaa cattctagca   1680
atgtttgact cagtgtcaag caggtgacaa ggaacatggt gctgtgtggg gggaacccat   1740
ggcccaggtg agggcttatt ggtgggtgaa gctgtgggtg ttcaggtggt ggagaaggcc   1800
ttaagggatg ggactgacac ctcagcactg aaggcaggag gaagctgtgg ctctgggttg   1860
cacccctgcc tggctccacc ctctctggca tctgtagaag ttacagctgg ttcttcctct   1920
cagccccatg ctcccagaaa taagactcag acccaaatta tagttacaaa taccttggcc   1980
atatagctag gctcttctca gactagctca taacttaact cattaatttt aacctccatc   2040
ctgccacatg gctggtggcc tgtgctcagg taccatgagt ccagctcttc acatctttcc   2100
ggatgaatct tccataattc tttctgcctc ctggatgttc caccttctat tccacctttt   2160
cctataggcc atggttttgt ttttgttttt tttttccaaa tttaatttaa ttaattaatt   2220
tatttatttt tggtttttcg agacagggtt tctctgtatc gccctggctg tcctggaact   2280
cactatgtaa gccaggctgg cctcaaactc agaaatccgc ctgcctctgc ctcctgagtg   2340
ctgggattaa aggcgtgcgc aaccatgccc ggtgtggttt tttttttttt ttaattgaca   2400
ggtggatgca tctatataat ccataacata ttctctctac aggtatctat taggttttgg   2460
gtgaggtgtg gagttctagg gaactctgag agaaattcct ggggagtaag tggtttatca   2520
agttgattgg aggagttttt aatgctatgg acagacagac agaaggacaa cagcatagtc   2580
ggggctacca gggagttcag gccccggcat cggagataga agcaggatgg ggtctttgaa   2640
gagattctga gcccacacag cagaggaggg actctctctt tagagctttt gaggatgagg   2700
gaggttgact gcaagagcct acagccaggc tcgaggcagg caggggggtgg ggagcaggat   2760
gtaaacccct tcgatgctga cagactcact tctggggtaa aatattatga gatgcctgtc   2820
agtgtctgtg aagagacctg agcagagtct ggattctgac atcaatcatg ttcttacaat   2880
```

```
actgaagacc tgagagcctg caatcttggt ttgtaaattg ctggtctccg tgcttccagt   2940
gaacttggac attcttctca tggttggtcc aggagaggcc aaagctgagg gcaccctgcc   3000
ttccaccccc agtccagctt gaccttttat ctggagcaac agtgtctaga tgatgggtgg   3060
gtgaggggtg ctatactgtc tgtccctctg ggaagggttc tgttactttt ggaggcagct   3120
aggaagtttc tctgtgcagc tgccccctgg tgctgtgtgg tgacctcatt gcctgtgacc   3180
ccaggatcac aggatctggg ctaaagtggt agtccataga aaccaaagac aatgatttgg   3240
tgtttagaaa gctactcttg gtctgggtga agtctggtgc ttaagggcta tcacaaagag   3300
cgtgtcaaac catctctcag cctgtgagtc agtggggagc ccaagggcat cagtgtttgg   3360
aaactggaat ccaaaccggg caatctcgga aggaaactgt ttaggaattg tgatgggacg   3420
ggccgtggct gtctctgaaa agggcctgcc agataactta ttacttttaa ggacaccttt   3480
ggctcttact aatttataaa gcattttata taaacacacc agggagtgca tggtgaacta   3540
cacgtatgat cagttaagtg ggctagaat taggtaggga gagcatcgga cctctgcctc   3600
ctcaacctca acttgcttgc tttctccact ggctccaaat ctttgtatag tcatcagcca   3660
tgaccacctc tctccctccc catctactac cagcagcgtt aatgggaata agtacccact   3720
tctctcaggt gtactataca gctgtgggtg tggtgtgtgt ttcctgtaat tcacacttta   3780
gaaaggaaac aagcaaacaa aagaaaccag gtgctgccca tactcctaag tgtagacagt   3840
gaaggtgtgt gtctcccatg cctgagtctc ctggaggcct agtgagctcc aggttcatgc   3900
aagcacatca ggaggaatca tataatctca gcacggttga tccagatggg ataagaaagg   3960
actctgggag agagaatgtg gttctagaga caaagtgtct aggctacaca gaagataaga   4020
ctgtcccaag gaaagaaaag aaaccaggaa ctagggtgca gctcagttgt cagaggactt   4080
ctctaggctt gaagcccaga gtccaatctc agcaccttat aaactgtgga gtgacaggca   4140
gtgacatcgg cctgtaatcc caacactcaa gcagtagagg caagaggatc ataagttcaa   4200
ggtcttcctt ggctatttag ggagttggag gttagctctg gctacatgag accctgtctc   4260
aaaaaaaaaa aaaaaaaaaa gtagaaactt ctgccttgct ttgagctgcc cctttctgga   4320
cgtttctcat cagtagagaa tattcctgcc accctatcag acaaaactcc cactggtttg   4380
gagtctctcc attctcagga acacctcagg agtcagacag tgagcagcag ggagcaatgt   4440
cttgacttgt aagcccctta gcaaggctgg ttcatttgtt tattaaaagc aggtgtgggt   4500
gaatttatgc aaatgagtat gcaaactagt ggaacagcag aaggattgaa tggatacacc   4560
aaaaataacc acaactgttt aagggaaaag ggtccataat aaatgtgggg aacaaaaaac   4620
aaataaatgt gattttttt agaaaaatg                                      4649
```

<210> SEQ ID NO 24
<211> LENGTH: 2753
<212> TYPE: DNA
<213> ORGANISM: Homo sapiens

<400> SEQUENCE: 24

```
agagagcgct tgcgggcgcc gggcggagct gctgcggatc aggacccgag ccgattcccg     60
atcccgaccc agatcctaac ccgcgccccc gccccgccgc cgccgccatg tacgacgcag    120
agcgcggctg gagcttgtcc ttcgcgggct gcggcttcct gggcttctac cacgtcgggg    180
cgacccgctg cctgagcgag cacgccccgc acctcctccg cgacgcgcgc atgttgttcg    240
gcgcttcggc cggggcgttg cactgcgtcg gcgtcctctc cggtatcccg ctggagcaga    300
```

-continued

```
ctctgcaggt cctctcagat cttgtgcgga aggccaggag tcggaacatt ggcatcttcc    360
atccatcctt caacttaagc aagttcctcc gacagggtct ctgcaaatgc ctcccggcca    420
atgtccacca gctcatctcc ggcaaaatag gcatctctct taccagagtg tctgatgggg    480
aaaacgttct ggtgtctgac tttcggtcca aagacgaagt cgtggatgcc ttggtatgtt    540
cctgcttcat ccccttctac agtggcctta tccctccttc cttcagaggc gtgcgatatg    600
tggatggagg agtgagtgac aacgtaccct tcattgatgc caaaacaacc atcaccgtgt    660
ccccttcta tggggagtac gacatctgcc ctaaagtcaa gtccacgaac tttcttcatg     720
tggacatcac caagctcagt ctacgcctct gcacagggaa cctctacctt ctctcgagag    780
cttttgtccc cccggatctc aaggtgctgg gagagatatg ccttcgagga tatttggatg    840
cattcaggtt cttggaagag aagggcatct gcaacaggcc ccagccaggc ctgaagtcat    900
cctcagaagg gatggatcct gaggtcgcca tgcccagctg ggcaaacatg agtctggatt    960
cttccccgga gtcggctgcc ttggctgtga ggctggaggg agatgagctg ctagaccacc   1020
tgcgtctcag catcctgccc tgggatgaga gcatcctgga caccctctcg cccaggctcg   1080
ctacagcact gagtgaagaa atgaaagaca aaggtggata catgagcaag atttgcaact   1140
tgctacccat taggataatg tcttatgtaa tgctgccctg taccctgcct gtggaatctg   1200
ccattgcgat tgtccagaga ctggtgacat ggcttccaga tatgcccgac gatgtcctgt   1260
ggttgcagtg ggtgacctca caggtgttca ctcgagtgct gatgtgtctg ctccccgcct   1320
ccaggtccca aatgccagtg agcagccaac aggcctcccc atgcacacct gagcaggact   1380
ggccctgctg gactccctgc tcccccaagg gctgtccagc agagaccaaa gcagaggcca   1440
ccccgcggtc catcctcagg tccagcctga acttcttctt gggcaataaa gtacctgctg   1500
gtgctgaggg gctctccacc tttcccagtt tttcactaga gaagagtctg tgagtcactt   1560
gaggaggcga gtctagcaga ttctttcaga ggtgctaaag tttcccatct ttgtgcagct   1620
acctccgcat tgctgtgtag tgacccctgc ctgtgacgtg gaggatccca gcctctgagc   1680
tgagttggtt ttatgaaaag ctaggaagca acctttcgcc tgtgcagcgg tccagcactt   1740
aactctaata catcagcatg cgttaattca gctggttggg aaatgacacc aggaagccca   1800
gtgcagaggg tcccttactg actgtttcgt ggccctatta atggtcagac tgttccagca   1860
tgaggttctt agaatgacag gtgtttggat gggtgggggc cttgtgatgg ggggtaggct   1920
ggcccatgtg tgatcttgtg gggtggaggg aagagaatag catgatccca cttccccatg   1980
ctgtgggaag gggtgcagtt cgtccccaag aacgacactg cctgtcaggt ggtctgcaaa   2040
gatgataacc ttgactacta aaaacgtctc catggcgggg gtaacaagat gataatctac   2100
ttaattttag aacacctttt tcacctaact aaaataatgt ttaaagagtt ttgtataaaa   2160
atgtaaggaa gcgttgttac ctgttgaatt ttgtattatg tgaatcagtg agatgttagt   2220
agaataagcc ttaaaaaaaa aaaaatcggt tgggtgcagt ggcacacggc tgtaatccca   2280
gcactttggg aggccaaggt tggcagatca cctgaggtca ggagttcaag accagtctgg   2340
ccaacatagc aaaaccctgt ctctactaaa aatacaaaaa ttatctgggc atggtggtgc   2400
atgcctgtaa tcccagctat tcggaaggct gaggcaggag aatcacttga acccaggagg   2460
cggaggttgc ggtgagctga gattgcacca tttcattcca gcctgggcaa catgagtgaa   2520
agtctgactc aaaaaaaaaa aatttaaaaa acaaaataat ctagtgtgca gggcattcac   2580
ctcagccccc caggcaggag ccaagcacag caggagcttc cgcctcctct ccactggagc   2640
acacaacttg aacctggctt attttctgca gggaccagcc ccacatggtc agtgagtttc   2700
```

tccccatgtg tggcgatgag agagtgtaga aataaagaca caagacaaag aga 2753

<210> SEQ ID NO 25
<211> LENGTH: 425
<212> TYPE: PRT
<213> ORGANISM: Rattus norvegicus

<400> SEQUENCE: 25

Met Tyr Asp Pro Glu Arg Arg Trp Ser Leu Ser Phe Ala Gly Cys Gly
1 5 10 15

Phe Leu Gly Phe Tyr His Ile Gly Ala Thr Leu Cys Leu Ser Glu Arg
20 25 30

Ala Pro His Ile Leu Arg Glu Ala Arg Thr Phe Phe Gly Cys Ser Ala
35 40 45

Gly Ala Leu His Ala Val Thr Phe Val Cys Ser Leu Pro Leu Asp His
50 55 60

Ile Met Glu Ile Leu Met Asp Leu Val Arg Lys Ala Arg Ser Arg Asn
65 70 75 80

Ile Gly Thr Leu His Pro Phe Phe Asn Ile Asn Lys Cys Val Arg Asp
85 90 95

Gly Leu Gln Glu Thr Leu Pro Asp Asn Val His Gln Ile Ile Ser Gly
100 105 110

Lys Val Tyr Ile Ser Leu Thr Arg Val Ser Asp Gly Glu Asn Val Leu
115 120 125

Val Ser Glu Phe His Ser Lys Asp Glu Val Val Asp Ala Leu Val Cys
130 135 140

Ser Cys Phe Ile Pro Leu Phe Ser Gly Leu Ile Pro Pro Ser Phe Arg
145 150 155 160

Gly Glu Arg Tyr Val Asp Gly Gly Val Ser Asp Asn Val Pro Val Leu
165 170 175

Asp Ala Lys Thr Thr Ile Thr Val Ser Pro Phe Tyr Gly Glu His Asp
180 185 190

Ile Cys Pro Lys Val Lys Ser Thr Asn Phe Leu Gln Val Asn Ile Thr
195 200 205

Asn Leu Ser Leu Arg Leu Cys Thr Gly Asn Leu His Leu Leu Thr Arg
210 215 220

Ala Leu Phe Pro Ser Asp Val Lys Val Met Gly Glu Leu Cys Phe Gln
225 230 235 240

Gly Tyr Leu Asp Ala Phe Arg Phe Leu Glu Glu Asn Gly Ile Cys Asn
245 250 255

Gly Pro Gln Arg Ser Leu Ser Leu Ser Leu Glu Lys Glu Met Ala Pro
260 265 270

Glu Thr Met Ile Pro Cys Leu Glu Asn Gly His Leu Val Ala Gly Asn
275 280 285

Lys Val Pro Val Ser Cys Val Cys Leu Thr Ala Val Pro Ser Asp Glu
290 295 300

Ser Ile Trp Glu Met Leu Ser Pro Lys Leu Ser Thr Ala Leu Thr Glu
305 310 315 320

Ala Ile Lys Asp Arg Gly Gly Tyr Leu Asn Lys Val Cys Asn Leu Leu
325 330 335

Pro Ile Arg Ile Leu Ser Tyr Ile Leu Leu Pro Cys Thr Leu Pro Val
340 345 350

Glu Ser Ala Ile Ala Ala Val His Arg Leu Val Met Trp Leu Pro Asp
355 360 365

-continued

```
Ile His Glu Asp Ile Gln Trp Leu Gln Trp Ala Thr Ser Gln Val Cys
    370                 375                 380

Ala Arg Met Thr Met Cys Leu Leu Pro Ser Thr Arg Ser Arg Ala Ser
385                 390                 395                 400

Lys Asp Asn His Gln Thr Leu Lys His Gly Tyr His Pro Ser Leu His
                405                 410                 415

Lys Pro Gln Gly Ser Ser Ala Gly Leu
            420                 425


<210> SEQ ID NO 26
<211> LENGTH: 2759
<212> TYPE: DNA
<213> ORGANISM: Rattus norvegicus

<400> SEQUENCE: 26

cccggagcag aattgagctg catcgccttc cggagcctcc agcgccatgt acgacccaga     60

gcgccgctgg agcctgtcgt tcgcaggctg cggcttccta ggcttctacc acatcggggc    120

tacgctatgt ctgagcgagc gcgctccgca catcctccgc gaagcgcgca ctttcttcgg    180

ctgctcggcc ggtgcactgc acgcggtcac cttcgtgtgc agtctccctc tcgatcacat    240

catggagatc ctcatggacc tcgtgcggaa agccaggagc cgcaacatcg gcaccctcca    300

cccgttcttc aacattaaca agtgcgtcag agacggcctt caggagaccc tcccagacaa    360

cgtccaccag atcatttctg gcaaggttta catctcactc accagagtgt ccgatgggga    420

gaacgtgctg gtgtctgagt tccattccaa agacgaagtg gtggatgccc tggtgtgctc    480

ctgcttcatt cctctcttct ctggcctaat ccctccttcc ttccgaggtg agcggtacgt    540

ggatggagga gtgagtgaca acgtccctgt gctggacgcc aaaaccacca tcacggtgtc    600

ccctttctat ggtgagcatg acatctgtcc caaagtgaag tccaccaact tcctccaggt    660

gaatatcacc aacctcagtc ttcgtctctg cactgggaac cttcatcttc tgaccagagc    720

actcttccca tctgatgtga aggtgatggg agagctgtgc tttcaagggt acctggacgc    780

cttccggttc ctggaagaga acggcatctg taatgggcca cagcgcagcc tgagtctgtc    840

cttggagaag gaaatggcgc cagaaaccat gataccctgc ttggaaaatg gccaccttgt    900

agcagggaac aaggtgccag taagctgtgt atgccttaca gctgtgccgt cggatgagag    960

catctgggag atgctgtccc ccaagctcag cacagctctg actgaagcga ttaaagacag   1020

ggggggctac ctgaacaaag tctgcaacct cctgcccatt aggatcctgt cctacatctt   1080

gctgccctgc actctgcccg tggagtcggc catcgctgca gtccacaggc tggtgatgtg   1140

gctccctgat atccatgaag atatccagtg gctacagtgg gcaacatccc aggtgtgtgc   1200

ccgaatgacc atgtgcctgc tcccctctac cagatccaga gcatccaagg ataaccatca   1260

aacactcaag catggatatc acccatctct ccacaaaccc caaggcagct ctgccggttt   1320

gtaaattgct ggtctccgtg cttccgatga acttgggcat tctccctgtg gatggttcca   1380

ggagaggcca tagctgaagg cactctgcct tccaccccaa gtccagtttg acctttatct   1440

agagcaacag tgtctagatg ataggtgggt ggggggtgct gtctctctgt ttccctctgg   1500

gaagggttct gttaactttt ggaggcagct aggaaatttc tctccaggag ctgagcctgt   1560

gcagctgccc ccttggtgct gtgtggtaac ctcattgcct gtgaccctag gatcatagga   1620

tctgggctaa ataggtagtt catagaaacc aaagacaata atttggtgtt tagaaaacta   1680

cttttggtct gggtgaagtc tggtgcttga gagttagtgc agagagaacg gtcaaaccgt   1740
```

-continued

```
ctctcagcct gtggatctat ggggattcca agggcttcag tgtttggaaa cggcaatcca   1800
aacgggcaat cttgtgcaat cttggaagga gaactgttca ggaagtgtga tgggatgagc   1860
tgtggctgtc tctgaaaagg gcctaccata taacttatta ctttcaagga tacctttggc   1920
tcttactaaa atagtttata aagcatttta tagaaacaca ccagggaatg cgtggtgaac   1980
tacatgtatg atcagtgaac tgtgactaga attaacctta aaatctcttg tatgtggggc   2040
cagagcaaca caggtgggaa acgcagcgga cctctgcctc ctcggcctca acatgaactt   2100
ggcttgcttt ctccaccgtc tccaaatctt tgtatagtca tcgaccatta ccacctctcc   2160
tttcccatct actacagcag ccttaatggg gataagtacc cccttttctc aggtgtccga   2220
ataagctgtg ggtgtggcct gtgtttcctg taattctgag gttagattgg aacataagca   2280
agcagacaaa caagcagaca aacaaacaag gttctactca tattcctaag cagtgacagt   2340
gaaggcatgt gtctcccatg cctgagtctc ctagggtcct agtgagctct gggttcatgc   2400
aagcacttcc ggaggaattg caccctccat ggaacacata atctccactg ggttgatcct   2460
gattggataa gaaaggatct cggggagaga atgtggttcc agaggcaaag tgtctaggct   2520
acacagaaaa ggtaagactg tccccaaggg aagaaaacaa actgggagct ggggtccagc   2580
tcaattgtta agagtgcttc tctagtatgc gtgaagccca gagtccaatc tcagtaccag   2640
atacacggta caggcagtga catatgcctg taatcccaac cctcaagcag tagaggcaag   2700
aggatcagaa gttcatggtc atccttgact acttatactt agggagttgg aggtcagcc    2759
```

<210> SEQ ID NO 27
<211> LENGTH: 1278
<212> TYPE: DNA
<213> ORGANISM: Rattus norvegicus

<400> SEQUENCE: 27

```
atgtacgacc cagagcgccg ctggagcctg tcgttcgcag gctgcggctt cctaggcttc     60
taccacatcg ggctacgct atgtctgagc gagcgcgctc cgcacatcct ccgcgaagcg    120
cgcactttct tcggctgctc ggccggtgca ctgcacgcgg tcaccttcgt gtgcagtctc    180
cctctcgatc acatcatgga gatcctcatg gacctcgtgc ggaaagccag gagccgcaac    240
atcggcaccc tccacccgtt cttcaacatt aacaagtgcg tcagagacgg ccttcaggag    300
accctcccag acaacgtcca ccagatcatt tctggcaagg tttacatctc actcaccaga    360
gtgtccgatg gggagaacgt gctggtgtct gagttccatt ccaaagacga agtggtggat    420
gccctggtgt gctcctgctt cattcctctc ttctctggcc taatccctcc ttccttccga    480
ggtgagcggt acgtggatgg aggagtgagt gacaacgtcc ctgtgctgga cgccaaaacc    540
accatcacgg tgtccccttt ctatggtgag catgacatct gtcccaaagt gaagtccacc    600
aacttcctcc aggtgaatat caccaacctc agtcttcgtc tctgcactgg gaaccttcat    660
cttctgacca gagcactctt cccatctgat gtgaaggtga tgggagagct gtgctttcaa    720
gggtacctgg acgccttccg gttcctggaa gagaacggca tctgtaatgg gccacagcgc    780
agcctgagtc tgtccttgga gaaggaaatg gcgccagaaa ccatgatacc ctgcttggaa    840
aatggccacc ttgtagcagg gaacaaggtg ccagtaagct gtgtatgcct tacagctgtg    900
ccgtcggatg agagcatctg ggagatgctg tcccccaagc tcagcacagc tctgactgaa    960
gcgattaaag acaggggggg ctacctgaac aaagtctgca acctcctgcc cattaggatc   1020
ctgtcctaca tcttgctgcc ctgcactctg cccgtggagt cggccatcgc tgcagtccac   1080
aggctggtga tgtggctccc tgatatccat gaagatatcc agtggctaca gtgggcaaca   1140
```

tcccaggtgt gtgcccgaat gaccatgtgc ctgctcccct ctaccagatc cagagcatcc 1200
aaggataacc atcaaacact caagcatgga tatcacccat ctctccacaa accccaaggc 1260
agctctgccg gtttgtaa 1278

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
agtgctcaac ggcaccggga 20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
ggagcattgg actgccacta 20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
ggaggttgca gactttgctc 20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
ggtccaactc aagccaagtg 20

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
tgcccgaaga aacctgtcc 19

<210> SEQ ID NO 33
<211> LENGTH: 19
<212> TYPE: DNA
<213> ORGANISM: Artificial Sequence
<220> FEATURE:
<223> OTHER INFORMATION: Synthetic

<400> SEQUENCE: 33
tccagctgag tgctcaacg 19

-continued

<210> SEQ ID NO 34
<211> LENGTH: 23
<212> TYPE: DNA
<213> ORGANISM: Artificial Sequence
<220> FEATURE:
<223> OTHER INFORMATION: Synthetic

<400> SEQUENCE: 34
agagctctca tccttcccgg tgc 23

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35
ccacccggca ttaggatgta ag 22

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
gtgccaggca aagacacatg 20

<210> SEQ ID NO 37
<211> LENGTH: 25
<212> TYPE: DNA
<213> ORGANISM: Artificial Sequence
<220> FEATURE:
<223> OTHER INFORMATION: Synthetic

<400> SEQUENCE: 37
aagcacacca tggagtggac tctca 25

<210> SEQ ID NO 38
<211> LENGTH: 23
<212> TYPE: DNA
<213> ORGANISM: Artificial Sequence
<220> FEATURE:
<223> OTHER INFORMATION: Synthetic

<400> SEQUENCE: 38
gctctgagtg aagcgattaa gga 23

<210> SEQ ID NO 39
<211> LENGTH: 19
<212> TYPE: DNA
<213> ORGANISM: Artificial Sequence
<220> FEATURE:
<223> OTHER INFORMATION: Synthetic

<400> SEQUENCE: 39
gcagggcagc atgatgtag 19

<210> SEQ ID NO 40
<211> LENGTH: 24
<212> TYPE: DNA
<213> ORGANISM: Artificial Sequence
<220> FEATURE:
<223> OTHER INFORMATION: Synthetic

<400> SEQUENCE: 40
agggctacct gagcaaagtc tgca 24

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
gcagtggcgt gatctcaact c 21

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
caggagaatg gcgtgaacct 20

<210> SEQ ID NO 43
<211> LENGTH: 16
<212> TYPE: DNA
<213> ORGANISM: Artificial Sequence
<220> FEATURE:
<223> OTHER INFORMATION: Synthetic

<400> SEQUENCE: 43
ctgcaagctc cacctc 16

<210> SEQ ID NO 44
<211> LENGTH: 22
<212> TYPE: DNA
<213> ORGANISM: Artificial Sequence
<220> FEATURE:
<223> OTHER INFORMATION: Synthetic

<400> SEQUENCE: 44
tgtcaggtgg tctgcaaaga tg 22

<210> SEQ ID NO 45
<211> LENGTH: 17
<212> TYPE: DNA
<213> ORGANISM: Artificial Sequence
<220> FEATURE:
<223> OTHER INFORMATION: Synthetic

<400> SEQUENCE: 45
gttacccccg ccatgga 17

<210> SEQ ID NO 46
<211> LENGTH: 22
<212> TYPE: DNA
<213> ORGANISM: Artificial Sequence
<220> FEATURE:
<223> OTHER INFORMATION: Synthetic

<400> SEQUENCE: 46
taaccttgac tactaaaaac gt 22

<210> SEQ ID NO 47

<211> LENGTH: 20
<212> TYPE: DNA
<213> ORGANISM: Artificial Sequence
<220> FEATURE:
<223> OTHER INFORMATION: Synthetic

<400> SEQUENCE: 47
ttgctttcac aggccttggt 20

<210> SEQ ID NO 48
<211> LENGTH: 23
<212> TYPE: DNA
<213> ORGANISM: Artificial Sequence
<220> FEATURE:
<223> OTHER INFORMATION: Synthetic

<400> SEQUENCE: 48
aaggagggat aaggccactg tag 23

<210> SEQ ID NO 49
<211> LENGTH: 17
<212> TYPE: DNA
<213> ORGANISM: Artificial Sequence
<220> FEATURE:
<223> OTHER INFORMATION: Synthetic

<400> SEQUENCE: 49
ttcctgcttc atgcctt 17

<210> SEQ ID NO 50
<211> LENGTH: 22
<212> TYPE: DNA
<213> ORGANISM: Artificial Sequence
<220> FEATURE:
<223> OTHER INFORMATION: Synthetic

<400> SEQUENCE: 50
gccatccaga acctgaaaga aa 22

<210> SEQ ID NO 51
<211> LENGTH: 19
<212> TYPE: DNA
<213> ORGANISM: Artificial Sequence
<220> FEATURE:
<223> OTHER INFORMATION: Synthetic

<400> SEQUENCE: 51
cgtgggcttt cccaaatcc 19

<210> SEQ ID NO 52
<211> LENGTH: 27
<212> TYPE: DNA
<213> ORGANISM: Artificial Sequence
<220> FEATURE:
<223> OTHER INFORMATION: Synthetic

<400> SEQUENCE: 52
agggtattca aagagccatt ctgccca 27

<210> SEQ ID NO 53
<211> LENGTH: 22
<212> TYPE: DNA
<213> ORGANISM: Artificial Sequence
<220> FEATURE:
<223> OTHER INFORMATION: Synthetic

<400> SEQUENCE: 53
cacgacttcc acctgctctt ct 22

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gagagggcct ttgactgaga 20

<210> SEQ ID NO 55
<211> LENGTH: 24
<212> TYPE: DNA
<213> ORGANISM: Artificial Sequence
<220> FEATURE:
<223> OTHER INFORMATION: Synthetic

<400> SEQUENCE: 55
cctctgtggc ctgtaggttc ttgg 24

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
ggcagaaggc acccagacta 20

<210> SEQ ID NO 57
<211> LENGTH: 17
<212> TYPE: DNA
<213> ORGANISM: Artificial Sequence
<220> FEATURE:
<223> OTHER INFORMATION: Synthetic

<400> SEQUENCE: 57
ggcaaccgga gcattgg 17

<210> SEQ ID NO 58
<211> LENGTH: 15
<212> TYPE: DNA
<213> ORGANISM: Artificial Sequence
<220> FEATURE:
<223> OTHER INFORMATION: Synthetic

<400> SEQUENCE: 58
aacaccctta gtggc 15

<210> SEQ ID NO 59
<211> LENGTH: 22
<212> TYPE: DNA
<213> ORGANISM: Artificial Sequence
<220> FEATURE:
<223> OTHER INFORMATION: Synthetic

<400> SEQUENCE: 59
cgtgtagctc acactggtca ca 22

<210> SEQ ID NO 60
<211> LENGTH: 21
<212> TYPE: DNA

<213> ORGANISM: Artificial Sequence
<220> FEATURE:
<223> OTHER INFORMATION: Synthetic

<400> SEQUENCE: 60
gggtgatgag gtccaactca a 21

<210> SEQ ID NO 61
<211> LENGTH: 14
<212> TYPE: DNA
<213> ORGANISM: Artificial Sequence
<220> FEATURE:
<223> OTHER INFORMATION: Synthetic

<400> SEQUENCE: 61
accaccacac ttgg 14

<210> SEQ ID NO 62
<211> LENGTH: 23264
<212> TYPE: DNA
<213> ORGANISM: Artificial Sequence
<220> FEATURE:
<223> OTHER INFORMATION: Synthetic

<400> SEQUENCE: 62
atgtacgacg cagagcgcgg ctggagcttg tccttcgcgg gctgcggctt cctgggcttc 60
taccacgtcg gggcgacccg ctgcctgagc gagcacgccc cgcacctcct ccgcgacgcg 120
cgcatgttgt tcggcgcttc ggccggggcg ttgcactgcg tcggcgtcct ctccggtatc 180
ccgctgggtg cgtctgggga cgctgcccgg gctccacgtg cggagtgggt gccccctagg 240
ccggggagcg ggggatcccc aggggtcgcg gggccctgga ggagcgggca tcggacgcgg 300
acacggcggg gtgcatcccg agggccccct ccgaggcaga tgcttcctgc gggggcgctg 360
ttcctgggcc cgggaagggg gcgttggaac cccgagcggt ccgggccgaa gcctgggact 420
ctcgtgcgtc cccacccccta cccccatcag gcgcccgtgc atgaagggag accctcacct 480
ccggactgag agtcggagcg tctcggagcg acggggagta gggagcggga cccggggcgg 540
agggtagtgc tggcccctgc ggactccggg tcccctgtgt cctctcggga ggggctggac 600
gggctgagct gccgaggggc cgatttgccc tgggccggac aaagagtggg gctttggccg 660
gtcccccacg gtgggctcct tccctctggg gattgaggga ctcaagacac cccgcgcctg 720
cgcttttctt ttcttttttt cttttttttt ttttgagacg gagtttcgct cagtcgccca 780
ggctggagtg cagtggcgtg atctcaactc actgcaagct ccacctccca ggttcacgcc 840
attctcctgc ctcagcctcc cgagtagctg ggactacagg cgccagccac caagcccggc 900
taattttttg tattttttag tagagacggg gtttcaccgt gttagccagg atggtctcga 960
tctcctgacc tcgtgatctg cccacctcgg cctcccagaa tgctggggtt acaggcgtga 1020
gccactgctc cctgctgcct acgctctctg ggtcgcagcc cagccttctg ggggctgggt 1080
agcctcccag aagggcaacc ctgggcatcc tccagggcag gctaactgga gtctagtggg 1140
gaggggtacc ttgaaagagg aaagttgttt cctcctcctc ctcctcctcc agtgtttggg 1200
acccttcctg gggctggag tgcatccctg gacacccccc aatcccatcc tcttctctag 1260
tttccactga cctaggccca ccctcccctc tccggctcag tactcctgga aatgagattc 1320
cgtacatttg aatcttgtcc taatgaaata tttgtccatg tgggtacctg tgtgtgtgtg 1380
gtgggggtgc agacggaggg tttgtttctc actagctgga actactgggg tgtggtatgc 1440
ttcctgggaa tttgtgtgcc acagtcctgg aggcgaggag gggggttgtga gccagtaggc 1500

-continued

```
aggggctggg gcaagtagca ttgtgaagct attgacaccc agacgtcccc aggcaggaga   1560
ttatgccccc attagccccc ttttatctgg gcttccttaa caatggactc tttgccctgc   1620
ctgccagagc cagcagggag tgactgttca gtggtgagga agcgggcaga ggaagccctg   1680
ccattgggta ggagcagtgg gcagcccctg ggctgactgg gaggtgggga ttagggatta   1740
gacagtcctg gctgtctgcc ttcccctaag ccagggggag aggagcaaag ggcacgaaat   1800
gtggcctcca ggaggattag accgccacat gatcatttgc acaccctggg gtttagcaac   1860
aataaaagtc agcttttttg tatcccaagg tggcctgtgg acacccacat ggacaaatgt   1920
ttacactggg acagaattca aatgcagagg tcccaggagc ctaaagtaca ctcactctgg   1980
tatagaaagg attccttact gggcagagga caggtgcagc ctggggcttt cccaggcagg   2040
acacagggag gctcaggaac caccaagtcc ctggaaggtg gatctggagg tgttggcagg   2100
agccactccc tgggttccag ggctccaggt tcctgcttta accccctgtc tcacagaggg   2160
ctgtgcactt gggggctgct gagcatgtcc cagaggctgc atcctggaca cagcacctca   2220
gtgcatctga gctgaggcta acttggcagg agggacaggc agaacctgcc agccacgtgc   2280
aattccaccc ctctggccac tcagggaagg agagctgtga gtcaagatca gatttgggtc   2340
aggacaggct ggggcctgcc tgtccctgtg catcccaaga tttatggctg gccaggggtt   2400
gggctgggag gggtggtctt gcatgccagg agagtgcaga tcagcctgag aggccaggcc   2460
agtaagtgag gtcagatctc ctgcacctga tagcattaag gccatctaca ccaaagctct   2520
aatgctgata tgttcctggc ctctatgtgg ggcatggagg tggggcatgg aggtgaggcc   2580
tgctcgcctg ggcttctgga agtgggagac tcattcctgt ggctgaggcc tacagcagtg   2640
ctgtgtggta ggaatacact ggaagccatg atgtcattgt gcattttcta gaagccacat   2700
tgaataaagt aaaagacaca ggtagaatta atttcattga gcccaatata tccaaaataa   2760
tatcattttc acatctattc aatataaaaa tttactaatg agatatttca tactaagcca   2820
ctgaaatcca gtttgtatct tacacatctc agttttgacg agccacattt caagggcgtg   2880
atagccacat gtggctccca tagtagacag tactggtcta gagaaatgtt ggtggcatcc   2940
ttgctgtctg gtttctggcc ttgccaaaag tattaccatc ccagtgtggt acattctttc   3000
atgtatttgt ctcctgtccc cagagcagac tctgcaggtc ctctcagatc ttgtgcggaa   3060
ggccaggagt cggaacattg gcatcttcca tccatccttc aacttaagca agttcctccg   3120
acagggtctc tgcaaatgcc tcccggccaa tgtccaccag ctcatctccg gcaaaatagg   3180
catctctctt accagagtgt ctgatgggga aaacgttctg gtgtctgact ttcggtccaa   3240
agacgaagtc gtggatgtaa gcagtttgct tatctggacg ttgtcaagtt agaaaagctg   3300
ttttgggatg ggtgtggtgg ctcatgcctg tcatcccggc actttgggag gccgaagcgg   3360
gtgggttgct tgagcccagg agctcgagac caacatgatg aaacccagtc tctacaaaaa   3420
ttacagaaaa attagctagg catggtgttg tgggcccata gtcccagcta ctagggaggc   3480
tgaggcagga gaattgcttg agcctgggag gtggaggttg cagtaagtca tgatcatgcc   3540
actgtactcc agcccgggtg acagtgagat gctgtctgga aaaaaaaaaa aaagaaagac   3600
tgttttgttt tggaagcaac acaggcagtt gtaggccccc tgtgccagag tgacataaac   3660
tctgtacacc tccagtgatt tggtccatgt ttgtaaaccc tgaatgttcc agggcagttt   3720
cttttcttca ctttttatct cttttttttg ggtggggggg cggggtacag agtcttgctc   3780
tgtctcccag gctggagtgc agtggcgcaa tctcaacctc ccgaggagct gggactacag   3840
```

-continued

```
gcacaggcca tcacaccttg ctaatgtttg tactttttgt agagacgggg ttttgccctg   3900
ttgcccaggc tggtcccaaa ctcctgcacc caagtaatct gcccacctct gcctggcagt   3960
tacaatttca aataattcct ccctttcctt caacacttgg ctcatgaccg tccagtccaa   4020
ggaacctgtc ctgcaggtgt gcctctcccg agcttcctct atgcatcttc cataatgaag   4080
atgccttctc actggaaacc ctacaagggt gggaacgtgc cttatttgcc tgtatcctca   4140
gggtctagca gagagaagat aatctgtaat accaaaacac cattaaattc agctgatgct   4200
ttcataagcg ctccttggag gaaggactcc atttacttga cagatctgtg caagacagca   4260
gcctggcgcg tctaacctgc agccagttgc atcctctgtt taaccttgtt tgtggaagct   4320
ttctctaaac agccagcact tgtctgttcc cacatgggtc cgttctccca gtgaatcacc   4380
gtggtgccta ctgactgctc tgtagcacag tgcttcgcaa agtgtgatcc tgggaccagc   4440
agagcagcag ctcctttgag cttattggaa tggcagaccc tcaggtccca cctctgacct   4500
gctgcatggg aattctgggg agggacgcag aatctctggt tccacaggct ctccggtgat   4560
gctaatgaat accggcattt gaacagcacc gatctagccc ctttcagtcc atgagccaac   4620
aacccttggt cctgtctgtg gtgacccagt gtgactctca tggggagcaa ggagaggaag   4680
ttgaagttca ctgacagggt tgttaagggg attatgcaat agatgagacc catgggcctg   4740
aagtccgagg gtgtatgtta gttccccgtt cttttgaccc atggattaac ctactctgtg   4800
caaagggcat tttcaagttt gttgccctgc tcacttggag aaagcttatg aaggatcagg   4860
aaaattaaaa gggtgctctc gcctataact tctctctcct ttgctttcac aggccttggt   4920
atgttcctgc ttcatgcctt tctacagtgg ccttatccct ccttccttca gaggcgtggt   4980
aagtcggctt tctctgctag cgctgagtcc tgggggcctc tgaagtgtgc tcacacatct   5040
cctgcctgca gggcactggt gtcaggcacc tcagggtctg tcccatggtg gagccccatg   5100
cctcactgcc tttcagacag agtagccaca gctggcccta tttccaggct acccgggcag   5160
caaaacttac tgcatgtgta attaattatt tggctatctg taaggtaaac tggctggttc   5220
acttaatctg caccttaagc atcagatagc ttctcagtga tctagttaaa ctatatgatg   5280
ttggccaggc gcggtggctc atgtctgtaa tcccagcact ttgggagcct gaagcaggca   5340
gatcacttga ggtcaggagt tcgagaccag cctggccaac agtgtgaaac tctgtctctc   5400
ctaaaaatac aaaaattagc tgggcatggt ggtgtgcacc tgtaatccca gctgctcggg   5460
aggctgaggc aggagaattg cttgaacttg ggaggcggaa gttgcagtga gccaagatcg   5520
caccactgca ctccatcctg ggtgacagag cgagactcta tctcaaaaag aaaaaaaaaa   5580
aaaaggtaaa taaagtatat gacactgaag aatctgttac ccctggaagg tggagcttta   5640
ctcttagggg gaactataac agtcatatat atatattttt ttcttttctt ttttttttt    5700
tttgagatgg agtctsgctc tgtctcccag gctggagtgc agtggtgcaa tctcggctca   5760
ctgcaacctc cacttcacag gttcaggcaa ttctcctgcc tcaacctccc gagtagctgg   5820
gattacaggt gcctgccgtt acgccaagct aatttttgta tttttagtag agacagggtt   5880
tcatcatatt ggccaggctg gtctccaact cctgacctca ggtgatccgc ccgccttggc   5940
ctcccaaagt gctgagatta caggcgtgag ccatggtgcc cggccaacaa tcacatgtgt   6000
tgtaaacaac aacaaaaatc tgtcagcctg gtctaaccta gatttgtgct ttgttttgtt   6060
ttgccacttt gtgatgcaca ggaggaagtt taggctgtaa aatactagcc ttttagggta   6120
atttttgaac tcacaagagc agcagcggaa cctttgatgc aatcctgtat gtagcaccag   6180
cagagccacg tggcagaggg actcacatta ggagcctccc attacagact acgtgctcct   6240
```

```
gtgcgttatc ttatagggtc cccacaacca aggggagatg tgattattca tcctgtgtgg   6300
ctgtggggaa cttgagagtc atacttgccc aaagagcacg gccagcgagc ttgcacccag   6360
gtcactctct gctcctctgt cagaacaggg catgtcttgg ttcactgcag ggcggctctt   6420
ctcattctct gtagtttggg gtccaggata gtggtccacg gagccactgg agtgcccagc   6480
cactgagtga ccaaagcata ttttggattt ccgacattgc cacagcatgg ttgggcatca   6540
gcaggacccc aaccccttgt tatgctggtg gctttatgtg gttatttgat cttccccaga   6600
actcagcagg agtgcaccca gcagcaccgt agtgatgctc tctggctccc cagtgcacgg   6660
ttctggcttt ccttcctggt cgagagtttc aagccctctg ggtcctactc tgtccttttc   6720
agcccatagc tttgttcaaa agctgctggc agtgttcaga tttggctgag ttcagtgaat   6780
atgtgcattg gctgatttct gagccatgcc agggggatgg agaagccgaa gcaggagtgt   6840
ttgttctgca ggctctggag taggcattgg gtctgtgccg gctcacttgc tagtcttgca   6900
tccttcccta accccctctg gggatgtctg gccacatcag aagacagttt gggttgtcag   6960
aactggggga gtaccaggcc gaggtgggtg gatcatgagg tcaggagatc gagaccatcc   7020
tggctaacac agtgaaacct catctctact aaacatacga aaaaaattag ctgggcgtgg   7080
tggcgggcgc ctgtagtccc agctactcgg gaggctgagg caggagaatg gtgtgaaccc   7140
gggggcgga gcttgcagtg agctgagatc ctgccactgc actccagcct gggcaacaaa   7200
gcgagactcc gtctcacaaa aaaaacaaaa caaaacaaaa caaaatctgg gggagtgcca   7260
ctggcatctg atgtatagag gcccgagatg ctgtgtcatc acccgttgag tgcgctcata   7320
ggcatcttcc tgacaattag aacccattat tcttcaaatt caatgcaagc aaattcaaag   7380
cattactatg tacataccgc gtgctaatca attgcaccac tggagctcct aaattcaaaa   7440
cattactata aaaaagttca aaatgcatgg aaaagttgta cgtggcagga gaatatttgg   7500
gcttctgact accccttgaa tgaagatgat ccaccagccg ccttcctcct tggtcttcac   7560
tccagattcc tagcatttca ttctgtgtct ctttatgcag tgaggttttt gtttgttttt   7620
tgagacagag tctcactgta tcacctaggc ctggagtgca gtggcgcgat ctcagctcac   7680
tgcaaccctc ggctcctggg tttaagcgat tctcctgcct cagcctcccg agcagctgag   7740
attacaagca cacatcccca tgcccagcta atttttgtat ttttagcaga gacagggttt   7800
caccatgttg cccaggctgg tctcgaactc ctggcctcaa gtgatccatg tgcctcagcc   7860
ttccaaagtg ctgggattac aggcgtgagc caccatgccc agctcctagt gaggtttttg   7920
atgccttgct acatctgccc tagaaattgt gtgactacga ttttggaaat gttgctgtgt   7980
aaacttgtga tcatttctgg actccaggca agaatcttga tggctaaggt gtggctgaac   8040
atgtctgatt ctctcctgga cctgttttag gccaaactct gctctgaaat tcctccgtgt   8100
ggaagggcgg gctggggaga gcctcccagc tggaatcttt tggatgcctt tctctgtggg   8160
tatctgatgg ctggctctga tggctggctg tgatggctgt ggctggaaat cattgttgac   8220
atgagtttca cagatgcagg ctctgtccaa actgtagcaa aagctgcctg ccccagccga   8280
gctatgggca ataaggtggt ttaaggatat agatgaagga aaactcaccc ttagaataat   8340
ttatccaaaa tgctgctgtg ttgtgggtta gaggacattt tctgaggtcc caggttcatt   8400
gtttcattta agtctcaaaa gtccctccag gtgttggttc taattgtcaa agcatggggg   8460
gagatgggct catgggttaa aggtcttatc ccagatttct gtatcctcct tgcaagcagc   8520
aaaggggtct ggatttgaat ccatgaccat gtttctcctt tgggtttcca tcacactctg   8580
```

-continued tccccgtgca ctgagcaccc tttagttcat atgacccoct taggcatgtt acatgggcac 8640
tcctataggt gcccatctgg ccctaggact tggccaacac aacatggact ccagtttcca 8700
tctgcctctt tgccaggcac ttttgtgcag tgcacacact gtacaacagt agacggcaac 8760
cctgagagcc agagtagagc ctgtcctagc accggaatgc tcggtaagga tttgtcgcag 8820
gagtgattcc aaagccaatg tcctccctcc atatcagcct gtttgtggct ctgagaagct 8880
ctgcccacat gtgaaagctt gttaagcact taagcactaa cccagagctt cagacagtac 8940
cagtcctttt tccccttctt taaaagcgat atgtggatgg aggagtgagt gacaacgtac 9000
ccttcattga tgccaaaaca accatcaccg tgtccccctt ctatggggag tacgacatct 9060
gccctaaagt caagtccacg aactttcttc atgtggacat caccaagctc agtctacgcc 9120
tctgcacagg gaacctctac cttctctcga gagcttttgt ccccccggat ctcaaggtga 9180
gttggtggtg agggggcagg tgttctgggg tgcagctctt ctttgcctcc ctgattgcca 9240
ggagctacca gttactgtct gcacaatcaa acagaaatag acctgttctt gatggttaac 9300
ggaaataaaa ggcgcttgtc ccagaagctc aggtgaggca ccaccctgat tatgggaatc 9360
acctgggaac atatacccag acctaaaact cagatccact tcccaggctg tggttatata 9420
gtcagggggg tgcagtatgg gtattaggat tttttatttt ttagttataa agattttttt 9480
ttgatttgtt tttgagacag ggtcttgctc tgccgcttag gctggagtgc agtggtgcaa 9540
tcatagctca ctgaagcctc agactcctgg gttcaagcag tcctcccacc tcagcctcct 9600
aaggagctgg gacccacagg catgcagcac cacacctggc taattttaa aaattttgtg 9660
gagtgttgcc caggctggtc tcacactcct ggcctcaagc gatcctccca ccccagcctc 9720
ccaatgtgtt gggattacag gcatgagcca ttgtacccag ccactaagat gattcttatt 9780
tggaaacacg gtcaagaaca actgcgttcg gtagtttaac ctttttgat tgtggtggtt 9840
ttagtatgcc ttaccactct accatagtaa gaaatttgca gaccatgtac accaaccttt 9900
ggtgctcctg gggagaaaga aagaaggcta tgcaatgcaa tgcatgctca cagtccaagg 9960
gagagggaaa gctgtctaac aggattggtt ttcccgtgtg ctttataagc agatgagtag 10020
aggagacagc tcttattgtc ctagtggcaa ttgggatagg ctgcaaagtt tgttagggtg 10080
gaggcttatt ccgggaccaa gggagcccaa agaaacaagc tcctgccagg cgcggtggct 10140
cacgcctgta atcccagcac tttgggaggc tgaggcaggt ggatcacctg aggtcaggag 10200
tttgagacca gcctggccaa catggtgaaa ccccgtctct atgaaaaata caaaaattac 10260
ccgggcatgg tggcgggcac ctgtaatccc agctactagg gaggctgagg caggaaaatg 10320
gcttgaacct cggaagcgga ggtggccgtt agccgagatc acgccactgc actccagcct 10380
gggcaacaga gcaagactct gccttaaaaa aaaaaaaaaa aaaaagaaaa gtaaaaggaa 10440
aaaaaagagg ctctggcctg ctggggtgcc tgcaaagtct ccgtggaagg gtgacattca 10500
agccgagacc tccagggaac tgtctcctgg gagcacagag ccctttgctc agcccccagg 10560
tggctcagtg cccccagcca gcagactcag agcttgcatg attctttggt gctctctgcg 10620
gtcttccaat gatgctgaaa taaatggtgc ttggtgtctc cctgctgtag tccccttgct 10680
tgctttgctc acaggtgctg ggagagatat gccttcgagg atatttggat gcattcaggt 10740
tcttggaaga gaagggtatg tatgggctgg gaggatcagc catgcccttt tgacaagcat 10800
ttactagcgg tcttggtaaa gacttgagat ttgccttagt tctaacactt agtgcccaac 10860
gccttccttg tgttgctcaa cctactcatg agcccaggag ataggaaatc tccgtcccat 10920
tgtacagatg gggaaacaga attttggaaa ggagagccaa gcagcacaca cccctccctg 10980

```
aggggcagag ccgagatttg aactgggatg tcatgactcc agggccctct ccctccccag  11040
ggtcccctta tctgaaggcg gtttttcttt ccagctcgac ctcttgtgac ccttagttta  11100
acaagggccg aagttaaaga gtttctgcgc ctggaccccca aatgaagcaa tcagatttct  11160
catctccagt caggtgtggg tccaagccca ctagacaagt ttgctcttcc cagagcacat  11220
ttctgccttc aagtcatcct ggcttgtcag ggctgggggga gttctgctct agaaatatta  11280
gagtggaagg aaaaagatgt gttgggagct atttttcttt aatactaaaa gttggttgat  11340
gaatttgtcg ttggccaaga ccaaggagac tgcattttta aggacatatg tgtatttatc  11400
tgctcagaaa atgttcattg ctgtgtgcta gggatactgc agtgaacaca gaggtgtgac  11460
ccttgccagc cttgtgagag aagtgagcag ataagtaagc agaagggtga tgctgtgtcg  11520
atgggaaagt acaggtgcca atgagaaggc acaggtgtca aggagaagac acaggatgct  11580
ggaggctcat gcaggatgga tctccaaggc ccaggggaag aagggcctct cggaggacgt  11640
gaatccacat taagactttg ggataagta ggagcgcctt aggcatgggg acccatggat  11700
gcgaggcctg taggacacag agaggatggc atgaaggcct gtgcaactgg aggggtgggg  11760
atggggacac taagagatgg ctggaagtgt gggggtgggg acactaagag atgactggag  11820
aagagggggt caggagtggt gaaaaatggg agaggagggc aggctgggcc ttttggatac  11880
agggggattg catcctgcag tggtagggag ccactgaggg ctgctgcagt aggagtgagg  11940
ggatcagagg agagctttgg aagccccctg gatgcgggac aggaagggag ataccagtgt  12000
ctaggaggcc agtgaggcag ccagaggctc caccaggatc agggctgcga gggtcatgag  12060
gaggaaacca atttgaagga gtccagggga ataggacttg gaaatgaccg atgggacatt  12120
tgggaagagg aagacagaag agcgcagtcc cagcttctgg ctttagcagt tgggcaaggg  12180
gagatgggga gatgtgccca tgggttgagg gttgaggaca ttaggaggga gccggtatgg  12240
caggaagagc tggtgtgcca gagatgctgg aagcagcatc tgcctgagaa cagatacctg  12300
gcaatattcc taagggaaag tgacatctcg gagggtgagg agggcatctg atagggcctg  12360
gaaagagccg gggcaagcat gaatgtgagg ttatcttggg gggcaaggct caggcgttga  12420
ggagcagccc ctggtctctt cagcctgaag ttggaagcca gagttgggcc aggtgcagct  12480
gtggttgtct gaagtccccc tcccccagcc cagtgtgcca atgctgtaag agcaagggcc  12540
gctcactggt gctggtggct gagtcccagc acccaggaca gggcctggca catactggtg  12600
cccaatcctc ccttctgggt gcttcttcca aggccttgtg atggaagtga gtaccctctt  12660
cgacatcaga cccagcttca aatcccggct ctgctatgta tcggctgcgt ggctttagac  12720
aagtctttta accttgctgt gcttctgatt tctcagctga aaaatggaga tgatgataat  12780
ggtttctgta aggccttatg gtgaagcacc tagctcaggg cctggaaggc aggtgtaacc  12840
agtggttcag ttgttataaa cgaacactaa ccctcgcctt tgcacctcat gaatccagat  12900
atgtagatgg agcccacaaa gctagcagga gccaagctca cgtgtgtcct gctttaaagc  12960
cccatacccc tttctccggg tgacaaacac ctgtgctcgt tctcttccct tcccctcttc  13020
cccttgcatt tggctaataa caggccagct gcctgcctcc ctgcagtttg gtagatgggt  13080
gggtaatgac caccactccc acgttcgcct gatgggcttg ttttccgtgc ccttcacagg  13140
catctgcaac aggccccagc caggcctgaa gtcatcctca gaagggatgg atcctgaggt  13200
cgccatgccc agctgggcaa acatgagtct ggattcttcc ccggagtcgg ctgccttggc  13260
tgtgaggctg gagggagatg agctgctaga ccacctgcgt ctcagcatcc tgccctggga  13320
```

-continued

```
tgagagcatc ctggacaccc tctcgcccag gctcgctaca ggtacccact cctcggggtg  13380
ggcacgggca gcaccttgtt ttctttcttg tgcattatgg aggaagatgg tactgccaca  13440
tgggagcgat agggtgaggc aaccatgaca ggtggttggg aacatctcct tccatgtgta  13500
cagcctgggc tgctgccatc actcccagca cagcccccaa cccccccaat cctggaacct  13560
tgccaagtct cccttcccgt ggggtcatga ccaggaggaa aacaaactcc agctgagccc  13620
cttggggttc cccatatagg ctcctgcctg tggcagctgg gccctctgta cccctttcca  13680
actctgtgtc cctaacatgg cacctgagct cctgccatcc tggatttcat ggaccccaag  13740
gatgggggtc ctgcatctgg gacttggcct attactcgga gctccttttc agccgcctcc  13800
ctccacctgt ccacccacct caaggctcct ttcttgagac ctctcctaat ttctcccttc  13860
ccctaaaccc acaattttga acctccatcg aatggtgctg tagtttataa tgtcatcaaa  13920
tatcaaatgg agacagtgct atggtccaaa tgattgtgta ccccccagaa tttgtctttt  13980
gaaatcctaa cccccaacat gatggtctta ggaggtgggg cctttgggag gagattaggt  14040
catgaggaaa gggctgtcat gaatgggatt ggtgccctta ttaaacagac ccaagagagg  14100
tcccttgtcc cttctactgt gtgaggactc agaaggtggt gtctatgaag aaggaggccc  14160
tcaccagaca ccaacacgtc tgctgcccct tgatctggga ccttgcagcc tctagaactc  14220
tgaaaaatcg atgtttgttg ttttataagc cactcagttg gtggcatttt gttagagtag  14280
cctgaacacg gactaagtca aacagaagaa cccacaaacc agctacagag ttgggcattt  14340
ggagaaattc aaaaatgagt cagacataac tccttattct tgaggtgccc taagagatgg  14400
gacacagcag ctgcccaggt gcattagttt gttctcacat tgctataaag aaatacctga  14460
gactgggtaa ctcataaaga aagaggttga attggctcac agttgcacag gctggacagg  14520
aagcatggtg ctggcatctg ctcagcttct ggggaggcct caggaaactt acaatcatgg  14580
cagaaggtga acgggaagca tgcacatccc atgactggag caggagtgag agagagaggg  14640
aaatagaggg aaggtgccat acacttttaa acaaccagat ctcacgagaa cacactcact  14700
atcaagagaa cagcaccagt ggggaaatcc gcccccacga tccaatcacc tcccatcagg  14760
ctccgcctcc aacactggga attacaattt gacatgagat gtgggcaggg acacagatcc  14820
aaaccatatg accagattaa tacgatttga ggcatcacga ggtcattaaa gagagggaat  14880
aaaagactgg ggctccagga agaaggctct ggaatccagc agagggtcaa ggaccagctt  14940
gtaaagctgg tggtgcctga gaagtaccta ggagaacata gatgctgtga cgtttgatgt  15000
agctgttttt tgttttgtgt tttggttttt gagacagagt ctcactctgt cgcccaggct  15060
ggagtgtgca gtggcgtgat cttggctcac tggagcctcc atctcccagg ttcaaatgat  15120
cctcatgcct cagcctcctg agttgctggg attacaggtg cacaccacca cgcctggcta  15180
atttttgtgt tttcagtaga gacagggttt caccatgttg gccaggctgg tcttgaactc  15240
ctgacctcaa gtgatccaac aacttcagcc tcccaaagtg ctgggatgac aggcatgagc  15300
caccatgccc agcctgatgt agctgtttct gtgcacatta tttgctgtgg ggtatattca  15360
gatttcttaa tacaagatga ttctttgcct catgacttac acaccatttt ctatttaatt  15420
tcagctatga tattggaaat ggacatgtct tttcaaggaa aataaaagca ggctttctgg  15480
aatggcgact tccaaacata tttgtcaatt taaaggagct gggagtgggg accctatgcc  15540
ccgtaagcac tctcttagct gttcttggct gtgctccccg cttcagcttc acactgccct  15600
tgctgtgaag ggagaagcct gggctgggcg cggtggctta cacctgtaat cctagcactt  15660
ttggaggccg aggtgggtgg atcacctgag gtcaggagtt caagaccagc ctggccaaca  15720
```

-continued

```
tggtgaaact ccatctctac taaaaataca aaaaattagc tgggcatggt ggcaggtgcc  15780
tgtaatccca gctacttggg aggctgaggc agaagaatcg cttgaaccca ggaggcggag  15840
gttgcagtga gccgagattg cgccattgca ctccagcctg ggggcaacaa gagcaaaact  15900
ctgtctggaa aaaaaagaaa ggagcagctt ggcaaacccc accttgtcgc ttctgtgagt  15960
gcctctgacc ctttggctgc caggacgggc gtattttatg gaaatgctaa gcaccaacag  16020
agtaaagtgg tttggttttt cacagtggtg ggagataata gctccaaatt gtctttttca  16080
gcactgagtg aagaaatgaa agacaaaggt ggatacatga gcaagatttg caacttgcta  16140
cccattagga taatgtctta tgtaatgctg ccctgtaccc tgcctgtgga atctgccatt  16200
gcgattgtcc agaggtgagc attttaggtg gctccgtgtc ttcctcacag ggttgatatg  16260
aggatgaaac aagatgatag atcatggtgg catgtagtct gggacccgga ttgtcgtgcc  16320
acagatcaca gctcacagtc tatgtgcaat gcccctgaat gttgcccacc tgtcctcaag  16380
ccacacatgc acctgtaact cagtgcaagc ccagaaactc cccgtgggga ctcctagagc  16440
tgtcagtggc ctcacatagc agctggtcca gtctcttgtg attgcccaag gaaactgagg  16500
cctggagagc ttggggtcgc tgctctgagg ccatagagat gcctagtaga agggccaggc  16560
ctagaagcag gatccttgct gcccctctga gctgtttcca tttaaaatca catgaaggcc  16620
ggcgccgtgg ctcacggctg taatcccagc attttgggag gccaaggtgg gtggatcatg  16680
tgaggtcagg agtttgagac cagcctggcc aacatggtga aatgccatct gtactaaaaa  16740
tacaaaaatt agtggagcat ggtggcacgt gcctgtactc ccagctactt ggaaggctgg  16800
ggcagaagaa tcgcttgagc ctgggaggca gaggttgtag tgagccaaga ttgtaccact  16860
gcactccagc ctgggtgaca ggagagaaac cctatctcaa aataaaatga aaggtaatga  16920
aatgaataaa ataataaatc aagtcacggc cgggcacggt ggctcacacc tgtaatccca  16980
gcgctttggg aggccgaggt gggtggataa tgaggtcagg agttcaagac cagcctggcc  17040
aacatggtga aaccatgtct ctactaaaaa tacaaaaatt agctgggcat ggtggtgcat  17100
gcctgtaatc ccagctactc cggaggctaa ggcaggagaa ttgcttgaag caggacctag  17160
gaggcagagg ttggttgcag tgagccgaga tcatgccact gcactctagc ctgggctaca  17220
gagcgaaact ccgactcaaa aaaaaaaaaa aaaaaaaatc aaatcacatg aaagtagaac  17280
atagggaatt ccatctttcg ttctaggcat agtttgttaa tatgattcag agccagcagt  17340
taggagaaca cagtgtgact ctcctagaac ttcttgattg ggcttcctct gattgggttt  17400
cctctgattg ggcttcctct gaaagtgggg gggatggggg gtggggagca gaatggtcag  17460
agcttggctc agcagtcaga ctgctcttct tcaaatcctg gctgcattgc ttactacagc  17520
tgtgtgactc cagatgactg aatccacctc tctgtgctgc agcttcccgt ctagagagat  17580
cacctggagc agagggtggt caggagactc aatctggtta ctgactcaca gtgcaggagt  17640
actcatccca tagtaagcat ccagctagag atgttgattt ctattttcag gtaataatga  17700
tgatcgtaaa attagagaca gataaaaggt atgggcatta gaccagggca ctgcaatttc  17760
taagctgtgt gacctcaggc aagttactcg acttctctga gcctcagcgg tttcatccgc  17820
aatatatgga taggaaaacc gacctcagtg ggttgtctga cagtggaggg cacttgatta  17880
aaaaaaaaaa aattaccctg gtctgaatat taccctggac tgaaagaaaa atattgagct  17940
aatacaggca tcaggaatgg ggctgcaggg agtccaggga agggagaacg aagagcctga  18000
aggtgtgagg aggtgcgagt gctgatctgt ctgctacaaa gaggctgctg agcctcctgt  18060
```

-continued ggatgtggcc ctggacttgg cagtttaata cctgagctgt taaaataacc tcagatgctg 18120
tgttctttaa ggggtaggat tcagattcct gctgaaatgc ttctgaaagg gagggaatga 18180
gccagcccat ccccagttgc tttttaagat cattgggaag ttctggtctt gccatttgtc 18240
cctggaccac tcttaggtcc tcctgcccca cttccatctg ggtgtgtgcc ctgggctgtc 18300
caccacacag ctacatcctg ccatcttccc tcctggagcc actgtgccat gcatggatct 18360
gtagcttcat ttttcttggc ttttccctgg tttttctgga gcagagtctc tagtaaactc 18420
ccaaggaaga aaacgtttga ctttatgtgt gttgggaaac gtgctttttt tctattacat 18480
ctcagtgata ggttggccat gtctagaatt gcaggttgaa aatcatttcc tctcagtata 18540
ttggttagtg agaagcctgg gactgagaca gtcacattct cacttctttg caggtgagtg 18600
ctcttaggac tgtcttttta tcccttatac tctgaaatgt catatgtctt ggtgtaagtc 18660
cttatttcag ttattgagct ggacaagtac tggagacccc ttcagtcaaa gccttctgtc 18720
attctccagc tctaggaaat tatcttctat tgttatttct gttattcctt cccttccatt 18780
ttcttttttc tttttttttt tttttttttg agacagggtc ttactctggt gcccaggctg 18840
gaatgcagtg acctgatcat ggtacactgc agcctgaacc tcccagactc aagtgatcct 18900
cccacctcaa cctcctaagt agctgggact gcaagcacac atcaccacac ccaacaaata 18960
tttttaaaa attttgtaag atgggatctt actatgttgc ccagactttt tcttcctctt 19020
cctggggctc ttattaggaa gatgtttgac ttcctgggtt ggattcctgt ctccgtgtct 19080
gactttctct ctttgtcata tttttcatca ctcgttgtct ttttgcgtct gctctgacag 19140
atttcctcaa attttgtctt ctagtcctat cctacagttt ttactttcag caaatataat 19200
ttaatctcca agagtactct cttgttcttt tttcttagca ttctgttctt gttttatgga 19260
tgtaacattc tcttggaata tttgctgtcc tctagatcat cccttctcca tttcttcttg 19320
ggctagtttt tctgtttctt catctttctc ttttatgcta cttattctgg gcgtgttctt 19380
ggtgggtttt ttcccatata gcaacagagg acttggagct cagggagaaa agggtaggtg 19440
catcacctgg cagagctccc agacagtgac aggcaggctg cgggaaggat gtctacttgg 19500
cggtgctacc gctttcctag aaaccctttc cctggagctg gttgaactgt tgggttttgc 19560
cctggtggtg aacgctggct ccccgtgctc tgcctgtttc atcaccagcc ccctcccctt 19620
ctgcctgggg tccagtaatc tgttgaaata tatatcttgc tcattggtga gctcctgctc 19680
cttcctcgtt gctcttgcag atttatcact tctcgtaagg ctgcgcttgt acttggggat 19740
tttctctgtg ccacactggg aaacataggg tggttgcatg ctgcagtcct gagcacttat 19800
ttcactcaca tctttacacg aagatttggt gggtgtttac tttgttttta gtaagttagt 19860
ctgtcatgtc ctttgatcct tttttttgt tttttgagat ggagtctctc tgtgtcctcc 19920
aggctggagt gcaatgtcgc gatctcagct cactgcaacc tccacctcct gggctcaaga 19980
gattctcctg cttcagtctc ctgagtagct gggattacag gcatgtgcca ccacacctgg 20040
ctaatttttg tatttttagt agaggtgggg tttggcatgt tggccagcct ggtctcaaac 20100
tcctgacctc ctgacctgcc tgccttggcc tcccaaagtg ctgggattac aggtgtgagc 20160
caccacacct ggccctgatt aatcttttaa tgcccagtct ctccttcaaa agccggctcc 20220
tttctctccc tcgccttcct agattccttc tccactcccc aggatcagcc tcctcctccc 20280
caccccacca ctgctggggg gatgtctgtg gtcaggcatt tatcagagac cctgaggtgg 20340
gggtccttta tgtgtctggg ggatggagag tctagaggag gtagcgttca gacctctcca 20400
tggtgcctct gctgggctca catgtgacca agcacagcaa accatgaggc aggggatggt 20460
cttgaccatg agagcccttg cagcagctgc catgggcctc agctcctctc caagctggga 20520
agagccctga aaagccaagg tgtttttttt tccctcttta tttcagtgta agtcccttga 20580
gctttcttga accagaagtg ggctcatttt gctttagaga tttcaggtgg gcttgtcctt 20640
gtcctagcat cccagatcca ccttctggga agtcatcaga ttggaggtga tgttggcagc 20700
ttttgtaaac aaagggtagt gttgtaagct gttgtgtctg cctatgtgtg tgtttgtgta 20760
cttggtctca tctctgcaga ctggtgacat ggcttccaga tatgcccgac gatgtcctgt 20820
ggttgcagtg ggtgacctca caggtgttca ctcgagtgct gatgtgtctg ctccccgcct 20880
ccaggtaaat actttggctg tgggtgtgtg ggccggacgg gcacctctct catctgatga 20940
ggcctcacac gacattctag aaacagctgg ctgaacacca agcaaggagc ttgcccttgg 21000
gtgtggggac cctgtctcat gggaggcagc tgagtcagtc agaggtcctg gcacacctgc 21060
tgagagctgc cacccaggcc aacctgaacc ggagcctggg aagacttccc gttggatgag 21120
tctctttgag ggcagcattg atggtggaag agcagagagg ccccagataa gcagggaaag 21180
gtgcttcaga cagagtggct gggatgagga ctggggagtg tcagatagcg ctggcgtgtc 21240
tgagcgaagg agctctggca cccatggcac aggaaggagg tgggaccctg gaggggcagg 21300
gctagcagag ctcctcggag cgtgtggcta ggtgcctggt aatgcaagcc ccctgtcctc 21360
caccctctgt tgtactgagt cacagtctcc ggggtgaagc ccagcagtct gcgttgacag 21420
gccccagggg atgccgctac ttcctgaatt ctgaattctg gaaactgagc cggagttcag 21480
ggcctggctc ccattaccag ggttggacgt tatcctgaaa atcataggcc ttggtttcct 21540
cacttggcta acaggggtga tccccatccc ctcaatgggt ttccgtgagc tcctgagagc 21600
ccgtagcatg gtacttggca catgctgggc atcaggaggt atggcctctc ttgctattgt 21660
tgttattggt agacacagaa ggatttaaaa gtaggggaat gcaaagatcc gatttgctag 21720
ggaagagggc agtagtggcc aagtagaggg tggatcctgg gccctggctg gcagcaggca 21780
gcaagggggg ctgccagggc ccaggcaggg acgacctgta gaccgagagg cttcctaagg 21840
ctcttggaca ggaggaggtg tcggttccaa gcctgaggag cggggcagcc ctggtgactg 21900
gtggtcagtg gtgccaggcg gtgggtggta ggacaccctg gcaggcaagt aggtttgtgt 21960
gggggaaact gataggcccc tccagggatt cgttggtgga caacacctgt gatgtccagt 22020
gggaggtgtc caggtagctg ggagggccac aggcttggaa gacctaggtg gtgacatcag 22080
cccagcactg agggctagaa gaagctgtgt ctctggctgt gacggcaccc tagagtgtgt 22140
gtggtgccct ctactggccg gcaatgtggg tccaccgtag ctcagactgc acactgcagc 22200
agcgggaacg gcctctaagc caacttcctc catgtgtttc aggtcccaaa tgccagtgag 22260
cagccaacag gcctccccat gcacacctga gcaggactgg ccctgctgga ctccctgctc 22320
ccccgagggc tgtccagcag agaccaaagc agaggccacc ccgcggtcca tcctcaggtc 22380
cagcctgaac ttcttcttgg gcaataaagt acctgctggt gctgaggggc tctccacctt 22440
tcccagtttt tcactagaga agagtctgtg agtcacttga ggaggcgagt ctagcagatt 22500
ctttcagagg tgctaaagtt tcccatcttt gtgcagctac ctccgcattg ctgtgtagtg 22560
acccctgcct gtgacgtgga ggatcccagc ctctgagctg agttggtttt atgaaaagct 22620
aggaagcaac ctttcgcctg tgcagcggtc cagcacttaa ctctaataca tcagcatgcg 22680
ttaattcagc tggttgggaa atgacaccag gaagcccagt gcagagggtc ccttactgac 22740
tgtttcgtgg ccctattaat ggtcagactg ttccagcatg aggttcttag aatgacaggt 22800

```
gtttggatgg gtgggggcct tgtgatgggg ggtaggctgg cccatgtgtg atcttgtggg  22860

gtggagggaa gagaatagca tgatcccact tccccatgct gtgggaaggg gtgcagttcg  22920

tccccaagaa cgacactgcc tgtcaggtgg tctgcaaaga tgataacctt gactactaaa  22980

aacgtctcca tggcgggggt aacaagatga taatctactt aattttagaa caccttttc   23040

acctaactaa aataatgttt aaagagtttt gtataaaaat gtaaggaagc gttgttacct  23100

gttgaatttt gtattatgtg aatcagtgag atgttagtag aataagcctt aaaaaaaaaa  23160

aaatcggttg ggtgcagcgg cacacggctg taatcccagc actttgggag gccaaggttg  23220

gcagatcacc tgaggtcagg agttcaagac cagtctggcc aaca                   23264


<210> SEQ ID NO 63
<211> LENGTH: 481
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(41)
<223> OTHER INFORMATION: Cytoplasmic Domain
<220> FEATURE:
<221> NAME/KEY: MISC_FEATURE
<222> LOCATION: (42)..(62)
<223> OTHER INFORMATION: Transmembrane Domain
<220> FEATURE:
<221> NAME/KEY: MISC_FEATURE
<222> LOCATION: (63)..(481)
<223> OTHER INFORMATION: Lumenal Domain

<400> SEQUENCE: 63

Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125

Val Ser Asp Phe Arg Ser Lys Asp Glu Val Val Asp Ala Leu Val Cys
    130                 135                 140

Ser Cys Phe Ile Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220
```

```
Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
            245                 250                 255

Arg Pro Gln Pro Gly Leu Lys Ser Ser Ser Glu Gly Met Asp Pro Glu
        260                 265                 270

Val Ala Met Pro Ser Trp Ala Asn Met Ser Leu Asp Ser Ser Pro Glu
    275                 280                 285

Ser Ala Ala Leu Ala Val Arg Leu Glu Gly Asp Glu Leu Leu Asp His
290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
            325                 330                 335

Gly Tyr Met Ser Lys Ile Cys Asn Leu Leu Pro Ile Arg Ile Met Ser
        340                 345                 350

Tyr Val Met Leu Pro Cys Thr Leu Pro Val Glu Ser Ala Ile Ala Ile
    355                 360                 365

Val Gln Arg Leu Val Thr Trp Leu Pro Asp Met Pro Asp Asp Val Leu
370                 375                 380

Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
            405                 410                 415

Ser Pro Cys Thr Pro Glu Gln Asp Trp Pro Cys Trp Thr Pro Cys Ser
        420                 425                 430

Pro Glu Gly Cys Pro Ala Glu Thr Lys Ala Glu Ala Thr Pro Arg Ser
    435                 440                 445

Ile Leu Arg Ser Ser Leu Asn Phe Phe Leu Gly Asn Lys Val Pro Ala
450                 455                 460

Gly Ala Glu Gly Leu Ser Thr Phe Pro Ser Phe Ser Leu Glu Lys Ser
465                 470                 475                 480

Leu

<210> SEQ ID NO 64
<211> LENGTH: 1446
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(123)
<223> OTHER INFORMATION: Cytoplasmic Domain
<220> FEATURE:
<221> NAME/KEY: misc_feature
<222> LOCATION: (124)..(186)
<223> OTHER INFORMATION: Transmembrane Domain
<220> FEATURE:
<221> NAME/KEY: misc_feature
<222> LOCATION: (187)..(1443)
<223> OTHER INFORMATION: Lumenal Domain

<400> SEQUENCE: 64

atgtacgacg cagagcgcgg ctggagcttg tccttcgcgg gctgcggctt cctgggcttc      60

taccacgtcg gggcgacccg ctgcctgagc gagcacgccc cgcacctcct ccgcgacgcg     120

cgcatgttgt tcggcgcttc ggccggggcg ttgcactgcg tcggcgtcct ctccggtatc     180
```

```
ccgctggagc agactctgca ggtcctctca gatcttgtgc ggaaggccag gagtcggaac    240

attggcatct tccatccatc cttcaactta agcaagttcc tccgacaggg tctctgcaaa    300

tgcctcccgg ccaatgtcca ccagctcatc tccggcaaaa taggcatctc tcttaccaga    360

gtgtctgatg gggaaaacgt tctggtgtct gactttcggt ccaaagacga agtcgtggat    420

gccttggtat gttcctgctt catccccttc tacagtggcc ttatccctcc ttccttcaga    480

ggcgtgcgat atgtggatgg aggagtgagt gacaacgtac ccttcattga tgccaaaaca    540

accatcaccg tgtcccctt ctatggggag tacgacatct gccctaaagt caagtccacg    600

aactttcttc atgtggacat caccaagctc agtctacgcc tctgcacagg gaacctctac    660

cttctctcga gagcttttgt ccccccggat ctcaaggtgc tgggagagat atgccttcga    720

ggatatttgg atgcattcag gttcttggaa gagaagggca tctgcaacag gccccagcca    780

ggcctgaagt catcctcaga agggatggat cctgaggtcg ccatgcccag ctgggcaaac    840

atgagtctgg attcttcccc ggagtcggct gccttggctg tgaggctgga gggagatgag    900

ctgctagacc acctgcgtct cagcatcctg ccctgggatg agagcatcct ggacaccctc    960

tcgcccaggc tcgctacagc actgagtgaa gaaatgaaag acaaaggtgg atacatgagc   1020

aagatttgca acttgctacc cattaggata atgtcttatg taatgctgcc ctgtaccctg   1080

cctgtggaat ctgccattgc gattgtccag agactggtga catggcttcc agatatgccc   1140

gacgatgtcc tgtggttgca gtgggtgacc tcacaggtgt tcactcgagt gctgatgtgt   1200

ctgctccccg cctccaggtc ccaaatgcca gtgagcagcc aacaggcctc cccatgcaca   1260

cctgagcagg actggccctg ctggactccc tgctccccg agggctgtcc agcagagacc   1320

aaagcagagg ccaccccgcg gtccatcctc aggtccagcc tgaacttctt cttgggcaat   1380

aaagtacctg ctggtgctga ggggctctcc acctttccca gtttttcact agagaagagt   1440

ctgtga                                                              1446
```

<210> SEQ ID NO 65
<211> LENGTH: 419
<212> TYPE: PRT
<213> ORGANISM: Artificial Sequence
<220> FEATURE:
<223> OTHER INFORMATION: Synthetic

<400> SEQUENCE: 65

```
Glu Gln Thr Leu Gln Val Leu Ser Asp Leu Val Arg Lys Ala Arg Ser
1               5                   10                  15

Arg Asn Ile Gly Ile Phe His Pro Ser Phe Asn Leu Ser Lys Phe Leu
            20                  25                  30

Arg Gln Gly Leu Cys Lys Cys Leu Pro Ala Asn Val His Gln Leu Ile
        35                  40                  45

Ser Gly Lys Ile Gly Ile Ser Leu Thr Arg Val Ser Asp Gly Glu Asn
    50                  55                  60

Val Leu Val Ser Asp Phe Arg Ser Lys Asp Glu Val Val Asp Ala Leu
65                  70                  75                  80

Val Cys Ser Cys Phe Ile Pro Phe Tyr Ser Gly Leu Ile Pro Pro Ser
                85                  90                  95

Phe Arg Gly Val Arg Tyr Val Asp Gly Gly Val Ser Asp Asn Val Pro
            100                 105                 110

Phe Ile Asp Ala Lys Thr Thr Ile Thr Val Ser Pro Phe Tyr Gly Glu
        115                 120                 125

Tyr Asp Ile Cys Pro Lys Val Lys Ser Thr Asn Phe Leu His Val Asp
```

```
    130                 135                 140

Ile Thr Lys Leu Ser Leu Arg Leu Cys Thr Gly Asn Leu Tyr Leu Leu
145                 150                 155                 160

Ser Arg Ala Phe Val Pro Pro Asp Leu Lys Val Leu Gly Glu Ile Cys
                165                 170                 175

Leu Arg Gly Tyr Leu Asp Ala Phe Arg Phe Leu Glu Glu Lys Gly Ile
            180                 185                 190

Cys Asn Arg Pro Gln Pro Gly Leu Lys Ser Ser Ser Glu Gly Met Asp
        195                 200                 205

Pro Glu Val Ala Met Pro Ser Trp Ala Asn Met Ser Leu Asp Ser Ser
    210                 215                 220

Pro Glu Ser Ala Ala Leu Ala Val Arg Leu Glu Gly Asp Glu Leu Leu
225                 230                 235                 240

Asp His Leu Arg Leu Ser Ile Leu Pro Trp Asp Glu Ser Ile Leu Asp
                245                 250                 255

Thr Leu Ser Pro Arg Leu Ala Thr Ala Leu Ser Glu Glu Met Lys Asp
            260                 265                 270

Lys Gly Gly Tyr Met Ser Lys Ile Cys Asn Leu Leu Pro Ile Arg Ile
        275                 280                 285

Met Ser Tyr Val Met Leu Pro Cys Thr Leu Pro Val Glu Ser Ala Ile
    290                 295                 300

Ala Ile Val Gln Arg Leu Val Thr Trp Leu Pro Asp Met Pro Asp Asp
305                 310                 315                 320

Val Leu Trp Leu Gln Trp Val Thr Ser Gln Val Phe Thr Arg Val Leu
                325                 330                 335

Met Cys Leu Leu Pro Ala Ser Arg Ser Gln Met Pro Val Ser Ser Gln
            340                 345                 350

Gln Ala Ser Pro Cys Thr Pro Glu Gln Asp Trp Pro Cys Trp Thr Pro
        355                 360                 365

Cys Ser Pro Glu Gly Cys Pro Ala Glu Thr Lys Ala Glu Ala Thr Pro
    370                 375                 380

Arg Ser Ile Leu Arg Ser Ser Leu Asn Phe Phe Leu Gly Asn Lys Val
385                 390                 395                 400

Pro Ala Gly Ala Glu Gly Leu Ser Thr Phe Pro Ser Phe Ser Leu Glu
                405                 410                 415

Lys Ser Leu


<210> SEQ ID NO 66
<211> LENGTH: 1257
<212> TYPE: DNA
<213> ORGANISM: Artificial Sequence
<220> FEATURE:
<223> OTHER INFORMATION: Synthetic

<400> SEQUENCE: 66

gagcagactc tgcaggtcct ctcagatctt gtgcggaagg ccaggagtcg gaacattggc      60

atcttccatc catccttcaa cttaagcaag ttcctccgac agggtctctg caaatgcctc     120

ccggccaatg tccaccagct catctccggc aaaataggca tctctcttac cagagtgtct     180

gatggggaaa acgttctggt gtctgacttt cggtccaaag acgaagtcgt ggatgccttg     240

gtatgttcct gcttcatccc cttctacagt ggccttatcc ctccttcctt cagaggcgtg     300

cgatatgtgg atggaggagt gagtgacaac gtacccttca ttgatgccaa aacaaccatc     360

accgtgtccc ccttctatgg ggagtacgac atctgcccta aagtcaagtc cacgaacttt     420
```

```
cttcatgtgg acatcaccaa gctcagtcta cgcctctgca cagggaacct ctaccttctc    480

tcgagagctt ttgtcccccc ggatctcaag gtgctgggag agatatgcct tcgaggatat    540

ttggatgcat tcaggttctt ggaagagaag ggcatctgca acaggcccca gccaggcctg    600

aagtcatcct cagaagggat ggatcctgag gtcgccatgc ccagctgggc aaacatgagt    660

ctggattctt ccccggagtc ggctgccttg gctgtgaggc tggagggaga tgagctgcta    720

gaccacctgc gtctcagcat cctgccctgg gatgagagca tcctggacac cctctcgccc    780

aggctcgcta cagcactgag tgaagaaatg aaagacaaag gtggatacat gagcaagatt    840

tgcaacttgc tacccattag gataatgtct tatgtaatgc tgccctgtac cctgcctgtg    900

gaatctgcca ttgcgattgt ccagagactg gtgacatggc ttccagatat gcccgacgat    960

gtcctgtggt tgcagtgggt gacctcacag gtgttcactc gagtgctgat gtgtctgctc   1020

cccgcctcca ggtcccaaat gccagtgagc agccaacagg cctccccatg cacacctgag   1080

caggactggc cctgctggac tccctgctcc cccgagggct gtccagcaga gaccaaagca   1140

gaggccaccc cgcggtccat cctcaggtcc agcctgaact tcttcttggg caataaagta   1200

cctgctggtg ctgaggggct ctccaccttt cccagttttt cactagagaa gagtctg      1257
```

```
<210> SEQ ID NO 67
<211> LENGTH: 36433
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(58)
<223> OTHER INFORMATION: Mouse Sequence
<220> FEATURE:
<221> NAME/KEY: misc_feature
<222> LOCATION: (59)..(23322)
<223> OTHER INFORMATION: Human Sequence
<220> FEATURE:
<221> NAME/KEY: misc_feature
<222> LOCATION: (59)..(61)
<223> OTHER INFORMATION: Start Codon
<220> FEATURE:
<221> NAME/KEY: misc_feature
<222> LOCATION: (4992)..(4994)
<223> OTHER INFORMATION: 148I (ATC)
<220> FEATURE:
<221> NAME/KEY: misc_feature
<222> LOCATION: (22381)..(22383)
<223> OTHER INFORMATION: 434E (GAG)
<220> FEATURE:
<221> NAME/KEY: misc_feature
<222> LOCATION: (22527)..(22529)
<223> OTHER INFORMATION: Stop Codon
<220> FEATURE:
<221> NAME/KEY: misc_feature
<222> LOCATION: (23323)..(28133)
<223> OTHER INFORMATION: Neo Self-Deleting Cassette
<220> FEATURE:
<221> NAME/KEY: misc_feature
<222> LOCATION: (23323)..(23328)
<223> OTHER INFORMATION: XhoI
<220> FEATURE:
<221> NAME/KEY: misc_feature
<222> LOCATION: (23329)..(23362)
<223> OTHER INFORMATION: LoxP1
<220> FEATURE:
<221> NAME/KEY: misc_feature
<222> LOCATION: (28061)..(28094)
<223> OTHER INFORMATION: LoxP2
<220> FEATURE:
<221> NAME/KEY: misc_feature
<222> LOCATION: (28102)..(28127)
<223> OTHER INFORMATION: I_Ceu
```

<220> FEATURE:
<221> NAME/KEY: misc_feature
<222> LOCATION: (28128)..(28133)
<223> OTHER INFORMATION: NheI
<220> FEATURE:
<221> NAME/KEY: misc_feature
<222> LOCATION: (28134)..(36433)
<223> OTHER INFORMATION: Mouse Sequence

<400> SEQUENCE: 67

```
agagcagcaa caccgggagc agagctgaac tgcagcgccg cccggagctt caagcaccat     60
gtacgacgca gagcgcggct ggagcttgtc cttcgcgggc tgcggcttcc tgggcttcta    120
ccacgtcggg gcgacccgct gcctgagcga gcacgccccg cacctcctcc gcgacgcgcg    180
catgttgttc ggcgcttcgg ccggggcgtt gcactgcgtc ggcgtcctct ccggtatccc    240
gctgggtgcg tctggggacg ctgcccgggc tccacgtgcg gagtgggtgc cccctaggcc    300
ggggagcggg ggatccccag gggtcgcggg gccctggagg agcgggcatc ggacgcggac    360
acggcggggt gcatcccgag ggccccctcc gaggcagatg cttcctgcgg gggcgctgtt    420
cctgggcccg ggaagggggc gttggaaccc cgagcggtcc gggccgaagc ctgggactct    480
cgtgcgtccc cacccctacc cccatcaggc gcccgtgcat gaagggagac cctcacctcc    540
ggactgagag tcggagcgtc tcggagcgac ggggagtagg gagcgggacc cggggcggag    600
ggtagtgctg gcccctgcgg actccgggtc ccctgtgtcc tctcgggagg ggctggacgg    660
gctgagctgc cgaggggccg atttgccctg ggccggacaa agagtggggc tttggccggt    720
cccccacggt gggctccttc cctctgggga ttgagggact caagacaccc cgcgcctgcg    780
cttttctttt cttttttct ttttttttt ttgagacgga gtttcgctca gtcgcccagg    840
ctggagtgca gtggcgtgat ctcaactcac tgcaagctcc acctcccagg ttcacgccat    900
tctcctgcct cagcctcccg agtagctggg actacaggcg ccagccacca agcccggcta    960
attttttgta ttttttagta gagacggggt ttcaccgtgt tagccaggat ggtctcgatc   1020
tcctgacctc gtgatctgcc cacctcggcc tcccagaatg ctggggttac aggcgtgagc   1080
cactgctccc tgctgcctac gctctctggg tcgcagccca gccttctggg ggctgggtag   1140
cctcccagaa gggcaaccct gggcatcctc cagggcaggc taactggagt ctagtgggga   1200
ggggtacctt gaaagaggaa agttgtttcc tcctcctcct cctcctccag tgtttgggac   1260
ccttcctggg ggctggagtg catccctgga caccccccaa tcccatcctc ttctctagtt   1320
tccactgacc taggcccacc ctcccctctc cggctcagta ctcctggaaa tgagattccg   1380
tacatttgaa tcttgtccta atgaaatatt tgtccatgtg ggtacctgtg tgtgtgtggt   1440
gggggtgcag acggagggtt tgtttctcac tagctggaac tactggggtg tggtatgctt   1500
cctgggaatt tgtgtgccac agtcctggag gcgaggaggg ggttgtgagc cagtaggcag   1560
gggctggggc aagtagcatt gtgaagctat tgacacccag acgtccccag gcaggagatt   1620
atgcccccat tagccccctt ttatctgggc ttccttaaca atggactctt tgccctgcct   1680
gccagagcca gcagggagtg actgttcagt ggtgaggaag cgggcagagg aagccctgcc   1740
attgggtagg agcagtgggc agcccctggg ctgactggga ggtggggatt agggattaga   1800
cagtcctggc tgtctgcctt cccctaagcc agggggagag gagcaaaggg cacgaaatgt   1860
ggcctccagg aggattagac cgccacatga tcatttgcac accctggggt ttagcaacaa   1920
taaaagtcag ctttttgta tcccaaggtg gcctgtggac acccacatgg acaaatgttt   1980
acactgggac agaattcaaa tgcagaggtc ccaggagcct aaagtacact cactctggta   2040
```

-continued

```
tagaaaggat tccttactgg gcagaggaca ggtgcagcct ggggctttcc caggcaggac   2100
acagggaggc tcaggaacca ccaagtccct ggaaggtgga tctggaggtg ttggcaggag   2160
ccactccctg ggttccaggg ctccaggttc ctgctttaac cccctgtctc acagagggct   2220
gtgcacttgg gggctgctga gcatgtccca gaggctgcat cctggacaca gcacctcagt   2280
gcatctgagc tgaggctaac ttggcaggag ggacaggcag aacctgccag ccacgtgcaa   2340
ttccacccct ctggccactc agggaaggag agctgtgagt caagatcaga tttgggtcag   2400
gacaggctgg ggcctgcctg tccctgtgca tcccaagatt tatggctggc caggggttgg   2460
gctgggaggg gtggtcttgc atgccaggag agtgcagatc agcctgagag gccaggccag   2520
taagtgaggt cagatctcct gcacctgata gcattaaggc catctacacc aaagctctaa   2580
tgctgatatg ttcctggcct ctatgtgggg catggaggtg gggcatggag gtgaggcctg   2640
ctcgcctggg cttctggaag tgggagactc attcctgtgg ctgaggccta cagcagtgct   2700
gtgtggtagg aatacactgg aagccatgat gtcattgtgc attttctaga agccacattg   2760
aataaagtaa aagacacagg tagaattaat ttcattgagc ccaatatatc caaaataata   2820
tcattttcac atctattcaa tataaaaatt tactaatgag atatttcata ctaagccact   2880
gaaatccagt ttgtatctta cacatctcag ttttgacgag ccacatttca agggcgtgat   2940
agccacatgt ggctcccata gtagacagta ctggtctaga gaaatgttgg tggcatcctt   3000
gctgtctggt ttctggcctt gccaaaagta ttaccatccc agtgtggtac attctttcat   3060
gtatttgtct cctgtcccca gagcagactc tgcaggtcct ctcagatctt gtgcggaagg   3120
ccaggagtcg gaacattggc atcttccatc catccttcaa cttaagcaag ttcctccgac   3180
agggtctctg caaatgcctc ccggccaatg tccaccagct catctccggc aaaataggca   3240
tctctcttac cagagtgtct gatgggggaaa acgttctggt gtctgacttt cggtccaaag   3300
acgaagtcgt ggatgtaagc agtttgctta tctggacgtt gtcaagttag aaaagctgtt   3360
ttgggatggg tgtggtggct catgcctgtc atcccggcac tttgggaggc cgaagcgggt   3420
gggttgcttg agcccaggag ctcgagacca acatgatgaa acccagtctc tacaaaaatt   3480
acagaaaaat tagctaggca tggtgttgtg ggcccatagt cccagctact agggaggctg   3540
aggcaggaga attgcttgag cctgggaggt ggaggttgca gtaagtcatg atcatgccac   3600
tgtactccag cccgggtgac agtgagatgc tgtctggaaa aaaaaaaaaa agaaagactg   3660
ttttgttttg gaagcaacac aggcagttgt aggccccctg tgccagagtg acataaactc   3720
tgtacacctc cagtgatttg gtccatgttt gtaaaccctg aatgttccag ggcagtttct   3780
tttcttcact ttttatctct tttttttggg tgggggggcg gggtacagag tcttgctctg   3840
tctcccaggc tggagtgcag tggcgcaatc tcaacctccc gaggagctgg gactacaggc   3900
acaggccatc acaccttgct aatgtttgta ctttttgtag agacggggtt ttgccctgtt   3960
gcccaggctg gtcccaaact cctgcaccca agtaatctgc ccacctctgc ctggcagtta   4020
caatttcaaa taattcctcc ctttccttca acacttggct catgaccgtc cagtccaagg   4080
aacctgtcct gcaggtgtgc ctctcccgag cttcctctat gcatcttcca taatgaagat   4140
gccttctcac tggaaaccct acaagggtgg gaacgtgcct tatttgcctg tatcctcagg   4200
gtctagcaga gagaagataa tctgtaatac caaaaacacca ttaaattcag ctgatgcttt   4260
cataagcgct ccttggagga aggactccat ttacttgaca gatctgtgca agacagcagc   4320
ctggcgcgtc taacctgcag ccagttgcat cctctgttta accttgtttg tggaagcttt   4380
ctctaaacag ccagcacttg tctgttccca catgggtccg ttctcccagt gaatcaccgt   4440
```

-continued ggtgcctact gactgctctg tagcacagtg cttcgcaaag tgtgatcctg ggaccagcag 4500
agcagcagct cctttgagct tattggaatg gcagaccctc aggtcccacc tctgacctgc 4560
tgcatgggaa ttctggggag ggacgcagaa tctctggttc cacaggctct ccggtgatgc 4620
taatgaatac cggcatttga acagcaccga tctagcccct ttcagtccat gagccaacaa 4680
cccttggtcc tgtctgtggt gacccagtgt gactctcatg gggagcaagg agaggaagtt 4740
gaagttcact gacagggttg ttaaggggat tatgcaatag atgagaccca tgggcctgaa 4800
gtccgagggt gtatgttagt tccccgttct tttgacccat ggattaacct actctgtgca 4860
aagggcattt tcaagtttgt tgccctgctc acttggagaa agcttatgaa ggatcaggaa 4920
aattaaaagg gtgctctcgc ctataacttc tctctccttt gctttcacag gccttggtat 4980
gttcctgctt catccctttc tacagtggcc ttatccctcc ttccttcaga ggcgtggtaa 5040
gtcggctttc tctgctagcg ctgagtcctg gggggcctctg aagtgtgctc acacatctcc 5100
tgcctgcagg gcactggtgt caggcacctc agggtctgtc ccatggtgga gccccatgcc 5160
tcactgcctt tcagacagag tagccacagc tggccctatt tccaggctac ccgggcagca 5220
aaacttactg catgtgtaat taattatttg gctatctgta aggtaaactg gctggttcac 5280
ttaatctgca ccttaagcat cagatagctt ctcagtgatc tagttaaact atatgatgtt 5340
ggccaggcgc ggtggctcat gtctgtaatc ccagcacttt gggagcctga agcaggcaga 5400
tcacttgagg tcaggagttc gagaccagcc tggccaacag tgtgaaactc tgtctctcct 5460
aaaaatacaa aaattagctg ggcatggtgg tgtgcacctg taatcccagc tgctcgggag 5520
gctgaggcag gagaattgct tgaacttggg aggcggaagt tgcagtgagc caagatcgca 5580
ccactgcact ccatcctggg tgacagagcg agactctatc tcaaaaagaa aaaaaaaaaa 5640
aaggtaaata aagtatatga cactgaagaa tctgttaccc ctggaaggtg gagctttact 5700
cttaggggga actataacag tcatatatat atattttttt cttttctttt tttttttttt 5760
tgagatggag tctsgctctg tctcccaggc tggagtgcag tggtgcaatc tcggctcact 5820
gcaacctcca cttcacaggt tcaggcaatt ctcctgcctc aacctcccga gtagctggga 5880
ttacaggtgc ctgccgttac gccaagctaa tttttgtatt tttagtagag acagggtttc 5940
atcatattgg ccaggctggt ctccaactcc tgacctcagg tgatccgccc gccttggcct 6000
cccaaagtgc tgagattaca ggcgtgagcc atggtgcccg gccaacaatc acatgtgttg 6060
taaacaacaa caaaaatctg tcagcctggt ctaacctaga tttgtgcttt gttttgtttt 6120
gccactttgt gatgcacagg aggaagttta ggctgtaaaa tactagcctt ttagggtaat 6180
ttttgaactc acaagagcag cagcggaacc tttgatgcaa tcctgtatgt agcaccagca 6240
gagccacgtg gcagagggac tcacattagg agcctcccat tacagactac gtgctcctgt 6300
gcgttatctt atagggtccc cacaaccaag gggagatgtg attattcatc ctgtgtggct 6360
gtggggaact tgagagtcat acttgcccaa agagcacggc cagcgagctt gcacccaggt 6420
cactctctgc tcctctgtca gaacagggca tgtcttggtt cactgcaggg cggctcttct 6480
cattctctgt agtttggggt ccaggatagt ggtccacgga gccactggag tgcccagcca 6540
ctgagtgacc aaagcatatt ttggatttcc gacattgcca cagcatggtt gggcatcagc 6600
aggaccccaa ccccttgtta tgctggtggc tttatgtggt tatttgatct tccccagaac 6660
tcagcaggag tgcacccagc agcaccgtag tgatgctctc tggctcccca gtgcacggtt 6720
ctggctttcc ttcctggtcg agagtttcaa gccctctggg tcctactctg tccttttcag 6780

-continued

```
cccatagctt tgttcaaaag ctgctggcag tgttcagatt tggctgagtt cagtgaatat   6840
gtgcattggc tgatttctga gccatgccag ggggatggag aagccgaagc aggagtgttt   6900
gttctgcagg ctctggagta ggcattgggt ctgtgccggc tcacttgcta gtcttgcatc   6960
cttccctaac cccctctggg gatgtctggc cacatcagaa gacagtttgg gttgtcagaa   7020
ctgggggagt accaggccga ggtgggtgga tcatgaggtc aggagatcga gaccatcctg   7080
gctaacacag tgaaacctca tctctactaa acatacgaaa aaaattagct gggcgtggtg   7140
gcgggcgcct gtagtcccag ctactcggga ggctgaggca ggagaatggt gtgaacccgg   7200
ggggcggagc ttgcagtgag ctgagatcct gccactgcac tccagcctgg gcaacaaagc   7260
gagactccgt ctcacaaaaa aaacaaaaca aaacaaaaca aaatctgggg gagtgccact   7320
ggcatctgat gtatagaggc ccgagatgct gtgtcatcac ccgttgagtg cgctcatagg   7380
catcttcctg acaattagaa cccattattc ttcaaattca atgcaagcaa attcaaagca   7440
ttactatgta cataccgcgt gctaatcaat tgcaccactg gagctcctaa attcaaaaca   7500
ttactataaa aaagttcaaa atgcatggaa aagttgtacg tggcaggaga atatttgggc   7560
ttctgactac cccttgaatg aagatgatcc accagccgcc ttcctccttg gtcttcactc   7620
cagattccta gcatttcatt ctgtgtctct ttatgcagtg aggtttttgt ttgtttttttg   7680
agacagagtc tcactgtatc acctaggcct ggagtgcagt ggcgcgatct cagctcactg   7740
caaccctcgg ctcctgggtt taagcgattc tcctgcctca gcctcccgag cagctgagat   7800
tacaagcaca catccccatg cccagctaat ttttgtattt ttagcagaga cagggtttca   7860
ccatgttgcc caggctggtc tcgaactcct ggcctcaagt gatccatgtg cctcagcctt   7920
ccaaagtgct gggattacag gcgtgagcca ccatgcccag ctcctagtga ggtttttgat   7980
gccttgctac atctgcccta gaaattgtgt gactacgatt ttggaaatgt tgctgtgtaa   8040
acttgtgatc atttctggac tccaggcaag aatcttgatg gctaaggtgt ggctgaacat   8100
gtctgattct ctcctggacc tgttttaggc caaactctgc tctgaaattc ctccgtgtgg   8160
aagggcgggc tggggagagc ctcccagctg gaatcttttg gatgcctttc tctgtgggta   8220
tctgatggct ggctctgatg gctggctgtg atggctgtgg ctggaaatca ttgttgacat   8280
gagtttcaca gatgcaggct ctgtccaaac tgtagcaaaa gctgcctgcc ccagccgagc   8340
tatgggcaat aaggtggttt aaggatatag atgaaggaaa actcaccctt agaataattt   8400
atccaaaatg ctgctgtgtt gtgggttaga ggacattttc tgaggtccca ggttcattgt   8460
ttcatttaag tctcaaaagt ccctccaggt gttggttcta attgtcaaag catgggggga   8520
gatgggctca tgggttaaag gtcttatccc agatttctgt atcctccttg caagcagcaa   8580
aggggtctgg atttgaatcc atgaccatgt ttctcctttg ggtttccatc acactctgtc   8640
cccgtgcact gagcaccctt tagttcatat gacccccctta ggcatgttac atgggcactc   8700
ctataggtgc ccatctggcc ctaggacttg gccaacacaa catggactcc agtttccatc   8760
tgcctctttg ccaggcactt ttgtgcagtg cacacactgt acaacagtag acggcaaccc   8820
tgagagccag agtagagcct gtcctagcac cggaatgctc ggtaaggatt tgtcgcagga   8880
gtgattccaa agccaatgtc ctccctccat atcagcctgt ttgtggctct gagaagctct   8940
gcccacatgt gaaagcttgt taagcactta agcactaacc cagagcttca gacagtacca   9000
gtccttttttc cccttcttta aaagcgatat gtggatggag gagtgagtga caacgtaccc   9060
ttcattgatg ccaaaacaac catcaccgtg tccccccttct atggggagta cgacatctgc   9120
cctaaagtca agtccacgaa ctttcttcat gtggacatca ccaagctcag tctacgcctc   9180
```

-continued

```
tgcacaggga acctctacct tctctcgaga gcttttgtcc ccccggatct caaggtgagt   9240
tggtggtgag gggcaggtg ttctggggtg cagctcttct ttgcctccct gattgccagg   9300
agctaccagt tactgtctgc acaatcaaac agaaatagac ctgttcttga tggttaacgg   9360
aaataaaagg cgcttgtccc agaagctcag gtgaggcacc accctgatta tgggaatcac   9420
ctgggaacat atacccagac ctaaaactca gatccacttc ccaggctgtg gttatatagt   9480
caggggggtg cagtatgggt attaggattt tttattttt agttataaag attttttttt   9540
gatttgtttt tgagacaggg tcttgctctg ccgcttaggc tggagtgcag tggtgcaatc   9600
atagctcact gaagcctcag actcctgggt tcaagcagtc ctcccacctc agcctcctaa   9660
ggagctggga cccacaggca tgcagcacca cacctggcta atttttaaaa attttgtgga   9720
gtgttgccca ggctggtctc acactcctgg cctcaagcga tcctcccacc ccagcctccc   9780
aatgtgttgg gattacaggc atgagccatt gtacccagcc actaagatga ttcttatttg   9840
gaaacacggt caagaacaac tgcgttcggt agtttaacct tttttgattg tggtggtttt   9900
agtatgcctt accactctac catagtaaga aatttgcaga ccatgtacac caacctttgg   9960
tgctcctggg gagaaagaaa gaaggctatg caatgcaatg catgctcaca gtccaaggga  10020
gagggaaagc tgtctaacag gattggtttt cccgtgtgct ttataagcag atgagtagag  10080
gagacagctc ttattgtcct agtggcaatt gggataggct gcaaagtttg ttagggtgga  10140
ggcttattcc gggaccaagg gagcccaaag aaacaagctc ctgccaggcg cggtggctca  10200
cgcctgtaat cccagcactt tgggaggctg aggcaggtgg atcacctgag gtcaggagtt  10260
tgagaccagc ctggccaaca tggtgaaacc ccgtctctat gaaaaataca aaaattaccc  10320
gggcatggtg gcgggcacct gtaatcccag ctactaggga ggctgaggca ggaaaatggc  10380
ttgaacctcg gaagcggagg tggccgttag ccgagatcac gccactgcac tccagcctgg  10440
gcaacagagc aagactctgc cttaaaaaaa aaaaaaaaaa aaagaaaagt aaaaggaaaa  10500
aaaagaggct ctggcctgct ggggtgcctg caaagtctcc gtggaagggt gacattcaag  10560
ccgagacctc cagggaactg tctcctggga gcacagagcc ctttgctcag cccccaggtg  10620
gctcagtgcc cccagccagc agactcagag cttgcatgat tctttggtgc tctctgcggt  10680
cttccaatga tgctgaaata aatggtgctt ggtgtctccc tgctgtagtc cccttgcttg  10740
ctttgctcac aggtgctggg agagatatgc cttcgaggat atttggatgc attcaggttc  10800
ttggaagaga agggtatgta tgggctggga ggatcagcca tgccctttttg acaagcattt  10860
actagcggtc ttggtaaaga cttgagattt gccttagttc taacacttag tgcccaacgc  10920
cttccttgtg ttgctcaacc tactcatgag cccaggagat aggaaatctc cgtcccattg  10980
tacagatggg gaaacagaat tttggaaagg agagccaagc agcacacacc cctccctgag  11040
gggcagagcc gagatttgaa ctgggatgtc atgactccag ggccctctcc ctccccaggg  11100
tccccttatc tgaaggcggt ttttctttcc agctcgacct cttgtgaccc ttagtttaac  11160
aagggccgaa gttaaagagt ttctgcgcct ggaccccaaa tgaagcaatc agatttctca  11220
tctccagtca ggtgtgggtc caagcccact agacaagttt gctcttccca gagcacattt  11280
ctgccttcaa gtcatcctgg cttgtcaggg ctgggggagt tctgctctag aaatattaga  11340
gtggaaggaa aaagatgtgt tgggagctat ttttctttaa tactaaaagt tggttgatga  11400
atttgtcgtt ggccaagacc aaggagactg catttttaag gacatatgtg tatttatctg  11460
ctcagaaaat gttcattgct gtgtgctagg gatactgcag tgaacacaga ggtgtgaccc  11520
```

-continued

```
ttgccagcct tgtgagagaa gtgagcagat aagtaagcag aagggtgatg ctgtgtcgat  11580
gggaaagtac aggtgccaat gagaaggcac aggtgtcaag gagaagacac aggatgctgg  11640
aggctcatgc aggatggatc tccaaggccc aggggaagaa gggcctctcg gaggacgtga  11700
atccacatta agactttggg gataagtagg agcgccttag gcatggggac ccatggatgc  11760
gaggcctgta ggacacagag aggatggcat gaaggcctgt gcaactggag gggtggggat  11820
ggggacacta agagatggct ggaagtgtgg gggtggggac actaagagat gactggagaa  11880
gagggggtca ggagtggtga aaaatgggag aggagggcag gctgggcctt ttggatacag  11940
ggggattgca tcctgcagtg gtagggagcc actgagggct gctgcagtag gagtgagggg  12000
atcagaggag agctttggaa gccccctgga tgcgggacag gaagggagat accagtgtct  12060
aggaggccag tgaggcagcc agaggctcca ccaggatcag ggctgcgagg gtcatgagga  12120
ggaaaccaat ttgaaggagt ccaggggaat aggacttgga aatgaccgat gggacatttg  12180
ggaagaggaa gacagaagag cgcagtccca gcttctggct ttagcagttg ggcaagggga  12240
gatggggaga tgtgcccatg ggttgagggt tgaggacatt aggagggagc cggtatggca  12300
ggaagagctg gtgtgccaga gatgctggaa gcagcatctg cctgagaaca gatacctggc  12360
aatattccta agggaaagtg acatctcgga gggtgaggag ggcatctgat agggcctgga  12420
aagagccggg gcaagcatga atgtgaggtt atcttggggg gcaaggctca ggcgttgagg  12480
agcagcccct ggtctcttca gcctgaagtt ggaagccaga gttgggccag gtgcagctgt  12540
ggttgtctga agtccccctc ccccagccca gtgtgccaat gctgtaagag caagggccgc  12600
tcactggtgc tggtggctga gtcccagcac ccaggacagg gcctggcaca tactggtgcc  12660
caatcctccc ttctgggtgc ttcttccaag gccttgtgat ggaagtgagt accctcttcg  12720
acatcagacc cagcttcaaa tcccggctct gctatgtatc ggctgcgtgg ctttagacaa  12780
gtcttttaac cttgctgtgc ttctgatttc tcagctgaaa aatggagatg atgataatgg  12840
tttctgtaag gccttatggt gaagcaccta gctcagggcc tggaaggcag gtgtaaccag  12900
tggttcagtt gttataaacg aacactaacc ctcgcctttg cacctcatga atccagatat  12960
gtagatggag cccacaaagc tagcaggagc caagctcacg tgtgtcctgc tttaaagccc  13020
catacccctt tctccgggtg acaaacacct gtgctcgttc tcttcccttc ccctcttccc  13080
cttgcatttg gctaataaca ggccagctgc ctgcctccct gcagtttggt agatgggtgg  13140
gtaatgacca ccactcccac gttcgcctga tgggcttgtt ttccgtgccc ttcacaggca  13200
tctgcaacag gccccagcca ggcctgaagt catcctcaga agggatggat cctgaggtcg  13260
ccatgcccag ctgggcaaac atgagtctgg attcttcccc ggagtcggct gccttggctg  13320
tgaggctgga gggagatgag ctgctagacc acctgcgtct cagcatcctg ccctgggatg  13380
agagcatcct ggacaccctc tcgcccaggc tcgctacagg tacccactcc tcggggtggg  13440
cacgggcagc accttgtttt ctttcttgtg cattatggag gaagatggta ctgccacatg  13500
ggagcgatag ggtgaggcaa ccatgacagg tggttgggaa catctccttc catgtgtaca  13560
gcctgggctg ctgccatcac tcccagcaca gcccccaacc cccccaatcc tggaaccttg  13620
ccaagtctcc cttcccgtgg ggtcatgacc aggaggaaaa caaactccag ctgagcccct  13680
tggggttccc catataggct cctgcctgtg gcagctgggc cctctgtacc cctttccaac  13740
tctgtgtccc taacatggca cctgagctcc tgccatcctg gatttcatgg accccaagga  13800
tgggggtcct gcatctggga cttggcctat tactcggagc tccttttcag ccgcctccct  13860
ccacctgtcc acccacctca aggctccttt cttgagacct ctcctaattt ctcccttccc  13920
```

```
ctaaacccac aattttgaac ctccatcgaa tggtgctgta gtttataatg tcatcaaata  13980
tcaaatggag acagtgctat ggtccaaatg attgtgtacc ccccagaatt tgtcttttga  14040
aatcctaacc cccaacatga tggtcttagg aggtggggcc tttgggagga gattaggtca  14100
tgaggaaagg gctgtcatga atgggattgg tgcccttatt aaacagaccc aagagaggtc  14160
ccttgtccct tctactgtgt gaggactcag aaggtggtgt ctatgaagaa ggaggccctc  14220
accagacacc aacacgtctg ctgccccttg atctgggacc ttgcagcctc tagaactctg  14280
aaaaatcgat gtttgttgtt ttataagcca ctcagttggt ggcattttgt tagagtagcc  14340
tgaacacgga ctaagtcaaa cagaagaacc cacaaaccag ctacagagtt gggcatttgg  14400
agaaattcaa aaatgagtca gacataactc cttattcttg aggtgcccta agagatggga  14460
cacagcagct gcccaggtgc attagtttgt tctcacattg ctataaagaa atacctgaga  14520
ctgggtaact cataaagaaa gaggttgaat tggctcacag ttgcacaggc tggacaggaa  14580
gcatggtgct ggcatctgct cagcttctgg ggaggcctca ggaaacttac aatcatggca  14640
gaaggtgaac gggaagcatg cacatcccat gactggagca ggagtgagag agagagggaa  14700
atagagggaa ggtgccatac acttttaaac aaccagatct cacgagaaca cactcactat  14760
caagagaaca gcaccagtgg ggaaatccgc ccccacgatc caatcacctc ccatcaggct  14820
ccgcctccaa cactgggaat tacaatttga catgagatgt gggcagggac acagatccaa  14880
accatatgac cagattaata cgatttgagg catcacgagg tcattaaaga gagggaataa  14940
aagactgggg ctccaggaag aaggctctgg aatccagcag agggtcaagg accagcttgt  15000
aaagctggtg gtgcctgaga agtacctagg agaacataga tgctgtgacg tttgatgtag  15060
ctgttttttg ttttgtgttt tggtttttga gacagagtct cactctgtcg cccaggctgg  15120
agtgtgcagt ggcgtgatct tggctcactg gagcctccat ctcccaggtt caaatgatcc  15180
tcatgcctca gcctcctgag ttgctgggat tacaggtgca caccaccacg cctggctaat  15240
ttttgtgttt tcagtagaga cagggtttca ccatgttggc caggctggtc ttgaactcct  15300
gacctcaagt gatccaacaa cttcagcctc ccaaagtgct gggatgacag gcatgagcca  15360
ccatgcccag cctgatgtag ctgtttctgt gcacattatt tgctgtgggg tatattcaga  15420
tttcttaata caagatgatt ctttgcctca tgacttacac accattttct atttaatttc  15480
agctatgata ttggaaatgg acatgtcttt tcaaggaaaa taaaagcagg ctttctggaa  15540
tggcgacttc caaacatatt tgtcaattta aaggagctgg gagtggggac cctatgcccc  15600
gtaagcactc tcttagctgt tcttggctgt gctccccgct tcagcttcac actgcccttg  15660
ctgtgaaggg agaagcctgg gctgggcgcg gtggcttaca cctgtaatcc tagcactttt  15720
ggaggccgag gtgggtggat cacctgaggt caggagttca agaccagcct ggccaacatg  15780
gtgaaactcc atctctacta aaaatacaaa aaattagctg ggcatggtgg caggtgcctg  15840
taatcccagc tacttgggag gctgaggcag aagaatcgct tgaacccagg aggcggaggt  15900
tgcagtgagc cgagattgcg ccattgcact ccagcctggg ggcaacaaga gcaaaactct  15960
gtctggaaaa aaaagaaagg agcagcttgg caaaccccac cttgtcgctt ctgtgagtgc  16020
ctctgaccct ttggctgcca ggacgggcgt attttatgga aatgctaagc accaacagag  16080
taaagtggtt tggtttttca cagtggtggg agataatagc tccaaattgt ctttttcagc  16140
actgagtgaa gaaatgaaag acaaaggtgg atacatgagc aagatttgca acttgctacc  16200
cattaggata atgtcttatg taatgctgcc ctgtaccctg cctgtggaat ctgccattgc  16260
```

-continued gattgtccag aggtgagcat tttaggtggc tccgtgtctt cctcacaggg ttgatatgag 16320
gatgaaacaa gatgatagat catggtggca tgtagtctgg gacccggatt gtcgtgccac 16380
agatcacagc tcacagtcta tgtgcaatgc ccctgaatgt tgcccacctg tcctcaagcc 16440
acacatgcac ctgtaactca gtgcaagccc agaaactccc cgtggggact cctagagctg 16500
tcagtggcct cacatagcag ctggtccagt ctcttgtgat tgcccaagga aactgaggcc 16560
tggagagctt ggggtcgctg ctctgaggcc atagagatgc ctagtagaag ggccaggcct 16620
agaagcagga tccttgctgc ccctctgagc tgtttccatt taaaatcaca tgaaggccgg 16680
cgccgtggct cacggctgta atcccagcat tttgggaggc caaggtgggt ggatcatgtg 16740
aggtcaggag tttgagacca gcctggccaa catggtgaaa tgccatctgt actaaaaata 16800
caaaaattag tggagcatgg tggcacgtgc ctgtactccc agctacttgg aaggctgggg 16860
cagaagaatc gcttgagcct gggaggcaga ggttgtagtg agccaagatt gtaccactgc 16920
actccagcct gggtgacagg agagaaaccc tatctcaaaa taaaatgaaa ggtaatgaaa 16980
tgaataaaat aataaatcaa gtcacggccg ggcacggtgg ctcacacctg taatcccagc 17040
gctttgggag gccgaggtgg gtggataatg aggtcaggag ttcaagacca gcctggccaa 17100
catggtgaaa ccatgtctct actaaaaata caaaaattag ctgggcatgg tggtgcatgc 17160
ctgtaatccc agctactccg gaggctaagg caggagaatt gcttgaagca ggacctagga 17220
ggcagaggtt ggttgcagtg agccgagatc atgccactgc actctagcct gggctacaga 17280
gcgaaactcc gactcaaaaa aaaaaaaaaa aaaaaatcaa atcacatgaa agtagaacat 17340
agggaattcc atctttcgtt ctaggcatag tttgttaata tgattcagag ccagcagtta 17400
ggagaacaca gtgtgactct cctagaactt cttgattggg cttcctctga ttgggtttcc 17460
tctgattggg cttcctctga aagtgggggg gatggggggt ggggagcaga atggtcagag 17520
cttggctcag cagtcagact gctcttcttc aaatcctggc tgcattgctt actacagctg 17580
tgtgactcca gatgactgaa tccacctctc tgtgctgcag cttcccgtct agagagatca 17640
cctggagcag agggtggtca ggagactcaa tctggttact gactcacagt gcaggagtac 17700
tcatcccata gtaagcatcc agctagagat gttgatttct attttcaggt aataatgatg 17760
atcgtaaaat tagagacaga taaaaggtat gggcattaga ccagggcact gcaatttcta 17820
agctgtgtga cctcaggcaa gttactcgac ttctctgagc ctcagcggtt tcatccgcaa 17880
tatatggata ggaaaaccga cctcagtggg ttgtctgaca gtggagggca cttgattaaa 17940
aaaaaaaaaa ttaccctggt ctgaatatta ccctggactg aaagaaaaat attgagctaa 18000
tacaggcatc aggaatgggg ctgcagggag tccagggaag ggagaacgaa gagcctgaag 18060
gtgtgaggag gtgcgagtgc tgatctgtct gctacaaaga ggctgctgag cctcctgtgg 18120
atgtggccct ggacttggca gtttaatacc tgagctgtta aaataacctc agatgctgtg 18180
ttctttaagg ggtaggattc agattcctgc tgaaatgctt ctgaaaggga gggaatgagc 18240
cagcccatcc ccagttgctt tttaagatca ttgggaagtt ctggtcttgc catttgtccc 18300
tggaccactc ttaggtcctc ctgccccact tccatctggg tgtgtgccct gggctgtcca 18360
ccacacagct acatcctgcc atcttccctc ctggagccac tgtgccatgc atggatctgt 18420
agcttcattt ttcttggctt ttccctggtt tttctggagc agagtctcta gtaaactccc 18480
aaggaagaaa acgtttgact ttatgtgtgt tgggaaacgt gcttttttttc tattacatct 18540
cagtgatagg ttggccatgt ctagaattgc aggttgaaaa tcatttcctc tcagtatatt 18600
ggttagtgag aagcctggga ctgagacagt cacattctca cttctttgca ggtgagtgct 18660

```
cttaggactg tctttttatc ccttatactc tgaaatgtca tatgtcttgg tgtaagtcct  18720
tatttcagtt attgagctgg acaagtactg gagacccctt cagtcaaagc cttctgtcat  18780
tctccagctc taggaaatta tcttctattg ttatttctgt tattccttcc cttccatttt  18840
ctttttcttt tttttttttt tttttttgag acagggtctt actctggtgc ccaggctgga  18900
atgcagtgac ctgatcatgg tacactgcag cctgaacctc ccagactcaa gtgatcctcc  18960
cacctcaacc tcctaagtag ctgggactgc aagcacacat caccacaccc aacaaatatt  19020
ttttaaaaat tttgtaagat gggatcttac tatgttgccc agactttttc ttcctcttcc  19080
tggggctctt attaggaaga tgtttgactt cctgggttgg attcctgtct ccgtgtctga  19140
ctttctctct ttgtcatatt tttcatcact cgttgtcttt ttgcgtctgc tctgacagat  19200
ttcctcaaat tttgtcttct agtcctatcc tacagttttt actttcagca aatataattt  19260
aatctccaag agtactctct tgttcttttt tcttagcatt ctgttcttgt tttatggatg  19320
taacattctc ttggaatatt tgctgtcctc tagatcatcc cttctccatt tcttcttggg  19380
ctagtttttc tgtttcttca tctttctctt ttatgctact tattctgggc gtgttcttgg  19440
tgggtttttt cccatatagc aacagaggac ttggagctca gggagaaaag ggtaggtgca  19500
tcacctggca gagctcccag acagtgacag gcaggctgcg ggaaggatgt ctacttggcg  19560
gtgctaccgc tttcctagaa accctttccc tggagctggt tgaactgttg ggttttgccc  19620
tggtggtgaa cgctggctcc ccgtgctctg cctgtttcat caccagcccc ctccccttct  19680
gcctggggtc cagtaatctg ttgaaatata tatcttgctc attggtgagc tcctgctcct  19740
tcctcgttgc tcttgcagat ttatcacttc tcgtaaggct gcgcttgtac ttggggattt  19800
tctctgtgcc acactgggaa acatagggtg gttgcatgct gcagtcctga gcacttattt  19860
cactcacatc tttacacgaa gatttggtgg gtgtttactt tgtttttagt aagttagtct  19920
gtcatgtcct ttgatccttt ttttttgttt tttgagatgg agtctctctg tgtcctccag  19980
gctggagtgc aatgtcgcga tctcagctca ctgcaacctc cacctcctgg gctcaagaga  20040
ttctcctgct tcagtctcct gagtagctgg gattacaggc atgtgccacc acacctggct  20100
aatttttgta tttttagtag aggtggggtt tggcatgttg gccagcctgg tctcaaactc  20160
ctgacctcct gacctgcctg ccttggcctc ccaaagtgct gggattacag gtgtgagcca  20220
ccacacctgg ccctgattaa tcttttaatg cccagtctct ccttcaaaag ccggctcctt  20280
tctctccctc gccttcctag attccttctc cactccccag gatcagcctc ctcctcccca  20340
ccccaccact gctgggggga tgtctgtggt caggcattta tcagagaccc tgaggtgggg  20400
gtcctttatg tgtctggggg atggagagtc tagaggaggt agcgttcaga cctctccatg  20460
gtgcctctgc tgggctcaca tgtgaccaag cacagcaaac catgaggcag gggatggtct  20520
tgaccatgag agcccttgca gcagctgcca tgggcctcag ctcctctcca agctgggaag  20580
agccctgaaa agccaaggtg ttttttttc cctctttatt tcagtgtaag tcccttgagc  20640
tttcttgaac cagaagtggg ctcattttgc tttagagatt tcaggtgggc ttgtccttgt  20700
cctagcatcc cagatccacc ttctgggaag tcatcagatt ggaggtgatg ttggcagctt  20760
ttgtaaacaa agggtagtgt tgtaagctgt tgtgtctgcc tatgtgtgtg tttgtgtact  20820
tggtctcatc tctgcagact ggtgacatgg cttccagata tgcccgacga tgtcctgtgg  20880
ttgcagtggg tgacctcaca ggtgttcact cgagtgctga tgtgtctgct ccccgcctcc  20940
aggtaaatac tttggctgtg ggtgtgtggg ccggacgggc acctctctca tctgatgagg  21000
```

-continued

```
cctcacacga cattctagaa acagctggct gaacaccaag caaggagctt gcccttgggt  21060
gtggggaccc tgtctcatgg gaggcagctg agtcagtcag aggtcctggc acacctgctg  21120
agagctgcca cccaggccaa cctgaaccgg agcctgggaa gacttcccgt tggatgagtc  21180
tctttgaggg cagcattgat ggtggaagag cagagaggcc ccagataagc agggaaaggt  21240
gcttcagaca gagtggctgg gatgaggact ggggagtgtc agatagcgct ggcgtgtctg  21300
agcgaaggag ctctggcacc catggcacag gaaggaggtg ggaccctgga ggggcagggc  21360
tagcagagct cctcggagcg tgtggctagg tgcctggtaa tgcaagcccc ctgtcctcca  21420
ccctctgttg tactgagtca cagtctccgg ggtgaagccc agcagtctgc gttgacaggc  21480
cccaggggat gccgctactt cctgaattct gaattctgga aactgagccg gagttcaggg  21540
cctggctccc attaccaggg ttggacgtta tcctgaaaat cataggcctt ggtttcctca  21600
cttggctaac aggggtgatc cccatcccct caatgggttt ccgtgagctc ctgagagccc  21660
gtagcatggt acttggcaca tgctgggcat caggaggtat ggcctctctt gctattgttg  21720
ttattggtag acacagaagg atttaaaagt aggggaatgc aaagatccga tttgctaggg  21780
aagagggcag tagtggccaa gtagagggtg gatcctgggc cctggctggc agcaggcagc  21840
aaggggggct gccagggccc aggcagggac gacctgtaga ccgagaggct tcctaaggct  21900
cttggacagg aggaggtgtc ggttccaagc ctgaggagcg gggcagccct ggtgactggt  21960
ggtcagtggt gccaggcggt gggtggtagg acaccctggc aggcaagtag gtttgtgtgg  22020
gggaaactga taggcccctc cagggattcg ttggtggaca acacctgtga tgtccagtgg  22080
gaggtgtcca ggtagctggg agggccacag gcttggaaga cctaggtggt gacatcagcc  22140
cagcactgag ggctagaaga agctgtgtct ctggctgtga cggcacccta gagtgtgtgt  22200
ggtgccctct actggccggc aatgtgggtc caccgtagct cagactgcac actgcagcag  22260
cgggaacggc ctctaagcca acttcctcca tgtgtttcag gtcccaaatg ccagtgagca  22320
gccaacaggc ctccccatgc acacctgagc aggactggcc ctgctggact ccctgctccc  22380
ccgagggctg tccagcagag accaaagcag aggccacccc gcggtccatc ctcaggtcca  22440
gcctgaactt cttcttgggc aataaagtac ctgctggtgc tgaggggctc tccacctttc  22500
ccagtttttc actagagaag agtctgtgag tcacttgagg aggcgagtct agcagattct  22560
ttcagaggtg ctaaagtttc ccatctttgt gcagctacct ccgcattgct gtgtagtgac  22620
ccctgcctgt gacgtggagg atcccagcct ctgagctgag ttggttttat gaaaagctag  22680
gaagcaacct ttcgcctgtg cagcggtcca gcacttaact ctaatacatc agcatgcgtt  22740
aattcagctg gttgggaaat gacaccagga agcccagtgc agagggtccc ttactgactg  22800
tttcgtggcc ctattaatgg tcagactgtt ccagcatgag gttcttagaa tgacaggtgt  22860
ttggatgggt gggggccttg tgatgggggg taggctggcc catgtgtgat cttgtggggt  22920
ggagggaaga gaatagcatg atcccacttc cccatgctgt gggaaggggt gcagttcgtc  22980
cccaagaacg acactgcctg tcaggtggtc tgcaaagatg ataaccttga ctactaaaaa  23040
cgtctccatg gcgggggtaa caagatgata atctacttaa ttttagaaca ccttttttcac  23100
ctaactaaaa taatgtttaa agagttttgt ataaaaatgt aaggaagcgt tgttacctgt  23160
tgaattttgt attatgtgaa tcagtgagat gttagtagaa taagccttaa aaaaaaaaaa  23220
atcggttggg tgcagcggca cacggctgta atcccagcac tttgggaggc caaggttggc  23280
agatcacctg aggtcaggag ttcaagacca gtctggccaa cactcgagat aacttcgtat  23340
aatgtatgct atacgaagtt atatgcatgc cagtagcagc acccacgtcc accttctgtc  23400
```

tagtaatgtc caacacctcc ctcagtccaa acactgctct gcatccatgt ggctcccatt 23460
tatacctgaa gcacttgatg gggcctcaat gttttactag agcccacccc cctgcaactc 23520
tgagaccctc tggatttgtc tgtcagtgcc tcactggggc gttggataat ttcttaaaag 23580
gtcaagttcc ctcagcagca ttctctgagc agtctgaaga tgtgtgcttt tcacagttca 23640
aatccatgtg gctgtttcac ccacctgcct ggccttgggt tatctatcag gacctagcct 23700
agaagcaggt gtgtggcact taacacctaa gctgagtgac taactgaaca ctcaagtgga 23760
tgccatcttt gtcacttctt gactgtgaca caagcaactc ctgatgccaa agccctgccc 23820
acccctctca tgcccatatt tggacatggt acaggtcctc actggccatg gtctgtgagg 23880
tcctggtcct ctttgacttc ataattccta ggggccacta gtatctataa gaggaagagg 23940
gtgctggctc ccaggccaca gcccacaaaa ttccacctgc tcacaggttg gctggctcga 24000
cccaggtggt gtcccctgct ctgagccagc tcccggccaa gccagcacca tgggaacccc 24060
caagaagaag aggaaggtgc gtaccgattt aaattccaat ttactgaccg tacaccaaaa 24120
tttgcctgca ttaccggtcg atgcaacgag tgatgaggtt cgcaagaacc tgatggacat 24180
gttcagggat cgccaggcgt tttctgagca tacctggaaa atgcttctgt ccgtttgccg 24240
gtcgtgggcg gcatggtgca agttgaataa ccggaaatgg tttcccgcag aacctgaaga 24300
tgttcgcgat tatcttctat atcttcaggc gcgcggtctg gcagtaaaaa ctatccagca 24360
acatttgggc cagctaaaca tgcttcatcg tcggtccggg ctgccacgac caagtgacag 24420
caatgctgtt tcactggtta tgcggcggat ccgaaaagaa aacgttgatg ccggtgaacg 24480
tgcaaaacag gtaaatataa aatttttaag tgtataatga tgttaaacta ctgattctaa 24540
ttgtttgtgt attttaggct ctagcgttcg aacgcactga tttcgaccag gttcgttcac 24600
tcatggaaaa tagcgatcgc tgccaggata tacgtaatct ggcatttctg gggattgctt 24660
ataacaccct gttacgtata gccgaaattg ccaggatcag ggttaaagat atctcacgta 24720
ctgacggtgg gagaatgtta atccatattg gcagaacgaa aacgctggtt agcaccgcag 24780
gtgtagagaa ggcacttagc ctgggggtaa ctaaactggt cgagcgatgg atttccgtct 24840
ctggtgtagc tgatgatccg aataactacc tgttttgccg ggtcagaaaa aatggtgttg 24900
ccgcgccatc tgccaccagc cagctatcaa ctcgcgccct ggaagggatt tttgaagcaa 24960
ctcatcgatt gatttacggc gctaaggatg actctggtca gagatacctg gcctggtctg 25020
gacacagtgc ccgtgtcgga gccgcgcgag atatggcccg cgctggagtt tcaataccgg 25080
agatcatgca agctggtggc tggaccaatg taaatattgt catgaactat atccgtaacc 25140
tggatagtga aacaggggca atggtgcgcc tgctggaaga tggcgattag gcggccggcc 25200
gctaatcagc cataccacat ttgtagaggt tttacttgct ttaaaaaacc tcccacacct 25260
ccccctgaac ctgaaacata aaatgaatgc aattgttgtt gttaacttgt ttattgcagc 25320
ttataatggt tacaaataaa gcaatagcat cacaaatttc acaaataaag catttttttc 25380
actgcattct agttgtggtt tgtccaaact catcaatgta tcttatcatg tctggatccc 25440
ccggctagag tttaaacact agaactagtg gatcccccgg gatcatggcc tccgcgccgg 25500
gttttggcgc ctcccgcggg cgcccccctc ctcacggcga gcgctgccac gtcagacgaa 25560
gggcgcagcg agcgtcctga tccttccgcc cggacgctca ggacagcggc ccgctgctca 25620
taagactcgg ccttagaacc ccagtatcag cagaaggaca ttttaggacg ggacttgggt 25680
gactctaggg cactggtttt ctttccagag agcggaacag gcgaggaaaa gtagtccctt 25740

```
ctcggcgatt ctgcggaggg atctccgtgg ggcggtgaac gccgatgatt atataaggac  25800
gcgccgggtg tggcacagct agttccgtcg cagccgggat ttgggtcgcg gttcttgttt  25860
gtggatcgct gtgatcgtca cttggtgagt agcgggctgc tgggctggcc ggggctttcg  25920
tggccgccgg gccgctcggt gggacggaag cgtgtggaga gaccgccaag ggctgtagtc  25980
tgggtccgcg agcaaggttg ccctgaactg ggggttgggg ggagcgcagc aaaatggcgg  26040
ctgttcccga gtcttgaatg gaagacgctt gtgaggcggg ctgtgaggtc gttgaaacaa  26100
ggtggggggc atggtgggcg gcaagaaccc aaggtcttga ggccttcgct aatgcgggaa  26160
agctcttatt cgggtgagat gggctggggc accatctggg gaccctgacg tgaagtttgt  26220
cactgactgg agaactcggt ttgtcgtctg ttgcgggggc ggcagttatg gcggtgccgt  26280
tgggcagtgc acccgtacct ttgggagcgc gcgccctcgt cgtgtcgtga cgtcacccgt  26340
tctgttggct tataatgcag ggtggggcca cctgccggta ggtgtgcggt aggcttttct  26400
ccgtcgcagg acgcagggtt cgggcctagg gtaggctctc ctgaatcgac aggcgccgga  26460
cctctggtga ggggagggat aagtgaggcg tcagtttctt tggtcggttt tatgtaccta  26520
tcttcttaag tagctgaagc tccggttttg aactatgcgc tcggggttgg cgagtgtgtt  26580
ttgtgaagtt ttttaggcac cttttgaaat gtaatcattt gggtcaatat gtaattttca  26640
gtgttagact agtaaattgt ccgctaaatt ctggccgttt ttggcttttt tgttagacgt  26700
gttgacaatt aatcatcggc atagtatatc ggcatagtat aatacgacaa ggtgaggaac  26760
taaaccatgg gatcggccat tgaacaagat ggattgcacg caggttctcc ggccgcttgg  26820
gtggagaggc tattcggcta tgactgggca caacagacaa tcggctgctc tgatgccgcc  26880
gtgttccggc tgtcagcgca ggggcgcccg gttctttttg tcaagaccga cctgtccggt  26940
gccctgaatg aactgcagga cgaggcagcg cggctatcgt ggctggccac gacgggcgtt  27000
ccttgcgcag ctgtgctcga cgttgtcact gaagcgggaa gggactggct gctattgggc  27060
gaagtgccgg ggcaggatct cctgtcatct caccttgctc ctgccgagaa agtatccatc  27120
atggctgatg caatgcggcg gctgcatacg cttgatccgg ctacctgccc attcgaccac  27180
caagcgaaac atcgcatcga gcgagcacgt actcggatgg aagccggtct tgtcgatcag  27240
gatgatctgg acgaagagca tcaggggctc gcgccagccg aactgttcgc caggctcaag  27300
gcgcgcatgc ccgacggcga tgatctcgtc gtgacccatg gcgatgcctg cttgccgaat  27360
atcatggtgg aaaatggccg cttttctgga ttcatcgact gtggccggct gggtgtggcg  27420
gaccgctatc aggacatagc gttggctacc cgtgatattg ctgaagagct tggcggcgaa  27480
tgggctgacc gcttcctcgt gctttacggt atcgccgctc ccgattcgca gcgcatcgcc  27540
ttctatcgcc ttcttgacga gttcttctga ggggatccgc tgtaagtctg cagaaattga  27600
tgatctatta aacaataaag atgtccacta aaatggaagt ttttcctgtc atactttgtt  27660
aagaagggtg agaacagagt acctacattt tgaatggaag gattggagct acgggggtgg  27720
gggtggggtg ggattagata aatgcctgct ctttactgaa ggctctttac tattgcttta  27780
tgataatgtt tcatagttgg atatcataat ttaaacaagc aaaaccaaat taagggccag  27840
ctcattcctc ccactcatga tctatagatc tatagatctc tcgtgggatc attgtttttc  27900
tcttgattcc cactttgtgg ttctaagtac tgtggtttcc aaatgtgtca gtttcatagc  27960
ctgaagaacg agatcagcag cctctgttcc acatacactt cattctcagt attgttttgc  28020
caagttctaa ttccatcaga cctcgacctg cagcccctag ataacttcgt ataatgtatg  28080
ctatacgaag ttatgctagg gtaactataa cggtcctaag gtagcgagct agccatgtgt  28140
```

ccagttcgca ggggggattt gtttgcatgt tgacttccct cgttggaaac ttcagagggt 28200
ttggttttgt tgttgctact tgggaattcg gggtgtttgc acaggcttac cagttaagca 28260
agttcaaaca ggtaaacatc tcagacgtgt tttgagcatc acaccaacgc tcagaaggct 28320
tctgactttt acactgggtg tggcggcaca cacctgtggt cccagcactg tggatggagg 28380
ctgaggcaga agagtcagga attcaaacct atcctgggcc acagagttag tcaaggccag 28440
cttgggcttt gtatagagac catgtctcat aactaagatg tgtctgggga cgtaactcag 28500
tggatagttt gcatggttca atccctgtgc taccattagg aaggagaagg gagggaagga 28560
gaaagagagg aagggaaaga gggaaagggg ggaaagagag agaagaaagg agagggggag 28620
aagaagagag ggaaggagag agggagaggg gaaaaacaga aagggcaaga ggaagagagt 28680
gagagggagg gaaggagaga gggaagaagg gggagaggaa gggagaaaac aagaggggaa 28740
gagagagtag gagggaggga aggagggaga ggaaggaagg gagaagaagg aagggaagga 28800
aggagagaaa aagaggaaag gagaggggag agaaggagag agagaggaag aagaggagga 28860
ggaagaggag gaggaggagg aaagaaagag gagggtgtgt tatctagagg ctctggatgt 28920
accttctgcc ctggactact cctggtctcc ttatcctgtc caatctgggc ccatgcctca 28980
gggacatgac ccagccctgc ccttccattt ctttgcaccc tctttttctt ggcactctcc 29040
cttgtttttc tgaagcgaag ccttcctaaa tccccaggga aacagcagcc tgccagcctc 29100
ctcagagcct cacctgttcc tgcactggct gctgggcagc tgctcgcagg cctgcgggca 29160
cagtctgtcc tctgagagcc tagctggggc tccgtaagat tatttattca cgacttccac 29220
ctgctcttct cctctgtggc ctgtaggttc ttggtctttc tttccaccga ctgctacttt 29280
ctcagtcaaa ggccctctct ctcctggttt ggggacatga ccatctgtaa ttaatgcctg 29340
tagtttcgtc tttcctgggg ctgtttcttc tctcttatga gactcttgtg agatgctttg 29400
cctggaactc tgtagaccag gctgacctta gactcacaga gatccacctg gttctggctt 29460
ctgagtgctg gggttaaagg aatgcaccat cgttgcctga catagaaact tctttattgg 29520
ggcagatggg aaatgagaaa cagatgtctt cagggtctga gggaaagcct agagcagaga 29580
agccttcatc ctgggagaaa gaacagatca gcagcttatg aagttgttag ggagtgccca 29640
ggggaatggt gaaggagagg tagtccccaa gagcgcccca gcggggccgg tagatctgga 29700
agatggtgat ccaggtggtg agaatgaatg atcaccaaga agaggaagcc cacagctgag 29760
cgccaaacat agcctttgat ttggctctgc tctgtgtagg ctggggcgag gaaagcctct 29820
ctaaagaacc agaaaatgtt gaccaaccaa agaaaaggca ggaacgcaaa tccaccaaga 29880
tagtacttcc ggcacaggtt caacttctcc tcattggata cccgctccaa gttcatagtt 29940
gcgctggagc ccggtggtcc taagggtctg cagagcaaga cccaaatgac aggcgcaaga 30000
tcacgagcaa ccacgcccca gtgcggttta tcccttctgc ctgggattcc tttgtgggag 30060
atttgcggga gatgccgcag ttttcagtgg agtttgttgt cgctttattt ttttcttctc 30120
ctgcccagcc cccctcgcac cccaccctct ccgccagttt tcagtggagt ttgttgtcgc 30180
tttatttttt tcttctcctg cccagccccc ctcgcactcc accccctccg ccgaaacttc 30240
tctttcttac atatttcagc cctttggctt tttgcctcca atctgaagtc ttctcagctt 30300
taccctccag ttctaccctt cggggtttta acattagcag catgagtgag catgctggtc 30360
ctttcttctg gttcctttac ttgagcattc tcagcttggt ttgtgggtgt tgggagaagt 30420
gtattggggg tgtgtctgtg gaagtgggtg tgtctgtatg ttgaggggta tttttacttt 30480

-continued

```
tatttatgtc tgtgtgcact gattggttga ttgattttgt gtgtgtgtgt gtgtgtgtgc  30540
gcgcgcacgc acacacacac aaactgtttg agcagacagg ctagccttga cttctagatc  30600
ctcctgcttc accctcttag cactaggata atagatatgc gcctctgtgc ttaggtgagt  30660
gtcctgccgt cctgtctttc tttcctggct atagcagggc cacagcctat gtgtggaggt  30720
cagaggacaa ctctcagaag gagttggccc tctccttcca ttttctgggt cctaaagatc  30780
agactcaagt tgtgagacag ggcagaaaac gtcattaccc tgtgaaccat gtctgcctcc  30840
tgtgtaagta cttctgagac agaattctag ttctgtagcc caagctggcc tagaacttac  30900
tgtgtagacc agactgacct tcaactcaag tcggacctct cccctgcatg cagggtgtag  30960
ggcttgattc acccctcccc catcccactc aaggtcttgt attaggggca tcagcctagc  31020
tcccaggcag ggagtagtgc tgagtcagcc tgcttctgga ggaagaaggg ctcccttgtg  31080
agggtggggg tggggggtg cttcctcctt gtccttcctg gaggattaga cacaaggcca  31140
agtttgactg tagtaccagt gctttgtggt gtctggctcc ctcccctctg gctgaggcta  31200
tgggatctca tagccagatc agtagttcac acttgcagcc agctcagctg cttaggggga  31260
agcccaggag gtctagacca gcctgtggag agagactccg tcctccctgc tccccgtcac  31320
tgtgctccct tagcatggga gcacctctgg ataagaggtg cagcaagcta ggcttagctt  31380
gtcctcaccc caccccacgt cctcgaattt gtatcttagc acattgcaca ggcccaacct  31440
ttagtttctc tatccaaacc ctggggcagc tttactgatc cagtgttccc cttcaacagc  31500
ttccccaccg acgtcatgat aaatcgaatt aagtcgaagt tgtaaaaagt caggtttatt  31560
ggggcagctc tgggtgggct caccaatgtc acaggaaggg gtcagcaaag ttgtagaagt  31620
tgccgggctg agctccagta gaggctgctg ggggagtggg ggaggggagt cgtgaagtga  31680
tggttattca tttggtaagt ttagggccct gtaggtgggt ctttaggtcc agcggttact  31740
ttggaatctg gaactgggag ctgactttgt ccagtgtttt agatgggctt ttgcaagcat  31800
gggcgcctgg tcagaagaga aagggggtag ggtctcttgg cccataccat cttaccggtg  31860
ttccaaactt ccagtctgcc acccctcaag ggaagttctt accagcaact tacctcttgc  31920
cagagtctac agagggtttt ggccccggtg gctccagttg gattcctagt ggccctgcac  31980
cgctggcttc tatggagcct aggcctcggc cagcacttgc cctcaaccct tgagaaatta  32040
ggtagaccca ccccacgctg ctgcctttcc cgttcattcc caggagcttt ctggaacctt  32100
atatggcctg tgtgctttaa gagatattct cagaggttca cctttgtgct gatatcccac  32160
atatgcctta gggaaggtat cagattgcgg ttagaggcga tacaggcagc tcactaggat  32220
taaggtcgcg gttgtctagt tggttgtgag ccaccacttg gttgctggga tttgaactta  32280
gaacctctga aagagcggcc cgtgctctta gccactgagc catctctcca gcaatgggac  32340
tgctttttat tgcagtgttg gctgcttttt attgacctct tttttttttt ttttctggtt  32400
taatctttac agtgaaccct tgtgtccatg tgatatttgt gcacatgtac atatatctgc  32460
atctgtgttt ctatgtgaag tatacatgca tggtgtctgt tatgaaaaat aacacaggat  32520
taaagggcca cctggagggc ccatgccaag gtgtctccct gagaaatccc accatgtgac  32580
agacctggct ggtataaggg aggtctattg tggggcaagg gaggggagac agaaaggggg  32640
agacagagac agggaggctg gcagggaaca tgtggggaca gagaaagaga gagagaataa  32700
gaaaggggag atagagaagg ggaccggggt aacatggtcc tcttacaagc tcccaggcca  32760
cccacacctg gtggcagctc aggtagcaat ggaggcaggt gatgacctaa gctgttgcta  32820
ggtctctgtt gttaggtccc tgggaggaaa ccagaatcac ctgtaagcca atagtgtcct  32880
```

tggcttcctt cccacaggct ggtgacatgg ctccctgata tccaggatga tatccagtgg 32940
ctacaatggg cgacatccca ggtttgtgcc cgaatgacga tgtgcctgct cccctctacc 33000
aggtaaatac ttgggcccag ggtgtgtggg ccagataggc atccctcccg gttgttccca 33060
gagctcttag ggtcagagct tgggtggtga cagccttaac aagccaggct cagccgcctg 33120
tccccagcat gccattaaag aaaccggtag cagagaaagc aggtttattc gaatataaaa 33180
aggttcaagc ccccacccgg ttaatcttta agataccaac aggaggctta agtttaaaca 33240
gagttacaca taaacagtct gaatcagggc gtggtcctgc ccaccattgt ctgggcttca 33300
aggttccttc tttctctccc tagcatgaga ttcctgggac aatcccaatt ccttggcctc 33360
cattgtatca aagggctgaa aaccaaaggg aaggcacagc tgtctcttca gcatgcctct 33420
tctgccagaa ccactgcaag gtttggtgct caggctgtgc aaacattcta gcaatgtttg 33480
actcagtgtc aagcaggtga caaggaacat ggtgctgtgt ggggggaacc catggcccag 33540
gtgagggctt attggtgggt gaagctgtgg gtgttcaggt ggtggagaag gccttaaggg 33600
atgggactga cacctcagca ctgaaggcag gaggaagctg tggctctggg ttgcacccct 33660
gcctggctcc accctctctg gcatctgtag aagttacagc tggttcttcc tctcagcccc 33720
atgctcccag aaataagact cagacccaaa ttatagttac aaataccttg gccatatagc 33780
taggctcttc tcagactagc tcataactta actcattaat tttaacctcc atcctgccac 33840
atggctggtg gcctgtgctc aggtaccatg agtccagctc ttcacatctt tccggatgaa 33900
tcttccataa ttctttctgc ctcctggatg ttccaccttc tattccacct tttcctatag 33960
gccatggttt tgtttttgtt ttttttttcc aaatttaatt taattaatta atttatttat 34020
ttttggtttt tcgagacagg gtttctctgt atcgccctgg ctgtcctgga actcactatg 34080
taagccaggc tggcctcaaa ctcagaaatc cgcctgcctc tgcctcctga gtgctgggat 34140
taaaggcgtg cgcaaccatg cccggtgtgg tttttttttt tttttaattg acaggtggat 34200
gcatctatat aatccataac atattctctc tacaggtatc tattaggttt tgggtgaggt 34260
gtggagttct agggaactct gagagaaatt cctggggagt aagtggttta tcaagttgat 34320
tggaggagtt tttaatgcta tggacagaca gacagaagga caacagcata gtcggggcta 34380
ccagggagtt caggccccgg catcggagat agaagcagga tggggtcttt gaagagattc 34440
tgagcccaca cagcagagga gggactctct ctttagagct tttgaggatg agggaggttg 34500
actgcaagag cctacagcca ggctcgaggc aggcaggggg tggggagcag gatgtaaacc 34560
ccttcgatgc tgacagactc acttctgggg taaaatatta tgagatgcct gtcagtgtct 34620
gtgaagagac ctgagcagag tctggattct gacatcaatc atgttcttac aatactgaag 34680
acctgagagc ctgcaatctt ggtttgtaaa ttgctggtct ccgtgcttcc agtgaacttg 34740
gacattcttc tcatggttgg tccaggagag gccaaagctg agggcaccct gccttccacc 34800
cccagtccag cttgaccttt tatctggagc aacagtgtct agatgatggg tgggtgaggg 34860
gtgctatact gtctgtccct ctgggaaggg ttctgttact tttggaggca gctaggaagt 34920
ttctctgtgc agctgccccc tggtgctgtg tggtgacctc attgcctgtg accccaggat 34980
cacaggatct gggctaaagt ggtagtccat agaaaccaaa gacaatgatt tggtgtttag 35040
aaagctactc ttggtctggg tgaagtctgg tgcttaaggg ctatcacaaa gagcgtgtca 35100
aaccatctct cagcctgtga gtcagtgggg agcccaaggg catcagtgtt tggaaactgg 35160
aatccaaacc gggcaatctc ggaaggaaac tgtttaggaa ttgtgatggg acgggccgtg 35220

-continued

```
gctgtctctg aaaagggcct gccagataac ttattacttt taaggacacc tttggctctt  35280

actaatttat aaagcatttt atataaacac accagggagt gcatggtgaa ctacacgtat  35340

gatcagttaa gtggggctag aattaggtag ggagagcatc ggacctctgc ctcctcaacc  35400

tcaacttgct tgctttctcc actggctcca aatctttgta tagtcatcag ccatgaccac  35460

ctctctccct ccccatctac taccagcagc gttaatggga ataagtaccc acttctctca  35520

ggtgtactat acagctgtgg gtgtggtgtg tgtttcctgt aattcacact ttagaaagga  35580

aacaagcaaa caaaagaaac caggtgctgc ccatactcct aagtgtagac agtgaaggtg  35640

tgtgtctccc atgcctgagt ctcctggagg cctagtgagc tccaggttca tgcaagcaca  35700

tcaggaggaa tcatataatc tcagcacggt tgatccagat gggataagaa aggactctgg  35760

gagagagaat gtggttctag agacaaagtg tctaggctac acagaagata agactgtccc  35820

aaggaaagaa aagaaaccag gaactagggt gcagctcagt tgtcagagga cttctctagg  35880

cttgaagccc agagtccaat ctcagcacct tataaactgt ggagtgacag gcagtgacat  35940

cggcctgtaa tcccaacact caagcagtag aggcaagagg atcataagtt caaggtcttc  36000

cttggctatt tagggagttg gaggttagct ctggctacat gagaccctgt ctcaaaaaaa  36060

aaaaaaaaaa aaagtagaaa cttctgcctt gctttgagct gcccctttct ggacgtttct  36120

catcagtaga gaatattcct gccaccctat cagacaaaac tcccactggt ttggagtctc  36180

tccattctca ggaacacctc aggagtcaga cagtgagcag cagggagcaa tgtcttgact  36240

tgtaagcccc ttagcaaggc tggttcattt gtttattaaa agcaggtgtg ggtgaattta  36300

tgcaaatgag tatgcaaact agtggaacag cagaaggatt gaatggatac accaaaaata  36360

accacaactg tttaagggaa aagggtccat aataaatgtg gggaacaaaa aacaaataaa  36420

tgtgattttt ttt                                                     36433
```

<210> SEQ ID NO 68
<211> LENGTH: 31701
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(58)
<223> OTHER INFORMATION: Mouse Sequence
<220> FEATURE:
<221> NAME/KEY: misc_feature
<222> LOCATION: (59)..(23322)
<223> OTHER INFORMATION: Human Sequence
<220> FEATURE:
<221> NAME/KEY: misc_feature
<222> LOCATION: (59)..(61)
<223> OTHER INFORMATION: Start Codon
<220> FEATURE:
<221> NAME/KEY: misc_feature
<222> LOCATION: (4992)..(4994)
<223> OTHER INFORMATION: 148I (ATC)
<220> FEATURE:
<221> NAME/KEY: misc_feature
<222> LOCATION: (22381)..(22383)
<223> OTHER INFORMATION: 434E (GAG)
<220> FEATURE:
<221> NAME/KEY: misc_feature
<222> LOCATION: (22527)..(22529)
<223> OTHER INFORMATION: Stop Codon
<220> FEATURE:
<221> NAME/KEY: misc_feature
<222> LOCATION: (23323)..(23328)
<223> OTHER INFORMATION: XhoI
<220> FEATURE:
<221> NAME/KEY: misc_feature
<222> LOCATION: (23329)..(23362)
<223> OTHER INFORMATION: LoxP
<220> FEATURE:
<221> NAME/KEY: misc_feature
<222> LOCATION: (23370)..(23395)
<223> OTHER INFORMATION: I_Ceu
<220> FEATURE:
<221> NAME/KEY: misc_feature
<222> LOCATION: (23396)..(23401)
<223> OTHER INFORMATION: NheI
<220> FEATURE:
<221> NAME/KEY: misc_feature
<222> LOCATION: (23402)..(31701)
<223> OTHER INFORMATION: Mouse Sequence

<400> SEQUENCE: 68
agagcagcaa caccgggagc agagctgaac tgcagcgccg cccggagctt caagcaccat 60
gtacgacgca gagcgcggct ggagcttgtc cttcgcgggc tgcggcttcc tgggcttcta 120
ccacgtcggg gcgacccgct gcctgagcga gcacgccccg cacctcctcc gcgacgcgcg 180
catgttgttc ggcgcttcgg ccggggcgtt gcactgcgtc ggcgtcctct ccggtatccc 240
gctgggtgcg tctggggacg ctgcccgggc tccacgtgcg gagtgggtgc cccctaggcc 300
ggggagcggg ggatccccag gggtcgcggg gccctggagg agcgggcatc ggacgcggac 360
acggcggggt gcatcccgag ggccccctcc gaggcagatg cttcctgcgg gggcgctgtt 420
cctgggcccg ggaagggggc gttggaaccc cgagcggtcc gggccgaagc ctgggactct 480
cgtgcgtccc cacccctacc cccatcaggc gcccgtgcat gaagggagac cctcacctcc 540
ggactgagag tcggagcgtc tcggagcgac ggggagtagg gagcgggacc cggggcggag 600
ggtagtgctg gcccctgcgg actccgggtc ccctgtgtcc tctcgggagg ggctggacgg 660
gctgagctgc cgaggggccg atttgccctg ggccggacaa agagtggggc tttggccggt 720
cccccacggt gggctccttc cctctgggga ttgagggact caagacaccc cgcgcctgcg 780
cttttctttt cttttttcct ttttttttt ttgagacgga gtttcgctca gtcgcccagg 840
ctggagtgca gtggcgtgat ctcaactcac tgcaagctcc acctcccagg ttcacgccat 900
tctcctgcct cagcctcccg agtagctggg actacaggcg ccagccacca agcccggcta 960
attttttgta ttttttagta gagacggggt ttcaccgtgt tagccaggat ggtctcgatc 1020
tcctgacctc gtgatctgcc cacctcggcc tcccagaatg ctggggttac aggcgtgagc 1080
cactgctccc tgctgcctac gctctctggg tcgcagccca gccttctggg ggctgggtag 1140
cctcccagaa gggcaaccct gggcatcctc cagggcaggc taactggagt ctagtgggga 1200
ggggtacctt gaaagaggaa agttgtttcc tcctcctcct cctcctccag tgtttgggac 1260
ccttcctggg ggctggagtg catccctgga caccccccaa tcccatcctc ttctctagtt 1320
tccactgacc taggcccacc ctcccctctc cggctcagta ctcctggaaa tgagattccg 1380
tacatttgaa tcttgtccta atgaaatatt tgtccatgtg ggtacctgtg tgtgtgtggt 1440
gggggtgcag acggagggtt tgtttctcac tagctggaac tactggggtg tggtatgctt 1500
cctgggaatt tgtgtgccac agtcctggag gcgaggaggg ggttgtgagc cagtaggcag 1560
gggctggggc aagtagcatt gtgaagctat tgacacccag acgtccccag gcaggagatt 1620
atgcccccat tagccccctt ttatctgggc ttccttaaca atggactctt tgccctgcct 1680
gccagagcca gcagggagtg actgttcagt ggtgaggaag cgggcagagg aagccctgcc 1740
attgggtagg agcagtgggc agcccctggg ctgactggga ggtggggatt agggattaga 1800
cagtcctggc tgtctgcctt cccctaagcc agggggagag gagcaaaggg cacgaaatgt 1860

-continued

```
ggcctccagg aggattagac cgccacatga tcatttgcac accctggggt ttagcaacaa   1920
taaaagtcag ctttttgta tcccaaggtg gcctgtggac acccacatgg acaaatgttt   1980
acactgggac agaattcaaa tgcagaggtc ccaggagcct aaagtacact cactctggta   2040
tagaaaggat tccttactgg gcagaggaca ggtgcagcct ggggctttcc caggcaggac   2100
acagggaggc tcaggaacca ccaagtccct ggaaggtgga tctggaggtg ttggcaggag   2160
ccactccctg ggttccaggg ctccaggttc ctgctttaac cccctgtctc acagagggct   2220
gtgcacttgg gggctgctga gcatgtccca gaggctgcat cctggacaca gcacctcagt   2280
gcatctgagc tgaggctaac ttggcaggag ggacaggcag aacctgccag ccacgtgcaa   2340
ttccacccct ctggccactc agggaaggag agctgtgagt caagatcaga tttgggtcag   2400
gacaggctgg ggcctgcctg tccctgtgca tcccaagatt tatggctggc caggggttgg   2460
gctgggaggg gtggtcttgc atgccaggag agtgcagatc agcctgagag gccaggccag   2520
taagtgaggt cagatctcct gcacctgata gcattaaggc catctacacc aaagctctaa   2580
tgctgatatg ttcctggcct ctatgtgggg catggaggtg ggcatggagg gtgaggcctg   2640
ctcgcctggg cttctggaag tgggagactc attcctgtgg ctgaggccta cagcagtgct   2700
gtgtggtagg aatacactgg aagccatgat gtcattgtgc attttctaga agccacattg   2760
aataaagtaa aagacacagg tagaattaat ttcattgagc ccaatatatc caaaataata   2820
tcattttcac atctattcaa tataaaaatt tactaatgag atatttcata ctaagccact   2880
gaaatccagt ttgtatctta cacatctcag ttttgacgag ccacatttca agggcgtgat   2940
agccacatgt ggctcccata gtagacagta ctggtctaga gaaatgttgg tggcatcctt   3000
gctgtctggt ttctggcctt gccaaaagta ttaccatccc agtgtggtac attctttcat   3060
gtatttgtct cctgtcccca gagcagactc tgcaggtcct ctcagatctt gtgcggaagg   3120
ccaggagtcg gaacattggc atcttccatc catccttcaa cttaagcaag ttcctccgac   3180
agggtctctg caaatgcctc ccggccaatg tccaccagct catctccggc aaaataggca   3240
tctctcttac cagagtgtct gatggggaaa acgttctggt gtctgacttt cggtccaaag   3300
acgaagtcgt ggatgtaagc agtttgctta tctggacgtt gtcaagttag aaaagctgtt   3360
ttgggatggg tgtggtggct catgcctgtc atcccggcac tttgggaggc cgaagcgggt   3420
gggttgcttg agcccaggag ctcgagacca acatgatgaa acccagtctc tacaaaaatt   3480
acagaaaaat tagctaggca tggtgttgtg ggcccatagt cccagctact agggaggctg   3540
aggcaggaga attgcttgag cctgggaggt ggaggttgca gtaagtcatg atcatgccac   3600
tgtactccag cccgggtgac agtgagatgc tgtctggaaa aaaaaaaaaa agaaagactg   3660
ttttgttttg gaagcaacac aggcagttgt aggccccctg tgccagagtg acataaactc   3720
tgtacacctc cagtgatttg gtccatgttt gtaaaccctg aatgttccag ggcagtttct   3780
tttcttcact ttttatctct tttttttggg tggggggcg gggtacagag tcttgctctg   3840
tctcccaggc tggagtgcag tggcgcaatc tcaacctccc gaggagctgg gactacaggc   3900
acaggccatc acaccttgct aatgtttgta ctttttgtag agacggggtt ttgccctgtt   3960
gcccaggctg gtcccaaact cctgcaccca agtaatctgc ccacctctgc ctggcagtta   4020
caatttcaaa taattcctcc ctttccttca acacttggct catgaccgtc cagtccaagg   4080
aacctgtcct gcaggtgtgc ctctcccgag cttcctctat gcatcttcca taatgaagat   4140
gccttctcac tggaaaccct acaagggtgg gaacgtgcct tatttgcctg tatcctcagg   4200
gtctagcaga gagaagataa tctgtaatac caaaacacca ttaaattcag ctgatgcttt   4260
```

-continued

```
cataagcgct ccttggagga aggactccat ttacttgaca gatctgtgca agacagcagc   4320
ctggcgcgtc taacctgcag ccagttgcat cctctgttta accttgtttg tggaagcttt   4380
ctctaaacag ccagcacttg tctgttccca catgggtccg ttctcccagt gaatcaccgt   4440
ggtgcctact gactgctctg tagcacagtg cttcgcaaag tgtgatcctg ggaccagcag   4500
agcagcagct cctttgagct tattggaatg gcagaccctc aggtcccacc tctgacctgc   4560
tgcatgggaa ttctggggag ggacgcagaa tctctggttc cacaggctct ccggtgatgc   4620
taatgaatac cggcatttga acagcaccga tctagcccct ttcagtccat gagccaacaa   4680
cccttggtcc tgtctgtggt gacccagtgt gactctcatg gggagcaagg agaggaagtt   4740
gaagttcact gacagggttg ttaaggggat tatgcaatag atgagaccca tgggcctgaa   4800
gtccgagggt gtatgttagt tccccgttct tttgacccat ggattaacct actctgtgca   4860
aagggcattt tcaagtttgt tgccctgctc acttggagaa agcttatgaa ggatcaggaa   4920
aattaaaagg gtgctctcgc ctataacttc tctctccttt gctttcacag gccttggtat   4980
gttcctgctt catccctttc tacagtggcc ttatccctcc ttccttcaga ggcgtggtaa   5040
gtcggctttc tctgctagcg ctgagtcctg ggggcctctg aagtgtgctc acacatctcc   5100
tgcctgcagg gcactggtgt caggcacctc agggtctgtc ccatggtgga gccccatgcc   5160
tcactgcctt tcagacagag tagccacagc tggccctatt tccaggctac ccgggcagca   5220
aaacttactg catgtgtaat taattatttg gctatctgta aggtaaactg gctggttcac   5280
ttaatctgca ccttaagcat cagatagctt ctcagtgatc tagttaaact atatgatgtt   5340
ggccaggcgc ggtggctcat gtctgtaatc ccagcacttt gggagcctga agcaggcaga   5400
tcacttgagg tcaggagttc gagaccagcc tggccaacag tgtgaaactc tgtctctcct   5460
aaaaatacaa aaattagctg ggcatggtgg tgtgcacctg taatcccagc tgctcgggag   5520
gctgaggcag gagaattgct tgaacttggg aggcggaagt tgcagtgagc caagatcgca   5580
ccactgcact ccatcctggg tgacagagcg agactctatc tcaaaaagaa aaaaaaaaaa   5640
aaggtaaata aagtatatga cactgaagaa tctgttaccc ctggaaggtg gagctttact   5700
cttaggggga actataacag tcatatatat atattttttt cttttctttt ttttttttt   5760
tgagatggag tctsgctctg tctcccaggc tggagtgcag tggtgcaatc tcggctcact   5820
gcaacctcca cttcacaggt tcaggcaatt ctcctgcctc aacctcccga gtagctggga   5880
ttacaggtgc ctgccgttac gccaagctaa tttttgtatt tttagtagag acagggtttc   5940
atcatattgg ccaggctggt ctccaactcc tgacctcagg tgatccgccc gccttggcct   6000
cccaaagtgc tgagattaca ggcgtgagcc atggtgcccg gccaacaatc acatgtgttg   6060
taaacaacaa caaaaatctg tcagcctggt ctaacctaga tttgtgcttt gttttgtttt   6120
gccactttgt gatgcacagg aggaagttta ggctgtaaaa tactagcctt ttagggtaat   6180
ttttgaactc acaagagcag cagcggaacc tttgatgcaa tcctgtatgt agcaccagca   6240
gagccacgtg gcagagggac tcacattagg agcctcccat tacagactac gtgctcctgt   6300
gcgttatctt atagggtccc cacaaccaag gggagatgtg attattcatc ctgtgtggct   6360
gtggggaact tgagagtcat acttgcccaa agagcacggc cagcgagctt gcacccaggt   6420
cactctctgc tcctctgtca gaacagggca tgtcttggtt cactgcaggg cggctcttct   6480
cattctctgt agtttggggt ccaggatagt ggtccacgga gccactggag tgcccagcca   6540
ctgagtgacc aaagcatatt ttggatttcc gacattgcca cagcatggtt gggcatcagc   6600
```

-continued

```
aggaccccaa ccccttgtta tgctggtggc tttatgtggt tatttgatct tccccagaac   6660
tcagcaggag tgcacccagc agcaccgtag tgatgctctc tggctcccca gtgcacggtt   6720
ctggctttcc ttcctggtcg agagtttcaa gccctctggg tcctactctg tccttttcag   6780
cccatagctt tgttcaaaag ctgctggcag tgttcagatt tggctgagtt cagtgaatat   6840
gtgcattggc tgatttctga gccatgccag gggatggag aagccgaagc aggagtgttt    6900
gttctgcagg ctctggagta ggcattgggt ctgtgccggc tcacttgcta gtcttgcatc   6960
cttccctaac cccctctggg gatgtctggc cacatcagaa gacagtttgg gttgtcagaa   7020
ctgggggagt accaggccga ggtgggtgga tcatgaggtc aggagatcga gaccatcctg   7080
gctaacacag tgaaacctca tctctactaa acatacgaaa aaaattagct gggcgtggtg   7140
gcgggcgcct gtagtcccag ctactcggga ggctgaggca ggagaatggt gtgaacccgg   7200
ggggcggagc ttgcagtgag ctgagatcct gccactgcac tccagcctgg gcaacaaagc   7260
gagactccgt ctcacaaaaa aaacaaaaca aaacaaaaca aaatctgggg gagtgccact   7320
ggcatctgat gtatagaggc ccgagatgct gtgtcatcac ccgttgagtg cgctcatagg   7380
catcttcctg acaattagaa cccattattc ttcaaattca atgcaagcaa attcaaagca   7440
ttactatgta cataccgcgt gctaatcaat tgcaccactg gagctcctaa attcaaaaca   7500
ttactataaa aaagttcaaa atgcatggaa aagttgtacg tggcaggaga atatttgggc   7560
ttctgactac cccttgaatg aagatgatcc accagccgcc ttcctccttg gtcttcactc   7620
cagattccta gcatttcatt ctgtgtctct ttatgcagtg aggtttttgt ttgtttttg    7680
agacagagtc tcactgtatc acctaggcct ggagtgcagt ggcgcgatct cagctcactg   7740
caaccctcgg ctcctgggtt taagcgattc tcctgcctca gcctcccgag cagctgagat   7800
tacaagcaca catccccatg cccagctaat ttttgtattt ttagcagaga cagggtttca   7860
ccatgttgcc caggctggtc tcgaactcct ggcctcaagt gatccatgtg cctcagcctt   7920
ccaaagtgct gggattacag gcgtgagcca ccatgcccag ctcctagtga ggtttttgat   7980
gccttgctac atctgcccta gaaattgtgt gactacgatt ttggaaatgt tgctgtgtaa   8040
acttgtgatc atttctggac tccaggcaag aatcttgatg gctaaggtgt ggctgaacat   8100
gtctgattct ctcctggacc tgttttaggc caaactctgc tctgaaattc ctccgtgtgg   8160
aagggcgggc tggggagagc ctcccagctg gaatcttttg gatgcctttc tctgtgggta   8220
tctgatggct ggctctgatg gctggctgtg atggctgtgg ctggaaatca ttgttgacat   8280
gagtttcaca gatgcaggct ctgtccaaac tgtagcaaaa gctgcctgcc ccagccgagc   8340
tatgggcaat aaggtggttt aaggatatag atgaaggaaa actcaccctt agaataattt   8400
atccaaaatg ctgctgtgtt gtgggttaga ggacattttc tgaggtccca ggttcattgt   8460
ttcatttaag tctcaaaagt ccctccaggt gttggttcta attgtcaaag catgggggga   8520
gatgggctca tgggttaaag gtcttatccc agatttctgt atcctccttg caagcagcaa   8580
aggggtctgg atttgaatcc atgaccatgt ttctcctttg ggtttccatc acactctgtc   8640
cccgtgcact gagcaccctt tagttcatat gaccccctta ggcatgttac atgggcactc   8700
ctataggtgc ccatctggcc ctaggacttg gccaacacaa catggactcc agtttccatc   8760
tgcctctttg ccaggcactt ttgtgcagtg cacacactgt acaacagtag acggcaaccc   8820
tgagagccag agtagagcct gtcctagcac cggaatgctc ggtaaggatt tgtcgcagga   8880
gtgattccaa agccaatgtc ctccctccat atcagcctgt ttgtggctct gagaagctct   8940
gcccacatgt gaaagcttgt taagcactta agcactaacc cagagcttca gacagtacca   9000
```

-continued

```
gtcctttttc cccttcttta aaagcgatat gtggatggag gagtgagtga caacgtaccc   9060
ttcattgatg ccaaaacaac catcaccgtg tccccctttct atggggagta cgacatctgc   9120
cctaaagtca agtccacgaa ctttcttcat gtggacatca ccaagctcag tctacgcctc   9180
tgcacaggga acctctacct tctctcgaga gcttttgtcc ccccggatct caaggtgagt   9240
tggtggtgag gggcaggtg ttctggggtg cagctcttct ttgcctccct gattgccagg   9300
agctaccagt tactgtctgc acaatcaaac agaaatagac ctgttcttga tggttaacgg   9360
aaataaaagg cgcttgtccc agaagctcag gtgaggcacc accctgatta tgggaatcac   9420
ctgggaacat atacccagac ctaaaactca gatccacttc ccaggctgtg gttatatagt   9480
caggggggtg cagtatgggt attaggattt tttattttt agttataaag attttttttt   9540
gatttgtttt tgagacaggg tcttgctctg ccgcttaggc tggagtgcag tggtgcaatc   9600
atagctcact gaagcctcag actcctgggt tcaagcagtc ctcccacctc agcctcctaa   9660
ggagctggga cccacaggca tgcagcacca cacctggcta atttttaaaa attttgtgga   9720
gtgttgccca ggctggtctc acactcctgg cctcaagcga tcctcccacc ccagcctccc   9780
aatgtgttgg gattacaggc atgagccatt gtacccagcc actaagatga ttcttatttg   9840
gaaacacggt caagaacaac tgcgttcggt agtttaacct tttttgattg tggtggtttt   9900
agtatgcctt accactctac catagtaaga aatttgcaga ccatgtacac caacctttgg   9960
tgctcctggg gagaaagaaa gaaggctatg caatgcaatg catgctcaca gtccaaggga  10020
gagggaaagc tgtctaacag gattggtttt cccgtgtgct ttataagcag atgagtagag  10080
gagacagctc ttattgtcct agtggcaatt gggataggct gcaaagtttg ttagggtgga  10140
ggcttattcc gggaccaagg gagcccaaag aaacaagctc ctgccaggcg cggtggctca  10200
cgcctgtaat cccagcactt tgggaggctg aggcaggtgg atcacctgag gtcaggagtt  10260
tgagaccagc ctggccaaca tggtgaaacc ccgtctctat gaaaaataca aaaattaccc  10320
gggcatggtg gcgggcacct gtaatcccag ctactaggga ggctgaggca ggaaaatggc  10380
ttgaacctcg gaagcggagg tggccgttag ccgagatcac gccactgcac tccagcctgg  10440
gcaacagagc aagactctgc cttaaaaaaa aaaaaaaaaa aaagaaaagt aaaaggaaaa  10500
aaaagaggct ctggcctgct ggggtgcctg caaagtctcc gtggaagggt gacattcaag  10560
ccgagacctc cagggaactg tctcctggga gcacagagcc ctttgctcag cccccaggtg  10620
gctcagtgcc cccagccagc agactcagag cttgcatgat tctttggtgc tctctgcggt  10680
cttccaatga tgctgaaata aatggtgctt ggtgtctccc tgctgtagtc cccttgcttg  10740
ctttgctcac aggtgctggg agagatatgc cttcgaggat atttggatgc attcaggttc  10800
ttggaagaga agggtatgta tgggctggga ggatcagcca tgccctttttg acaagcattt  10860
actagcggtc ttggtaaaga cttgagattt gccttagttc taacacttag tgcccaacgc  10920
cttccttgtg ttgctcaacc tactcatgag cccaggagat aggaaatctc cgtcccattg  10980
tacagatggg gaaacagaat tttggaaagg agagccaagc agcacacacc cctccctgag  11040
gggcagagcc gagatttgaa ctgggatgtc atgactccag ggccctctcc ctccccaggg  11100
tccccttatc tgaaggcggt ttttctttcc agctcgacct cttgtgaccc ttagtttaac  11160
aagggccgaa gttaaagagt ttctgcgcct ggaccccaaa tgaagcaatc agatttctca  11220
tctccagtca ggtgtgggtc caagcccact agacaagttt gctcttccca gagcacattt  11280
ctgccttcaa gtcatcctgg cttgtcaggg ctgggggagt tctgctctag aaatattaga  11340
```

-continued gtggaaggaa aaagatgtgt tgggagctat ttttctttaa tactaaaagt tggttgatga 11400
atttgtcgtt ggccaagacc aaggagactg catttttaag gacatatgtg tatttatctg 11460
ctcagaaaat gttcattgct gtgtgctagg gatactgcag tgaacacaga ggtgtgaccc 11520
ttgccagcct tgtgagagaa gtgagcagat aagtaagcag aagggtgatg ctgtgtcgat 11580
gggaaagtac aggtgccaat gagaaggcac aggtgtcaag gagaagacac aggatgctgg 11640
aggctcatgc aggatggatc tccaaggccc aggggaagaa gggcctctcg gaggacgtga 11700
atccacatta agactttggg gataagtagg agcgccttag gcatggggac ccatggatgc 11760
gaggcctgta ggacacagag aggatggcat gaaggcctgt gcaactggag gggtggggat 11820
ggggacacta agagatggct ggaagtgtgg gggtggggac actaagagat gactggagaa 11880
gagggggtca ggagtggtga aaaatgggag aggagggcag gctgggcctt ttggatacag 11940
ggggattgca tcctgcagtg gtagggagcc actgagggct gctgcagtag gagtgagggg 12000
atcagaggag agctttggaa gccccctgga tgcgggacag gaagggagat accagtgtct 12060
aggaggccag tgaggcagcc agaggctcca ccaggatcag ggctgcgagg gtcatgagga 12120
ggaaaccaat ttgaaggagt ccaggggaat aggacttgga aatgaccgat gggacatttg 12180
ggaagaggaa gacagaagag cgcagtccca gcttctggct ttagcagttg ggcaagggga 12240
gatggggaga tgtgcccatg ggttgagggt tgaggacatt aggagggagc cggtatggca 12300
ggaagagctg gtgtgccaga gatgctggaa gcagcatctg cctgagaaca gatacctggc 12360
aatattccta agggaaagtg acatctcgga gggtgaggag ggcatctgat agggcctgga 12420
aagagccggg gcaagcatga atgtgaggtt atcttggggg gcaaggctca ggcgttgagg 12480
agcagcccct ggtctcttca gcctgaagtt ggaagccaga gttgggccag gtgcagctgt 12540
ggttgtctga agtcccccctc ccccagccca gtgtgccaat gctgtaagag caagggccgc 12600
tcactggtgc tggtggctga gtcccagcac ccaggacagg gcctggcaca tactggtgcc 12660
caatcctccc ttctgggtgc ttcttccaag gccttgtgat ggaagtgagt accctcttcg 12720
acatcagacc cagcttcaaa tcccggctct gctatgtatc ggctgcgtgg ctttagacaa 12780
gtcttttaac cttgctgtgc ttctgatttc tcagctgaaa aatggagatg atgataatgg 12840
tttctgtaag gccttatggt gaagcaccta gctcagggcc tggaaggcag gtgtaaccag 12900
tggttcagtt gttataaacg aacactaacc ctcgcctttg cacctcatga atccagatat 12960
gtagatggag cccacaaagc tagcaggagc caagctcacg tgtgtcctgc tttaaagccc 13020
catacccctt tctccgggtg acaaacacct gtgctcgttc tcttcccttc ccctcttccc 13080
cttgcatttg gctaataaca ggccagctgc ctgcctccct gcagtttggt agatgggtgg 13140
gtaatgacca ccactcccac gttcgcctga tgggcttgtt ttccgtgccc ttcacaggca 13200
tctgcaacag gccccagcca ggcctgaagt catcctcaga agggatggat cctgaggtcg 13260
ccatgcccag ctgggcaaac atgagtctgg attcttcccc ggagtcggct gccttggctg 13320
tgaggctgga gggagatgag ctgctagacc acctgcgtct cagcatcctg ccctgggatg 13380
agagcatcct ggacaccctc tcgcccaggc tcgctacagg tacccactcc tcggggtggg 13440
cacgggcagc accttgtttt ctttcttgtg cattatggag gaagatggta ctgccacatg 13500
ggagcgatag ggtgaggcaa ccatgacagg tggttgggaa catctccttc catgtgtaca 13560
gcctgggctg ctgccatcac tcccagcaca gcccccaacc cccccaatcc tggaaccttg 13620
ccaagtctcc cttcccgtgg ggtcatgacc aggaggaaaa caaactccag ctgagcccct 13680
tggggttccc catataggct cctgcctgtg gcagctgggc cctctgtacc cctttccaac 13740

```
tctgtgtccc taacatggca cctgagctcc tgccatcctg gatttcatgg accccaagga  13800
tgggggtcct gcatctggga cttggcctat tactcggagc tccttttcag ccgcctccct  13860
ccacctgtcc acccacctca aggctccttt cttgagacct ctcctaattt ctcccttccc  13920
ctaaacccac aattttgaac ctccatcgaa tggtgctgta gtttataatg tcatcaaata  13980
tcaaatggag acagtgctat ggtccaaatg attgtgtacc ccccagaatt tgtcttttga  14040
aatcctaacc cccaacatga tggtcttagg aggtggggcc tttgggagga gattaggtca  14100
tgaggaaagg gctgtcatga atgggattgg tgcccttatt aaacagaccc aagagaggtc  14160
ccttgtccct tctactgtgt gaggactcag aaggtggtgt ctatgaagaa ggaggccctc  14220
accagacacc aacacgtctg ctgccccttg atctgggacc ttgcagcctc tagaactctg  14280
aaaaatcgat gtttgttgtt ttataagcca ctcagttggt ggcattttgt tagagtagcc  14340
tgaacacgga ctaagtcaaa cagaagaacc cacaaaccag ctacagagtt gggcatttgg  14400
agaaattcaa aaatgagtca gacataactc cttattcttg aggtgcccta agagatggga  14460
cacagcagct gcccaggtgc attagtttgt tctcacattg ctataaagaa atacctgaga  14520
ctgggtaact cataaagaaa gaggttgaat tggctcacag ttgcacaggc tggacaggaa  14580
gcatggtgct ggcatctgct cagcttctgg ggaggcctca ggaaacttac aatcatggca  14640
gaaggtgaac gggaagcatg cacatcccat gactggagca ggagtgagag agagagggaa  14700
atagagggaa ggtgccatac acttttaaac aaccagatct cacgagaaca cactcactat  14760
caagagaaca gcaccagtgg ggaaatccgc ccccacgatc caatcacctc ccatcaggct  14820
ccgcctccaa cactgggaat tacaatttga catgagatgt gggcagggac acagatccaa  14880
accatatgac cagattaata cgatttgagg catcacgagg tcattaaaga gagggaataa  14940
aagactgggg ctccaggaag aaggctctgg aatccagcag agggtcaagg accagcttgt  15000
aaagctggtg gtgcctgaga agtacctagg agaacataga tgctgtgacg tttgatgtag  15060
ctgtttttg ttttgtgttt tggtttttga gacagagtct cactctgtcg cccaggctgg  15120
agtgtgcagt ggcgtgatct tggctcactg gagcctccat ctcccaggtt caaatgatcc  15180
tcatgcctca gcctcctgag ttgctgggat tacaggtgca caccaccacg cctggctaat  15240
ttttgtgttt tcagtagaga cagggtttca ccatgttggc caggctggtc ttgaactcct  15300
gacctcaagt gatccaacaa cttcagcctc ccaaagtgct gggatgacag gcatgagcca  15360
ccatgcccag cctgatgtag ctgtttctgt gcacattatt tgctgtgggg tatattcaga  15420
tttcttaata caagatgatt ctttgcctca tgacttacac accattttct atttaatttc  15480
agctatgata ttggaaatgg acatgtcttt tcaaggaaaa taaaagcagg ctttctggaa  15540
tggcgacttc caaacatatt tgtcaattta aaggagctgg gagtggggac cctatgcccc  15600
gtaagcactc tcttagctgt tcttggctgt gctccccgct tcagcttcac actgcccttg  15660
ctgtgaaggg agaagcctgg gctgggcgcg gtggcttaca cctgtaatcc tagcactttt  15720
ggaggccgag gtgggtggat cacctgaggt caggagttca agaccagcct ggccaacatg  15780
gtgaaactcc atctctacta aaaatacaaa aaattagctg ggcatggtgg caggtgcctg  15840
taatcccagc tacttgggag gctgaggcag aagaatcgct tgaacccagg aggcggaggt  15900
tgcagtgagc cgagattgcg ccattgcact ccagcctggg ggcaacaaga gcaaaactct  15960
gtctggaaaa aaaagaaagg agcagcttgg caaaccccac cttgtcgctt ctgtgagtgc  16020
ctctgaccct ttggctgcca ggacgggcgt attttatgga aatgctaagc accaacagag  16080
```

```
taaagtggtt tggtttttca cagtggtggg agataatagc tccaaattgt ctttttcagc  16140
actgagtgaa gaaatgaaag acaaaggtgg atacatgagc aagatttgca acttgctacc  16200
cattaggata atgtcttatg taatgctgcc ctgtaccctg cctgtggaat ctgccattgc  16260
gattgtccag aggtgagcat tttaggtggc tccgtgtctt cctcacaggg ttgatatgag  16320
gatgaaacaa gatgatagat catggtggca tgtagtctgg gacccggatt gtcgtgccac  16380
agatcacagc tcacagtcta tgtgcaatgc ccctgaatgt tgcccacctg tcctcaagcc  16440
acacatgcac ctgtaactca gtgcaagccc agaaactccc cgtggggact cctagagctg  16500
tcagtggcct cacatagcag ctggtccagt ctcttgtgat tgcccaagga aactgaggcc  16560
tggagagctt ggggtcgctg ctctgaggcc atagagatgc ctagtagaag ggccaggcct  16620
agaagcagga tccttgctgc ccctctgagc tgtttccatt taaaatcaca tgaaggccgg  16680
cgccgtggct cacggctgta atcccagcat tttgggaggc caaggtgggt ggatcatgtg  16740
aggtcaggag tttgagacca gcctggccaa catggtgaaa tgccatctgt actaaaaata  16800
caaaaattag tggagcatgg tggcacgtgc ctgtactccc agctacttgg aaggctgggg  16860
cagaagaatc gcttgagcct gggaggcaga ggttgtagtg agccaagatt gtaccactgc  16920
actccagcct gggtgacagg agagaaaccc tatctcaaaa taaaatgaaa ggtaatgaaa  16980
tgaataaaat aataaatcaa gtcacggccg ggcacggtgg ctcacacctg taatcccagc  17040
gctttgggag gccgaggtgg gtggataatg aggtcaggag ttcaagacca gcctggccaa  17100
catggtgaaa ccatgtctct actaaaaata caaaaattag ctgggcatgg tggtgcatgc  17160
ctgtaatccc agctactccg gaggctaagg caggagaatt gcttgaagca ggacctagga  17220
ggcagaggtt ggttgcagtg agccgagatc atgccactgc actctagcct gggctacaga  17280
gcgaaactcc gactcaaaaa aaaaaaaaaa aaaaaatcaa atcacatgaa agtagaacat  17340
agggaattcc atctttcgtt ctaggcatag tttgttaata tgattcagag ccagcagtta  17400
ggagaacaca gtgtgactct cctagaactt cttgattggg cttcctctga ttgggtttcc  17460
tctgattggg cttcctctga aagtgggggg gatggggggt ggggagcaga atggtcagag  17520
cttggctcag cagtcagact gctcttcttc aaatcctggc tgcattgctt actacagctg  17580
tgtgactcca gatgactgaa tccacctctc tgtgctgcag cttcccgtct agagagatca  17640
cctggagcag agggtggtca ggagactcaa tctggttact gactcacagt gcaggagtac  17700
tcatcccata gtaagcatcc agctagagat gttgatttct attttcaggt aataatgatg  17760
atcgtaaaat tagagacaga taaaaggtat gggcattaga ccagggcact gcaatttcta  17820
agctgtgtga cctcaggcaa gttactcgac ttctctgagc ctcagcggtt tcatccgcaa  17880
tatatggata ggaaaaccga cctcagtggg ttgtctgaca gtggagggca cttgattaaa  17940
aaaaaaaaaa ttaccctggt ctgaatatta ccctggactg aaagaaaaat attgagctaa  18000
tacaggcatc aggaatgggg ctgcagggag tccagggaag ggagaacgaa gagcctgaag  18060
gtgtgaggag gtgcgagtgc tgatctgtct gctacaaaga ggctgctgag cctcctgtgg  18120
atgtggccct ggacttggca gtttaatacc tgagctgtta aaataacctc agatgctgtg  18180
ttctttaagg ggtaggattc agattcctgc tgaaatgctt ctgaaaggga gggaatgagc  18240
cagcccatcc ccagttgctt tttaagatca ttgggaagtt ctggtcttgc catttgtccc  18300
tggaccactc ttaggtcctc ctgccccact tccatctggg tgtgtgccct gggctgtcca  18360
ccacacagct acatcctgcc atcttccctc ctggagccac tgtgccatgc atggatctgt  18420
agcttcattt ttcttggctt ttccctggtt tttctggagc agagtctcta gtaaactccc  18480
```

aaggaagaaa acgtttgact ttatgtgtgt tgggaaacgt gctttttttc tattacatct 18540
cagtgatagg ttggccatgt ctagaattgc aggttgaaaa tcatttcctc tcagtatatt 18600
ggttagtgag aagcctggga ctgagacagt cacattctca cttctttgca ggtgagtgct 18660
cttaggactg tctttttatc ccttatactc tgaaatgtca tatgtcttgg tgtaagtcct 18720
tatttcagtt attgagctgg acaagtactg gagacccctt cagtcaaagc cttctgtcat 18780
tctccagctc taggaaatta tcttctattg ttatttctgt tattccttcc cttccatttt 18840
ctttttcttt tttttttttt tttttttgag acagggtctt actctggtgc ccaggctgga 18900
atgcagtgac ctgatcatgg tacactgcag cctgaacctc ccagactcaa gtgatcctcc 18960
cacctcaacc tcctaagtag ctgggactgc aagcacacat caccacaccc aacaaatatt 19020
ttttaaaaat tttgtaagat gggatcttac tatgttgccc agactttttc ttcctcttcc 19080
tggggctctt attaggaaga tgtttgactt cctgggttgg attcctgtct ccgtgtctga 19140
ctttctctct ttgtcatatt tttcatcact cgttgtcttt ttgcgtctgc tctgacagat 19200
ttcctcaaat tttgtcttct agtcctatcc tacagttttt actttcagca aatataattt 19260
aatctccaag agtactctct tgttcttttt tcttagcatt ctgttcttgt tttatggatg 19320
taacattctc ttggaatatt tgctgtcctc tagatcatcc cttctccatt tcttcttggg 19380
ctagtttttc tgtttcttca tctttctctt ttatgctact tattctgggc gtgttcttgg 19440
tgggtttttt cccatatagc aacagaggac ttggagctca gggagaaaag ggtaggtgca 19500
tcacctggca gagctcccag acagtgacag gcaggctgcg ggaaggatgt ctacttggcg 19560
gtgctaccgc tttcctagaa accctttccc tggagctggt tgaactgttg ggttttgccc 19620
tggtggtgaa cgctggctcc ccgtgctctg cctgtttcat caccagcccc ctccccttct 19680
gcctggggtc cagtaatctg ttgaaatata tatcttgctc attggtgagc tcctgctcct 19740
tcctcgttgc tcttgcagat ttatcacttc tcgtaaggct gcgcttgtac ttggggattt 19800
tctctgtgcc acactgggaa acatagggtg gttgcatgct gcagtcctga gcacttattt 19860
cactcacatc tttacacgaa gatttggtgg gtgtttactt tgtttttagt aagttagtct 19920
gtcatgtcct ttgatccttt ttttttgttt tttgagatgg agtctctctg tgtcctccag 19980
gctggagtgc aatgtcgcga tctcagctca ctgcaacctc cacctcctgg gctcaagaga 20040
ttctcctgct tcagtctcct gagtagctgg gattacaggc atgtgccacc acacctggct 20100
aatttttgta tttttagtag aggtggggtt tggcatgttg gccagcctgg tctcaaactc 20160
ctgacctcct gacctgcctg ccttggcctc ccaaagtgct gggattacag gtgtgagcca 20220
ccacacctgg ccctgattaa tcttttaatg cccagtctct ccttcaaaag ccggctcctt 20280
tctctccctc gccttcctag attccttctc cactccccag gatcagcctc ctcctcccca 20340
ccccaccact gctgggggga tgtctgtggt caggcattta tcagagaccc tgaggtgggg 20400
gtcctttatg tgtctggggg atggagagtc tagaggaggt agcgttcaga cctctccatg 20460
gtgcctctgc tgggctcaca tgtgaccaag cacagcaaac catgaggcag gggatggtct 20520
tgaccatgag agcccttgca gcagctgcca tgggcctcag ctcctctcca agctgggaag 20580
agccctgaaa agccaaggtg tttttttttc cctctttatt tcagtgtaag tcccttgagc 20640
tttcttgaac cagaagtggg ctcattttgc tttagagatt tcaggtgggc ttgtccttgt 20700
cctagcatcc cagatccacc ttctgggaag tcatcagatt ggaggtgatg ttggcagctt 20760
ttgtaaacaa agggtagtgt tgtaagctgt tgtgtctgcc tatgtgtgtg tttgtgtact 20820
tggtctcatc tctgcagact ggtgacatgg cttccagata tgcccgacga tgtcctgtgg 20880
ttgcagtggg tgacctcaca ggtgttcact cgagtgctga tgtgtctgct ccccgcctcc 20940
aggtaaatac tttggctgtg ggtgtgtggg ccggacgggc acctctctca tctgatgagg 21000
cctcacacga cattctagaa acagctggct gaacaccaag caaggagctt gcccttgggt 21060
gtggggaccc tgtctcatgg gaggcagctg agtcagtcag aggtcctggc acacctgctg 21120
agagctgcca cccaggccaa cctgaaccgg agcctgggaa gacttcccgt tggatgagtc 21180
tctttgaggg cagcattgat ggtggaagag cagagaggcc ccagataagc agggaaaggt 21240
gcttcagaca gagtggctgg gatgaggact ggggagtgtc agatagcgct ggcgtgtctg 21300
agcgaaggag ctctggcacc catggcacag gaaggaggtg ggaccctgga ggggcagggc 21360
tagcagagct cctcggagcg tgtggctagg tgcctggtaa tgcaagcccc ctgtcctcca 21420
ccctctgttg tactgagtca cagtctccgg ggtgaagccc agcagtctgc gttgacaggc 21480
cccaggggat gccgctactt cctgaattct gaattctgga aactgagccg gagttcaggg 21540
cctggctccc attaccaggg ttggacgtta tcctgaaaat cataggcctt ggtttcctca 21600
cttggctaac aggggtgatc cccatcccct caatgggttt ccgtgagctc ctgagagccc 21660
gtagcatggt acttggcaca tgctgggcat caggaggtat ggcctctctt gctattgttg 21720
ttattggtag acacagaagg atttaaaagt aggggaatgc aaagatccga tttgctaggg 21780
aagagggcag tagtggccaa gtagagggtg gatcctgggc cctggctggc agcaggcagc 21840
aagggggggct gccagggccc aggcagggac gacctgtaga ccgagaggct tcctaaggct 21900
cttggacagg aggaggtgtc ggttccaagc ctgaggagcg gggcagccct ggtgactggt 21960
ggtcagtggt gccaggcggt gggtggtagg acaccctggc aggcaagtag gtttgtgtgg 22020
gggaaactga taggcccctc cagggattcg ttggtggaca acacctgtga tgtccagtgg 22080
gaggtgtcca ggtagctggg agggccacag gcttggaaga cctaggtggt gacatcagcc 22140
cagcactgag ggctagaaga agctgtgtct ctggctgtga cggcacccta gagtgtgtgt 22200
ggtgccctct actggccggc aatgtgggtc caccgtagct cagactgcac actgcagcag 22260
cgggaacggc ctctaagcca acttcctcca tgtgtttcag gtcccaaatg ccagtgagca 22320
gccaacaggc ctccccatgc acacctgagc aggactggcc ctgctggact ccctgctccc 22380
ccgagggctg tccagcagag accaaagcag aggccacccc gcggtccatc ctcaggtcca 22440
gcctgaactt cttcttgggc aataaagtac ctgctggtgc tgaggggctc tccacctttc 22500
ccagtttttc actagagaag agtctgtgag tcacttgagg aggcgagtct agcagattct 22560
ttcagaggtg ctaaagtttc ccatctttgt gcagctacct ccgcattgct gtgtagtgac 22620
ccctgcctgt gacgtggagg atcccagcct ctgagctgag ttggttttat gaaaagctag 22680
gaagcaacct ttcgcctgtg cagcggtcca gcacttaact ctaatacatc agcatgcgtt 22740
aattcagctg gttgggaaat gacaccagga agcccagtgc agagggtccc ttactgactg 22800
tttcgtggcc ctattaatgg tcagactgtt ccagcatgag gttcttagaa tgacaggtgt 22860
ttggatgggt gggggccttg tgatgggggg taggctggcc catgtgtgat cttgtggggt 22920
ggagggaaga gaatagcatg atcccacttc cccatgctgt gggaaggggt gcagttcgtc 22980
cccaagaacg acactgcctg tcaggtggtc tgcaaagatg ataaccttga ctactaaaaa 23040
cgtctccatg gcgggggtaa caagatgata atctacttaa ttttagaaca cctttttcac 23100
ctaactaaaa taatgtttaa agagttttgt ataaaaatgt aaggaagcgt tgttacctgt 23160
tgaattttgt attatgtgaa tcagtgagat gttagtagaa taagccttaa aaaaaaaaaa 23220
atcggttggg tgcagcggca cacggctgta atcccagcac tttgggaggc caaggttggc 23280
agatcacctg aggtcaggag ttcaagacca gtctggccaa cactcgagat aacttcgtat 23340
aatgtatgct atacgaagtt atgctagggt aactataacg gtcctaaggt agcgagctag 23400
ccatgtgtcc agttcgcagg ggggatttgt ttgcatgttg acttccctcg ttggaaactt 23460
cagagggttt ggttttgttg ttgctacttg ggaattcggg gtgtttgcac aggcttacca 23520
gttaagcaag ttcaaacagg taaacatctc agacgtgttt tgagcatcac accaacgctc 23580
agaaggcttc tgacttttac actgggtgtg gcggcacaca cctgtggtcc cagcactgtg 23640
gatggaggct gaggcagaag agtcaggaat tcaaacctat cctgggccac agagttagtc 23700
aaggccagct tgggctttgt atagagacca tgtctcataa ctaagatgtg tctggggacg 23760
taactcagtg gatagtttgc atggttcaat ccctgtgcta ccattaggaa ggagaaggga 23820
gggaaggaga aagagaggaa gggaaagagg gaaagggggg aaagagagag aagaaaggag 23880
agggggagaa gaagagaggg aaggagagag ggagagggga aaaacagaaa gggcaagagg 23940
aagagagtga gagggaggga aggagagagg gaagaagggg gagaggaagg gagaaaacaa 24000
gaggggaaga gagagtagga gggagggaag gagggagagg aaggaaggga gaagaaggaa 24060
gggaaggaag gagagaaaaa gaggaaagga gaggggagag aaggagagag agaggaagaa 24120
gaggaggagg aagaggagga ggaggaggaa agaaagagga gggtgtgtta tctagaggct 24180
ctggatgtac cttctgccct ggactactcc tggtctcctt atcctgtcca atctgggccc 24240
atgcctcagg gacatgaccc agccctgccc ttccatttct ttgcaccctc tttttcttgg 24300
cactctccct tgtttttctg aagcgaagcc ttcctaaatc cccagggaaa cagcagcctg 24360
ccagcctcct cagagcctca cctgttcctg cactggctgc tgggcagctg ctcgcaggcc 24420
tgcgggcaca gtctgtcctc tgagagccta gctggggctc cgtaagatta tttattcacg 24480
acttccacct gctcttctcc tctgtggcct gtaggttctt ggtctttctt tccaccgact 24540
gctactttct cagtcaaagg ccctctctct cctggtttgg ggacatgacc atctgtaatt 24600
aatgcctgta gtttcgtctt tcctggggct gtttcttctc tcttatgaga ctcttgtgag 24660
atgctttgcc tggaactctg tagaccaggc tgaccttaga ctcacagaga tccacctggt 24720
tctggcttct gagtgctggg gttaaaggaa tgcaccatcg ttgcctgaca tagaaacttc 24780
tttattgggg cagatgggaa atgagaaaca gatgtcttca gggtctgagg gaaagcctag 24840
agcagagaag ccttcatcct gggagaaaga acagatcagc agcttatgaa gttgttaggg 24900
agtgcccagg ggaatggtga aggagaggta gtccccaaga gcgcccccagc ggggccggta 24960
gatctggaag atggtgatcc aggtggtgag aatgaatgat caccaagaag aggaagccca 25020
cagctgagcg ccaaacatag cctttgattt ggctctgctc tgtgtaggct ggggcgagga 25080
aagcctctct aaagaaccag aaaatgttga ccaaccaaag aaaaggcagg aacgcaaatc 25140
caccaagata gtacttccgg cacaggttca acttctcctc attggatacc cgctccaagt 25200
tcatagttgc gctggagccc ggtggtccta agggtctgca gagcaagacc caaatgacag 25260
gcgcaagatc acgagcaacc acgccccagt gcggtttatc ccttctgcct gggattcctt 25320
tgtgggagat ttgcgggaga tgccgcagtt ttcagtggag tttgttgtcg ctttattttt 25380
ttcttctcct gcccagcccc cctcgcaccc caccctctcc gccagttttc agtggagttt 25440
gttgtcgctt tattttttc ttctcctgcc cagccccccct cgcactccac cccctccgcc 25500
gaaacttctc tttcttacat atttcagccc tttggctttt tgcctccaat ctgaagtctt 25560

```
ctcagcttta ccctccagtt ctacccttcg gggttttaac attagcagca tgagtgagca  25620
tgctggtcct ttcttctggt tcctttactt gagcattctc agcttggttt gtgggtgttg  25680
ggagaagtgt attgggggtg tgtctgtgga agtgggtgtg tctgtatgtt gaggggtatt  25740
tttactttta tttatgtctg tgtgcactga ttggttgatt gattttgtgt gtgtgtgtgt  25800
gtgtgtgcgc gcgcacgcac acacacacaa actgtttgag cagacaggct agccttgact  25860
tctagatcct cctgcttcac cctcttagca ctaggataat agatatgcgc ctctgtgctt  25920
aggtgagtgt cctgccgtcc tgtctttctt tcctggctat agcagggcca cagcctatgt  25980
gtggaggtca gaggacaact ctcagaagga gttggccctc tccttccatt ttctgggtcc  26040
taaagatcag actcaagttg tgagacaggg cagaaaacgt cattaccctg tgaaccatgt  26100
ctgcctcctg tgtaagtact tctgagacag aattctagtt ctgtagccca agctggccta  26160
gaacttactg tgtagaccag actgaccttc aactcaagtc ggacctctcc cctgcatgca  26220
gggtgtaggg cttgattcac ccctccccca tcccactcaa ggtcttgtat taggggcatc  26280
agcctagctc ccaggcaggg agtagtgctg agtcagcctg cttctggagg aagaagggct  26340
cccttgtgag ggtgggggtg ggggggtgct tcctccttgt ccttcctgga ggattagaca  26400
caaggccaag tttgactgta gtaccagtgc tttgtggtgt ctggctccct cccctctggc  26460
tgaggctatg ggatctcata gccagatcag tagttcacac ttgcagccag ctcagctgct  26520
tagggggaag cccaggaggt ctagaccagc ctgtggagag agactccgtc ctccctgctc  26580
cccgtcactg tgctccctta gcatgggagc acctctggat aagaggtgca gcaagctagg  26640
cttagcttgt cctcacccca ccccacgtcc tcgaatttgt atcttagcac attgcacagg  26700
cccaaccttt agtttctcta tccaaaccct ggggcagctt tactgatcca gtgttcccct  26760
tcaacagctt ccccaccgac gtcatgataa atcgaattaa gtcgaagttg taaaaagtca  26820
ggtttattgg ggcagctctg ggtgggctca ccaatgtcac aggaaggggt cagcaaagtt  26880
gtagaagttg ccgggctgag ctccagtaga ggctgctggg ggagtggggg aggggagtcg  26940
tgaagtgatg gttattcatt tggtaagttt agggccctgt aggtgggtct ttaggtccag  27000
cggttacttt ggaatctgga actgggagct gactttgtcc agtgttttag atgggctttt  27060
gcaagcatgg gcgcctggtc agaagagaaa gggggtaggg tctcttggcc cataccatct  27120
taccggtgtt ccaaacttcc agtctgccac ccctcaaggg aagttcttac cagcaactta  27180
cctcttgcca gagtctacag agggttttgg ccccggtggc tccagttgga ttcctagtgg  27240
ccctgcaccg ctggcttcta tggagcctag gcctcggcca gcacttgccc tcaacccttg  27300
agaaattagg tagacccacc ccacgctgct gcctttcccg ttcattccca ggagctttct  27360
ggaaccttat atggcctgtg tgctttaaga gatattctca gaggttcacc tttgtgctga  27420
tatcccacat atgccttagg gaaggtatca gattgcggtt agaggcgata caggcagctc  27480
actaggatta aggtcgcggt tgtctagttg gttgtgagcc accacttggt tgctgggatt  27540
tgaacttaga acctctgaaa gagcggcccg tgctcttagc cactgagcca tctctccagc  27600
aatgggactg ctttttattg cagtgttggc tgctttttat tgacctcttt tttttttttt  27660
ttctggttta atctttacag tgaacccttg tgtccatgtg atatttgtgc acatgtacat  27720
atatctgcat ctgtgtttct atgtgaagta tacatgcatg gtgtctgtta tgaaaaataa  27780
cacaggatta aagggccacc tggagggccc atgccaaggt gtctccctga gaaatcccac  27840
catgtgacag acctggctgg tataagggag gtctattgtg gggcaaggga ggggagacag  27900
aaagggggag acagagacag ggaggctggc agggaacatg tggggacaga gaaagagaga  27960
```

gagaataaga aaggggagat agagaagggg accggggtaa catggtcctc ttacaagctc 28020
ccaggccacc cacacctggt ggcagctcag gtagcaatgg aggcaggtga tgacctaagc 28080
tgttgctagg tctctgttgt taggtccctg ggaggaaacc agaatcacct gtaagccaat 28140
agtgtccttg gcttccttcc cacaggctgg tgacatggct ccctgatatc caggatgata 28200
tccagtggct acaatgggcg acatcccagg tttgtgcccg aatgacgatg tgcctgctcc 28260
cctctaccag gtaaatactt gggcccaggg tgtgtgggcc agataggcat ccctcccggt 28320
tgttcccaga gctcttaggg tcagagcttg ggtggtgaca gccttaacaa gccaggctca 28380
gccgcctgtc cccagcatgc cattaaagaa accggtagca gagaaagcag gtttattcga 28440
atataaaaag gttcaagccc ccacccggtt aatctttaag ataccaacag gaggcttaag 28500
tttaaacaga gttacacata aacagtctga atcagggcgt ggtcctgccc accattgtct 28560
gggcttcaag gttccttctt tctctcccta gcatgagatt cctgggacaa tcccaattcc 28620
ttggcctcca ttgtatcaaa gggctgaaaa ccaaagggaa ggcacagctg tctcttcagc 28680
atgcctcttc tgccagaacc actgcaaggt ttggtgctca ggctgtgcaa acattctagc 28740
aatgtttgac tcagtgtcaa gcaggtgaca aggaacatgg tgctgtgtgg ggggaaccca 28800
tggcccaggt gagggcttat tggtgggtga agctgtgggt gttcaggtgg tggagaaggc 28860
cttaagggat gggactgaca cctcagcact gaaggcagga ggaagctgtg gctctgggtt 28920
gcacccctgc ctggctccac cctctctggc atctgtagaa gttacagctg gttcttcctc 28980
tcagccccat gctcccagaa ataagactca gacccaaatt atagttacaa ataccttggc 29040
catatagcta ggctcttctc agactagctc ataacttaac tcattaattt taacctccat 29100
cctgccacat ggctggtggc ctgtgctcag gtaccatgag tccagctctt cacatctttc 29160
cggatgaatc ttccataatt ctttctgcct cctggatgtt ccaccttcta ttccaccttt 29220
tcctataggc catggttttg tttttgtttt ttttttccaa atttaattta attaattaat 29280
ttatttattt ttggtttttc gagacagggt ttctctgtat cgccctggct gtcctggaac 29340
tcactatgta agccaggctg gcctcaaact cagaaatccg cctgcctctg cctcctgagt 29400
gctgggatta aaggcgtgcg caaccatgcc cggtgtggtt tttttttttt tttaattgac 29460
aggtggatgc atctatataa tccataacat attctctcta caggtatcta ttaggttttg 29520
ggtgaggtgt ggagttctag ggaactctga gagaaattcc tggggagtaa gtggtttatc 29580
aagttgattg gaggagtttt taatgctatg gacagacaga cagaaggaca acagcatagt 29640
cggggctacc agggagttca ggccccggca tcggagatag aagcaggatg gggtctttga 29700
agagattctg agcccacaca gcagaggagg gactctctct ttagagcttt tgaggatgag 29760
ggaggttgac tgcaagagcc tacagccagg ctcgaggcag gcagggggtg gggagcagga 29820
tgtaaacccc ttcgatgctg acagactcac ttctggggta aaatattatg agatgcctgt 29880
cagtgtctgt gaagagacct gagcagagtc tggattctga catcaatcat gttcttacaa 29940
tactgaagac ctgagagcct gcaatcttgg tttgtaaatt gctggtctcc gtgcttccag 30000
tgaacttgga cattcttctc atggttggtc caggagaggc caaagctgag ggcaccctgc 30060
cttccacccc cagtccagct tgacctttta tctggagcaa cagtgtctag atgatgggtg 30120
ggtgaggggt gctatactgt ctgtccctct gggaagggtt ctgttacttt tggaggcagc 30180
taggaagttt ctctgtgcag ctgccccctg gtgctgtgtg gtgacctcat tgcctgtgac 30240
cccaggatca caggatctgg gctaaagtgg tagtccatag aaaccaaaga caatgatttg 30300

```
gtgtttagaa agctactctt ggtctgggtg aagtctggtg cttaagggct atcacaaaga  30360
gcgtgtcaaa ccatctctca gcctgtgagt cagtggggag cccaagggca tcagtgtttg  30420
gaaactggaa tccaaaccgg gcaatctcgg aaggaaactg tttaggaatt gtgatgggac  30480
gggccgtggc tgtctctgaa aagggcctgc cagataactt attactttta aggacacctt  30540
tggctcttac taatttataa agcattttat ataaacacac cagggagtgc atggtgaact  30600
acacgtatga tcagttaagt ggggctagaa ttaggtaggg agagcatcgg acctctgcct  30660
cctcaacctc aacttgcttg ctttctccac tggctccaaa tctttgtata gtcatcagcc  30720
atgaccacct ctctccctcc ccatctacta ccagcagcgt taatgggaat aagtacccac  30780
ttctctcagg tgtactatac agctgtgggt gtggtgtgtg tttcctgtaa ttcacacttt  30840
agaaaggaaa caagcaaaca aaagaaacca ggtgctgccc atactcctaa gtgtagacag  30900
tgaaggtgtg tgtctcccat gcctgagtct cctggaggcc tagtgagctc caggttcatg  30960
caagcacatc aggaggaatc atataatctc agcacggttg atccagatgg gataagaaag  31020
gactctggga gagagaatgt ggttctagag acaaagtgtc taggctacac agaagataag  31080
actgtcccaa ggaaagaaaa gaaaccagga actagggtgc agctcagttg tcagaggact  31140
tctctaggct tgaagcccag agtccaatct cagcacctta taaactgtgg agtgacaggc  31200
agtgacatcg gcctgtaatc ccaacactca agcagtagag gcaagaggat cataagttca  31260
aggtcttcct tggctattta gggagttgga ggttagctct ggctacatga gaccctgtct  31320
caaaaaaaaa aaaaaaaaaa agtagaaact tctgccttgc tttgagctgc ccctttctgg  31380
acgtttctca tcagtagaga atattcctgc caccctatca gacaaaactc ccactggttt  31440
ggagtctctc cattctcagg aacacctcag gagtcagaca gtgagcagca gggagcaatg  31500
tcttgacttg taagcccctt agcaaggctg gttcatttgt ttattaaaag caggtgtggg  31560
tgaatttatg caaatgagta tgcaaactag tggaacagca gaaggattga atggatacac  31620
caaaaataac cacaactgtt taagggaaaa gggtccataa taaatgtggg gaacaaaaaa  31680
caaataaatg tgattttttt t                                            31701
```

```
<210> SEQ ID NO 69
<211> LENGTH: 23264
<212> TYPE: DNA
<213> ORGANISM: Artificial Sequence
<220> FEATURE:
<223> OTHER INFORMATION: Synthetic

<400> SEQUENCE: 69
```

```
atgtacgacg cagagcgcgg ctggagcttg tccttcgcgg gctgcggctt cctgggcttc     60
taccacgtcg ggcgacccg ctgcctgagc gagcacgccc cgcacctcct ccgcgacgcg    120
cgcatgttgt tcggcgcttc ggccggggcg ttgcactgcg tcggcgtcct ctccggtatc    180
ccgctgggtg cgtctgggga cgctgcccgg gctccacgtg cggagtgggt gcccccctagg   240
ccggggagcg ggggatcccc aggggtcgcg gggccctgga ggagcgggca tcggacgcgg    300
acacggcggg gtgcatcccg agggccccct ccgaggcaga tgcttcctgc gggggcgctg    360
ttcctgggcc cgggaagggg gcgttggaac cccgagcggt ccgggccgaa gcctgggact    420
ctcgtgcgtc cccacccta cccccatcag gcgcccgtgc atgaagggag accctcacct    480
ccggactgag agtcggagcg tctcggagcg acggggagta gggagcggga cccggggcgg    540
agggtagtgc tggcccctgc ggactccggg tcccctgtgt cctctcggga ggggctggac    600
gggctgagct gccgaggggc cgatttgccc tgggccggac aaagagtggg gctttggccg    660
```

```
gtcccccacg gtgggctcct tccctctggg gattgaggga ctcaagacac cccgcgcctg    720
cgcttttctt ttcttttttt cttttttttt ttttgagacg gagtttcgct cagtcgccca    780
ggctggagtg cagtggcgtg atctcaactc actgcaagct ccacctccca ggttcacgcc    840
attctcctgc ctcagcctcc cgagtagctg ggactacagg cgccagccac caagcccggc    900
taattttttg tatttttttag tagagacggg gtttcaccgt gttagccagg atggtctcga    960
tctcctgacc tcgtgatctg cccacctcgg cctcccagaa tgctggggtt acaggcgtga   1020
gccactgctc cctgctgcct acgctctctg ggtcgcagcc cagccttctg gggctgggt    1080
agcctcccag aagggcaacc ctgggcatcc tccagggcag gctaactgga gtctagtggg   1140
gaggggtacc ttgaaagagg aaagttgttt cctcctcctc ctcctcctcc agtgtttggg   1200
acccttcctg ggggctggag tgcatccctg gacacccccc aatcccatcc tcttctctag   1260
tttccactga cctaggccca ccctcccctc tccggctcag tactcctgga aatgagattc   1320
cgtacatttg aatcttgtcc taatgaaata tttgtccatg tgggtacctg tgtgtgtgtg   1380
gtgggggtgc agacggaggg tttgtttctc actagctgga actactgggg tgtggtatgc   1440
ttcctgggaa tttgtgtgcc acagtcctgg aggcgaggag ggggttgtga gccagtaggc   1500
aggggctggg gcaagtagca ttgtgaagct attgacaccc agacgtcccc aggcaggaga   1560
ttatgccccc attagccccc ttttatctgg gcttccttaa caatggactc tttgccctgc   1620
ctgccagagc cagcagggag tgactgttca gtggtgagga agcgggcaga ggaagccctg   1680
ccattgggta ggagcagtgg gcagcccctg ggctgactgg gaggtgggga ttagggatta   1740
gacagtcctg gctgtctgcc ttcccctaag ccagggggag aggagcaaag ggcacgaaat   1800
gtggcctcca ggaggattag accgccacat gatcatttgc acaccctggg gtttagcaac   1860
aataaaagtc agcttttttg tatcccaagg tggcctgtgg acacccacat ggacaaatgt   1920
ttacactggg acagaattca aatgcagagg tcccaggagc ctaaagtaca ctcactctgg   1980
tatagaaagg attccttact gggcagagga caggtgcagc ctggggcttt cccaggcagg   2040
acacagggag gctcaggaac caccaagtcc ctggaaggtg gatctggagg tgttggcagg   2100
agccactccc tgggttccag ggctccaggt tcctgcttta accccctgtc tcacagaggg   2160
ctgtgcactt gggggctgct gagcatgtcc cagaggctgc atcctggaca cagcacctca   2220
gtgcatctga gctgaggcta acttggcagg agggacaggc agaacctgcc agccacgtgc   2280
aattccaccc ctctggccac tcagggaagg agagctgtga gtcaagatca gatttgggtc   2340
aggacaggct ggggcctgcc tgtccctgtg catcccaaga tttatggctg gccaggggtt   2400
gggctgggag gggtggtctt gcatgccagg agagtgcaga tcagcctgag aggccaggcc   2460
agtaagtgag gtcagatctc ctgcacctga tagcattaag gccatctaca ccaaagctct   2520
aatgctgata tgttcctggc ctctatgtgg ggcatggagg tggggcatgg aggtgaggcc   2580
tgctcgcctg ggcttctgga agtgggagac tcattcctgt ggctgaggcc tacagcagtg   2640
ctgtgtggta ggaatacact ggaagccatg atgtcattgt gcatttctta gaagccacat   2700
tgaataaagt aaaagacaca ggtagaatta atttcattga gcccaatata tccaaaataa   2760
tatcattttc acatctattc aatataaaaa tttactaatg agatatttca tactaagcca   2820
ctgaaatcca gtttgtatct tacacatctc agttttgacg agccacattt caagggcgtg   2880
atagccacat gtggctccca tagtagacag tactggtcta gagaaatgtt ggtggcatcc   2940
ttgctgtctg gtttctggcc ttgccaaaag tattaccatc ccagtgtggt acattctttc   3000
```

```
atgtatttgt ctcctgtccc cagagcagac tctgcaggtc ctctcagatc ttgtgcggaa   3060
ggccaggagt cggaacattg gcatcttcca tccatccttc aacttaagca agttcctccg   3120
acagggtctc tgcaaatgcc tcccggccaa tgtccaccag ctcatctccg gcaaaatagg   3180
catctctctt accagagtgt ctgatgggga aaacgttctg gtgtctgact ttcggtccaa   3240
agacgaagtc gtggatgtaa gcagtttgct tatctggacg ttgtcaagtt agaaaagctg   3300
ttttgggatg ggtgtggtgg ctcatgcctg tcatcccggc actttgggag gccgaagcgg   3360
gtgggttgct tgagcccagg agctcgagac caacatgatg aaacccagtc tctacaaaaa   3420
ttacagaaaa attagctagg catggtgttg tgggcccata gtcccagcta ctagggaggc   3480
tgaggcagga gaattgcttg agcctgggag gtggaggttg cagtaagtca tgatcatgcc   3540
actgtactcc agcccgggtg acagtgagat gctgtctgga aaaaaaaaaa aaagaaagac   3600
tgttttgttt tggaagcaac acaggcagtt gtaggccccc tgtgccagag tgacataaac   3660
tctgtacacc tccagtgatt tggtccatgt ttgtaaaccc tgaatgttcc agggcagttt   3720
cttttcttca ctttttatct cttttttttg ggtggggggg cggggtacag agtcttgctc   3780
tgtctcccag gctggagtgc agtggcgcaa tctcaacctc ccgaggagct gggactacag   3840
gcacaggcca tcacaccttg ctaatgtttg tactttttgt agagacgggg ttttgccctg   3900
ttgcccaggc tggtcccaaa ctcctgcacc caagtaatct gcccacctct gcctggcagt   3960
tacaatttca aataattcct ccctttcctt caacacttgg ctcatgaccg tccagtccaa   4020
ggaacctgtc ctgcaggtgt gcctctcccg agcttcctct atgcatcttc cataatgaag   4080
atgccttctc actggaaacc ctacaagggt gggaacgtgc cttatttgcc tgtatcctca   4140
gggtctagca gagagaagat aatctgtaat accaaaacac cattaaattc agctgatgct   4200
ttcataagcg ctccttggag gaaggactcc atttacttga cagatctgtg caagacagca   4260
gcctggcgcg tctaacctgc agccagttgc atcctctgtt taaccttgtt tgtggaagct   4320
ttctctaaac agccagcact tgtctgttcc cacatgggtc cgttctccca gtgaatcacc   4380
gtggtgccta ctgactgctc tgtagcacag tgcttcgcaa agtgtgatcc tgggaccagc   4440
agagcagcag ctcctttgag cttattggaa tggcagaccc tcaggtccca cctctgacct   4500
gctgcatggg aattctgggg agggacgcag aatctctggt tccacaggct ctccggtgat   4560
gctaatgaat accggcattt gaacagcacc gatctagccc ctttcagtcc atgagccaac   4620
aacccttggt cctgtctgtg gtgacccagt gtgactctca tggggagcaa ggagaggaag   4680
ttgaagttca ctgacagggt tgttaagggg attatgcaat agatgagacc catgggcctg   4740
aagtccgagg gtgtatgtta gttccccgtt cttttgaccc atggattaac ctactctgtg   4800
caaagggcat tttcaagttt gttgccctgc tcacttggag aaagcttatg aaggatcagg   4860
aaaattaaaa gggtgctctc gcctataact tctctctcct ttgctttcac aggccttggt   4920
atgttcctgc ttcatccctt tctacagtgg ccttatccct ccttccttca gaggcgtggt   4980
aagtcggctt tctctgctag cgctgagtcc tgggggcctc tgaagtgtgc tcacacatct   5040
cctgcctgca gggcactggt gtcaggcacc tcagggtctg tcccatggtg gagccccatg   5100
cctcactgcc tttcagacag agtagccaca gctggcccta tttccaggct acccgggcag   5160
caaaacttac tgcatgtgta attaattatt tggctatctg taaggtaaac tggctggttc   5220
acttaatctg caccttaagc atcagatagc ttctcagtga tctagttaaa ctatatgatg   5280
ttggccaggc gcggtggctc atgtctgtaa tcccagcact ttgggagcct gaagcaggca   5340
gatcacttga ggtcaggagt tcgagaccag cctggccaac agtgtgaaac tctgtctctc   5400
```

```
ctaaaaatac aaaaattagc tgggcatggt ggtgtgcacc tgtaatccca gctgctcggg   5460
aggctgaggc aggagaattg cttgaacttg ggaggcggaa gttgcagtga gccaagatcg   5520
caccactgca ctccatcctg ggtgacagag cgagactcta tctcaaaaag aaaaaaaaaa   5580
aaaaggtaaa taaagtatat gacactgaag aatctgttac ccctggaagg tggagcttta   5640
ctcttagggg gaactataac agtcatatat atatattttt ttcttttctt tttttttttt   5700
tttgagatgg agtctsgctc tgtctcccag gctggagtgc agtggtgcaa tctcggctca   5760
ctgcaacctc cacttcacag gttcaggcaa ttctcctgcc tcaacctccc gagtagctgg   5820
gattacaggt gcctgccgtt acgccaagct aatttttgta tttttagtag agacagggtt   5880
tcatcatatt ggccaggctg gtctccaact cctgacctca ggtgatccgc ccgccttggc   5940
ctcccaaagt gctgagatta caggcgtgag ccatggtgcc cggccaacaa tcacatgtgt   6000
tgtaaacaac aacaaaaatc tgtcagcctg gtctaaccta gatttgtgct ttgttttgtt   6060
ttgccacttt gtgatgcaca ggaggaagtt taggctgtaa aatactagcc ttttagggta   6120
atttttgaac tcacaagagc agcagcggaa cctttgatgc aatcctgtat gtagcaccag   6180
cagagccacg tggcagaggg actcacatta ggagcctccc attacagact acgtgctcct   6240
gtgcgttatc ttatagggtc cccacaacca aggggagatg tgattattca tcctgtgtgg   6300
ctgtggggaa cttgagagtc atacttgccc aaagagcacg gccagcgagc ttgcacccag   6360
gtcactctct gctcctctgt cagaacaggg catgtcttgg ttcactgcag ggcggctctt   6420
ctcattctct gtagtttggg gtccaggata gtggtccacg gagccactgg agtgcccagc   6480
cactgagtga ccaaagcata ttttggattt ccgacattgc cacagcatgg ttgggcatca   6540
gcaggacccc aacccccttgt tatgctggtg gctttatgtg gttatttgat cttccccaga   6600
actcagcagg agtgcaccca gcagcaccgt agtgatgctc tctggctccc cagtgcacgg   6660
ttctggcttt ccttcctggt cgagagtttc aagccctctg ggtcctactc tgtccttttc   6720
agcccatagc tttgttcaaa agctgctggc agtgttcaga tttggctgag ttcagtgaat   6780
atgtgcattg gctgatttct gagccatgcc agggggatgg agaagccgaa gcaggagtgt   6840
ttgttctgca ggctctggag taggcattgg gtctgtgccg gctcacttgc tagtcttgca   6900
tccttcccta accccctctg gggatgtctg gccacatcag aagacagttt gggttgtcag   6960
aactggggga gtaccaggcc gaggtgggtg gatcatgagg tcaggagatc gagaccatcc   7020
tggctaacac agtgaaacct catctctact aaacatacga aaaaaattag ctgggcgtgg   7080
tggcgggcgc ctgtagtccc agctactcgg gaggctgagg caggagaatg gtgtgaaccc   7140
ggggggcgga gcttgcagtg agctgagatc ctgccactgc actccagcct gggcaacaaa   7200
gcgagactcc gtctcacaaa aaaaacaaaa caaaacaaaa caaaatctgg gggagtgcca   7260
ctggcatctg atgtatagag gcccgagatg ctgtgtcatc acccgttgag tgcgctcata   7320
ggcatcttcc tgacaattag aacccattat tcttcaaatt caatgcaagc aaattcaaag   7380
cattactatg tacataccgc gtgctaatca attgcaccac tggagctcct aaattcaaaa   7440
cattactata aaaaagttca aaatgcatgg aaaagttgta cgtggcagga gaatatttgg   7500
gcttctgact accccttgaa tgaagatgat ccaccagccg ccttcctcct tggtcttcac   7560
tccagattcc tagcatttca ttctgtgtct ctttatgcag tgaggttttt gtttgttttt   7620
tgagacagag tctcactgta tcacctaggc ctggagtgca gtggcgcgat ctcagctcac   7680
tgcaaccctc ggctcctggg tttaagcgat tctcctgcct cagcctcccg agcagctgag   7740
```

-continued

```
attacaagca cacatcccca tgcccagcta atttttgtat ttttagcaga gacagggttt   7800
caccatgttg cccaggctgg tctcgaactc ctggcctcaa gtgatccatg tgcctcagcc   7860
ttccaaagtg ctgggattac aggcgtgagc caccatgccc agctcctagt gaggtttttg   7920
atgccttgct acatctgccc tagaaattgt gtgactacga ttttggaaat gttgctgtgt   7980
aaacttgtga tcatttctgg actccaggca agaatcttga tggctaaggt gtggctgaac   8040
atgtctgatt ctctcctgga cctgttttag gccaaactct gctctgaaat tcctccgtgt   8100
ggaagggcgg gctggggaga gcctcccagc tggaatcttt tggatgcctt tctctgtggg   8160
tatctgatgg ctggctctga tggctggctg tgatggctgt ggctggaaat cattgttgac   8220
atgagtttca cagatgcagg ctctgtccaa actgtagcaa aagctgcctg ccccagccga   8280
gctatgggca ataaggtggt ttaaggatat agatgaagga aaactcaccc ttagaataat   8340
ttatccaaaa tgctgctgtg ttgtgggtta gaggacattt tctgaggtcc caggttcatt   8400
gtttcattta agtctcaaaa gtccctccag gtgttggttc taattgtcaa agcatggggg   8460
gagatgggct catgggttaa aggtcttatc ccagatttct gtatcctcct tgcaagcagc   8520
aaaggggtct ggatttgaat ccatgaccat gtttctcctt tgggtttcca tcacactctg   8580
tccccgtgca ctgagcaccc tttagttcat atgaccccct taggcatgtt acatgggcac   8640
tcctataggt gcccatctgg ccctaggact tggccaacac aacatggact ccagtttcca   8700
tctgcctctt tgccaggcac ttttgtgcag tgcacacact gtacaacagt agacggcaac   8760
cctgagagcc agagtagagc ctgtcctagc accggaatgc tcggtaagga tttgtcgcag   8820
gagtgattcc aaagccaatg tcctccctcc atatcagcct gtttgtggct ctgagaagct   8880
ctgcccacat gtgaaagctt gttaagcact taagcactaa cccagagctt cagacagtac   8940
cagtcctttt tccccttctt taaaagcgat atgtggatgg aggagtgagt gacaacgtac   9000
ccttcattga tgccaaaaca accatcaccg tgtccccctt ctatggggag tacgacatct   9060
gccctaaagt caagtccacg aactttcttc atgtggacat caccaagctc agtctacgcc   9120
tctgcacagg gaacctctac cttctctcga gagcttttgt ccccccggat ctcaaggtga   9180
gttggtggtg agggggcagg tgttctgggg tgcagctctt ctttgcctcc ctgattgcca   9240
ggagctacca gttactgtct gcacaatcaa acagaaatag acctgttctt gatggttaac   9300
ggaaataaaa ggcgcttgtc ccagaagctc aggtgaggca ccaccctgat tatgggaatc   9360
acctgggaac atatacccag acctaaaact cagatccact tcccaggctg tggttatata   9420
gtcagggggg tgcagtatgg gtattaggat tttttatttt ttagttataa agattttttt   9480
ttgatttgtt tttgagacag ggtcttgctc tgccgcttag gctggagtgc agtggtgcaa   9540
tcatagctca ctgaagcctc agactcctgg gttcaagcag tcctcccacc tcagcctcct   9600
aaggagctgg gacccacagg catgcagcac cacacctggc taatttttaa aaattttgtg   9660
gagtgttgcc caggctggtc tcacactcct ggcctcaagc gatcctccca ccccagcctc   9720
ccaatgtgtt gggattacag gcatgagcca ttgtacccag ccactaagat gattcttatt   9780
tggaaacacg gtcaagaaca actgcgttcg gtagtttaac ctttttttgat tgtggtggtt   9840
ttagtatgcc ttaccactct accatagtaa gaaatttgca gaccatgtac accaaccttt   9900
ggtgctcctg gggagaaaga aagaaggcta tgcaatgcaa tgcatgctca cagtccaagg   9960
gagagggaaa gctgtctaac aggattggtt ttcccgtgtg ctttataagc agatgagtag  10020
aggagacagc tcttattgtc ctagtggcaa ttgggatagg ctgcaaagtt tgttagggtg  10080
gaggcttatt ccgggaccaa gggagcccaa agaaacaagc tcctgccagg cgcggtggct  10140
```

```
cacgcctgta atcccagcac tttgggaggc tgaggcaggt ggatcacctg aggtcaggag  10200
tttgagacca gcctggccaa catggtgaaa ccccgtctct atgaaaaata caaaaattac  10260
ccgggcatgg tggcgggcac ctgtaatccc agctactagg gaggctgagg caggaaaatg  10320
gcttgaacct cggaagcgga ggtggccgtt agccgagatc acgccactgc actccagcct  10380
gggcaacaga gcaagactct gccttaaaaa aaaaaaaaaa aaaaagaaaa gtaaaaggaa  10440
aaaaaagagg ctctggcctg ctggggtgcc tgcaaagtct ccgtggaagg gtgacattca  10500
agccgagacc tccagggaac tgtctcctgg gagcacagag ccctttgctc agcccccagg  10560
tggctcagtg cccccagcca gcagactcag agcttgcatg attctttggt gctctctgcg  10620
gtcttccaat gatgctgaaa taaatggtgc ttggtgtctc cctgctgtag tccccttgct  10680
tgctttgctc acaggtgctg ggagagatat gccttcgagg atatttggat gcattcaggt  10740
tcttggaaga gaagggtatg tatgggctgg gaggatcagc catgcccttt tgacaagcat  10800
ttactagcgg tcttggtaaa gacttgagat ttgccttagt tctaacactt agtgcccaac  10860
gccttccttg tgttgctcaa cctactcatg agcccaggag ataggaaatc tccgtcccat  10920
tgtacagatg gggaaacaga attttggaaa ggagagccaa gcagcacaca cccctccctg  10980
aggggcagag ccgagatttg aactgggatg tcatgactcc agggccctct ccctccccag  11040
ggtcccctta tctgaaggcg gtttttcttt ccagctcgac ctcttgtgac ccttagttta  11100
acaagggccg aagttaaaga gtttctgcgc ctggacccca aatgaagcaa tcagatttct  11160
catctccagt caggtgtggg tccaagccca ctagacaagt ttgctcttcc cagagcacat  11220
ttctgccttc aagtcatcct ggcttgtcag ggctgggga gttctgctct agaaatatta  11280
gagtggaagg aaaaagatgt gttgggagct atttttcttt aatactaaaa gttggttgat  11340
gaatttgtcg ttggccaaga ccaaggagac tgcattttta aggacatatg tgtatttatc  11400
tgctcagaaa atgttcattg ctgtgtgcta gggatactgc agtgaacaca gaggtgtgac  11460
ccttgccagc cttgtgagag aagtgagcag ataagtaagc agaagggtga tgctgtgtcg  11520
atgggaaagt acaggtgcca atgagaaggc acaggtgtca aggagaagac acaggatgct  11580
ggaggctcat gcaggatgga tctccaaggc ccaggggaag aagggcctct cggaggacgt  11640
gaatccacat taagactttg ggataagta ggagcgcctt aggcatgggg acccatggat  11700
gcgaggcctg taggacacag agaggatggc atgaaggcct gtgcaactgg aggggtgggg  11760
atggggacac taagagatgg ctggaagtgt gggggtgggg acactaagag atgactggag  11820
aagaggggt caggagtggt gaaaaatggg agaggagggc aggctgggcc ttttggatac  11880
agggggattg catcctgcag tggtagggag ccactgaggg ctgctgcagt aggagtgagg  11940
ggatcagagg agagctttgg aagccccctg gatgcgggac aggaagggag ataccagtgt  12000
ctaggaggcc agtgaggcag ccagaggctc caccaggatc agggctgcga gggtcatgag  12060
gaggaaacca atttgaagga gtccagggga ataggacttg gaaatgaccg atgggacatt  12120
tgggaagagg aagacagaag agcgcagtcc cagcttctgg ctttagcagt tgggcaaggg  12180
gagatgggga gatgtgccca tgggttgagg gttgaggaca ttaggaggga gccggtatgg  12240
caggaagagc tggtgtgcca gagatgctgg aagcagcatc tgcctgagaa cagatacctg  12300
gcaatattcc taagggaaag tgacatctcg gagggtgagg agggcatctg atagggcctg  12360
gaaagagccg gggcaagcat gaatgtgagg ttatcttggg gggcaaggct caggcgttga  12420
ggagcagccc ctggtctctt cagcctgaag ttggaagcca gagttgggcc aggtgcagct  12480
```

-continued

```
gtggttgtct gaagtccccc tcccccagcc cagtgtgcca atgctgtaag agcaagggcc  12540
gctcactggt gctggtggct gagtcccagc acccaggaca gggcctggca catactggtg  12600
cccaatcctc ccttctgggt gcttcttcca aggccttgtg atggaagtga gtaccctctt  12660
cgacatcaga cccagcttca aatcccggct ctgctatgta tcggctgcgt ggctttagac  12720
aagtctttta accttgctgt gcttctgatt tctcagctga aaaatggaga tgatgataat  12780
ggtttctgta aggccttatg gtgaagcacc tagctcaggg cctggaaggc aggtgtaacc  12840
agtggttcag ttgttataaa cgaacactaa ccctcgcctt tgcacctcat gaatccagat  12900
atgtagatgg agcccacaaa gctagcagga gccaagctca cgtgtgtcct gctttaaagc  12960
cccataccc tttctccggg tgacaaacac ctgtgctcgt tctcttccct tcccctcttc  13020
cccttgcatt tggctaataa caggccagct gcctgcctcc ctgcagtttg gtagatgggt  13080
gggtaatgac caccactccc acgttcgcct gatgggcttg ttttccgtgc ccttcacagg  13140
catctgcaac aggccccagc caggcctgaa gtcatcctca gaagggatgg atcctgaggt  13200
cgccatgccc agctgggcaa acatgagtct ggattcttcc ccggagtcgg ctgccttggc  13260
tgtgaggctg gagggagatg agctgctaga ccacctgcgt ctcagcatcc tgccctggga  13320
tgagagcatc ctggacaccc tctcgcccag gctcgctaca ggtacccact cctcggggtg  13380
ggcacgggca gcaccttgtt ttctttcttg tgcattatgg aggaagatgg tactgccaca  13440
tgggagcgat agggtgaggc aaccatgaca ggtggttggg aacatctcct tccatgtgta  13500
cagcctgggc tgctgccatc actcccagca cagcccccaa cccccccaat cctggaacct  13560
tgccaagtct cccttcccgt ggggtcatga ccaggaggaa aacaaactcc agctgagccc  13620
cttggggttc cccatatagg ctcctgcctg tggcagctgg gccctctgta cccctttcca  13680
actctgtgtc cctaacatgg cacctgagct cctgccatcc tggatttcat ggaccccaag  13740
gatgggggtc ctgcatctgg gacttggcct attactcgga gctccttttc agccgcctcc  13800
ctccacctgt ccacccacct caaggctcct ttcttgagac ctctcctaat ttctcccttc  13860
ccctaaaccc acaattttga acctccatcg aatggtgctg tagtttataa tgtcatcaaa  13920
tatcaaatgg agacagtgct atggtccaaa tgattgtgta ccccccagaa tttgtctttt  13980
gaaatcctaa cccccaacat gatggtctta ggaggtgggg cctttgggag gagattaggt  14040
catgaggaaa gggctgtcat gaatgggatt ggtgccctta ttaaacagac ccaagagagg  14100
tcccttgtcc cttctactgt gtgaggactc agaaggtggt gtctatgaag aaggaggccc  14160
tcaccagaca ccaacacgtc tgctgcccct tgatctggga ccttgcagcc tctagaactc  14220
tgaaaaatcg atgtttgttg ttttataagc cactcagttg gtggcatttt gttagagtag  14280
cctgaacacg gactaagtca aacagaagaa cccacaaacc agctacagag ttgggcattt  14340
ggagaaattc aaaaatgagt cagacataac tccttattct tgaggtgccc taagagatgg  14400
gacacagcag ctgcccaggt gcattagttt gttctcacat tgctataaag aaatacctga  14460
gactgggtaa ctcataaaga aagaggttga attggctcac agttgcacag gctggacagg  14520
aagcatggtg ctggcatctg ctcagcttct ggggaggcct caggaaactt acaatcatgg  14580
cagaaggtga acgggaagca tgcacatccc atgactggag caggagtgag agagagaggg  14640
aaatagaggg aaggtgccat acacttttaa acaaccagat ctcacgagaa cacactcact  14700
atcaagagaa cagcaccagt ggggaaatcc gcccccacga tccaatcacc tcccatcagg  14760
ctccgcctcc aacactggga attacaattt gacatgagat gtgggcaggg acacagatcc  14820
aaaccatatg accagattaa tacgatttga ggcatcacga ggtcattaaa gagagggaat  14880
```

```
aaaagactgg ggctccagga agaaggctct ggaatccagc agagggtcaa ggaccagctt  14940
gtaaagctgg tggtgcctga gaagtaccta ggagaacata gatgctgtga cgtttgatgt  15000
agctgttttt tgttttgtgt tttggttttt gagacagagt ctcactctgt cgcccaggct  15060
ggagtgtgca gtggcgtgat cttggctcac tggagcctcc atctcccagg ttcaaatgat  15120
cctcatgcct cagcctcctg agttgctggg attacaggtg cacaccacca cgcctggcta  15180
atttttgtgt tttcagtaga gacagggttt caccatgttg gccaggctgg tcttgaactc  15240
ctgacctcaa gtgatccaac aacttcagcc tcccaaagtg ctgggatgac aggcatgagc  15300
caccatgccc agcctgatgt agctgtttct gtgcacatta tttgctgtgg ggtatattca  15360
gatttcttaa tacaagatga ttctttgcct catgacttac acaccatttt ctatttaatt  15420
tcagctatga tattggaaat ggacatgtct tttcaaggaa aataaaagca ggctttctgg  15480
aatggcgact tccaaacata tttgtcaatt taaaggagct gggagtgggg accctatgcc  15540
ccgtaagcac tctcttagct gttcttggct gtgctccccg cttcagcttc acactgccct  15600
tgctgtgaag ggagaagcct gggctgggcg cggtggctta cacctgtaat cctagcactt  15660
ttggaggccg aggtgggtgg atcacctgag gtcaggagtt caagaccagc ctggccaaca  15720
tggtgaaact ccatctctac taaaaataca aaaaattagc tgggcatggt ggcaggtgcc  15780
tgtaatccca gctacttggg aggctgaggc agaagaatcg cttgaaccca ggaggcggag  15840
gttgcagtga gccgagattg cgccattgca ctccagcctg gggcaacaa gagcaaaact  15900
ctgtctggaa aaaaaagaaa ggagcagctt ggcaaacccc accttgtcgc ttctgtgagt  15960
gcctctgacc ctttggctgc caggacgggc gtattttatg gaaatgctaa gcaccaacag  16020
agtaaagtgg tttggttttt cacagtggtg ggagataata gctccaaatt gtctttttca  16080
gcactgagtg aagaaatgaa agacaaaggt ggatacatga gcaagatttg caacttgcta  16140
cccattagga taatgtctta tgtaatgctg ccctgtaccc tgcctgtgga atctgccatt  16200
gcgattgtcc agaggtgagc attttaggtg gctccgtgtc ttcctcacag ggttgatatg  16260
aggatgaaac aagatgatag atcatggtgg catgtagtct gggacccgga ttgtcgtgcc  16320
acagatcaca gctcacagtc tatgtgcaat gcccctgaat gttgcccacc tgtcctcaag  16380
ccacacatgc acctgtaact cagtgcaagc ccagaaactc cccgtgggga ctcctagagc  16440
tgtcagtggc ctcacatagc agctggtcca gtctcttgtg attgcccaag gaaactgagg  16500
cctggagagc ttggggtcgc tgctctgagg ccatagagat gcctagtaga agggccaggc  16560
ctagaagcag gatccttgct gcccctctga gctgtttcca tttaaaatca catgaaggcc  16620
ggcgccgtgg ctcacggctg taatcccagc attttgggag gccaaggtgg gtggatcatg  16680
tgaggtcagg agtttgagac cagcctggcc aacatggtga aatgccatct gtactaaaaa  16740
tacaaaaatt agtggagcat ggtggcacgt gcctgtactc ccagctactt ggaaggctgg  16800
ggcagaagaa tcgcttgagc ctgggaggca gaggttgtag tgagccaaga ttgtaccact  16860
gcactccagc ctgggtgaca ggagagaaac cctatctcaa aataaaatga aaggtaatga  16920
aatgaataaa ataataaatc aagtcacggc cgggcacggt ggctcacacc tgtaatccca  16980
gcgctttggg aggccgaggt gggtggataa tgaggtcagg agttcaagac cagcctggcc  17040
aacatggtga aaccatgtct ctactaaaaa tacaaaaatt agctgggcat ggtggtgcat  17100
gcctgtaatc ccagctactc cggaggctaa ggcaggagaa ttgcttgaag caggacctag  17160
gaggcagagg ttggttgcag tgagccgaga tcatgccact gcactctagc ctgggctaca  17220
```

-continued

```
gagcgaaact ccgactcaaa aaaaaaaaaa aaaaaaaatc aaatcacatg aaagtagaac  17280
atagggaatt ccatctttcg ttctaggcat agtttgttaa tatgattcag agccagcagt  17340
taggagaaca cagtgtgact ctcctagaac ttcttgattg ggcttcctct gattgggttt  17400
cctctgattg ggcttcctct gaaagtgggg gggatggggg gtggggagca gaatggtcag  17460
agcttggctc agcagtcaga ctgctcttct tcaaatcctg gctgcattgc ttactacagc  17520
tgtgtgactc cagatgactg aatccacctc tctgtgctgc agcttcccgt ctagagagat  17580
cacctggagc agagggtggt caggagactc aatctggtta ctgactcaca gtgcaggagt  17640
actcatccca tagtaagcat ccagctagag atgttgattt ctattttcag gtaataatga  17700
tgatcgtaaa attagagaca gataaaaggt atgggcatta gaccagggca ctgcaatttc  17760
taagctgtgt gacctcaggc aagttactcg acttctctga gcctcagcgg tttcatccgc  17820
aatatatgga taggaaaacc gacctcagtg ggttgtctga cagtggaggg cacttgatta  17880
aaaaaaaaaa aattaccctg gtctgaatat taccctggac tgaaagaaaa atattgagct  17940
aatacaggca tcaggaatgg ggctgcaggg agtccaggga agggagaacg aagagcctga  18000
aggtgtgagg aggtgcgagt gctgatctgt ctgctacaaa gaggctgctg agcctcctgt  18060
ggatgtggcc ctggacttgg cagtttaata cctgagctgt taaaataacc tcagatgctg  18120
tgttctttaa ggggtaggat tcagattcct gctgaaatgc ttctgaaagg gagggaatga  18180
gccagcccat ccccagttgc tttttaagat cattgggaag ttctggtctt gccatttgtc  18240
cctggaccac tcttaggtcc tcctgcccca cttccatctg ggtgtgtgcc ctgggctgtc  18300
caccacacag ctacatcctg ccatcttccc tcctggagcc actgtgccat gcatggatct  18360
gtagcttcat ttttcttggc ttttccctgg tttttctgga gcagagtctc tagtaaactc  18420
ccaaggaaga aaacgtttga ctttatgtgt gttgggaaac gtgctttttt tctattacat  18480
ctcagtgata ggttggccat gtctagaatt gcaggttgaa aatcatttcc tctcagtata  18540
ttggttagtg agaagcctgg gactgagaca gtcacattct cacttctttg caggtgagtg  18600
ctcttaggac tgtcttttta tcccttatac tctgaaatgt catatgtctt ggtgtaagtc  18660
cttatttcag ttattgagct ggacaagtac tggagacccc ttcagtcaaa gccttctgtc  18720
attctccagc tctaggaaat tatcttctat tgttatttct gttattcctt cccttccatt  18780
ttctttttc ttttttttt ttttttttg agacagggtc ttactctggt gcccaggctg  18840
gaatgcagtg acctgatcat ggtacactgc agcctgaacc tcccagactc aagtgatcct  18900
cccacctcaa cctcctaagt agctgggact gcaagcacac atcaccacac ccaacaaata  18960
ttttttaaaa attttgtaag atgggatctt actatgttgc ccagactttt tcttcctctt  19020
cctggggctc ttattaggaa gatgtttgac ttcctgggtt ggattcctgt ctccgtgtct  19080
gactttctct ctttgtcata tttttcatca ctcgttgtct ttttgcgtct gctctgacag  19140
atttcctcaa attttgtctt ctagtcctat cctacagttt ttactttcag caaatataat  19200
ttaatctcca agagtactct cttgttcttt tttcttagca ttctgttctt gttttatgga  19260
tgtaacattc tcttggaata tttgctgtcc tctagatcat cccttctcca tttcttcttg  19320
ggctagtttt tctgtttctt catctttctc ttttatgcta cttattctgg gcgtgttctt  19380
ggtgggtttt ttcccatata gcaacagagg acttggagct cagggagaaa agggtaggtg  19440
catcacctgg cagagctccc agacagtgac aggcaggctg cgggaaggat gtctacttgg  19500
cggtgctacc gctttcctag aaaccctttc cctggagctg gttgaactgt tgggttttgc  19560
cctggtggtg aacgctggct ccccgtgctc tgcctgtttc atcaccagcc ccctcccctt  19620
```

```
ctgcctgggg tccagtaatc tgttgaaata tatatcttgc tcattggtga gctcctgctc  19680
cttcctcgtt gctcttgcag atttatcact tctcgtaagg ctgcgcttgt acttggggat  19740
tttctctgtg ccacactggg aaacataggg tggttgcatg ctgcagtcct gagcacttat  19800
ttcactcaca tctttacacg aagatttggt gggtgtttac tttgttttta gtaagttagt  19860
ctgtcatgtc ctttgatcct tttttttgt tttttgagat ggagtctctc tgtgtcctcc  19920
aggctggagt gcaatgtcgc gatctcagct cactgcaacc tccacctcct gggctcaaga  19980
gattctcctg cttcagtctc ctgagtagct gggattacag gcatgtgcca ccacacctgg  20040
ctaatttttg tatttttagt agaggtgggg tttggcatgt tggccagcct ggtctcaaac  20100
tcctgacctc ctgacctgcc tgccttggcc tcccaaagtg ctgggattac aggtgtgagc  20160
caccacacct ggccctgatt aatcttttaa tgcccagtct ctccttcaaa agccggctcc  20220
tttctctccc tcgccttcct agattccttc tccactcccc aggatcagcc tcctcctccc  20280
caccccacca ctgctgggg gatgtctgtg gtcaggcatt tatcagagac cctgaggtgg  20340
gggtccttta tgtgtctggg ggatggagag tctagaggag gtagcgttca gacctctcca  20400
tggtgcctct gctgggctca catgtgacca agcacagcaa accatgaggc aggggatggt  20460
cttgaccatg agagcccttg cagcagctgc catgggcctc agctcctctc caagctggga  20520
agagccctga aaagccaagg tgtttttttt tccctcttta tttcagtgta agtcccttga  20580
gctttcttga accagaagtg ggctcatttt gctttagaga tttcaggtgg gcttgtcctt  20640
gtcctagcat cccagatcca ccttctggga agtcatcaga ttggaggtga tgttggcagc  20700
ttttgtaaac aaagggtagt gttgtaagct gttgtgtctg cctatgtgtg tgtttgtgta  20760
cttggtctca tctctgcaga ctggtgacat ggcttccaga tatgcccgac gatgtcctgt  20820
ggttgcagtg ggtgacctca caggtgttca ctcgagtgct gatgtgtctg ctccccgcct  20880
ccaggtaaat actttggctg tgggtgtgtg ggccggacgg gcacctctct catctgatga  20940
ggcctcacac gacattctag aaacagctgg ctgaacacca agcaaggagc ttgcccttgg  21000
gtgtggggac cctgtctcat gggaggcagc tgagtcagtc agaggtcctg gcacacctgc  21060
tgagagctgc cacccaggcc aacctgaacc ggagcctggg aagacttccc gttggatgag  21120
tctctttgag ggcagcattg atggtggaag agcagagagg ccccagataa gcagggaaag  21180
gtgcttcaga cagagtggct gggatgagga ctggggagtg tcagatagcg ctggcgtgtc  21240
tgagcgaagg agctctggca cccatggcac aggaaggagg tgggaccctg gaggggcagg  21300
gctagcagag ctcctcggag cgtgtggcta ggtgcctggt aatgcaagcc ccctgtcctc  21360
caccctctgt tgtactgagt cacagtctcc ggggtgaagc ccagcagtct gcgttgacag  21420
gccccagggg atgccgctac ttcctgaatt ctgaattctg gaaactgagc cggagttcag  21480
ggcctggctc ccattaccag ggttggacgt tatcctgaaa atcataggcc ttggtttcct  21540
cacttggcta acaggggtga tccccatccc ctcaatgggt ttccgtgagc tcctgagagc  21600
ccgtagcatg gtacttggca catgctgggc atcaggaggt atggcctctc ttgctattgt  21660
tgttattggt agacacagaa ggatttaaaa gtaggggaat gcaaagatcc gatttgctag  21720
ggaagagggc agtagtggcc aagtagaggg tggatcctgg gccctggctg gcagcaggca  21780
gcaagggggg ctgccagggc ccaggcaggg acgacctgta gaccgagagg cttcctaagg  21840
ctcttggaca ggaggaggtg tcggttccaa gcctgaggag cggggcagcc ctggtgactg  21900
gtggtcagtg gtgccaggcg gtgggtggta ggacaccctg gcaggcaagt aggtttgtgt  21960
```

-continued

```
gggggaaact gataggcccc tccagggatt cgttggtgga caacacctgt gatgtccagt  22020
gggaggtgtc caggtagctg ggagggccac aggcttggaa gacctaggtg gtgacatcag  22080
cccagcactg agggctagaa gaagctgtgt ctctggctgt gacggcaccc tagagtgtgt  22140
gtggtgccct ctactggccg gcaatgtggg tccaccgtag ctcagactgc acactgcagc  22200
agcgggaacg gcctctaagc caacttcctc catgtgtttc aggtcccaaa tgccagtgag  22260
cagccaacag gcctccccat gcacacctga gcaggactgg ccctgctgga ctccctgctc  22320
ccccgagggc tgtccagcag agaccaaagc agaggccacc ccgcggtcca tcctcaggtc  22380
cagcctgaac ttcttcttgg gcaataaagt acctgctggt gctgaggggc tctccacctt  22440
tcccagtttt tcactagaga agagtctgtg agtcacttga ggaggcgagt ctagcagatt  22500
ctttcagagg tgctaaagtt tcccatcttt gtgcagctac ctccgcattg ctgtgtagtg  22560
acccctgcct gtgacgtgga ggatcccagc ctctgagctg agttggtttt atgaaaagct  22620
aggaagcaac ctttcgcctg tgcagcggtc cagcacttaa ctctaataca tcagcatgcg  22680
ttaattcagc tggttgggaa atgacaccag gaagcccagt gcagagggtc ccttactgac  22740
tgtttcgtgg ccctattaat ggtcagactg ttccagcatg aggttcttag aatgacaggt  22800
gtttggatgg gtgggggcct tgtgatgggg ggtaggctgg cccatgtgtg atcttgtggg  22860
gtggagggaa gagaatagca tgatcccact tccccatgct gtgggaaggg gtgcagttcg  22920
tccccaagaa cgacactgcc tgtcaggtgg tctgcaaaga tgataacctt gactactaaa  22980
aacgtctcca tggcgggggt aacaagatga taatctactt aattttagaa cacctttttc  23040
acctaactaa aataatgttt aaagagtttt gtataaaaat gtaaggaagc gttgttacct  23100
gttgaatttt gtattatgtg aatcagtgag atgttagtag aataagcctt aaaaaaaaaa  23160
aaatcggttg ggtgcagcgg cacacggctg taatcccagc actttgggag gccaaggttg  23220
gcagatcacc tgaggtcagg agttcaagac cagtctggcc aaca                   23264
```

GENETICALLY MODIFIED MOUSE WITH A HUMANIZED PNPLA3 GENE AND METHODS OF USE

CROSS REFERENCE TO RELATED APPLICATIONS

This application claims the benefit of U.S. Application No. 62/966,837, filed Jan. 28, 2020, which is herein incorporated by reference in its entirety for all purposes.

REFERENCE TO A SEQUENCE LISTING SUBMITTED AS A TEXT FILE VIA EFS WEB

The Sequence Listing written in file 554248SEQLIST.txt is 308 kilobytes, was created on Jan. 27, 2021, and is hereby incorporated by reference.

BACKGROUND

Patatin-like phospholipase domain containing 3 (PNPLA3) is a lipid-droplet-associated protein with highest expression in liver and adipose tissue. It has been identified as a gene involved in steatosis, fibrosis, and cirrhosis of the liver. There is a large unmet need in chronic liver disease indications. It is of great interest to understand the biological role for PNPLA3 in the molecular mechanisms of steatosis and steatohepatitis.

SUMMARY

Non-human animals, non-human animal cells, and non-human animal genomes comprising a humanized PNPLA3 locus are provided, as well as methods of making and using such non-human animals, non-human animal cells, and non-human animal genomes. Also provided are humanized non-human animal PNPLA3 genes, nuclease agents and/or targeting vectors for use in humanizing a non-human animal PNPLA3 gene, and methods of making and using such humanized PNPLA3 genes.

In one aspect, provided are non-human animals, non-human animal cells, and non-human animal genomes comprising a humanized PNPLA3 locus. In one aspect, provided are non-human animals, non-human animal cells, and non-human animal genomes comprising a humanized PNPLA3 locus, wherein a humanized PNPLA3 protein is expressed from the humanized PNPLA3 locus. In some such non-human animals, non-human animal cells, and non-human animal genomes, the non-human animals, non-human animal cells, and non-human animal genomes comprise in their genome a humanized endogenous Pnpla3 locus in which a segment of the endogenous Pnpla3 locus has been deleted and replaced with a corresponding human PNPLA3 sequence.

In some such non-human animals, non-human animal cells, and non-human animal genomes, the humanized endogenous Pnpla3 locus encodes a PNPLA3 protein comprising a human PNPLA3 lumenal domain. In some such non-human animals, non-human animal cells, and non-human animal genomes, the human PNPLA3 lumenal domain is wild type at the position corresponding to position 148 of SEQ ID NO: 5. In some such non-human animals, non-human animal cells, and non-human animal genomes, the human PNPLA3 lumenal domain comprises an I148M mutation and/or a K434E mutation. Optionally, the human PNPLA3 lumenal domain comprises the I148M mutation and the K434E mutation. Optionally, the human PNPLA3 lumenal domain comprises the sequence set forth in SEQ ID NO: 10, optionally wherein the human PNPLA3 lumenal domain is encoded by the coding sequence set forth in SEQ ID NO: 20. Optionally, the human PNPLA3 lumenal domain comprises the K434E mutation but not the I148M mutation. Optionally, the human PNPLA3 lumenal domain comprises the sequence set forth in SEQ ID NO: 65, optionally wherein the human PNPLA3 lumenal domain is encoded by the coding sequence set forth in SEQ ID NO: 66. In some such non-human animals, non-human animal cells, and non-human animal genomes, the human PNPLA3 lumenal domain is a wild type human PNPLA3 lumenal domain. Optionally, the human PNPLA3 lumenal domain comprises the sequence set forth in SEQ ID NO: 8, optionally wherein the human PNPLA3 lumenal domain is encoded by the coding sequence set forth in SEQ ID NO: 18.

In some such non-human animals, non-human animal cells, and non-human animal genomes, the humanized endogenous Pnpla3 locus encodes a PNPLA3 protein comprising a human PNPLA3 transmembrane domain. Optionally, the human PNPLA3 transmembrane domain comprises the sequence set forth in SEQ ID NO: 7, optionally wherein the human PNPLA3 transmembrane domain is encoded by the coding sequence set forth in SEQ ID NO: 17.

In some such non-human animals, non-human animal cells, and non-human animal genomes, the humanized endogenous Pnpla3 locus encodes a PNPLA3 protein comprising a human PNPLA3 cytoplasmic domain. Optionally, the human PNPLA3 cytoplasmic domain comprises the sequence set forth in SEQ ID NO: 6, optionally wherein the human PNPLA3 cytoplasmic domain is encoded by the coding sequence set forth in SEQ ID NO: 16.

In some such non-human animals, non-human animal cells, and non-human animal genomes, a region of the endogenous Pnpla3 locus comprising both coding sequence and non-coding sequence has been deleted and replaced with a corresponding human PNPLA3 sequence comprising both coding sequence and non-coding sequence. In some such non-human animals, non-human animal cells, and non-human animal genomes, the humanized endogenous Pnpla3 locus comprises an endogenous Pnpla3 promoter, wherein the human PNPLA3 sequence is operably linked to the endogenous Pnpla3 promoter. In some such non-human animals, non-human animal cells, and non-human animal genomes, at least one intron and at least one exon of the endogenous Pnpla3 locus have been deleted and replaced with a corresponding human PNPLA3 sequence.

In some such non-human animals, non-human animal cells, and non-human animal genomes, an entire human PNPLA3 coding sequence has been inserted into the endogenous Pnpla3 locus. Optionally, a region of the human PNPLA3 locus comprising the sequence between the human PNPLA3 start codon and the human PNPLA3 stop codon has been inserted into the endogenous Pnpla3 locus.

In some such non-human animals, non-human animal cells, and non-human animal genomes, the 5'UTR of the human PNPLA3 locus has been inserted into the endogenous Pnpla3 locus, the 3' UTR of human PNPLA3 locus has been inserted into the endogenous Pnpla3 locus, or both the 5'UTR of the human PNPLA3 locus and the 3' UTR of human PNPLA3 locus have been inserted into the endogenous Pnpla3 locus.

In some such non-human animals, non-human animal cells, and non-human animal genomes, all of the endogenous Pnpla3 exons except for the last exon have been deleted in the humanized endogenous Pnpla3 locus. Optionally, a region of the endogenous Pnpla3 locus from the first exon to the penultimate exon including all intervening introns has been deleted in the humanized endogenous Pnpla3 locus.

In some such non-human animals, non-human animal cells, and non-human animal genomes, all or part of the last intron of the endogenous Pnpla3 locus has not been deleted in the humanized endogenous Pnpla3 locus. Optionally, the part of the last intron of the endogenous Pnpla3 locus that has not been deleted in the humanized endogenous Pnpla3 locus comprises a regulatory element that affects expression of a gene downstream of the endogenous Pnpla3 locus.

In some such non-human animals, non-human animal cells, and non-human animal genomes, a region of the endogenous Pnpla3 locus from the first exon to the penultimate exon including all intervening introns has been deleted in the humanized endogenous Pnpla3 locus and has been replaced with a region of the human PNPLA3 locus comprising the sequence between the human PNPLA3 start codon and the human PNPLA3 stop codon, and the humanized endogenous Pnpla3 locus comprises an endogenous Pnpla3 promoter, wherein the human PNPLA3 sequence is operably linked to the endogenous Pnpla3 promoter. Optionally, the PNPLA3 protein encoded by the humanized PNPLA3 locus comprises an I148M mutation and/or a K434E mutation. Optionally, the PNPLA3 protein encoded by the humanized PINPLA3 locus is a wild type human PNPLA3 protein.

In some such non-human animals, non-human animal cells, and non-human animal genomes, (i) the human PNPLA3 sequence at the humanized endogenous PNPLA3 locus comprises a sequence at least 90%, at least 95%, at least 96%, at least 97%, at least 98%, at least 99%, or 100% identical to the sequence set forth in SEQ ID NO: 62 or 69; and/or (ii) the humanized endogenous PNPLA3 locus encodes a protein comprising a sequence at least 90%, at least 95%, at least 96%, at least 97%, at least 98%, at least 99%, or 100% identical to the sequence set forth in SEQ ID NO: 5, 9, or 63; and/or (iii) the humanized endogenous PNPLA3 locus comprises a coding sequence comprising a sequence at least 90%, at least 95%, at least 96%, at least 97%, at least 98%, at least 99%, or 100% identical to the sequence set forth in SEQ ID NO: 15, 19, or 64; and/or (iv) the humanized endogenous PNPLA3 locus comprises a sequence at least 90%, at least 95%, at least 96%, at least 97%, at least 98%, at least 99%, or 100% identical to the sequence set forth in SEQ ID NO: 21, 22, 67, or 68.

In some such non-human animals, non-human animal cells, and non-human animal genomes, the humanized endogenous PNPLA3 locus does not comprise a selection cassette or a reporter gene.

In some such non-human animals, non-human animal cells, and non-human animal genomes, the non-human animal is homozygous for the humanized endogenous PNPLA3 locus.

In some such non-human animals, non-human animal cells, and non-human animal genomes, the non-human animal comprises the humanized endogenous PNPLA3 locus in its germline.

In some such non-human animals, non-human animal cells, and non-human animal genomes, the non-human animal is a mammal. Optionally, the non-human animal is a rat or mouse. Optionally, the non-human animal is a mouse.

In some such non-human animals, non-human animal cells, and non-human animal genomes, RNA expression from the humanized endogenous PNPLA3 locus in the liver of the non-human animal (e.g., under chow-fed conditions) or in the non-human animal cells or from the non-human animal genomes is higher than RNA expression from a non-humanized endogenous Pnpla3 locus in the liver of a control non-human animal (e.g., under chow-fed conditions) or in control non-human animal cells or from a control non-human animal genome. Optionally, the RNA expression from the humanized endogenous PNPLA3 locus in the liver of the non-human animal under chow-fed conditions is at least 5%, at least 10%, at least 15%, at least 20%, or at least 25% of the RNA expression from the humanized endogenous PNPLA3 locus in the liver of the non-human animal under high sucrose diet (HSD) or high fructose diet (HFD) conditions.

In another aspect, provided are targeting vectors for generating a humanized endogenous PNPLA3 locus in which a segment of the endogenous Pnpla3 locus has been deleted and replaced with a corresponding human PNPLA3 sequence. In some such targeting vectors, the targeting vector comprises an insert nucleic acid comprising the corresponding human PNPLA3 sequence flanked by a 5' homology arm targeting a 5' target sequence at the endogenous Pnpla3 locus and a 3' homology arm targeting a 3' target sequence at the endogenous Pnpla3 locus.

In another aspect, provided are humanized non-human animal PNPLA3 genes in which a segment of the non-human animal Pnpla3 gene has been deleted and replaced with a corresponding human PNPLA3 sequence.

In another aspect, provided are methods of assessing the activity of a human-PNPLA3-targeting reagent in vivo. Some such methods comprise: (a) administering the human-PNPLA3-targeting reagent to any of the above non-human animals comprising a humanized PNPLA3 locus; and (b) assessing the activity of the human-PNPLA3-targeting reagent in the non-human animal.

In some such methods, the administering comprises adeno-associated virus (AAV)-mediated delivery, lipid nanoparticle (LNP)-mediated delivery, hydrodynamic delivery (HDD), or injection.

In some such methods, step (b) comprises assessing the activity of the human-PNPLA3-targeting reagent in the liver of the non-human animal. In some such methods, step (b) comprises measuring hepatic fat content and/or measuring PNPLA3 levels in hepatic lipid droplets in the non-human animal.

In some such methods, step (b) comprises measuring expression of an PNPLA3 messenger RNA encoded by the humanized endogenous PNPLA3 locus. In some such methods, step (b) comprises measuring expression of a PNPLA3 protein encoded by the humanized endogenous PNPLA3 locus.

In some such methods, the human-PNPLA3-targeting reagent is a genome-editing agent, and step (b) comprises assessing modification of the humanized endogenous PNPLA3 locus. Optionally, step (b) comprises measuring the frequency of insertions or deletions within the humanized endogenous PNPLA3 locus.

In some such methods, the human-PNPLA3-targeting reagent comprises a nuclease agent designed to target a region of a human PNPLA3 gene. Optionally, the nuclease agent comprises a Cas protein and a guide RNA designed to target a guide RNA target sequence in the human PNPLA3 gene. Optionally, the Cas protein is a Cas9 protein.

In some such methods, the human-PNPLA3-targeting reagent comprises an exogenous donor nucleic acid, wherein the exogenous donor nucleic acid is designed to target the human PNPLA3 gene. Optionally, the exogenous donor nucleic acid is delivered via AAV. In some such methods, the human-PNPLA3-targeting reagent is an RNAi agent or an antisense oligonucleotide. In some such methods, the human-PNPLA3-targeting reagent is an antigen-binding protein. In some such methods, the human-PNPLA3-targeting reagent is small molecule.

In another aspect, provided are methods of optimizing the activity of a human-PNPLA3-targeting reagent in vivo. Some such methods comprise: (I) performing any of the above methods of assessing the activity of a human-PNPLA3-targeting reagent in vivo a first time in a first non-human animal comprising in its genome a humanized endogenous PNPLA3 locus; (II) changing a variable and performing the method of step (I) a second time with the changed variable in a second non-human animal comprising in its genome a humanized endogenous PNPLA3 locus; and (III) comparing the activity of the human-PNPLA3-targeting reagent in step (I) with the activity of the human-PNPLA3-targeting reagent in step (II), and selecting the method resulting in the higher activity.

In some such methods, the changed variable in step (II) is the delivery method of introducing the human-PNPLA3-targeting reagent into the non-human animal. In some such methods, the changed variable in step (II) is the route of administration of introducing the human-PNPLA3-targeting reagent into the non-human animal. In some such methods, the changed variable in step (II) is the concentration or amount of the human-PNPLA3-targeting reagent introduced into the non-human animal. In some such methods, the changed variable in step (II) is the form of the human-PNPLA3-targeting reagent introduced into the non-human animal. In some such methods, the changed variable in step (II) is the human-PNPLA3-targeting reagent introduced into the non-human animal.

In another aspect, provided are methods of making any of the above non-human animals comprising a humanized PNPLA3 locus.

Some such methods comprise: (a) introducing into a non-human animal host embryo a genetically modified non-human animal embryonic stem (ES) cell comprising in its genome a humanized endogenous Pnpla3 locus in which a segment of the endogenous Pnpla3 locus has been deleted and replaced with a corresponding human PNPLA3 sequence; and (b) gestating the non-human animal host embryo in a surrogate mother, wherein the surrogate mother produces an F0 progeny genetically modified non-human animal comprising the humanized endogenous Pnpla3 locus.

Some such methods comprise: (a) modifying the genome of a non-human animal one-cell stage embryo to comprise in its genome a humanized endogenous Pnpla3 locus in which a segment of the endogenous Pnpla3 locus has been deleted and replaced with a corresponding human PNPLA3 sequence, thereby generating a non-human animal genetically modified embryo; and (b) gestating the non-human animal genetically modified embryo in a surrogate mother, wherein the surrogate mother produces an F0 progeny genetically modified non-human animal comprising the humanized endogenous Pnpla3 locus.

Some such methods comprise: (a) introducing into a non-human animal embryonic stem (ES) cell a targeting vector comprising a nucleic acid insert comprising the human PNPLA3 sequence flanked by a 5' homology arm corresponding to a 5' target sequence in the endogenous Pnpla3 locus and a 3' homology arm corresponding to a 3' target sequence in the endogenous Pnpla3 locus, wherein the targeting vector recombines with the endogenous Pnpla3 locus to produce a genetically modified non-human ES cell comprising in its genome the humanized endogenous PNPLA3 locus comprising the human PNPLA3 sequence; (b) introducing the genetically modified non-human ES cell into a non-human animal host embryo; and (c) gestating the non-human animal host embryo in a surrogate mother, wherein the surrogate mother produces an F0 progeny genetically modified non-human animal comprising in its genome the humanized endogenous PNPLA3 locus comprising the human PNPLA3 sequence. Optionally, the targeting vector is a large targeting vector at least 10 kb in length or in which the sum total of the 5' and 3' homology arms is at least 10 kb in length.

Some such methods comprise: (a) introducing into a non-human animal one-cell stage embryo a targeting vector comprising a nucleic acid insert comprising the human PNPLA3 sequence flanked by a 5' homology arm corresponding to a 5' target sequence in the endogenous Pnpla3 locus and a 3' homology arm corresponding to a 3' target sequence in the endogenous Pnpla3 locus, wherein the targeting vector recombines with the endogenous Pnpla3 locus to produce a genetically modified non-human one-cell stage embryo comprising in its genome the humanized endogenous PNPLA3 locus comprising the human PNPLA3 sequence; (b) gestating the genetically modified non-human animal one-cell stage embryo in a surrogate mother to produce a genetically modified F0 generation non-human animal comprising in its genome the humanized endogenous PNPLA3 locus comprising the human PNPLA3 sequence.

In some such methods, step (a) further comprises introducing a nuclease agent that targets a target sequence in the endogenous Pnpla3 locus. Optionally, the nuclease agent comprises a Cas protein and a guide RNA. Optionally, the Cas protein is a Cas9 protein. Optionally, step (a) further comprises introducing a second guide RNA that targets a second target sequence within the endogenous Pnpla3 locus. Optionally, step (a) further comprises introducing a third guide RNA that targets a third target sequence within the endogenous Pnpla3 locus and a fourth guide RNA that targets a fourth target sequence within the endogenous Pnpla3 locus.

In some such methods, the non-human animal is a mouse or a rat. Optionally, the non-human animal is a mouse.

BRIEF DESCRIPTION OF THE FIGURES

FIG. 3 shows an alignment of the wild type mouse PNPLA3 protein, the wild type human PNPLA3 protein, and a human PNPLA3 protein with I148M and K434E mutations (mPNPLA3, hPNPLA3, and hPNPLA3_mut, respectively). The cytoplasmic domain, transmembrane domain, and lumenal domain are indicated, and the locations of the I148M and K434E mutations are boxed.

DEFINITIONS

Figure 1:
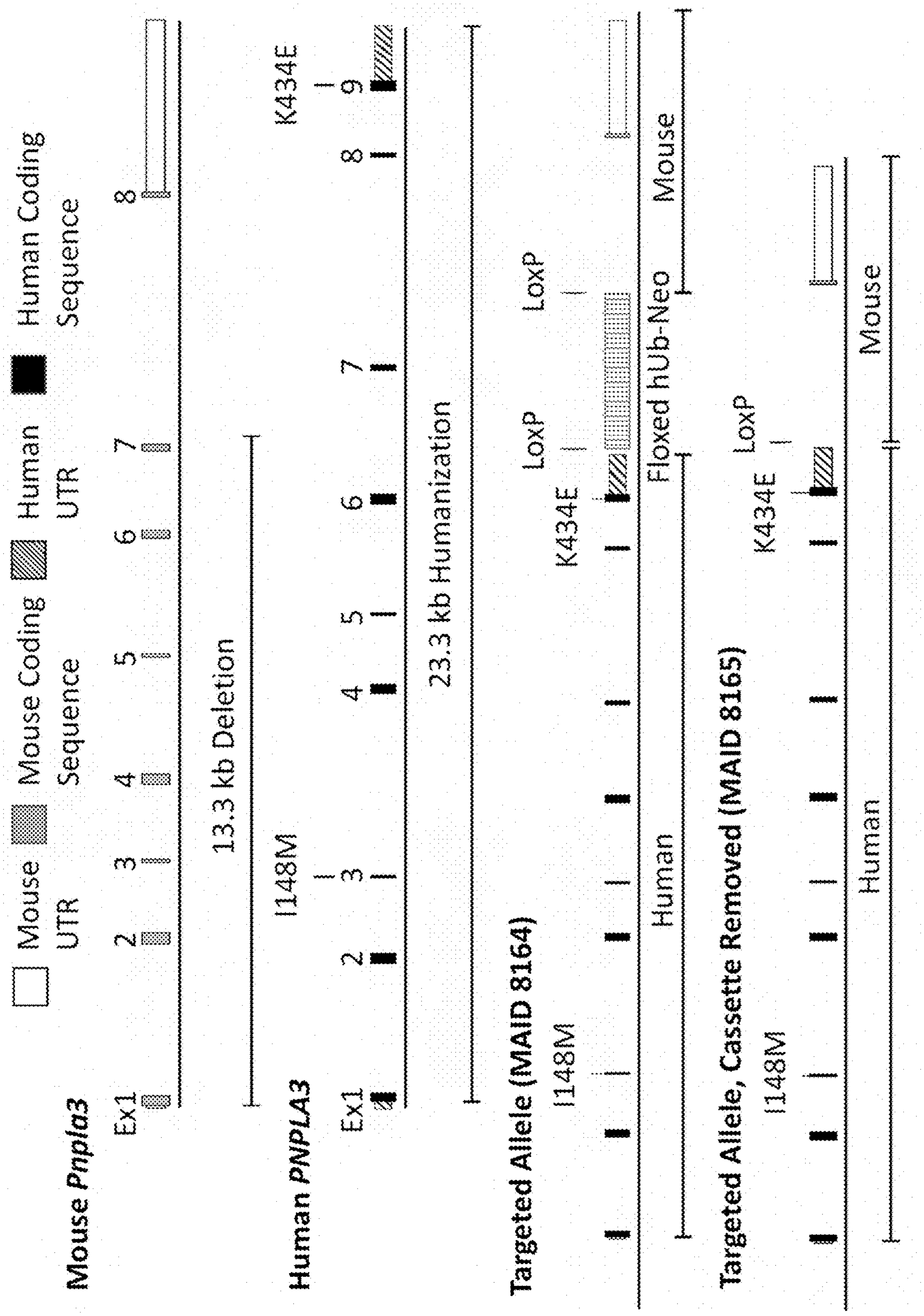
FIG. 1 (not to scale) shows a schematic of the targeting scheme for humanization of the mouse Pnpla3 locus. The top portion of the figure shows the endogenous wild type mouse Pnpla3 locus and the endogenous human PNPLA3 locus with I148M and K434E mutations, and the bottom portion of the figure shows the humanized PNPLA3 locus with or without the self-deleting selection cassette. Mouse 5' and 3' untranslated regions (UTRs) are designated by white boxes, mouse exons (coding sequence) are designated by light gray boxes, human 5' and 3' UTRs are designated by boxes with forward diagonal lines, and human exons (coding sequence) are designated by black boxes. The self-deleting ubiquitin puromycin selection cassette is designated by the box with vertical lines.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells in vitro, ex vivo, or in vivo. Numerous forms of viral vectors are known.

The term "isolated" with respect to cells, tissues (e.g., liver samples), lipid droplets, proteins, and nucleic acids includes cells, tissues (e.g., liver samples), lipid droplets, proteins, and nucleic acids that are relatively purified with respect to other bacterial, viral, cellular, or other components that may normally be present in situ, up to and including a substantially pure preparation of the cells, tissues (e.g., liver samples), lipid droplets, proteins, and nucleic acids. The term "isolated" also includes cells, tissues (e.g., liver samples), lipid droplets, proteins, and nucleic acids that have no naturally occurring counterpart, have been chemically synthesized and are thus substantially uncontaminated by other cells, tissues (e.g., liver samples), lipid droplets, proteins, and nucleic acids, or has been separated or purified from most other components (e.g., cellular components) with which they are naturally accompanied (e.g., other cellular proteins, polynucleotides, or cellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a rat cell or rat. For example, an endogenous Pnpla3 sequence of a mouse refers to a native Pnpla3 sequence that naturally occurs at the Pnpla3 locus in the mouse.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a PNPLA3 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, a "Pnpla3 locus" may refer to the specific location of a Pnpla3 gene, Pnpla3 DNA sequence, PNPLA3-encoding sequence, or Pnpla3 position on a chromosome of the genome of an organism that has been identified as to where such a sequence resides. A "Pnpla3 locus" may comprise a regulatory element of a Pnpla3 gene, including, for example, an enhancer, a promoter, 5' and/or 3' untranslated region (UTR), or a combination thereof.

The term "gene" refers to DNA sequences in a chromosome that may contain, if naturally present, at least one coding and at least one non-coding region. The DNA sequence in a chromosome that codes for a product (e.g., but not limited to, an RNA product and/or a polypeptide product) can include the coding region interrupted with non-coding introns and sequence located adjacent to the coding region on both the 5' and 3' ends such that the gene corresponds to the full-length mRNA (including the 5' and 3' untranslated sequences). Additionally, other non-coding sequences including regulatory sequences (e.g., but not limited to, promoters, enhancers, and transcription factor binding sites), polyadenylation signals, internal ribosome entry sites, silencers, insulating sequence, and matrix attachment regions may be present in a gene. These sequences may be close to the coding region of the gene (e.g., but not limited to, within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a mouse cell, a rat cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The methods and compositions provided herein employ a variety of different components. Some components throughout the description can have active variants and fragments. The term "functional" refers to the innate ability of a protein or nucleic acid (or a fragment or variant thereof) to exhibit a biological activity or function. The biological functions of functional fragments or variants may be the same or may in fact be changed (e.g., with respect to their specificity or selectivity or efficacy) in comparison to the original molecule, but with retention of the molecule's basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment," when referring to a protein, means a protein that is shorter or has fewer amino acids than the full-length protein. The term "fragment," when referring to a nucleic acid, means a nucleic acid that is shorter or has fewer nucleotides than the full-length nucleic acid. A fragment can be, for example, when referring to a protein fragment, an N-terminal fragment (i.e., removal of a portion of the C-terminal end of the protein), a C-terminal fragment (i.e., removal of a portion of the N-terminal end of the protein), or an internal fragment (i.e., removal of a portion of each of the N-terminal and C-terminal ends of the protein). A fragment can be, for example, when referring to a nucleic acid fragment, a 5' fragment (i.e., removal of a portion of the 3' end of the nucleic acid), a 3' fragment (i.e., removal of a portion of the 5' end of the nucleic acid), or an internal fragment (i.e., removal of a portion each of the 5' and 3' ends of the nucleic acid).

"Sequence identity" or "identity" in the context of two polynucleotides or polypeptide sequences refers to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

TABLE 1

Amino Acid Categorizations.

| | | | | | |
|---|---|---|---|---|---|
| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube or an isolated cell or cell line). The term "in vivo" includes natural environments (e.g., a cell or organism or body) and to processes or reactions that occur within a natural environment. The term "ex vivo" includes cells that have been removed from the body of an individual and processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreen1), yellow fluorescent proteins (e.g., YFP, eYFP, Citrine, Venus, YPet, PhiYFP, and ZsYellow1), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyan1, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Semin. Cell Dev. Biol.* 22(8):886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLoS ONE* 7:e45768:1-9; and Wang et al. (2013) *Nat. Biotechnol.* 31:530-532, each of which is herein incorporated by reference in its entirety for all purposes.

Non-homologous end joining (NHEJ) includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which the event or circumstance does not.

Designation of a range of values includes all integers within or defining the range, and all subranges defined by integers within the range.

Unless otherwise apparent from the context, the term "about" encompasses values±5 of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means $p \leq 0.05$.

DETAILED DESCRIPTION

I. Overview

Disclosed herein are non-human animal genomes, non-human animal cells, and non-human animals comprising a humanized PNPLA3 locus and methods of making and using such non-human animal cells and non-human animals. Also disclosed herein are humanized non-human animal Pnpla3 genes comprising a targeted genetic modification that humanizes the non-human animal Pnpla3 genes and nuclease agents and targeting vectors for use in humanizing a non-human animal Pnpla3 gene. Also disclosed herein are isolated liver samples (e.g., fractioned liver samples) prepared from the non-human animals comprising a humanized PNPLA3 locus and isolated lipid droplets prepared from the non-human animals comprising a humanized PNPLA3 locus.

PNPLA3 is a lipid-droplet-associated protein with highest expression in liver and adipose tissue. It has been identified through human genetics analyses as a gene involved in steatosis, fibrosis and cirrhosis of the liver. A common missense mutation (I148M or Ile148→Met148) in PNPLA3 is associated with higher risk of steatosis, non-alcoholic steatohepatitis (NASH), cirrhosis and liver carcinoma. Although PNPLA3 I148M mice have been generated, the understanding of human PNPLA3 function is very limited because of the low similarity between mouse and human PNPLA3 protein. In addition, human and mouse PNPLA3 expression patterns are very different. Mouse liver Pnpla3 RNA expression levels under chow-fed conditions are very low, which is not consistent with what is observed in humans. The humanized PNPLA3 mice disclosed herein show higher PNPLA3 RNA expression levels under chow-fed conditions, more consistent with what is observed in humans. The humanized PNPLA3 wild type and I148M mice generated here are novel models to study human PNPLA3 wild type and I148M function. The humanized PNPLA3 I148M mice showed higher basal RNA expression than non-humanized mice, which is more consistent with what is observed in humans.

II. Non-Human Animals Comprising a Humanized PNPLA3 Locus

The non-human animal genomes, non-human animal cells, and non-human animals disclosed herein comprise a humanized PNPLA3 locus. Cells or non-human animals comprising a humanized PNPLA3 locus express a human PNPLA3 protein or a partially humanized, chimeric PNPLA3 protein in which one or more fragments of the native PNPLA3 protein have been replaced with corresponding fragments from human PNPLA3 (e.g., all or part of the extracellular domain).

A. PNPLA3

The cells and non-human animals described herein comprise a humanized PNPLA3 locus. 1-acylglycerol-3-phosphate O-acyltransferase PNPLA3 (also known as PNPLA3, acylglycerol transacylase, adiponutrin, ADPN, calcium-independent phospholipase A2-epsilon, iPLA2-epsilon, lysophosphatidic acid acyltransferase, and patatin-like phospholipase domain-containing protein 3) is encoded by the PNPLA3 gene (also known as patatin-like phospholipase domain containing 3, ADPN, C22orf20, iPLA2-epsilon, and iPLA(2)epsilon). PNPLA3 is a lipid-droplet-associated protein with highest expression in liver and adipose tissue. PNPLA3 is a triacylglycerol lipase that mediates triacylglycerol hydrolysis in adipocytes. PNPLA3, which appears to be membrane bound, may be involved in the balance of energy usage/storage in adipocytes. PNPLA3 specifically catalyzes coenzyme A (CoA)-dependent acylation of 1-acyl-sn-glycerol 3-phosphate (2-lysophosphatidic acid/LPA) to generate phosphatidic acid (PA), an important metabolic intermediate and precursor for both triglycerides and glycerophospholipids. It does not esterify other lysophospholipids. It additionally possesses low triacylglycerol lipase and CoA-independent acylglycerol transacylase activities and thus may play a role in acyl-chain remodeling of triglycerides.

Polymorphic variation at position 148 influences insulin secretion levels and obesity. A common missense mutation (I148M or Ile148→Met148) in PNPLA3 is associated with risk for non-alcoholic fatty liver disease, as well as advanced forms of non-alcoholic steatohepatitis (NASH) and cirrhosis. The I148M variant is associated with increased hepatic fat content and serum aspartate aminotransferase concentrations. The I148M variant increases 1-acylglycerol-3-phosphate O-acyltransferase activity. In obese subjects the body mass index and waist are higher in carriers of the Ile-148 allele. The Ile-148 carriers also display decreased insulin secretion in response to oral glucose tolerance test. Met-148 allele carriers are seemingly more insulin resistant at a lower body mass index.

In subjects with and without non-alcoholic fatty liver disease (NAFLD), the I148M K434E variant was associated with histological NAFLD and steatohepatitis, whereas I148M without the K434E variant was not. Presence of a lysine at position 434 decreases PNPLA3 expression, lessening the effect of the I148M variant on the predisposition to steatosis and liver damage. See Donati et al. (2016) *Hepatology* 63(3):787-798, herein incorporated by reference in its entirety for all purposes. The K434E mutation enhances the I148M phenotype but is not sufficient to produce the phenotype by itself.

Human PNPLA3 maps to 22q13.31 on chromosome 22 (NCBI RefSeq Gene ID 80339; Assembly GRCh38.p13 (GCF_000001405.39); location NC_000022.11 (43923805 . . . 43947582)). The gene has been reported to have 9 exons. The wild type human PNPLA3 protein has been assigned UniProt accession number Q9NST1. At least two isoforms of human PNPLA3 are known (Q9NST1-1 and Q9NST1-2). The sequence for one isoform (canonical isoform), NCBI Accession No. NP_079501.2 (Q9NST1-1), is set forth in SEQ ID NO: 5. An mRNA (cDNA) encoding this isoform is assigned NCBI Accession No. NM_025225.3 and is set forth in SEQ ID NO: 24. An exemplary coding sequence (CDS) is set forth in SEQ ID NO: 15 (CCDS ID CCDS14054.1). The sequence for a human PNPLA3 protein having I148M and K434E mutations is set forth in SEQ ID NO: 9, with a corresponding coding sequence set forth in SEQ ID NO: 19. The sequence for a human PNPLA3 protein having a K434E mutation is set forth in SEQ ID NO: 63, with a corresponding coding sequence set forth in SEQ ID NO: 64. The full-length human PNPLA3 protein set forth in SEQ ID NO: 5 has 481 amino acids, including a cytoplasmic domain (amino acids 1-41), a transmembrane domain (amino acids 42-62), and a lumenal domain (amino acids 63-481). Delineations between these domains are as designated in UniProt. Reference to human PNPLA3 includes the canonical (wild type) forms as well as all allelic forms and isoforms. Any other forms of human PNPLA3 have amino acids numbered for maximal alignment with the wild type form, aligned amino acids being designated the same number.

Mouse Pnpla3 maps to 15; 15 E2 on chromosome 15 (NCBI RefSeq Gene ID 116939; Assembly GRCm38.p6 (GCF_000001635.26); location NC_000081.6 (84167776 . . . 84189521)). The gene has been reported to have 8 exons. The wild type mouse PNPLA3 protein has been assigned UniProt accession number Q91WW7. A sequence for mouse PNPLA3, NCBI Accession No. NP_473429.2, is set forth in SEQ ID NO: 1. An exemplary mRNA (cDNA) encoding mouse PNPLA3 is assigned NCBI Accession No. NM_054088.3 and is set forth in SEQ ID NO: 23. An exemplary coding sequence (CDS) is set forth in SEQ ID NO: 11 (CCDS ID CCDS37165.1). The canonical full-length mouse PNPLA3 protein set forth in SEQ ID NO: 1 has 413 amino acids, including a cytoplasmic domain (amino acids 1-42), a transmembrane domain (amino acids 43-63), and a lumenal domain (amino acids 64-413). Delineations between these domains are as designated in UniProt. Reference to mouse PNPLA3 includes the canonical (wild type) forms as well as all allelic forms and isoforms. Any other forms of mouse PNPLA3 have amino acids numbered for maximal alignment with the wild type form, aligned amino acids being designated the same number.

Rat Pnpla3 maps to 7q34 on chromosome 7 (NCBI RefSeq Gene ID 362972; Assembly Rnor_6.0 (GCF_000001895.5); location NC_005106.4 (125034760 . . . 125056165)). The gene has been reported to have 9 exons. The wild type rat PNPLA3 protein has been assigned UniProt accession number D3Z9J9. The sequence for rat PNPLA3, NCBI Accession No. NP_001269253.1, is set forth in SEQ ID NO: 25. An mRNA (cDNA) encoding rat PNPLA3 is assigned NCBI Accession No. NM_001282324.1 and is set forth in SEQ ID NO: 26. An exemplary coding sequence (CDS) is set forth in SEQ ID NO: 27. The canonical full-length rat PNPLA3 protein set forth in SEQ ID NO: 25 has 425 amino acids. Delineations between these domains are as designated in UniProt. Reference to rat PNPLA3 includes the canonical (wild type) forms as well as all allelic forms and isoforms. Any other forms of rat PNPLA3 have amino acids numbered for maximal alignment with the wild type form, aligned amino acids being designated the same number.

B. Humanized PNPLA3 Loci

Disclosed herein are humanized endogenous PNPLA3 loci in which a segment of an endogenous Pnpla3 locus has been deleted and replaced with a corresponding human PNPLA3 sequence (e.g., a corresponding human PNPLA3 genomic sequence), wherein a humanized PNPLA3 protein is expressed from the humanized endogenous PNPLA3 locus. A humanized PNPLA3 locus can be a Pnpla3 locus in which the entire Pnpla3 gene is replaced with the corresponding orthologous human PNPLA3 sequence, or it can be a Pnpla3 locus in which only a portion of the Pnpla3 gene is replaced with the corresponding orthologous human PNPLA3 sequence (i.e., humanized), or it can be a Pnpla3 locus in a portion of the Pnpla3 gene is deleted and a portion of the orthologous human PNPLA3 locus is inserted. In some examples, the portion of the orthologous human PNPLA3 locus that is inserted comprises more of the human PNPLA3 locus than is deleted from the endogenous Pnpla3 locus. A human PNPLA3 sequence corresponding to a particular segment of endogenous Pnpla3 sequence refers to the region of human PNPLA3 that aligns with the particular segment of endogenous Pnpla3 sequence when human PNPLA3 and the endogenous Pnpla3 are optimally aligned (greatest number of perfectly matched residues). The corresponding orthologous human sequence can comprise, for example, complementary DNA (cDNA) or genomic DNA. Optionally, a codon-optimized version of the corresponding orthologous human PNPLA3 sequence can be used and is modified to be codon-optimized based on codon usage in the non-human animal. Replaced or inserted (i.e., humanized) regions can include coding regions such as an exon, non-coding regions such as an intron, an untranslated region, or a regulatory region (e.g., a promoter, an enhancer, or a transcriptional repressor-binding element), or any combination thereof. As one example, exons corresponding to 1, 2, 3, 4, 5, 6, 7, 8, or all 9 exons of the human PNPLA3 gene can be humanized. For example, exons corresponding to exons 1-9 of the human PNPLA3 gene can be humanized. As an example, 1, 2, 3, 4, 5, 6, 7, 8, or all 9 exons of the human PNPLA3 gene can be inserted into the endogenous Pnpla3 locus, and/or endogenous Pnpla3 exons corresponding to 1, 2, 3, 4, 5, 6, 7, 8, or all 9 exons of the human PNPLA3 gene can be deleted form the endogenous Pnpla3 locus (for example, all endogenous exons except for the last exon can be deleted and replaced with all 9 exons of the human PNPLA3 gene). Alternatively, a region of PNPLA3 encoding an epitope recognized by an anti-human-PNPLA3 antigen-binding protein or a region targeted by human-PNPLA3-targeting reagent (e.g., a small molecule) can be humanized. Likewise, introns corresponding to 1, 2, 3, 4, 5, 6, 7, or all 8 introns of the human PNPLA3 gene can be humanized or can remain endogenous. For example, introns corresponding to the introns between exons 1 and 9 (i.e., introns 1-8) of the human PNPLA3 gene can be humanized. As an example, 1, 2, 3, 4, 5, 6, 7, or all 8 introns of the human PNPLA3 gene can be inserted into the endogenous Pnpla3 locus, and/or endogenous Pnpla3 introns corresponding to 1, 2, 3, 4, 5, 6, 7, or all 8 introns of the human PNPLA3 gene can be deleted form the endogenous Pnpla3 locus (for example, all endogenous introns except for a portion of the last intron can be deleted and replaced with all 8 introns of the human PNPLA3 gene). As a specific example, all or part of the last intron of the endogenous Pnpla3 locus has not been deleted in the humanized endogenous Pnpla3 locus. For example, the part of the last intron of the endogenous Pnpla3 locus that has not been deleted in the humanized endogenous Pnpla3 locus can comprise a regulatory element or a putative or predicted regulatory element. The regulatory element or putative or predicted regulatory element can affect expression of a gene downstream of the endogenous Pnpla3 locus (e.g., the gene immediately downstream of the endogenous Pnpla3 gene, such as Samm50 in the mouse).

Flanking untranslated regions including regulatory sequences can also be humanized or remain endogenous. For example, the 5' untranslated region (UTR), the 3' UTR, or both the 5' UTR and the 3' UTR can be humanized, or the 5' UTR, the 3' UTR, or both the 5' UTR and the 3' UTR can remain endogenous. One or both of the human 5' and 3'

UTRs can be inserted, and/or one or both of the endogenous 5' and 3' UTRs can be deleted. In a specific example, both the 5' UTR and the 3' UTR remain endogenous. In another specific example, the human 3' UTR is inserted into the endogenous Pnpla3 locus but the endogenous Pnpla3 3' UTR is not deleted. Depending on the extent of replacement by orthologous sequences, regulatory sequences, such as a promoter, can be endogenous or supplied by the replacing human orthologous sequence. For example, the humanized PNPLA3 locus can include the endogenous non-human animal Pnpla3 promoter.

Some humanized PNPLA3 loci can encode a wild type human or chimeric (non-human animal/human) PNPLA3 protein. A wild type PNPLA3 protein is one that does not comprise any mutations from the canonical PNPLA3 protein (e.g., canonical human PNPLA3 protein). Some humanized PNPLA3 loci can encode a human or chimeric (non-human animal/human) PNPLA3 protein that is wild type at position 148. A PNPLA3 protein is wild type at position 148 if a position in the humanized PNPLA3 corresponding to position 1148 in the canonical human PNPLA3 protein (SEQ ID NO: 5) when the humanized PNPLA3 protein is optimally aligned with the canonical human PNPLA3 protein remains wild type (e.g., 148I). Some humanized PNPLA3 loci can encode a human or chimeric (non-human animal/human) PNPLA3 protein comprising I148M and/or K434E mutations. An I148M mutation in a humanized PNPLA3 protein is a mutation to a methionine (M) at a position in the humanized PNPLA3 corresponding to position 1148 in the canonical human PNPLA3 protein (SEQ ID NO: 5) when the humanized PNPLA3 protein is optimally aligned with the canonical human PNPLA3 protein. Likewise, a K434E mutation in a humanized PNPLA3 protein is a mutation to a glutamate (E) at a position in the humanized PNPLA3 corresponding to position K434 in the canonical human PNPLA3 protein (SEQ ID NO: 5) when the humanized PNPLA3 protein is optimally aligned with the canonical human PNPLA3 protein. A humanized PNPLA3 protein and the canonical human PNPLA3 protein are optimally aligned when there is the greatest number of perfectly matched residues. Some humanized PNPLA3 loci can encode a human or chimeric (non-human animal/human) PNPLA3 protein comprising an I148M mutation but not a K434E mutation. Some humanized PNPLA3 loci can encode a human or chimeric (non-human animal/human) PNPLA3 protein comprising a K434E mutation but not an I148M mutation. Some humanized PNPLA3 loci can encode a human or chimeric (non-human animal/human) PNPLA3 protein comprising neither a I148M mutation nor a K434E mutation. Some humanized PNPLA3 loci can encode a human or chimeric (non-human animal/human) PNPLA3 protein that does not comprise an I148M mutation. Some humanized PNPLA3 loci can encode a human or chimeric (non-human animal/human) PNPLA3 protein that does not comprise a K434E mutation.

One or more or all of the regions encoding the cytoplasmic domain, the transmembrane domain, and the lumenal domain can be humanized, or one or more of such regions can remain endogenous. Exemplary coding sequences for a mouse PNPLA3 cytoplasmic domain, transmembrane domain, and lumenal domain are set forth in SEQ ID NOS: 12-14, respectively. Exemplary coding sequences for a human PNPLA3 cytoplasmic domain, transmembrane domain, and lumenal domain are set forth in SEQ ID NOS: 16-18, respectively. An exemplary coding sequence for a human PNPLA3 lumenal domain with I148M and K434E mutations is set forth in SEQ ID NO: 20. An exemplary coding sequence for a human PNPLA3 lumenal domain with a K434E mutation is set forth in SEQ ID NO: 66.

For example, all or part of the region of the Pnpla3 locus encoding the cytoplasmic domain can be humanized, and/or all or part of the region of the Pnpla3 locus encoding the transmembrane domain can be humanized, and/or all or part of the region of the Pnpla3 locus encoding the lumenal domain can be humanized. In one example, all or part of the region of the Pnpla3 locus encoding all three domains (cytoplasmic, transmembrane, and lumenal domains) is humanized. Optionally, the CDS of the human PNPLA3 cytoplasmic domain comprises a sequence, consists essentially of a sequence, or consists of a sequence that is at least about 85%, at least about 90%, at least about 95%, at least about 96%, at least about 97%, at least about 98%, at least about 99%, or about 100% identical to SEQ ID NO: 16 (or degenerates thereof) (e.g., at least 85%, at least 90%, at least 95%, at least 96%, at least 97%, at least 98%, at least 99%, or 100% identical to SEQ ID NO: 16 (or degenerates thereof)). The humanized PNPLA3 protein can retain the activity of the native PNPLA3 and/or human PNPLA3. Optionally, the CDS of the human PNPLA3 transmembrane domain comprises a sequence, consists essentially of a sequence, or consists of a sequence that is at least about 85%, at least about 90%, at least about 95%, at least about 96%, at least about 97%, at least about 98%, at least about 99%, or about 100% identical to SEQ ID NO: 17 (or degenerates thereof) (e.g., at least 85%, at least 90%, at least 95%, at least 96%, at least 97%, at least 98%, at least 99%, or 100% identical to SEQ ID NO: 17 (or degenerates thereof)). The humanized PNPLA3 protein can retain the activity of the native PNPLA3 and/or human PNPLA3. Optionally, the CDS of the human PNPLA3 lumenal domain comprises a sequence, consists essentially of a sequence, or consists of a sequence that is at least about 85%, at least about 90%, at least about 95%, at least about 96%, at least about 97%, at least about 98%, at least about 99%, or about 100% identical to SEQ ID NO: 18, 20, or 66 (or degenerates thereof) (e.g., at least 85%, at least 90%, at least 95%, at least 96%, at least 97%, at least 98%, at least 99%, or 100% identical to SEQ ID NO: 18, 20, or 66 (or degenerates thereof)). The humanized PNPLA3 protein can retain the activity of the native PNPLA3 and/or human PNPLA3. For example, the region of the Pnpla3 locus encoding the all of the cytoplasmic, transmembrane, and lumenal domains can be humanized such that a humanized PNPLA3 protein is produced with a human PNPLA3 cytoplasmic domain, a human PNPLA3 transmembrane domain, and a human PNPLA3 lumenal domain.

One or more of the regions encoding the cytoplasmic domain, the transmembrane domain, or the lumenal domain can remain endogenous. Optionally, the CDS of the endogenous PNPLA3 cytoplasmic domain comprises a sequence, consists essentially of a sequence, or consists of a sequence that is at least about 85%, at least about 90%, at least about 95%, at least about 96%, at least about 97%, at least about 98%, at least about 99%, or about 100% identical to SEQ ID NO: 12 (or degenerates thereof) (e.g., at least 85%, at least 90%, at least 95%, at least 96%, at least 97%, at least 98%, at least 99%, or 100% identical to SEQ ID NO: 12 (or degenerates thereof)). Optionally, the CDS of the endogenous PNPLA3 transmembrane domain comprises a sequence, consists essentially of a sequence, or consists of a sequence that is at least about 85%, at least about 90%, at least about 95%, at least about 96%, at least about 97%, at least about 98%, at least about 99%, or about 100% identical to SEQ ID NO: 13 (or degenerates thereof) (e.g., at least 85%, at least 90%, at least 95%, at least 96%, at least 97%, at least 98%, at least 99%, or 100% identical to SEQ ID NO: 13 (or degenerates thereof)). Optionally, the CDS of the endogenous PNPLA3 lumenal domain comprises a sequence, consists essentially of a sequence, or consists of a sequence that is at least about 85%, at least about 90%, at least about 95%, at least about 96%, at least about 97%, at least about 98%, at least about 99%, or about 100% identical to SEQ ID NO: 14 (or degenerates thereof) (e.g., at least 85%, at least 90%, at least 95%, at least 96%, at least 97%, at least 98%, at least 99%, or 100% identical to SEQ ID NO: 14 (or degenerates thereof)). In each case, the humanized PNPLA3 protein can retain the activity of the native PNPLA3 and/or human PNPLA3.

The PNPLA3 protein encoded by the humanized PNPLA3 locus can comprise one or more domains that are from a human PNPLA3 protein and/or one or more domains that are from an endogenous (i.e., native) PNPLA3 protein. Exemplary amino acid sequences for a mouse PNPLA3 cytoplasmic domain, transmembrane domain, and lumenal domain are set forth in SEQ ID NOS: 2-4, respectively. Exemplary amino acid sequences for a human PNPLA3 cytoplasmic domain, transmembrane domain, and lumenal domain are set forth in SEQ ID NOS: 6-8, respectively. An exemplary amino acid sequence for a human PNPLA3 lumenal domain with I148M and K434E mutations is set forth in SEQ ID NO: 10. An exemplary amino acid sequence for a human PNPLA3 lumenal domain with a K434E mutation is set forth in SEQ ID NO: 65.

The PNPLA3 protein can comprise one or more or all of a human PNPLA3 cytoplasmic domain, a human PNPLA3 transmembrane domain, and a human PNPLA3 lumenal domain. As one example, the PNPLA3 protein can comprise a human PNPLA3 cytoplasmic domain, a human PNPLA3 transmembrane domain, and a human PNPLA3 lumenal domain.

The PNPLA3 protein encoded by the humanized PNPLA3 locus can also comprise one or more domains that are from the endogenous (i.e., native) non-human animal PNPLA3 protein. As one example, the PNPLA3 protein encoded by the humanized PNPLA3 locus can comprise a cytoplasmic domain from the endogenous (i.e., native) non-human animal PNPLA3 protein and/or a transmembrane domain from the endogenous (i.e., native) non-human animal PNPLA3 protein and/or a lumenal domain from the endogenous (i.e., native) non-human animal PNPLA3 protein.

Domains in a humanized PNPLA3 protein that are from a human PNPLA3 protein can be encoded by a fully humanized sequence (i.e., the entire sequence encoding that domain is inserted orthologous human PNPLA3 sequence) or can be encoded by a partially humanized sequence (i.e., some of the sequence encoding that domain is inserted orthologous human PNPLA3 sequence, and the remaining endogenous (i.e., native) sequence encoding that domain encodes the same amino acids as the orthologous human PNPLA3 sequence such that the encoded domain is identical to that domain in the human PNPLA3 protein). For example, part of the region of the Pnpla3 locus encoding the cytoplasmic domain (e.g., encoding the N-terminal region of the cytoplasmic domain) can remain endogenous Pnpla3 sequence, wherein the amino acid sequence of the region of the cytoplasmic domain encoded by the remaining endogenous Pnpla3 sequence is identical to the corresponding orthologous human PNPLA3 amino acid sequence. As another example, part of the region of the Pnpla3 locus encoding the lumenal domain (e.g., encoding the C-terminal region of the lumenal domain) can remain endogenous Pnpla3 sequence, wherein the amino acid sequence of the region of the lumenal domain encoded by the remaining endogenous Pnpla3 sequence is identical to the corresponding orthologous human PNPLA3 amino acid sequence.

Likewise, domains in a humanized PNPLA3 protein that are from the endogenous PNPLA3 protein can be encoded by a fully endogenous sequence (i.e., the entire sequence encoding that domain is the endogenous Pnpla3 sequence) or can be encoded by a partially humanized sequence (i.e., some of the sequence encoding that domain is replaced with the orthologous human PNPLA3 sequence, but the orthologous human PNPLA3 sequence encodes the same amino acids as the replaced endogenous Pnpla3 sequence such that the encoded domain is identical to that domain in the endogenous PNPLA3 protein). For example, part of the region of the Pnpla3 locus encoding the cytoplasmic domain (e.g., encoding the N-terminal region of the cytoplasmic domain) can be replaced with orthologous human PNPLA3 sequence, wherein the amino acid sequence of the region of the cytoplasmic domain encoded by the orthologous human PNPLA3 sequence is identical to the corresponding endogenous amino acid sequence. As another example, part of the region of the Pnpla3 locus encoding the lumenal domain (e.g., encoding the C-terminal region of the lumenal domain) can be replaced with orthologous human PNPLA3 sequence, wherein the amino acid sequence of the region of the lumenal domain encoded by the orthologous human PNPLA3 sequence is identical to the corresponding endogenous amino acid sequence.

As one example, the humanized PNPLA3 protein encoded by the humanized PNPLA3 locus can comprise a human PNPLA3 cytoplasmic domain. Optionally, the human PNPLA3 cytoplasmic domain comprises a sequence, consists essentially of a sequence, or consists of a sequence that is at least about 85%, at least about 90%, at least about 95%, at least about 96%, at least about 97%, at least about 98%, at least about 99%, or about 100% identical to SEQ ID NO: 6 (e.g., at least 85%, at least 90%, at least 95%, at least 96%, at least 97%, at least 98%, at least 99%, or 100% identical to SEQ ID NO: 6). As another example, the humanized PNPLA3 protein encoded by the humanized PNPLA3 locus can comprise a human PNPLA3 transmembrane domain. Optionally, the human PNPLA3 transmembrane domain comprises a sequence, consists essentially of a sequence, or consists of a sequence that is at least about 85%, at least about 90%, at least about 95%, at least about 96%, at least about 97%, at least about 98%, at least about 99%, or about 100% identical to SEQ ID NO: 7 (e.g., at least 85%, at least 90%, at least 95%, at least 96%, at least 97%, at least 98%, at least 99%, or 100% identical to SEQ ID NO: 7). As another example, the humanized PNPLA3 protein encoded by the humanized PNPLA3 locus can comprise a human PNPLA3 lumenal domain. Optionally, the human PNPLA3 lumenal domain comprises a sequence, consists essentially of a sequence, or consists of a sequence that is at least about 85%, at least about 90%, at least about 95%, at least about 96%, at least about 97%, at least about 98%, at least about 99%, or about 100% identical to SEQ ID NO: 8, 10, or 65 (e.g., at least 85%, at least 90%, at least 95%, at least 96%, at least 97%, at least 98%, at least 99%, or 100% identical to SEQ ID NO: 8, 10, or 65). The human PNPLA3 lumenal domain can comprise I148M and/or K434E mutations or can lack I148M and/or K434E mutations (e.g., can be a wild type human PNPLA3 lumenal domain). For example, the human PNLA3 lumenal domain can comprise both I148M and K434E mutations (e.g., SEQ ID NO: 10).

Alternatively, the human PNLA3 lumenal domain can comprise just the K434E mutation (e.g., SEQ ID NO: 65). Alternatively, the human PNPLA3 lumenal domain can lack both I148M and K434E mutations or can retain 1148 and K434 as in wild type human PNPLA3 (e.g., SEQ ID NO: 8). In each case, the humanized PNPLA3 protein can retain the activity of the native PNPLA3 and/or can retain the activity of human PNPLA3. For example, the humanized PNPLA3 protein encoded by the humanized PNPLA3 locus can comprise a sequence, consist essentially of a sequence, or consist of a sequence that is at least about 85%, at least about 90%, at least about 95%, at least about 96%, at least about 97%, at least about 98%, at least about 99%, or about 100% identical to SEQ ID NO: 5, 9, or 63 (e.g., at least 85%, at least 90%, at least 95%, at least 96%, at least 97%, at least 98%, at least 99%, or 100% identical to SEQ ID NO: 5, 9, or 63). Optionally, the humanized PNPLA3 CDS encoded by the humanized PNPLA3 locus can comprise a sequence, consist essentially of a sequence, or consist of a sequence that is at least about 85%, at least about 90%, at least about 95%, at least about 96%, at least about 97%, at least about 98%, at least about 99%, or about 100% identical to SEQ ID NO: 15, 19, or 64 (or degenerates thereof) (e.g., at least 85%, at least 90%, at least 95%, at least 96%, at least 97%, at least 98%, at least 99%, or 100% identical to SEQ ID NO: 15, 19, or 64 (or degenerates thereof)). The human PNPLA3 protein can comprise I148M and/or K434E mutations or can lack I148M and/or K434E mutations (e.g., can be a wild type human PNPLA3 protein). For example, the human PNPLA3 protein can comprise both I148M and K434E mutations (e.g., SEQ ID NO: 9, encoded, e.g., by SEQ ID NO: 19). Alternatively, the human PNPLA3 protein can comprise a K434E mutation but retain 1148 (e.g., SEQ ID NO: 63, encoded, e.g., by SEQ ID NO: 64). Alternatively, the human PNPLA3 protein can lack both I148M and K434E mutations or can retain 1148 and K434 as in wild type human PNPLA3. For example, the human PNPLA3 protein can be a wild type human PNPLA3 protein (e.g., SEQ ID NO: 5, encoded, e.g., by SEQ ID NO: 15). In each case, the humanized PNPLA3 protein can retain the activity of the native PNPLA3 and/or can retain the activity of human PNPLA3.

Optionally, a humanized PNPLA3 locus can comprise other elements. Examples of such elements can include selection cassettes, reporter genes, recombinase recognition sites, or other elements. Alternatively, the humanized PNPLA3 locus can lack other elements (e.g., can lack a selection marker or selection cassette). Examples of suitable reporter genes and reporter proteins are disclosed elsewhere herein. Examples of suitable selection markers include neomycin phosphotransferase ($neo_r$), hygromycin B phosphotransferase ($hyg_r$), puromycin-N-acetyltransferase ($puro_r$), blasticidin S deaminase ($bsr_r$), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The humanized PNPLA3 locus can also be a conditional allele. For example, the conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

Figure 4:
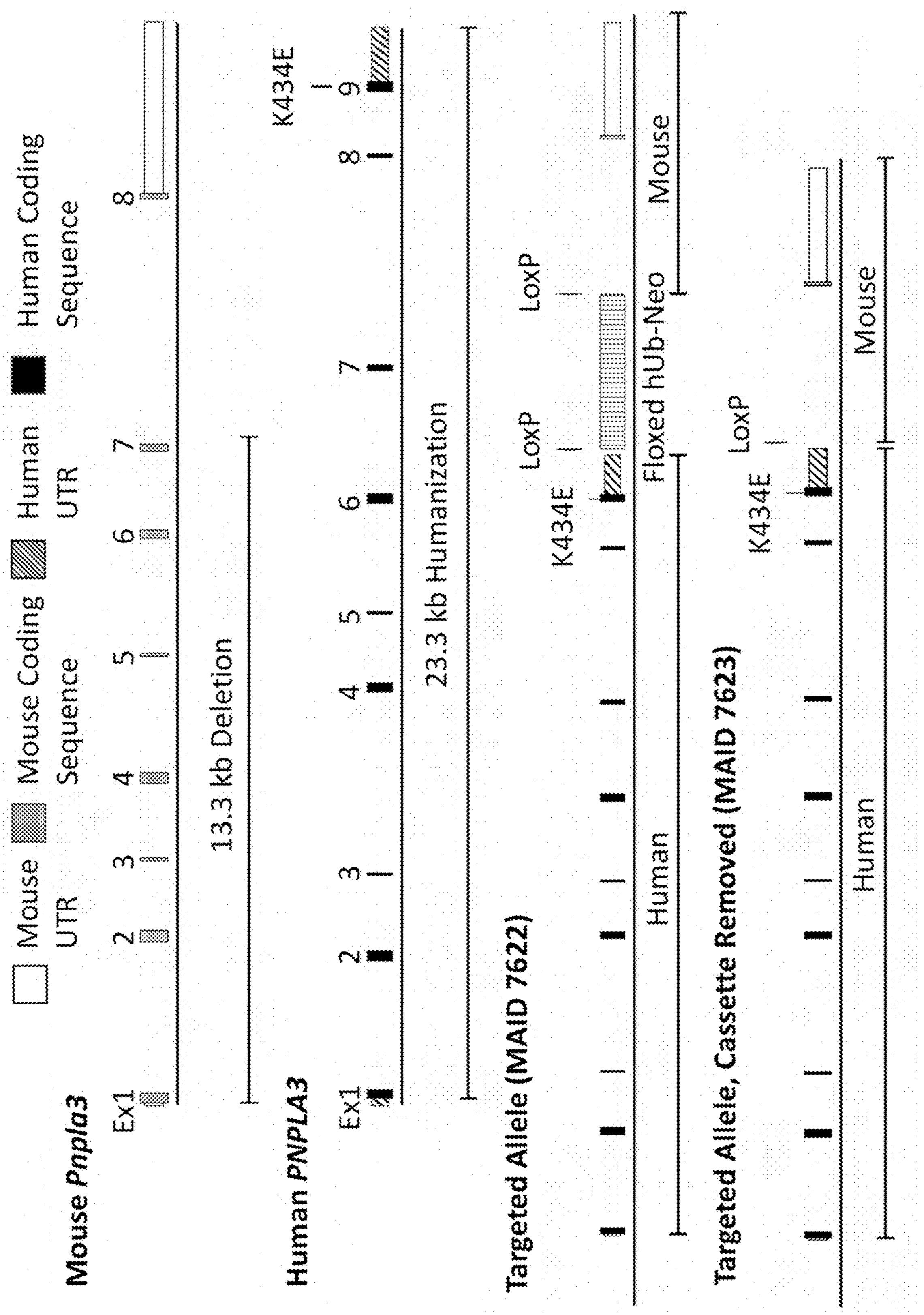
FIG. 4 (not to scale) shows a schematic of the targeting scheme for humanization of the mouse Pnpla3 locus. The top portion of the figure shows the endogenous wild type mouse Pnpla3 locus and the endogenous human PNPLA3 locus with a K434E mutation, and the bottom portion of the figure shows the humanized PNPLA3 locus with or without the self-deleting selection cassette. Mouse 5' and 3' untranslated regions (UTRs) are designated by white boxes, mouse exons (coding sequence) are designated by light gray boxes, human 5' and 3' UTRs are designated by boxes with forward diagonal lines, and human exons (coding sequence) are designated by black boxes. The self-deleting ubiquitin puromycin selection cassette is designated by the box with vertical lines.

In one exemplary humanized PNPLA3 locus (e.g., a humanized mouse PNPLA3 locus or a humanized rat PNPLA3 locus), a region of the endogenous Pnpla3 locus from the first exon to the penultimate exon including all intervening introns is deleted in the humanized PNPLA3 locus and replaced with a region of the human PNPLA3 locus comprising the sequence between the human PNPLA3 start codon and the human PNPLA3 stop codon. In a specific example, the humanized Pnpla3 locus comprises an endogenous Pnpla3 promoter, wherein the human PNPLA3 sequence is operably linked to the endogenous Pnpla3 promoter. One exemplary humanized PNPLA3 locus (e.g., a humanized mouse PNPLA3 locus or a humanized rat PNPLA3 locus) is one in which a region between from exon 1 through exon 7 of the endogenous Pnpla3 locus (e.g., an endogenous mouse Pnpla3 locus) is deleted (e.g., preserving some of intron 7 and preserving exon 8 (e.g., preserving some of mouse intron 7 and preserving mouse exon 8)) and is replaced with a region of human PNPLA3 from exon 1 through exon 9, including the 3' UTR and all introns between exons 1 and 9). The human PNPLA3 sequence replacing the deleted endogenous Pnpla3 sequence encodes a fully human PNPLA3 protein. See FIGS. 1 and 4. Exemplary sequences for a humanized PNPLA3 locus are set forth in SED ID NOS: 21, 22, 67, and 68.

In one specific example, the human PNPLA3 sequence at the humanized endogenous PNPLA3 locus can comprise a sequence, consist essentially of a sequence, or consist of a sequence at least about 85%, at least about 90%, at least about 95%, at least about 96%, at least about 97%, at least about 98%, at least about 99%, or about 100% identical to the sequence set forth in SEQ ID NO: 62 or 69 (e.g., at least 85%, at least 90%, at least 95%, at least 96%, at least 97%, at least 98%, at least 99%, or 100% identical to the sequence set forth in SEQ ID NO: 62 or 69). In another specific example, the humanized endogenous PNPLA3 locus can encode a protein comprising a sequence, consisting essentially of a sequence, or consisting of a sequence at least about 85%, at least about 90%, at least about 95%, at least about 96%, at least about 97%, at least about 98%, at least about 99%, or about 100% identical to the sequence set forth in SEQ ID NO: 5, 9, or 63 (at least 85%, at least 90%, at least 95%, at least 96%, at least 97%, at least 98%, at least 99%, or 100% identical to the sequence set forth in SEQ ID NO: 5, 9, or 63). In another specific example, the humanized endogenous PNPLA3 locus can comprise a coding sequence comprising a sequence, consisting essentially of a sequence, or consisting of a sequence at least about 85%, at least about 90%, at least about 95%, at least about 96%, at least about 97%, at least about 98%, at least about 99%, or about 100% identical to the sequence set forth in SEQ ID NO: 15, 19, or 64 (e.g., at least 85%, at least 90%, at least 95%, at least 96%, at least 97%, at least 98%, at least 99%, or 100% identical to the sequence set forth in SEQ ID NO: 15, 19, or 64). In another specific example, the humanized endogenous PNPLA3 locus can comprise a sequence, consist essentially of a sequence, or consist of a sequence at least about 85%, at least about 90%, at least about 95%, at least about 96%, at least about 97%, at least about 98%, at least about 99%, or about 100% identical to the sequence set forth in SEQ ID NO: 21, 22, 67, or 68 (e.g., at least 85%, at least 90%, at least 95%, at least 96%, at least 97%, at least 98%, at least 99%, or 100% identical to the sequence set forth in SEQ ID NO: 21, 22, 67, or 68).

C. Non-Human Animal Genomes, Non-Human Animal Cells, and Non-Human Animals Comprising a Humanized PNPLA3 Locus Non-human animal genomes, non-human animal cells, and non-human animals comprising a humanized PNPLA3 locus as described elsewhere herein are provided. The genomes, cells, or non-human animals can express a humanized PNPLA3 protein encoded by the humanized PNPLA3 locus. The genomes, cells, or non-human animals can be male or female. The genomes, cells, or non-human animals can be heterozygous or homozygous for the humanized PNPLA3 locus. A diploid organism has two alleles at each genetic locus. Each pair of alleles represents the genotype of a specific genetic locus. Genotypes are described as homozygous if there are two identical alleles at a particular locus and as heterozygous if the two alleles differ. A non-human animal comprising a humanized PNPLA3 locus can comprise the humanized PNPLA3 locus in its germline.

The non-human animal genomes or cells provided herein can be, for example, any non-human animal genome or cell comprising a Pnpla3 locus or a genomic locus homologous or orthologous to the human PNPLA3 locus. The genomes can be from or the cells can be eukaryotic cells, which include, for example, animal cells, mammalian cells, non-human mammalian cells, and human cells. The term "animal" includes any member of the animal kingdom, including, for example, mammals, fishes, reptiles, amphibians, birds, and worms. A mammalian cell can be, for example, a non-human mammalian cell, a rodent cell, a rat cell, or a mouse cell. Other non-human mammals include, for example, non-human primates. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell (e.g., a non-ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, such as hepatoblasts or hepatocytes.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, hepatocytes.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. A specific example of an immortalized cell line is the HepG2 human liver cancer cell line. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a humanized PNPLA3 locus as described herein can be made by the methods described elsewhere herein. The term "animal" includes any member of the animal kingdom, including, for example, mammals, fishes, reptiles, amphibians, birds, and worms. In a specific example, the non-human animal is a non-human mammal. Non-human mammals include, for example, non-human primates and rodents (e.g., mice and rats). The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 12959/SvEvH, 129S6 (129/SvEvTac), 129S7, 129S8, 129T1, and 129T2. See, e.g., Festing et al. (1999) *Mamm. Genome* 10(8):836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/01a. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

RNA expression from the humanized PNPLA3 locus in the liver (or in cells) of a non-human animal comprising the humanized locus can be higher than RNA expression from a non-humanized endogenous Pnpla3 locus (e.g., an endogenous wild type Pnpla3 locus or an endogenous Pnpla3 locus comprising I148M and/or K434E mutations) in the liver of a control non-human animal (e.g., a non-human animal with a non-humanized endogenous Pnpla3 locus, such as with a wild type endogenous Pnpla3 locus) or control non-human animal cell (e.g., a non-human animal cell without a humanized endogenous Pnpla3 locus, such as with a wild type endogenous Pnpla3 locus). For example, RNA expression from the humanized PNPLA3 locus in the liver (or in cells) of a non-human animal comprising the humanized locus under chow-fed conditions (e.g., for about 4 weeks or for 4 weeks) can be higher than RNA expression from a non-humanized endogenous Pnpla3 locus (e.g., an endogenous wild type Pnpla3 locus or an endogenous Pnpla3 locus comprising I148M and/or K434E mutations) in the liver (or in cells) of a control non-human animal (e.g., a non-human animal with a non-humanized endogenous Pnpla3 locus, such as with a wild type endogenous Pnpla3 locus) under chow-fed conditions (e.g., for about 4 weeks or for 4 weeks). For example, the expression can be at least about 1.5-fold higher, at least about 2-fold higher, at least about 3-fold higher, at least about 4-fold higher, at least about 5-fold higher, at least about 6-fold higher, at least about 7-fold higher, at least about 8-fold higher, at least about 9-fold higher, at least about 10-fold higher, at least about 11-fold higher, at least about 12-fold higher, at least about 13-fold higher, at least about 14-fold higher, at least about 15-fold higher, at least about 16-fold higher, at least about 17-fold higher, at least about 18-fold higher, at least about 19-fold higher, or at least about 20-fold higher from the humanized PNPLA3 locus compared to from a wild type Pnpla3 locus (e.g., at least 1.5-fold higher, at least 2-fold higher, at least 3-fold higher, at least 4-fold higher, at least 5-fold higher, at least 6-fold higher, at least 7-fold higher, at least 8-fold higher, at least 9-fold higher, at least 10-fold higher, at least 11-fold higher, at least 12-fold higher, at least 13-fold higher, at least 14-fold higher, at least 15-fold higher, at least 16-fold higher, at least 17-fold higher, at least 18-fold higher, at least 19-fold higher, or at least 20-fold higher from the humanized PNPLA3 locus compared to from a wild type Pnpla3 locus). Additionally or alternatively, RNA expression from the humanized PNPLA3 locus in the liver (or in cells) of a non-human animal comprising the humanized locus under chow-fed conditions (e.g., for about 4 weeks or for 4 weeks) can be at least about 5%, at least about 10%, at least about 15%, at least about 20%, at least about 25%, or at least about 30% of RNA expression from the humanized PNPLA3 locus in the liver (or in cells) of a non-human animal comprising the humanized locus under high sucrose diet (HSD) or high fructose diet (HFruD) conditions (e.g., for about 4 weeks or for 4 weeks) (e.g., at least 5%, at least 10%, at least 15%, at least 20%, at least 25%, or at least 30% of RNA expression from the humanized PNPLA3 locus in the liver (or in cells) of a non-human animal comprising the humanized locus under high sucrose diet (HSD) or high fructose diet (HFruD) conditions (e.g., for about 4 weeks or for 4 weeks)).

III. Methods of Making Non-Human Animals Comprising a Humanized PNPLA3 Locus

Various methods are provided for making a non-human animal genome, non-human animal cell, or non-human animal comprising a humanized PNPLA3 locus as disclosed elsewhere herein. Likewise, various methods are provided for making a humanized PNPLA3 gene or locus or for making a non-human animal genome or non-human animal cell comprising a humanized PNPLA3 locus as disclosed elsewhere herein. Any convenient method or protocol for producing a genetically modified organism is suitable for producing such a genetically modified non-human animal. See, e.g., Poueymirou et al. (2007) *Nat. Biotechnol.* 25(1): 91-99; U.S. Pat. Nos. 7,294,754; 7,576,259; 7,659,442; 8,816,150; 9,414,575; 9,730,434; and 10,039,269, each of which is herein incorporated by reference in its entirety for all purposes (describing mouse ES cells and the VELOCIMOU5E® method for making a genetically modified mouse). See also US 2014/0235933 A1, US 2014/0310828 A1, each of which is herein incorporated by reference in its entirety for all purposes (describing rat ES cells and methods for making a genetically modified rat). See also Cho et al. (2009) *Curr. Protoc. Cell. Biol.* 42:19.11.1-19.11.22 (doi: 10.1002/0471143030.cb1911s42) and Gama Sosa et al. (2010) *Brain Struct. Funct.* 214(2-3): 91-109, each of which is herein incorporated by reference in its entirety for all purposes. Such genetically modified non-human animals can be generated, for example, through gene knock-in at a targeted PNPLA3 locus.

For example, the method of producing a non-human animal comprising a humanized PNPLA3 locus can comprise: (1) providing a pluripotent cell (e.g., an embryonic stem (ES) cell such as a mouse ES cell or a rat ES cell)

comprising the humanized PNPLA3 locus; (2) introducing the genetically modified pluripotent cell into a non-human animal host embryo; and (3) gestating the host embryo in a surrogate mother.

As another example, the method of producing a non-human animal comprising a humanized PNPLA3 locus can comprise: (1) modifying the genome of a pluripotent cell (e.g., an embryonic stem (ES) cell such as a mouse ES cell or a rat ES cell) to comprise the humanized PNPLA3 locus; (2) identifying or selecting the genetically modified pluripotent cell comprising the humanized PNPLA3 locus; (3) introducing the genetically modified pluripotent cell into a non-human animal host embryo; and (4) gestating the host embryo in a surrogate mother. The donor cell can be introduced into a host embryo at any stage, such as the blastocyst stage or the pre-morula stage (i.e., the 4-cell stage or the 8-cell stage). Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized PNPLA3 locus (and capable of transmitting the genetic modification through the germline).

Alternatively, the method of producing the non-human animals described elsewhere herein can comprise: (1) modifying the genome of a one-cell stage embryo to comprise the humanized PNPLA3 locus using the methods described above for modifying pluripotent cells; (2) selecting the genetically modified embryo; and (3) gestating the genetically modified embryo in a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The modified cell or one-cell stage embryo can be generated, for example, through recombination by (a) introducing into the cell one or more exogenous donor nucleic acids (e.g., targeting vectors) comprising an insert nucleic acid flanked, for example, by 5' and 3' homology arms corresponding to 5' and 3' target sites (e.g., target sites flanking the endogenous sequences intended for deletion and replacement with the insert nucleic acid), wherein the insert nucleic acid comprises a human PNPLA3 sequence to generate a humanized PNPLA3 locus; and (b) identifying at least one cell comprising in its genome the insert nucleic acid integrated at the endogenous Pnpla3 locus (i.e., identifying at least one cell comprising the humanized PNPLA3 locus). Likewise, a modified non-human animal genome or humanized non-human animal PNPLA3 gene can be generated, for example, through recombination by (a) contacting the genome or gene with one or more exogenous donor nucleic acids (e.g., targeting vectors) comprising 5' and 3' homology arms corresponding to 5' and 3' target sites (e.g., target sites flanking the endogenous sequences intended for deletion and/or replacement with an insert nucleic acid (e.g., comprising a human PNPLA3 sequence to generate a humanized PNPLA3 locus) flanked by the 5' and 3' homology arms), wherein the exogenous donor nucleic acids are designed for humanization of the endogenous non-human animal Pnpla3 locus.

Alternatively, the modified pluripotent cell or one-cell stage embryo can be generated by (a) introducing into the cell: (i) a nuclease agent, wherein the nuclease agent induces a nick or double-strand break at a target site within the endogenous Pnpla3 locus; and (ii) one or more exogenous donor nucleic acids (e.g., targeting vectors) comprising an insert nucleic acid flanked by, for example, 5' and 3' homology arms corresponding to 5' and 3' target sites (e.g., target sites flanking the endogenous sequences intended for deletion and replacement with the insert nucleic acid), wherein the insert nucleic acid comprises a human PNPLA3 sequence to generate a humanized PNPLA3 locus; and (c) identifying at least one cell comprising in its genome the insert nucleic acid integrated at the endogenous Pnpla3 locus (i.e., identifying at least one cell comprising the humanized PNPLA3 locus). Likewise, a modified non-human animal genome or humanized non-human animal PNPLA3 gene can be generated by contacting the genome or gene with: (i) a nuclease agent, wherein the nuclease agent induces a nick or double-strand break at a target site within the endogenous Pnpla3 locus or gene; and (ii) one or more exogenous donor nucleic acids (e.g., targeting vectors) comprising an insert nucleic acid (e.g., comprising a human PNPLA3 sequence to generate a humanized PNPLA3 locus) flanked by, for example, 5' and 3' homology arms corresponding to 5' and 3' target sites (e.g., target sites flanking the endogenous sequences intended for deletion and/or replacement with the insert nucleic acid), wherein the exogenous donor nucleic acids are designed for humanization of the endogenous Pnpla3 locus. Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems (e.g., CRISPR/Cas9 systems) or components of such systems (e.g., CRISPR/Cas9). See, e.g., US 2013/0309670 and US 2015/0159175, each of which is herein incorporated by reference in its entirety for all purposes. In one example, the nuclease comprises a Cas9 protein and a guide RNA. For example, the guide RNA can target a guide RNA target sequence comprising any one of SEQ ID NOS: 28-31. In another example, the nuclease comprises a Cas9 protein and two or more, three or more, or four or more guide RNAs (e.g., guide RNAs targeting all of SEQ ID NOS: 28-31).

The step of modifying the genome can, for example, utilize exogenous repair templates (e.g., targeting vectors) to modify a Pnpla3 locus to comprise a humanized PNPLA3 locus disclosed herein. As one example, the targeting vector can be for generating a humanized PNPLA3 gene at an endogenous Pnpla3 locus (e.g., endogenous non-human animal Pnpla3 locus), wherein the targeting vector comprises a nucleic acid insert comprising human PNPLA3 sequence to be integrated in the Pnpla3 locus flanked by a 5' homology arm targeting a 5' target sequence at the endogenous Pnpla3 locus and a 3' homology arm targeting a 3' target sequence at the endogenous Pnpla3 locus. Integration of a nucleic acid insert in the Pnpla3 locus can result in addition of a nucleic acid sequence of interest in the Pnpla3 locus, deletion of a nucleic acid sequence of interest in the Pnpla3 locus, or replacement of a nucleic acid sequence of interest in the Pnpla3 locus (i.e., deleting a segment of the endogenous Pnpla3 locus and replacing with an orthologous human PNPLA3 sequence).

The exogenous repair templates can be for non-homologous-end-joining-mediated insertion or homologous recombination. Exogenous repair templates can comprise deoxyribonucleic acid (DNA) or ribonucleic acid (RNA), they can be single-stranded or double-stranded, and they can be in linear or circular form. For example, a repair template can be a single-stranded oligodeoxynucleotide (ssODN). Exogenous repair templates can also comprise a heterologous sequence that is not present at an untargeted endogenous Pnpla3 locus. For example, an exogenous repair template can comprise a selection cassette, such as a selection cassette flanked by recombinase recognition sites.

In cells other than one-cell stage embryos, the exogenous repair template can be a "large targeting vector" or "LTVEC," which includes targeting vectors that comprise homology arms that correspond to and are derived from nucleic acid sequences larger than those typically used by other approaches intended to perform homologous recombination in cells. See, e.g., US 2004/0018626; WO 2013/163394; U.S. Pat. Nos. 9,834,786; 10,301,646; WO 2015/088643; U.S. Pat. Nos. 9,228,208; 9,546,384; 10,208,317; and US 2019-0112619, each of which is herein incorporated by reference in its entirety for all purposes. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein). LTVECs can be of any length and are typically at least 10 kb in length. The sum total of the 5' homology arm and the 3' homology arm in an LTVEC is typically at least 10 kb. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) *Nat. Biotechnol.* 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes.

The methods can further comprise identifying a cell or animal having a modified target genomic locus. Various methods can be used to identify cells and animals having a targeted genetic modification. The screening step can comprise, for example, a quantitative assay for assessing modification-of-allele (MOA) of a parental chromosome. See, e.g., US 2004/0018626; US 2014/0178879; US 2016/0145646; WO 2016/081923; and Frendewey et al. (2010) *Methods Enzymol.* 476:295-307, each of which is herein incorporated by reference in its entirety for all purposes. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

The various methods provided herein allow for the generation of a genetically modified non-human F0 animal wherein the cells of the genetically modified F0 animal comprise the humanized PNPLA3 locus. It is recognized that depending on the method used to generate the F0 animal, the number of cells within the F0 animal that have the humanized PNPLA3 locus will vary. With mice, for example, the introduction of the donor ES cells into a pre-morula stage embryo from the mouse (e.g., an 8-cell stage mouse embryo) via, for example, the VELOCIMOUSE® method allows for a greater percentage of the cell population of the F0 mouse to comprise cells having the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification. The cells of the genetically modified F0 animal can be heterozygous for the humanized PNPLA3 locus or can be homozygous for the humanized PNPLA3 locus.

IV. Methods of Using Non-Human Animals Comprising a Humanized PNPLA3 Locus for Assessing Delivery or Efficacy of Human-PNPLA3-Targeting Reagents In Vivo or Ex Vivo Various methods are provided for using the non-human animals comprising a humanized PNPLA3 locus as described elsewhere herein for assessing delivery or efficacy of human-PNPLA3-targeting reagents in vivo or ex vivo. Because the non-human animals comprise a humanized PNPLA3 locus, the non-human animals will more accurately reflect the efficacy of a human-PNPLA3-targeting reagent.

A. Methods of Testing Efficacy of Human-PNPLA3-Targeting Reagents In Vivo or Ex Vivo Various methods are provided for assessing delivery or efficacy of human-PNPLA3-targeting reagents in vivo using non-human animals comprising a humanized PNPLA3 locus as described elsewhere herein. Such methods can comprise: (a) introducing into the non-human animal a human-PNPLA3-targeting reagent; and (b) assessing the activity of the human-PNPLA3-targeting reagent.

The human-PNPLA3-targeting reagent can be a human-PNPLA3-targeting antibody or antigen-binding protein or any other large molecule or small molecule that targets human PNPLA3. Alternatively, the human-PNPLA3-targeting reagent can be any biological or chemical agent that targets the human PNPLA3 locus (the human PNPLA3 gene), the human PNPLA3 mRNA, or the human PNPLA3 protein. Examples of human-PNPLA3-targeting reagents are disclosed elsewhere herein.

Such human-PNPLA3-targeting reagents can be administered by any delivery method (e.g., AAV, LNP, HDD, or injection) and by any route of administration. Means of delivering complexes and molecules and routes of administration are disclosed in more detail elsewhere herein. In particular methods, the reagents delivered via AAV-mediated delivery. For example, AAV8 can be used to target the liver. In other particular methods, the reagents are delivered by LNP-mediated delivery. In other particular methods, the reagents are delivered by hydrodynamic delivery (HDD). The dose can be any suitable dose.

Methods for assessing activity of the human-PNPLA3-targeting reagent are well-known and are provided elsewhere herein. Assessment of activity can be in any cell type, any tissue type, or any organ type. In some methods, assessment of activity is in the liver.

If the human-PNPLA3-targeting reagent is a genome editing reagent (e.g., a nuclease agent), such methods can comprise assessing modification of the humanized PNPLA3 locus. As one example, the assessing can comprise measuring non-homologous end joining (NHEJ) activity at the humanized PNPLA3 locus. This can comprise, for example, measuring the frequency of insertions or deletions within the humanized PNPLA3 locus. For example, the assessing can comprise sequencing the humanized PNPLA3 locus in one or more cells isolated from the non-human animal (e.g., next-generation sequencing). Assessment can comprise isolating a target organ or tissue (e.g., liver) from the non-human animal and assessing modification of humanized PNPLA3 locus in the target organ or tissue. Assessment can also comprise assessing modification of humanized PNPLA3 locus in two or more different cell types within the target organ or tissue. Similarly, assessment can comprise isolating a non-target organ or tissue (e.g., two or more non-target organs or tissues) from the non-human animal and assessing modification of humanized PNPLA3 locus in the non-target organ or tissue.

Such methods can also comprise measuring expression levels of the mRNA produced by the humanized PNPLA3 locus, or by measuring expression levels of the protein encoded by the humanized PNPLA3 locus. For example, protein levels can be measured in a particular cell, tissue, or organ type (e.g., liver). Methods for assessing expression of PNPLA3 mRNA or PNPLA3 protein expressed from the humanized PNPLA3 locus are provided elsewhere herein and are well-known.

As one specific example, if the human-PNPLA3-targeting reagent is a genome editing reagent (e.g., a nuclease agent), percent editing (e.g., total number of insertions or deletions observed over the total number of sequences read in the PCR reaction from a pool of lysed cells) at the humanized PNPLA3 locus can be assessed (e.g., in liver cells).

Measuring the activity of human-PNPLA3-targeting reagents can also or alternatively comprise measuring hepatic fat content (e.g., on a high-sucrose diet) and/or measuring PNPLA3 levels in hepatic lipid droplets. For example, a decrease in hepatic fat content or a decrease in PNPLA3 levels in hepatic lipid droplets can indicate higher activity of a human-PNPLA3-targeting reagent. Other activity readouts can include other known readouts (e.g., signs or symptoms) of non-alcoholic fatty liver disease (NAFLD) or hepatic steatosis. Increased activity can be shown by a decrease in a sign or symptom of NAFLD or hepatic steatosis.

The various methods provided above for assessing activity in vivo can also be used to assess the activity of human-PNPLA3-targeting reagents ex vivo (e.g., in a liver comprising a humanized PNPLA3 locus) or in vitro (e.g., in a cell comprising a humanized PNPLA3 locus) as described elsewhere herein.

B. Methods of Optimizing Delivery or Efficacy of Human-PNPLA3-Targeting Reagent In Vivo or Ex Vivo Various methods are provided for optimizing delivery of human-PNPLA3-targeting reagents to a cell or non-human animal or optimizing the activity or efficacy of human-PNPLA3-targeting reagents in vivo. Such methods can comprise, for example: (a) performing the method of testing the efficacy of a human-PNPLA3-targeting reagents as described above a first time in a first non-human animal or first cell comprising a humanized PNPLA3 locus; (b) changing a variable and performing the method a second time in a second non-human animal (i.e., of the same species) or a second cell comprising a humanized PNPLA3 locus with the changed variable; and (c) comparing the activity of the human-PNPLA3-targeting reagents in step (a) with the activity of the human-PNPLA3-targeting reagents in step (b), and selecting the method resulting in the higher activity.

Methods of measuring delivery, efficacy, or activity of human-PNPLA3-targeting reagents are disclosed elsewhere herein. For example, such methods can comprise measuring modification of the humanized PNPLA3 locus. More effective modification of the humanized PNPLA3 locus can mean different things depending on the desired effect within the non-human animal or cell. For example, more effective modification of the humanized PNPLA3 locus can mean one or more or all of higher levels of modification, higher precision, higher consistency, or higher specificity. Higher levels of modification (i.e., higher efficacy) of the humanized PNPLA3 locus refers to a higher percentage of cells is targeted within a particular target cell type, within a particular target tissue, or within a particular target organ (e.g., liver). Higher precision refers to more precise modification of the humanized PNPLA3 locus (e.g., a higher percentage of targeted cells having the same modification or having the desired modification without extra unintended insertions and deletions (e.g., NHEJ indels)). Higher consistency refers to more consistent modification of the humanized PNPLA3 locus among different types of targeted cells, tissues, or organs if more than one type of cell, tissue, or organ is being targeted (e.g., modification of a greater number of cell types within the liver). If a particular organ is being targeted, higher consistency can also refer to more consistent modification throughout all locations within the organ (e.g., the liver). Higher specificity can refer to higher specificity with respect to the genomic locus or loci targeted, higher specificity with respect to the cell type targeted, higher specificity with respect to the tissue type targeted, or higher specificity with respect to the organ targeted. For example, increased genomic locus specificity refers to less modification of off-target genomic loci (e.g., a lower percentage of targeted cells having modifications at unintended, off-target genomic loci instead of or in addition to modification of the target genomic locus). Likewise, increased cell type, tissue, or organ type specificity refers to less modification of off-target cell types, tissue types, or organ types if a particular cell type, tissue type, or organ type is being targeted (e.g., when a particular organ is targeted (e.g., the liver), there is less modification of cells in organs or tissues that are not intended targets).

Alternatively, such methods can comprise measuring expression of PNPLA3 mRNA or PNPLA3 protein. In one example, a more effective human-PNPLA3-targeting agent results in a greater decrease in PNPLA3 mRNA or PNPLA3 protein expression. Alternatively, such methods can comprise measuring PNPLA3 activity. In one example, a more effective human-PNPLA3-targeting agent results in a greater decrease in PNPLA3 activity.

The variable that is changed can be any parameter. As one example, the changed variable can be the packaging or the delivery method by which the human-PNPLA3-targeting reagent or reagents are introduced into the cell or non-human animal. Examples of delivery methods, such as LNP, HDD, and AAV, are disclosed elsewhere herein. For example, the changed variable can be the AAV serotype. Similarly, the administering can comprise LNP-mediated delivery, and the changed variable can be the LNP formulation. As another example, the changed variable can be the route of administration for introduction of the human-PNPLA3-targeting reagent or reagents into the cell or non-human animal. Examples of routes of administration, such as intravenous, intravitreal, intraparenchymal, and nasal instillation, are disclosed elsewhere herein.

As another example, the changed variable can be the concentration or amount of the human-PNPLA3-targeting reagent or reagents introduced. As another example, the changed variable can be the concentration or the amount of one human-PNPLA3-targeting reagent introduced (e.g., guide RNA, Cas protein, exogenous donor nucleic acid, RNAi agent, or ASO) relative to the concentration or the amount another human-PNPLA3-targeting reagent introduced (e.g., guide RNA, Cas protein, exogenous donor nucleic acid, RNAi agent, or ASO).

As another example, the changed variable can be the timing of introducing the human-PNPLA3-targeting reagent or reagents relative to the timing of assessing the activity or efficacy of the reagents. As another example, the changed variable can be the number of times or frequency with which the human-PNPLA3-targeting reagent or reagents are introduced. As another example, the changed variable can be the timing of introduction of one human-PNPLA3-targeting reagent introduced (e.g., guide RNA, Cas protein, exogenous donor nucleic acid, RNAi agent, or ASO) relative to the timing of introduction of another human-PNPLA3-targeting reagent introduced (e.g., guide RNA, Cas protein, exogenous donor nucleic acid, RNAi agent, or ASO).

As another example, the changed variable can be the form in which the human-PNPLA3-targeting reagent or reagents are introduced. For example, a guide RNA can be introduced in the form of DNA or in the form of RNA. A Cas protein (e.g., Cas9) can be introduced in the form of DNA, in the form of RNA, or in the form of a protein (e.g., complexed with a guide RNA). An exogenous donor nucleic acid can be DNA, RNA, single-stranded, double-stranded, linear, circular, and so forth. Similarly, each of the components can comprise various combinations of modifications for stability, to reduce off-target effects, to facilitate delivery, and so forth. Likewise, RNAi agents and ASOs, for example, can comprise various combinations of modifications for stability, to reduce off-target effects, to facilitate delivery, and so forth.

As another example, the changed variable can be the human-PNPLA3-targeting reagent or reagents that are introduced. For example, if the human-PNPLA3-targeting reagent comprises a guide RNA, the changed variable can be introducing a different guide RNA with a different sequence (e.g., targeting a different guide RNA target sequence). Similarly, if the human-PNPLA3-targeting reagent comprises an RNAi agent or an ASO, the changed variable can be introducing a different RNAi agent or ASO with a different sequence. Likewise, if the human-PNPLA3-targeting reagent comprises a Cas protein, the changed variable can be introducing a different Cas protein (e.g., introducing a different Cas protein with a different sequence, or a nucleic acid with a different sequence (e.g., codon-optimized) but encoding the same Cas protein amino acid sequence. Likewise, if the human-PNPLA3-targeting reagent comprises an exogenous donor nucleic acid, the changed variable can be introducing a different exogenous donor nucleic acid with a different sequence (e.g., a different insert nucleic acid or different homology arms (e.g., longer or shorter homology arms or homology arms targeting a different region of the human PNPLA3 gene)).

In a specific example, the human-PNPLA3-targeting reagent comprises a Cas protein and a guide RNA designed to target a guide RNA target sequence in a human PNPLA3 gene. In such methods, the changed variable can be the guide RNA sequence and/or the guide RNA target sequence. In some such methods, the Cas protein and the guide RNA can each be administered in the form of RNA, and the changed variable can be the ratio of Cas mRNA to guide RNA (e.g., in an LNP formulation). In some such methods, the changed variable can be guide RNA modifications (e.g., a guide RNA with a modification is compared to a guide RNA without the modification).

C. Human-PNPLA3-Targeting Reagents

A human-PNPLA3-targeting reagent can be any reagent that targets a human PNPLA3 protein, a human PNPLA3 gene, or a human PNPLA3 mRNA. A human-PNPLA3-targeting reagent can be, for example, a known human-PNPLA3-targeting reagent, can be a putative human-PNPLA3-targeting reagent (e.g., candidate reagents designed to target human PNPLA3), or can be a reagent being screened for human-PNPLA3-targeting activity.

For example, a human-PNPLA3-targeting reagent can be an antigen-binding protein (e.g., agonist antibody) targeting an epitope of a human PNPLA3 protein. The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a $F(ab)_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes).

Other human-PNPLA3-targeting reagents include small molecules targeting a human PNPLA3 protein.

Other human-PNPLA3-targeting reagents can include genome editing reagents such as a nuclease agent (e.g., a Clustered Regularly Interspersed Short Palindromic Repeats (CRISPR)/CRISPR-associated (Cas) (CRISPR/Cas) nuclease, a zinc finger nuclease (ZFN), or a Transcription Activator-Like Effector Nuclease (TALEN)) that cleaves a recognition site within the human PNPLA3 gene. Likewise, a human-PNPLA3-targeting reagent can be an exogenous donor nucleic acid (e.g., a targeting vector or single-stranded oligodeoxynucleotide (ssODN)) designed to recombine with the human PNPLA3 gene.

Other human-PNPLA3-targeting reagents can include RNAi agents. An "RNAi agent" is a composition that comprises a small double-stranded RNA or RNA-like (e.g., chemically modified RNA) oligonucleotide molecule capable of facilitating degradation or inhibition of translation of a target RNA, such as messenger RNA (mRNA), in a sequence-specific manner. The oligonucleotide in the RNAi agent is a polymer of linked nucleosides, each of which can be independently modified or unmodified. RNAi agents operate through the RNA interference mechanism (i.e., inducing RNA interference through interaction with the RNA interference pathway machinery (RNA-induced silencing complex or RISC) of mammalian cells). While it is believed that RNAi agents, as that term is used herein, operate primarily through the RNA interference mechanism, the disclosed RNAi agents are not bound by or limited to any particular pathway or mechanism of action. RNAi agents disclosed herein comprise a sense strand and an antisense strand, and include, but are not limited to, short interfering RNAs (siRNAs), double-stranded RNAs (dsRNA), micro RNAs (miRNAs), short hairpin RNAs (shRNA), and dicer substrates. The antisense strand of the RNAi agents described herein is at least partially complementary to a sequence (i.e., a succession or order of nucleobases or nucleotides, described with a succession of letters using standard nomenclature) in the target RNA.

Other human-PNPLA3-targeting reagents can include antisense oligonucleotides (ASOs). Single-stranded ASOs and RNA interference (RNAi) share a fundamental principle in that an oligonucleotide binds a target RNA through Watson-Crick base pairing. Without wishing to be bound by theory, during RNAi, a small RNA duplex (RNAi agent) associates with the RNA-induced silencing complex (RISC), one strand (the passenger strand) is lost, and the remaining strand (the guide strand) cooperates with RISC to bind complementary RNA. Argonaute 2 (Ago2), the catalytic component of the RISC, then cleaves the target RNA. The guide strand is always associated with either the complementary sense strand or a protein (RISC). In contrast, an ASO must survive and function as a single strand. ASOs bind to the target RNA and block ribosomes or other factors, such as splicing factors, from binding the RNA or recruit proteins such as nucleases. Different modifications and target regions are chosen for ASOs based on the desired mechanism of action. A gapmer is an ASO oligonucleotide containing 2-5 chemically modified nucleotides (e.g. LNA or 2'-MOE) on each terminus flanking a central 8-10 base gap of DNA. After binding the target RNA, the DNA-RNA hybrid acts substrate for RNase H.

D. Administering Human-PNPLA3-Targeting Reagents to Non-Human Animals or Cells The methods disclosed herein can comprise introducing into a non-human animal or cell various molecules (e.g., human-PNPLA3-targeting reagents such as therapeutic molecules or complexes), including nucleic acids, proteins, nucleic-acid-protein complexes, protein complexes, or small molecules. "Introducing" includes presenting to the cell or non-human animal the molecule (e.g., nucleic acid or protein) in such a manner that it gains access to the interior of the cell or to the interior of cells within the non-human animal. The introducing can be accomplished by any means, and two or more of the components (e.g., two of the components, or all of the components) can be introduced into the cell or non-human animal simultaneously or sequentially in any combination. For example, a Cas protein can be introduced into a cell or non-human animal before introduction of a guide RNA, or it can be introduced following introduction of the guide RNA. As another example, an exogenous donor nucleic acid can be introduced prior to the introduction of a Cas protein and a guide RNA, or it can be introduced following introduction of the Cas protein and the guide RNA (e.g., the exogenous donor nucleic acid can be administered about 1, 2, 3, 4, 8, 12, 24, 36, 48, or 72 hours before or after introduction of the Cas protein and the guide RNA). See, e.g., US 2015/0240263 and US 2015/0110762, each of which is herein incorporated by reference in its entirety for all purposes. In addition, two or more of the components can be introduced into the cell or non-human animal by the same delivery method or different delivery methods. Similarly, two or more of the components can be introduced into a non-human animal by the same route of administration or different routes of administration.

In some methods, components of a CRISPR/Cas system are introduced into a non-human animal or cell. A guide RNA can be introduced into a non-human animal or cell in the form of an RNA (e.g., in vitro transcribed RNA) or in the form of a DNA encoding the guide RNA. When introduced in the form of a DNA, the DNA encoding a guide RNA can be operably linked to a promoter active in a cell in the non-human animal. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Likewise, Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a mammalian cell, a rodent cell, a mouse cell, a rat cell, or any other host cell of interest, as compared to the naturally occurring polynucleotide sequence. When a nucleic acid encoding the Cas protein is introduced into a non-human animal, the Cas protein can be transiently, conditionally, or constitutively expressed in a cell in the non-human animal.

Nucleic acids encoding Cas proteins or guide RNAs can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding one or more gRNAs. Alternatively, it can be in a vector or plasmid that is separate from the vector comprising the DNA encoding one or more gRNAs. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allows for the generation of compact expression cassettes to facilitate delivery.

Molecules (e.g., Cas proteins or guide RNAs or RNAi agents or ASOs) introduced into the non-human animal or cell can be provided in compositions comprising a carrier increasing the stability of the introduced molecules (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of molecule (e.g., a nucleic acid or protein) into a cell or non-human animal. Methods for introducing molecules into various cell types are known and include, for example, stable transfection methods, transient transfection methods, and virus-mediated methods.

Transfection protocols as well as protocols for introducing molecules into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, sonoporation, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of molecules (e.g., nucleic acids or proteins) into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a Cas protein or a polynucleotide encoding a Cas protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a Cas protein is injected into the cytoplasm, the Cas protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109: 9354-9359.

Other methods for introducing molecules (e.g., nucleic acid or proteins) into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids and proteins into cells or non-human animals can be accomplished by hydrodynamic delivery (HDD). For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4):694-701, herein incorporated by reference in its entirety for all purposes.

Introduction of nucleic acids can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediate AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a combination of Cas mRNA and guide RNA or a combination of Cas protein and guide RNA. Delivery through such methods results in transient Cas expression, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) *Cell Reports* 22:1-9 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an mRNA encoding a Cas nuclease, such as Cas9, and a guide RNA or a nucleic acid encoding a guide RNA.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. See, e.g., Finn et al. (2018) *Cell Reports* 22:1-9 and WO 2017/173054 A1, each of which is herein incorporated by reference in its entirety for all purposes. Another example of a suitable lipid is Lipid B, which is ((5-((dimethylamino)methyl)-1,3-phenylene)bis(oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino)propoxy)carbonyl)oxy)hexadecanoyl)oxy)propane-1,3-diyl (9Z,9'Z,12Z,12'Z)-bis(octadeca-9,12-dienoate). Another example of a suitable lipid is Lipid D, which is 3-(((3-(dimethylamino)propoxy)carbonyl)oxy)-13-(octanoyloxy)tridecyl 3-octylundecanoate. Other suitable lipids include heptatriaconta-6,9,28,31-tetraen-19-yl 4-(dimethylamino)butanoate (also known as Dlin-MC3-DMA (MC3))).

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine di stearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-di stearoylglycerol (PEG-DSPE), PEG-dilaurylglycamide, PEG-dimyristylglycamide, PEG-dipalmitoylglycamide, and PEG-di stearoylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5. The N/P ratio can also be from about 4 to about 7 or from about 4.5 to about 6. In specific examples, the N/P ratio can be 4.5 or can be 6.

In some LNPs, the cargo can comprise Cas mRNA and gRNA. The Cas mRNA and gRNAs can be in different ratios. For example, the LNP formulation can include a ratio of Cas mRNA to gRNA nucleic acid ranging from about 25:1 to about 1:25, ranging from about 10:1 to about 1:10, ranging from about 5:1 to about 1:5, or about 1:1. Alternatively, the LNP formulation can include a ratio of Cas mRNA to gRNA nucleic acid from about 1:1 to about 1:5, or about 10:1. Alternatively, the LNP formulation can include a ratio of Cas mRNA to gRNA nucleic acid of about 1:10, 25:1, 10:1, 5:1, 3:1, 1:1, 1:3, 1:5, 1:10, or 1:25. Alternatively, the LNP formulation can include a ratio of Cas mRNA to gRNA nucleic acid of from about 1:1 to about 1:2. In specific examples, the ratio of Cas mRNA to gRNA can be about 1:1 or about 1:2.

In some LNPs, the cargo can comprise exogenous donor nucleic acid and gRNA. The exogenous donor nucleic acid and gRNAs can be in different ratios. For example, the LNP formulation can include a ratio of exogenous donor nucleic acid to gRNA nucleic acid ranging from about 25:1 to about 1:25, ranging from about 10:1 to about 1:10, ranging from about 5:1 to about 1:5, or about 1:1. Alternatively, the LNP formulation can include a ratio of exogenous donor nucleic acid to gRNA nucleic acid from about 1:1 to about 1:5, about 5:1 to about 1:1, about 10:1, or about 1:10. Alternatively, the LNP formulation can include a ratio of exogenous donor nucleic acid to gRNA nucleic acid of about 1:10, 25:1, 10:1, 5:1, 3:1, 1:1, 1:3, 1:5, 1:10, or 1:25.

A specific example of a suitable LNP has a nitrogen-to-phosphate (N/P) ratio of 4.5 and contains biodegradable cationic lipid, cholesterol, DSPC, and PEG2k-DMG in a 45:44:9:2 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. See, e.g., Finn et al. (2018) *Cell Reports* 22:1-9, herein incorporated by reference in its entirety for all purposes. The Cas9 mRNA can be in a 1:1 ratio by weight to the guide RNA. Another specific example of a suitable LNP contains Dlin-MC3-DMA (MC3), cholesterol, DSPC, and PEG-DMG in a 50:38.5:10:1.5 molar ratio.

Another specific example of a suitable LNP has a nitrogen-to-phosphate (N/P) ratio of 6 and contains biodegradable cationic lipid, cholesterol, DSPC, and PEG2k-DMG in a 50:38:9:3 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. The Cas9 mRNA can be in a 1:2 ratio by weight to the guide RNA.

The mode of delivery can be selected to decrease immunogenicity. For example, a Cas protein and a gRNA may be delivered by different modes (e.g., bi-modal delivery). These different modes may confer different pharmacodynamics or pharmacokinetic properties on the subject delivered molecule (e.g., Cas or nucleic acid encoding, gRNA or nucleic acid encoding, or exogenous donor nucleic acid/repair template). For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein). Delivery of Cas proteins in a more transient manner, for example as mRNA or protein, can ensure that the Cas/gRNA complex is only present and active for a short period of time and can reduce immunogenicity caused by peptides from the bacterially-derived Cas enzyme being displayed on the surface of the cell by WIC molecules. Such transient delivery can also reduce the possibility of off-target modifications.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyms, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically.

Administration in vivo can be by any suitable route including, for example, parenteral, intravenous, oral, subcutaneous, intra-arterial, intracranial, intrathecal, intraperitoneal, topical, intranasal, or intramuscular. A specific example is intravenous infusion. Compositions comprising the guide RNAs and/or Cas proteins (or nucleic acids encoding the guide RNAs and/or Cas proteins) can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can depend on the half-life of the exogenous donor nucleic acids, guide RNAs, or Cas proteins (or nucleic acids encoding the guide RNAs or Cas proteins) and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

E. Measuring Delivery, Activity, or Efficacy of Human-PNPLA3-Targeting Reagents In Vivo or Ex Vivo The methods disclosed herein can further comprise detecting or measuring activity of human-PNPLA3-targeting reagents. Measuring the activity of such reagents can comprise measuring hepatic fat content (e.g., on a high-sucrose diet) and/or measuring PNPLA3 levels in hepatic lipid droplets. For example, a decrease in hepatic fat content or a decrease in PNPLA3 levels in hepatic lipid droplets can indicate higher activity of a human-PNPLA3-targeting reagent. Other activity readouts can include other known readouts (e.g., signs or symptoms) of non-alcoholic fatty liver disease (NAFLD) or hepatic steatosis. Increased activity can be shown by a decrease in a sign or symptom of NAFLD or hepatic steatosis.

If the human-PNPLA3-targeting reagent is a genome editing reagent, the measuring can comprise assessing the humanized PNPLA3 locus for modifications. Various methods can be used to identify cells having a targeted genetic modification. The screening can comprise a quantitative assay for assessing modification-of-allele (MOA) of a parental chromosome. See, e.g., US 2004/0018626; US 2014/0178879; US 2016/0145646; WO 2016/081923; and Frendewey et al. (2010) *Methods Enzymol.* 476:295-307, each of which is herein incorporated by reference in its entirety for all purposes. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes). Next-generation sequencing (NGS) can also be used for screening. Next-generation sequencing can also be referred to as "NGS" or "massively parallel sequencing" or "high throughput sequencing." NGS can be used as a screening tool in addition to the MOA assays to define the exact nature of the targeted genetic modification and whether it is consistent across cell types or tissue types or organ types.

If the reagent is designed to inactivate the humanized PNPLA3 locus, affect expression of the humanized PNPLA3 locus, or prevent translation of the humanized PNPLA3 mRNA, the measuring can comprise assessing humanized PNPLA3 mRNA or protein expression.

The assessing in a non-human animal can be in any cell type from any tissue or organ. For example, the assessment can be in multiple cell types from the same tissue or organ (e.g., liver) or in cells from multiple locations within the tissue or organ. This can provide information about which cell types within a target tissue or organ are being targeted or which sections of a tissue or organ are being reached by the human-PNPLA3-targeting reagent. As another example, the assessment can be in multiple types of tissue or in multiple organs. In methods in which a particular tissue, organ, or cell type is being targeted, this can provide information about how effectively that tissue or organ is being targeted and whether there are off-target effects in other tissues or organs.

One example of an assay that can be used are the RNASCOPE™ and BASESCOPE™ RNA in situ hybridization (ISH) assays, which are methods that can quantify cell-specific edited transcripts, including single nucleotide changes, in the context of intact fixed tissue. The BASESCOPE™ RNA ISH assay can complement NGS and qPCR in characterization of gene editing. Whereas NGS/qPCR can provide quantitative average values of wild type and edited sequences, they provide no information on heterogeneity or percentage of edited cells within a tissue. The BASESCOPE™ ISH assay can provide a landscape view of an entire tissue and quantification of wild type versus edited transcripts with single-cell resolution, where the actual number of cells within the target tissue containing the edited mRNA transcript can be quantified. The BASESCOPE™ assay achieves single-molecule RNA detection using paired oligo ("ZZ") probes to amplify signal without non-specific background. However, the BASESCOPE™ probe design and signal amplification system enables single-molecule RNA detection with a ZZ probe, and it can differentially detect single nucleotide edits and mutations in intact fixed tissue.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | Protein | Mouse PNPLA3 Protein (UniProt Q91WW7.1; NCBI NP_473429.2) |
| 2 | Protein | Mouse PNPLA3 Protein Cytoplasmic Domain |
| 3 | Protein | Mouse PNPLA3 Protein Transmembrane Domain |
| 4 | Protein | Mouse PNPLA3 Protein Lumenal Domain |
| 5 | Protein | Human PNPLA3 Protein (UniProt Q9NST1.1; NCBI NP_079501) |
| 6 | Protein | Human PNPLA3 Protein Cytoplasmic Domain |
| 7 | Protein | Human PNPLA3 Protein Transmembrane Domain |
| 8 | Protein | Human PNPLA3 Protein Lumenal Domain |
| 9 | Protein | Humanized PNPLA3 protein (I148M/K434E) |
| 10 | Protein | Humanized PNPLA3 protein Lumenal Domain (I148M/K434E) |
| 11 | DNA | Mouse Pnpla3 CDS (CCDS37165.1) |
| 12 | DNA | Mouse Pnpla3 Cytoplasmic Domain CDS |
| 13 | DNA | Mouse Pnpla3 Transmembrane Domain CDS |
| 14 | DNA | Mouse Pnpla3 Lumenal Domain CDS |
| 15 | DNA | Human PNPLA3 CDS (CCDS14054.1) |
| 16 | DNA | Human PNPLA3 Cytoplasmic Domain CDS |
| 17 | DNA | Human PNPLA3 Transmembrane Domain CDS |
| 18 | DNA | Human PNPLA3 Lumenal Domain CDS |
| 19 | DNA | Humanized PNPLA3 CDS (I148M/K434E) |
| 20 | DNA | Humanized PNPLA3 Lumenal Domain CDS (I148M/K434E) |
| 21 | DNA | MAID 8164 Humanized PNPLA3 Locus with Self-Deleting Cassette |
| 22 | DNA | MAID 8165 Humanized PNPLA3 Locus without Self-Deleting Cassette |

TABLE 2-continued

Description of Sequences.

| SEQ ID NO | Type | Description |
|---|---|---|
| 23 | DNA | Mouse Pnpla3 mRNA (NM_054088.3) |
| 24 | DNA | Human PNPLA3 mRNA (NM_025225.3) |
| 25 | DNA | Rat PNPLA3 Protein (NP_001269253.1) |
| 26 | DNA | Rat Pnpla3 mRNA (NM_001282324.1) |
| 27 | DNA | Rat Pnpla3 CDS |
| 28-31 | DNA | Mouse Pnpla3 gRNA Target Sequences |
| 32-61 | DNA | Humanization Screening Assay Primers and Probes |
| 62 | DNA | Human PNPLA3 Sequence in Humanized Locus (I148M/K434E) |
| 63 | Protein | Humanized PNPLA3 Protein (K434E) |
| 64 | DNA | Humanized PNPLA3 CDS (K434E) |
| 65 | Protein | Humanized PNPLA3 Protein Lumenal Domain (K434E) |
| 66 | DNA | Humanized PNPLA3 Lumenal Domain CDS (K434E) |
| 67 | DNA | MAID 7622 Humanized PNPLA3 Locus with Self-Deleting Cassette |
| 68 | DNA | MAID 7623 Humanized PNPLA3 Locus without Self-Deleting Cassette |
| 69 | DNA | Human PNPLA3 Sequence in Humanized Locus (K434E) |

EXAMPLES

Example 1. Generation of Mice Comprising a Humanized PNPLA3 I148M/K434E Locus A large targeting vector (LTVEC) comprising a 5' homology arm comprising 20.0 kb of the mouse Pnpla3 locus and 3' homology arm comprising 8.9 kb of the mouse Pnpla3 locus was generated to replace a region of 13.3 kb from the mouse Pnpla3 gene with 23.3 kb of the corresponding sequence of the human PNPLA3 gene including mutations encoding PNPLA3 missense mutations I148M and K434E. Information on mouse and human PNPLA3 genes is provided in Table 3. A description of the generation of the large targeting vector is provided in Table 4. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) *Nat. Biotechnol.* 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes.

TABLE 3

| Mouse and Human PNPLA3. | | | | | | |
|---|---|---|---|---|---|---|
| | Gene Symbol | NCBI Gene ID | RefSeq mRNA ID | UniProt ID | Genomic Assembly | Chromosomal Location |
| Mouse | Pnpla3 | 116939 | NM_054088.3 | Q91WW7 | GRCm38.p6/ mm10 | Chr 15: 84,167,837-84,187,236 (+) |
| Human | PNPLA3 | 80339 | NM_025225.3 | Q9NST1 | GRCh38/ hg38 | Chr 22: 43,923,792-43,964,488 (+) |

TABLE 4

| Mouse Pnpla3 Large Targeting Vector. | | | | |
|---|---|---|---|---|
| | Genome Build | Start | End | Length (bp) |
| 5' Mouse Arm | GRCm38.p6/ mm10 | Chr15: 84,147,838 | Chr15: 84,167,873 | 20,036 |
| Human Insert | GRCh38/ hg38 | Chr22: 43,923,912 | Chr22: 43,947,175 | 23,264 |
| 3' Mouse Arm | GRCm38.p6/ mm10 | Chr15: 84,181,213 | Chr15: 84,190,149 | 8,937 |

Specifically, a region starting in exon 1 (coding exon 1; from amino acid 1) through exon 7, including the first 160 base pairs of intron 7 and all introns between exons 1 and 7 (i.e., between coding exon 1 and exon 7) was deleted from the mouse Pnpla3 locus (preserving the Pnpla3 mouse exon 8 and the adjacent 4764 base pairs of intron 7). Chromatin immunoprecipitation sequencing (ChIP-Seq) suggests that the last intron of mouse Pnpla3 has regulatory elements that could affect the expression of the gene downstream (Samm50), so we decided not to delete or modify that region. A region from human PNPLA3, including exon 1/coding exon 1 (from amino acid 1) through exon 9, including the 3' UTR and all introns between exons 1 and 9 (i.e., between coding exon 1 and exon 9) was inserted in place of the deleted mouse region (this human DNA fragment encodes the variants I148M, in coding exon 3, and K434E, in coding exon 9). The I148M mutation is associated with a high risk for non-alcoholic steatohepatitis (NASH). The K434E mutation makes the I148M phenotype stronger. A loxP-mPrm1-Crei-pA-hUb1-em7-Neo-pA-loxP cassette was inserted downstream of the human PNPLA3 3' UTR. This is the MAID 8164 allele (SEQ ID NO: 21). See FIG. 1. After cassette deletion, loxP and cloning sites remained downstream of the human PNPLA3 3' UTR. This is the MAID 8165 (SEQ ID NO: 22). See FIG. 1.

Sequences for the mouse PNPLA3 cytoplasmic domain, transmembrane domain, and lumenal domain are set forth in SEQ ID NOS: 2-4, respectively, with the corresponding coding sequence set forth in SEQ ID NOS: 12-14, respectively. Sequences for the human PNPLA3 cytoplasmic domain, transmembrane domain, and lumenal domain (comprising I148M and K434E mutations) are set forth in SEQ ID NOS: 6, 7, and 10, respectively, with the corresponding coding sequences set forth in SEQ ID NOS: 16, 17, and 20, respectively. The sequence of the wild type human PNLPA3 lumenal domain (without the I148M and K434E mutations) is set forth in SEQ ID NO: 8, with the corresponding coding sequence set forth in SEQ ID NO: 18. The expected encoded humanized PNLPA3 protein has human PNLPA3 cytoplasmic, transmembrane, and lumenal domains, along with the I148M and K434E mutations. See FIG. 1. An alignment of the wild type mouse PNPLA3 protein, the wild type human PNLPA3 protein, and the expected encoded human PNPLA3 protein with the I148M and K434E mutations is provided in FIG. 3. The mouse Pnpla3 coding sequence and the human PNPLA3 coding sequence (encoding a human PNPLA3 protein comprising I148M and K434E mutations) are set forth in SEQ ID NOS: 11 and 19, respectively. The mouse wild type PNPLA3 protein sequence and the human PNPLA3 protein sequence (comprising I148M and K434E mutations) are set forth in SEQ ID NOS: 1 and 9, respectively. The wild type human PNPLA3 coding sequence is set forth in SEQ ID NO: 15, and the wild type human PNPLA3 protein sequence is set forth in SEQ ID NO: 5. The sequences for the expected humanized PNPLA3 coding sequence and the expected humanized PNPLA3 protein are set forth in SEQ ID NOS: 19 and 9, respectively.

Figure 2:
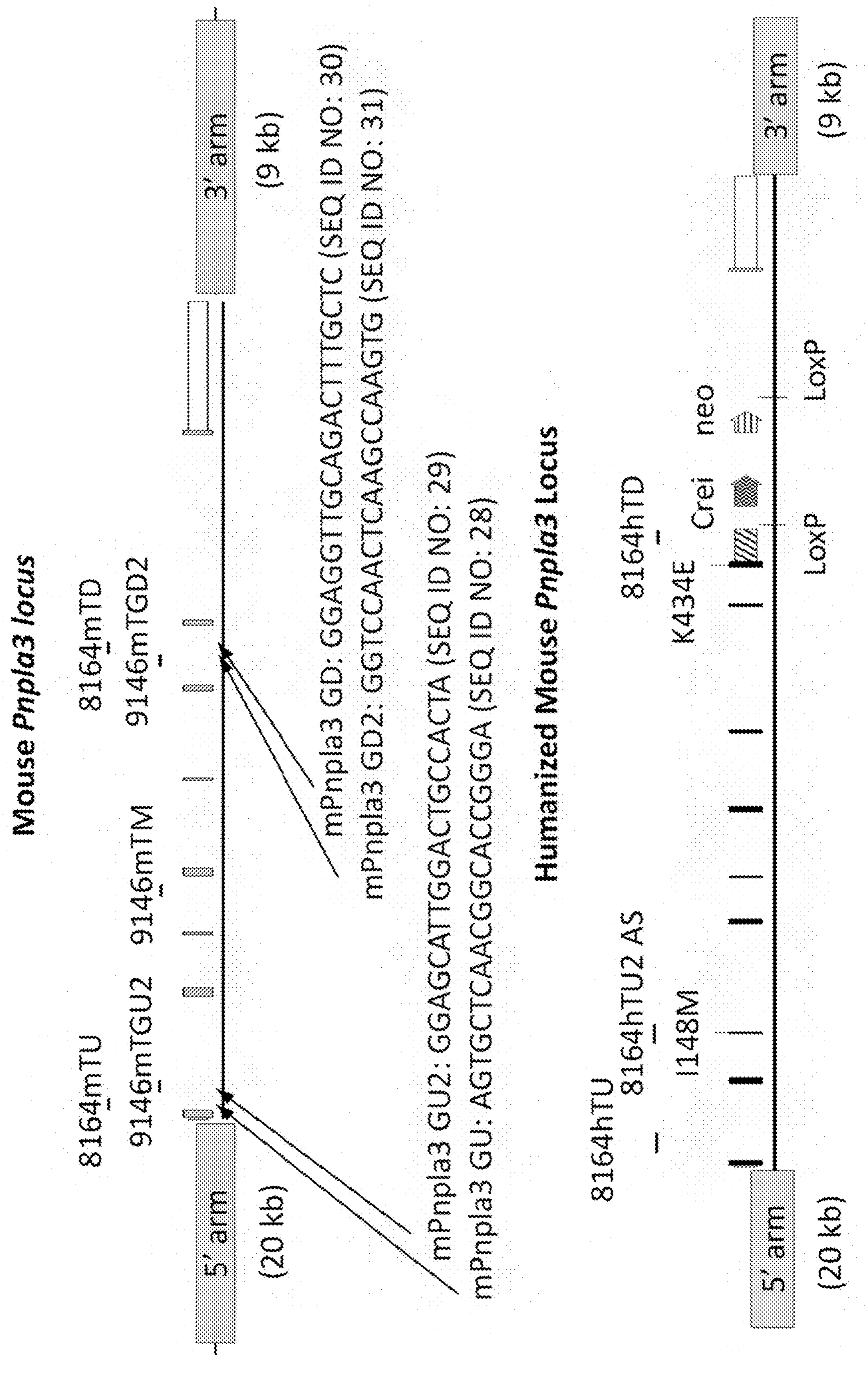
FIG. 2 (not to scale) shows a schematic of the TAQMAN® assays for screening humanization of the mouse Pnpla3 locus. Gain-of-allele (GOA) assays include 8164hTU and 8164hTD. Loss-of-allele (LOA) assays include 8164mTU, 9146mTM, and 8164mTD. CRISPR assays include 9146mTGU2 and 9146mTGD2. The mutation assay is indicated as 8164hTU AS. Locations of the guide RNA target sequences for mPnpla3 GU, GU2, GD, and GD2 are also indicated, and the guide RNA target sequences are provided.

To generate the mutant allele, CRISPR/Cas9 components including four guide RNAs (guide RNA target sequences set forth in SEQ ID NOS: 28-31) were introduced into F1H4 mouse embryonic stem (ES) cells together with the large targeting vector described above. F1H4 mouse ES cells were derived from hybrid embryos produced by crossing a female C57BL/6NTac mouse to a male 12956/SvEvTac mouse. See, e.g., US 2015-0376651 and WO 2015/200805, each of which is herein incorporated by reference in its entirety for all purposes. Specifically, a nucleofection process was carried out with $2\times10^6$ mouse ES cells (line F1H4) plus 0.4 μg PNPLA3 LTVEC; 5 μg Cas9; and 2.5 μg each of the gRNAs: gU, gU2, gD and gD2. Antibiotic selection was performed using G418 at a concentration of 100 μg/mL. Following antibiotic selection, colonies were picked, expanded, and screened by TAQMAN®. See FIG. 2. Loss-of-allele assays were performed to detect loss of the endogenous mouse allele, gain-of-allele assays were performed to detect gain of the humanized allele, an allele-specific assay was used to detect the I148M-encoding mutation, and CRISPR and retention assays were performed using the primers and probes set forth in Table 5.

TABLE 5

| Screening Assays. | | | | |
|---|---|---|---|---|
| Assay | Description | Primer/Probe | Sequence | SEQ ID NO |
| 8164mTU | Upstream Mouse LOA | Forward | TGCCCGAAGAAACCTGTCC | 32 |
| | | Reverse | TCCAGCTGAGTGCTCAACG | 33 |
| | | Probe(BHQ1 FAM) | AGAGCTCTCATCCTTCCCGGTGC | 34 |

TABLE 5-continued

Screening Assays.

| Assay | Description | Primer/Probe | Sequence | SEQ ID NO |
|---|---|---|---|---|
| 9146mTM | Middle Mouse LOA | Forward | CCACCCGGCATTAGGATGTAAG | 35 |
| | | Reverse | GTGCCAGGCAAAGACACATG | 36 |
| | | Probe(ABY-QSY) | AAGCACACCATGGAGTGGACTCTCA | 37 |
| 8164mTD | Downstream Mouse LOA | Forward | GCTCTGAGTGAAGCGATTAAGGA | 38 |
| | | Reverse | GCAGGGCAGCATGATGTAG | 39 |
| | | Probe(BHQ1 CAL) | AGGGCTACCTGAGCAAAGTCTGCA | 40 |
| 8164hTU | Upstream Human GOA | Forward | GCAGTGGCGTGATCTCAACTC | 41 |
| | | Reverse | CAGGAGAATGGCGTGAACCT | 42 |
| | | Probe(MGB FAM) | CTGCAAGCTCCACCTC | 43 |
| 8164hTD | Downstream Human GOA | Forward | TGTCAGGTGGTCTGCAAAGATG | 44 |
| | | Reverse | GTTACCCCCGCCATGGA | 45 |
| | | Probe(MGB VIC) | TAACCTTGACTACTAAAAACGT | 46 |
| 8164hTU2 (AS) | Human Mutation Assay | Forward | TTGCTTTCACAGGCCTTGGT | 47 |
| | | Reverse | AAGGAGGGATAAGGCCACTGTAG | 48 |
| | | Probe(MGB FAM) | TTCCTGCTTCATGCCTT | 49 |
| 9146retU | Upstream Retention Assay | Forward | GCCATCCAGAACCTGAAAGAAA | 50 |
| | | Reverse | CGTGGGCTTTCCCAAATCC | 51 |
| | | Probe(BHQ1 FAM) | AGGGTATTCAAAGAGCCATTCTGCCCA | 52 |
| 9146retD | Downstream Retention Assay | Forward | CACGACTTCCACCTGCTCTTCT | 53 |
| | | Reverse | GAGAGGGCCTTTGACTGAGA | 54 |
| | | Probe(BHQ1 CAL) | CCTCTGTGGCCTGTAGGTTCTTGG | 55 |
| 9146mTGU2 | Upstream CRISPR Assay | Forward | GGCAGAAGGCACCCAGACTA | 56 |
| | | Reverse | GGCAACCGGAGCATTGG | 57 |
| | | Probe(MGB FAM) | AACACCCTTAGTGGC | 58 |
| 9146mTGD2 | Downstream CRISPR Assay | Forward | CGTGTAGCTCACACTGGTCACA | 59 |
| | | Reverse | GGGTGATGAGGTCCAACTCAA | 60 |
| | | Probe(MGB VIC) | ACCACCACACTTGG | 61 |

Modification-of-allele (MOA) assays including loss-of-allele (LOA) and gain-of-allele (GOA) assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. The loss-of-allele (LOA) assay inverts the conventional screening logic and quantifies the number of copies in a genomic DNA sample of the native locus to which the mutation was directed. In a correctly targeted heterozygous cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector in a genomic DNA sample.

Retention assays are described in US 2016/0145646 and WO 2016/081923, each of which is herein incorporated by reference in its entirety for all purposes. Retention assays distinguish between correct targeted insertions of a nucleic acid insert into a target genomic locus from random transgenic insertions of the nucleic acid insert into genomic locations outside of the target genomic locus by assessing copy numbers of DNA templates from 5' and 3' target sequences corresponding to the 5' and 3' homology arms of the targeting vector, respectively. Specifically, retention assays determine copy numbers in a genomic DNA sample of a 5' target sequence DNA template intended to be retained in the modified target genomic locus and/or the 3' target sequence DNA template intended to be retained in the modified target genomic locus. In diploid cells, correctly targeted clones will retain a copy number of two. Copy numbers greater than two generally indicate transgenic integration of the targeting vector randomly outside of the target genomic locus rather than at the target genomic locus. Copy numbers of less than generally indicate large deletions extending beyond the region targeted for deletion.

CRISPR assays are TAQMAN® assays designed to cover the region that is disrupted by the CRISPR gRNAs. When a CRISPR gRNA cuts and creates an indel (insertion or deletion), the TAQMAN® assay will fail to amplify and thus reports CRISPR cleavage.

F0 mice were generated from the modified ES cells using the VELOCIMOUSE® method. Specifically, mouse ES cell clones comprising the humanized PNPLA3 locus described above that were selected by the MOA assay described above were injected into 8-cell stage embryos using the VELOCIMOUSE® method. See, e.g., U.S. Pat. Nos. 7,576,259; 7,659,442; 7,294,754; US 2008/0078000; and Poueymirou et al. (2007) Nat. Biotechnol. 25(1):91-99, each of which is herein incorporated by reference in its entirety for all purposes. In the VELOCIMOUSE® method, targeted mouse ES cells are injected through laser-assisted injection into pre-morula stage embryos, e.g., eight-cell-stage embryos, which efficiently yields F0 generation mice that are fully ES-cell-derived. In the VELOCIMOUSE method, the injected pre-morula stage embryos are cultured to the blastocyst stage, and the blastocyst-stage embryos are introduced into and gestated in surrogate mothers to produce the F0 generation mice. When starting with mouse ES cell clones homozygous for the targeted modification, F0 mice homozygous for the targeted modification are produced. When starting with mouse ES cell clones heterozygous for the targeted modification, subsequent breeding can be performed to produce mice homozygous for the targeted modification.

Example 2. Phenotyping of Mice Comprising a Humanized PNPLA3 I148M/K434E Locus

Figure 5:
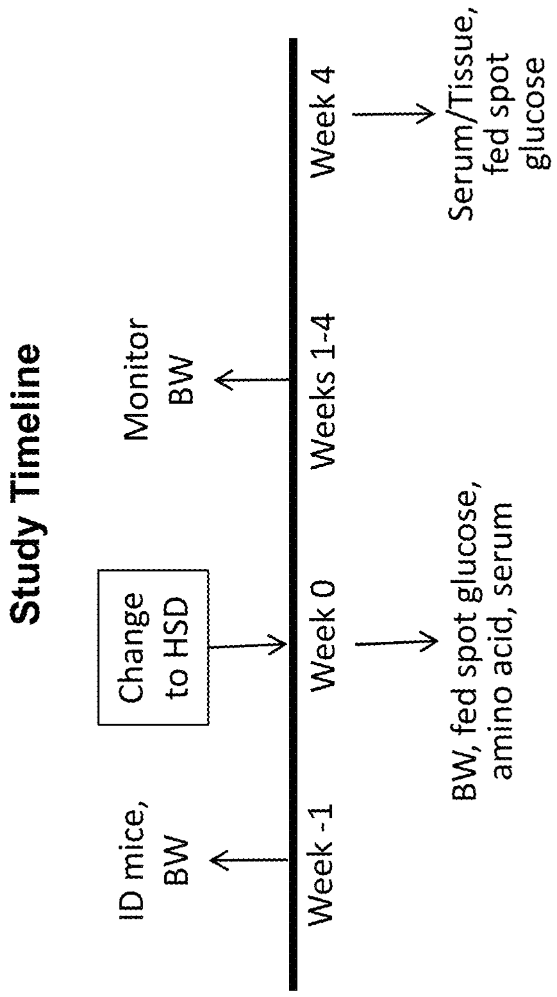
FIG. 5 shows a study timeline for phenotyping and characterizing the humanized PNPLA3 mice. BW=body weight. HSD=high sucrose diet.

FIG. 5 shows the study timeline for phenotyping and characterizing the humanized PNPLA3 mice generated in Example 1. The mice were randomized based on body weight at week −1. At week 0, the mice were switched to high sucrose diet or high fructose diet for 4 weeks. At week 4, the mice were sacrificed, and blood and tissues were collected.

Figure 6:
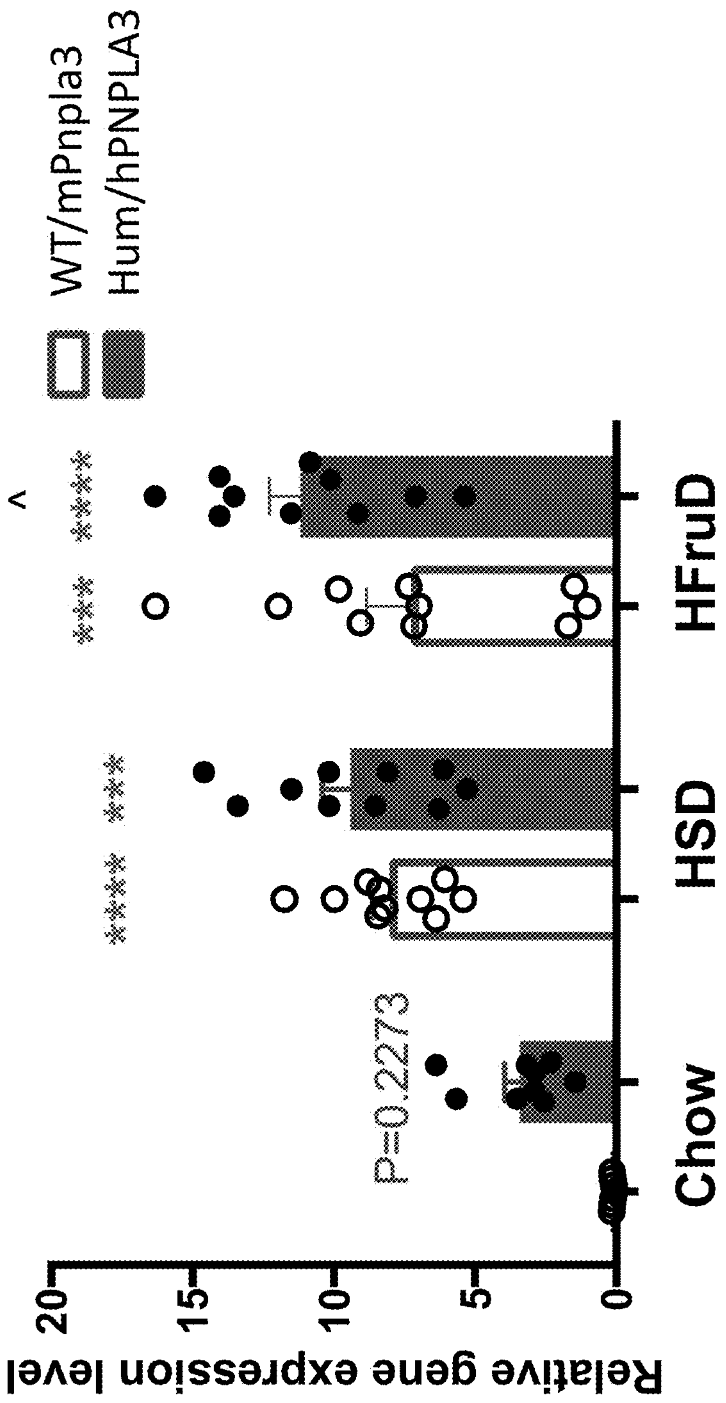
FIG. 6 shows RT-PCR of humanized PNPLA3 and mouse Pnpla3 from mouse Pnpla3 wild type liver and humanized mouse PNPLA3-I148M/K434E liver. RNA levels were normalized to mTBP. Mice were on chow, high sucrose diet (HSD) or high fructose diet (HFruD) for 4 weeks. *=compared between chow and HSD or HFD. ^=compared between WT and humanized on same diet. =$p<0.01$. *=$p<0.001$. ****=$p<0.0001$.
Figure 7:
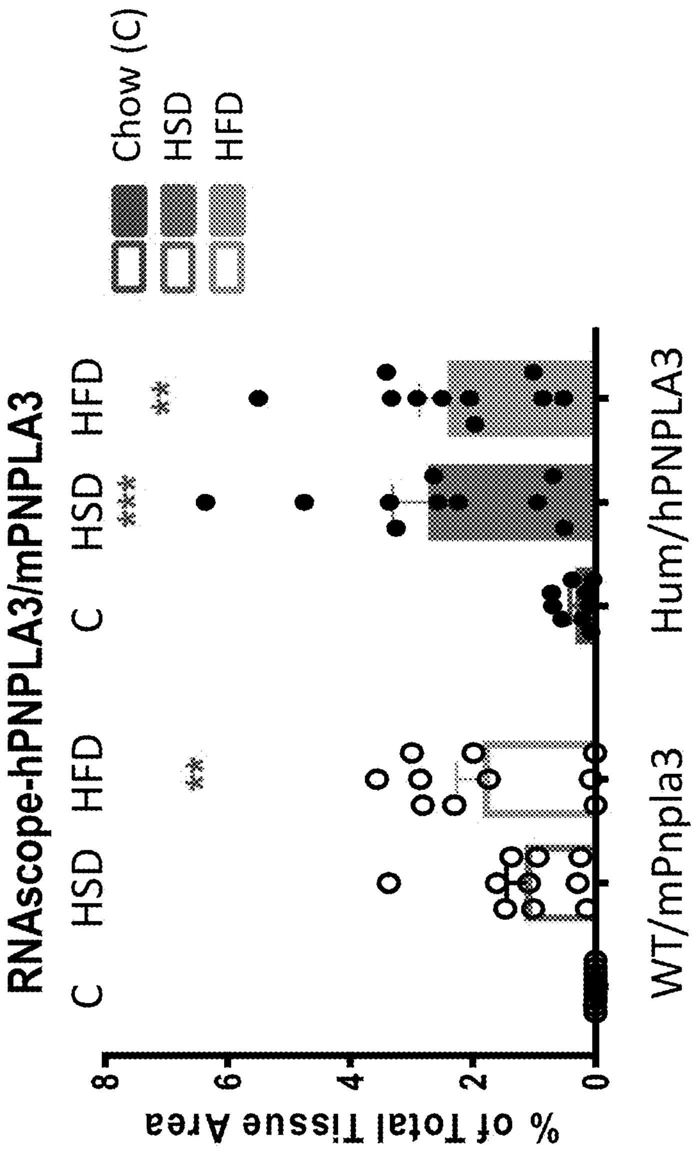
FIG. 7 shows RNA in situ hybridization of human PNPLA3 and mouse Pnpla3 from mouse Pnpla3 wild type and humanized PNPLA3-I148M/K434E mouse livers. Mice were on chow, high sucrose diet (HSD) or high fructose diet (HFD) for 4 weeks. =$p<0.01$. *=$p<0.001$.

To characterize the humanized mice generated in Example 1, mouse Pnpla3 and human PNPLA3 RNA levels were assessed in liver samples of wild type mice and mice comprising a humanized PNPLA3 I148M/K434E locus, respectively, after different diet treatments. FIG. 6 shows RT-PCR of human PNPLA3 and mouse Pnpla3 from mouse Pnpla3 wild type liver and humanized mouse PNPLA3-I148M/K434E liver. FIG. 7 shows RNA in situ hybridization of human PNPLA3 and mouse Pnpla3 from mouse Pnpla3 wild type and humanized PNPLA3-I148M/K434E mouse livers. Mice were on chow, high sucrose diet (HSD) or high fructose diet (HFD or HFruD) for 4 weeks. Liver samples were collected for RNA extraction and RT-PCR. On chow diet, PNPLA3 RNA expression levels in the humanized PNPLA3 I148M/K434E mice were much higher than the corresponding levels in the wild type mice (p=0.22 due to higher RNA level variability in humanized PNPLA3 I148M/K434E mice). HSD and HFruD strongly induced PNPLA3 expression in both the wild type mice and the humanized PNPLA3 I148M/K434E mice. These results show that human and mouse PNPLA3 expression patterns are different. Mouse liver Pnpla3 RNA expression levels at chow fed conditions were very low, which is not consistent with humans. The humanized PNPLA3 mice had higher PNPLA3 RNA expression at chow fed conditions, which is more consistent with what occurs in humans.

Example 3. Generation of Mice Comprising a Humanized PNPLA3 Wild Type (I148) Locus The large targeting vector (LTVEC) described in Example 1 was modified by homologous recombination and Gibson assembly using a 322 bp DNA fragment carrying the wild type allele 148I, to revert PNPLA3 148M to PNPLA3 148I. The variant 434E was not modified, as it came with the original unmodified bacterial artificial chromosome (BAC) used in Example 1. The PNPLA 148I and 434E version can be used as a wild type PNPLA3 because the enzymatic activity is similar to 148I/434K, and there is no liver damage, similar to 148I/434K. Although the human canonic PNPLA3 protein sequence is 148I/434K, the 434E variant is a naturally occurring variant in the human BAC used to generate the LTVEC in Example 1. As in Example 1, a loxP-mPrm1-Crei-pA-hUb1-em7-Neo-pA-loxP cassette was inserted downstream of the human PNPLA3 3' UTR. This is the MAID 7622 allele (SEQ ID NO: 67). See FIG. 4. After cassette deletion, loxP and cloning sites remained downstream of the human PNPLA3 3' UTR. This is the MAID 7623 (SEQ ID NO: 68). See FIG. 4.

Sequences for the mouse PNPLA3 cytoplasmic domain, transmembrane domain, and lumenal domain are set forth in SEQ ID NOS: 2-4, respectively, with the corresponding coding sequence set forth in SEQ ID NOS: 12-14, respectively. Sequences for the human PNPLA3 cytoplasmic domain, transmembrane domain, and lumenal domain (comprising 148I and 434E) are set forth in SEQ ID NOS: 6, 7, and 65, respectively, with the corresponding coding sequences set forth in SEQ ID NOS: 16, 17, and 66, respectively. The sequence of the wild type human PNLPA3 lumenal domain (without the K434E mutation) is set forth in SEQ ID NO: 8, with the corresponding coding sequence set forth in SEQ ID NO: 18. The expected encoded humanized PNLPA3 protein has human PNLPA3 cytoplasmic, transmembrane, and lumenal domains, along with the 148I and 434E. See FIG. 4. The mouse Pnpla3 coding sequence and the human PNPLA3 coding sequence (encoding a human PNPLA3 protein comprising 148I and 434E) are set forth in SEQ ID NOS: 11 and 64, respectively. The mouse wild type PNPLA3 protein sequence and the human PNPLA3 protein sequence (comprising 148I and 434E) are set forth in SEQ ID NOS: 1 and 63, respectively. The wild type human PNPLA3 coding sequence is set forth in SEQ ID NO: 15, and the wild type human PNPLA3 protein sequence is set forth in SEQ ID NO: 5. The sequences for the expected humanized PNPLA3 coding sequence and the expected humanized PNPLA3 protein are set forth in SEQ ID NOS: 64 and 63, respectively.

To generate the mutant allele, CRISPR/Cas9 components including four guide RNAs (guide RNA target sequences set forth in SEQ ID NOS: 28-31) were introduced into F1H4 mouse embryonic stem (ES) cells together with the large targeting vector described above. F1H4 mouse ES cells were derived from hybrid embryos produced by crossing a female C57BL/6NTac mouse to a male 12956/SvEvTac mouse. See, e.g., US 2015-0376651 and WO 2015/200805, each of which is herein incorporated by reference in its entirety for all purposes. Specifically, a nucleofection process was carried out with $2\times10^6$ mouse ES cells (line F1H4) plus 0.4 μg PNPLA3 LTVEC; 5 μg Cas9; and 2.5 μg each of the gRNAs: gU, gU2, gD and gD2. Antibiotic selection was performed using G418 at a concentration of 100 μg/mL. Following antibiotic selection, colonies were picked, expanded, and screened by TAQMAN®. See FIG. 2. Loss-of-allele assays were performed to detect loss of the endogenous mouse allele, gain-of-allele assays were performed to detect gain of the humanized allele, an allele-specific assay was used to detect the I148M-encoding mutation, and CRISPR and retention assays were performed using the primers and probes set forth in Table 5.

Modification-of-allele (MOA) assays including loss-of-allele (LOA) and gain-of-allele (GOA) assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. The loss-of-allele (LOA) assay inverts the conventional screening logic and quantifies the number of copies in a genomic DNA sample of the native locus to which the mutation was directed. In a correctly targeted heterozygous cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector in a genomic DNA sample.

Retention assays are described in US 2016/0145646 and WO 2016/081923, each of which is herein incorporated by reference in its entirety for all purposes. Retention assays distinguish between correct targeted insertions of a nucleic acid insert into a target genomic locus from random transgenic insertions of the nucleic acid insert into genomic locations outside of the target genomic locus by assessing copy numbers of DNA templates from 5' and 3' target sequences corresponding to the 5' and 3' homology arms of the targeting vector, respectively. Specifically, retention assays determine copy numbers in a genomic DNA sample of a 5' target sequence DNA template intended to be retained in the modified target genomic locus and/or the 3' target sequence DNA template intended to be retained in the modified target genomic locus. In diploid cells, correctly targeted clones will retain a copy number of two. Copy numbers greater than two generally indicate transgenic integration of the targeting vector randomly outside of the target genomic locus rather than at the target genomic locus. Copy numbers of less than generally indicate large deletions extending beyond the region targeted for deletion.

CRISPR assays are TAQMAN® assays designed to cover the region that is disrupted by the CRISPR gRNAs. When a CRISPR gRNA cuts and creates an indel (insertion or deletion), the TAQMAN® assay will fail to amplify and thus reports CRISPR cleavage.

F0 mice were generated from the modified ES cells using the VELOCIMOUSE® method. Specifically, mouse ES cell clones comprising the humanized PNPLA3 locus described above that were selected by the MOA assay described above were injected into 8-cell stage embryos using the VELOCIMOUSE® method. See, e.g., U.S. Pat. Nos. 7,576,259; 7,659,442; 7,294,754; US 2008/0078000; and Poueymirou et al. (2007) *Nat. Biotechnol.* 25(1):91-99, each of which is herein incorporated by reference in its entirety for all purposes. In the VELOCIMOUSE® method, targeted mouse ES cells are injected through laser-assisted injection into pre-morula stage embryos, e.g., eight-cell-stage embryos, which efficiently yields F0 generation mice that are fully ES-cell-derived. In the VELOCIMOUSE® method, the injected pre-morula stage embryos are cultured to the blastocyst stage, and the blastocyst-stage embryos are introduced into and gestated in surrogate mothers to produce the F0 generation mice. When starting with mouse ES cell clones homozygous for the targeted modification, F0 mice homozygous for the targeted modification are produced. When starting with mouse ES cell clones heterozygous for the targeted modification, subsequent breeding can be performed to produce mice homozygous for the targeted modification.

We claim:

1. A genetically modified mouse whose genome comprises a humanized patatin-like phospholipase domain containing 3 (PNPLA3) gene comprising an endogenous PNPLA3 promoter, and a replacement of an endogenous nucleic acid sequence from the first exon through the penultimate exon including all intervening introns of a PNPLA3 gene with an exogenous nucleic acid sequence comprising the start codon through the stop codon of a human PNPLA3 gene, wherein the mouse functionally expresses human PNPLA3 and exhibits increased expression of PNLPA3 in liver tissue when given standard chow as compared to a wild-type mouse given standard chow.

2. The genetically modified mouse of claim 1, wherein the humanized PNPLA3 gene encodes a PNPLA3 protein comprising a human PNPLA3 lumenal domain that is wild type at the position corresponding to position 148 of SEQ ID NO: 5.

3. The genetically modified mouse of claim 1, wherein the humanized PNPLA3 gene encodes a PNPLA3 protein comprising a human PNPLA3 lumenal domain comprising an I148M mutation and/or a K434E mutation.

4. The genetically modified mouse of claim 3, wherein the human PNPLA3 lumenal domain comprises the I148M mutation and the K434E mutation.

5. The genetically modified mouse of claim 4, wherein the human PNPLA3 lumenal domain comprises the sequence set forth in SEQ ID NO: 10, optionally wherein the human PNPLA3 lumenal domain is encoded by the coding sequence set forth in SEQ ID NO: 20.

6. The genetically modified mouse of claim 3, wherein the human PNPLA3 lumenal domain comprises the K434E mutation but not the I148M mutation.

7. The genetically modified mouse of claim 6, wherein the human PNPLA3 lumenal domain comprises the sequence set forth in SEQ ID NO: 65, optionally wherein the human PNPLA3 lumenal domain is encoded by the coding sequence set forth in SEQ ID NO: 66.

8. The genetically modified mouse of claim 1, wherein the humanized PNPLA3 gene encodes a PNPLA3 protein comprising a human PNPLA3 lumenal domain that is a wild type human PNPLA3 lumenal domain.

9. The genetically modified mouse of claim 8, wherein the human PNPLA3 lumenal domain comprises the sequence set forth in SEQ ID NO: 8, optionally wherein the human PNPLA3 lumenal domain is encoded by the coding sequence set forth in SEQ ID NO: 18.

10. The genetically modified mouse of claim 1, wherein the humanized PNPLA3 gene encodes a PNPLA3 protein comprising a human PNPLA3 transmembrane domain comprising the sequence set forth in SEQ ID NO: 7, optionally wherein the human PNPLA3 transmembrane domain is encoded by the coding sequence set forth in SEQ ID NO: 17.

11. The genetically modified mouse of claim 1, wherein the humanized PNPLA3 gene encodes a PNPLA3 protein comprising a human PNPLA3 cytoplasmic domain comprising the sequence set forth in SEQ ID NO: 6, optionally wherein the human PNPLA3 cytoplasmic domain is encoded by the coding sequence set forth in SEQ ID NO: 16.

12. The genetically modified mouse of claim 1, wherein the PNPLA3 protein produced by the humanized PNPLA3 gene comprises an I148M mutation and/or a K434E mutation.

13. The genetically modified mouse of claim 1, wherein the PNPLA3 protein produced by the humanized PNPLA3 gene is a wild type PNPLA3 protein.

14. The genetically modified mouse of claim 1, wherein the 3' UTR of the human PNPLA3 gene has been inserted into the endogenous PNPLA3 gene.

15. The genetically modified mouse of claim 1, wherein all or part of the last intron of the endogenous PNPLA3 gene has not been deleted in the humanized PNPLA3 gene.

16. The genetically modified mouse of claim 15, wherein the part of the last intron of the endogenous PNPLA3 gene that has not been deleted in the humanized PNPLA3 gene comprises a regulatory element that affects expression of a SAMM50 gene downstream of the endogenous PNPLA3 gene.

17. The genetically modified mouse of claim 1, wherein:

(i) the human PNPLA3 gene sequence at the humanized PNPLA3 gene comprises a sequence identical to the sequence set forth in SEQ ID NO: 62 or 69; and/or (ii) the humanized PNPLA3 gene encodes a protein comprising a sequence identical to the sequence set forth in SEQ ID NO: 5, 9, or 63; and/or (iii) the humanized PNPLA3 gene comprises a coding sequence comprising a sequence identical to the sequence set forth in SEQ ID NO: 15, 19, or 64; and/or (iv) the humanized PNPLA3 gene comprises a sequence identical to the sequence set forth in SEQ ID NO: 21, 22, 67, or 68.

18. The genetically modified mouse of claim 1, wherein the humanized PNPLA3 gene does not comprise a selection cassette or a reporter gene.

19. The genetically modified mouse of claim 1, wherein the mouse is homozygous for the humanized PNPLA3 gene.

20. The genetically modified mouse of claim 1, wherein the mouse comprises the humanized PNPLA3 gene in its germline.

21. A method of assessing the activity of inhibitory or antisense RNA that binds human PNPLA3 RNA in vivo, the method comprising:

a) administering the inhibitory or antisense RNA to the genetically modified mouse of claim 1;

b) measuring expression levels of human PNPLA3 in the mouse obtained in step a).

22. A method of making a genetically modified mouse with a humanized patatin-like phospholipase domain containing 3 (PNPLA3) gene, the method comprising:

(I) (a) introducing an embryonic stem (ES) cell whose genome comprises a replacement of an endogenous nucleic acid sequence from the first exon through the penultimate exon including all intervening introns of a PNPLA3 gene with an exogenous nucleic acid sequence comprising the start codon through the stop codon of a human PNPLA3 gene into a mouse embryo;

(b) implanting the embryo obtained in step (a) into a recipient female; and (c) obtaining a genetically modified mouse from the embryo implanted in step (b), wherein the germline genome of the mouse comprises a replacement of an endogenous nucleic acid sequence from the first exon through the penultimate exon including all intervening introns of a PNPLA3 gene with an exogenous nucleic acid sequence comprising the start codon through the stop codon of a human PNPLA3 gene, wherein the mouse functionally expresses human PNPLA3 and exhibits increased expression of PNLPA3 in liver tissue when given standard chow as compared to a wild-type mouse given standard chow; or (II) (a) implanting a one-cell mouse embryo whose genome comprises a replacement of an endogenous nucleic acid sequence from the first exon through the penultimate exon including all intervening introns of a PNPLA3 gene with an exogenous nucleic acid sequence comprising the start codon through the stop codon of a human PNPLA3 gene into a recipient female; and (b) obtaining a genetically modified mouse from the embryo implanted in step (a), wherein the germline genome of the mouse comprises a replacement of an endogenous nucleic acid sequence from the first exon through the penultimate exon including all intervening introns of a PNPLA3 gene with an exogenous nucleic acid sequence comprising the start codon through the stop codon of a human PNPLA3 gene, wherein the mouse functionally expresses human PNPLA3 and exhibits increased expression of PNLPA3 in liver tissue when given standard chow as compared to a wild-type mouse given standard chow.

23. A method of assessing the activity of a genome editing reagent that targets a human PNPLA3 gene in vivo, the method comprising:

a) administering the genome editing reagent to the genetically modified mouse of claim 1;

b) measuring the activity of the genome editing reagent in the mouse obtained in step a).

* * * * *